United States Patent
Ding et al.

(10) Patent No.: US 8,552,002 B2
(45) Date of Patent: Oct. 8, 2013

(54) COMPOUNDS AND COMPOSITIONS AS PROTEIN KINASE INHIBITORS

(75) Inventors: Qiang Ding, Beijing (CN); Nathanael Schiander Gray, Boston, MA (US); Bing Li, Northborough, MA (US); Yi Liu, San Diego, CA (US); Taebo Sim, Seoul (KR); Tetsuo Uno, San Diego, CA (US); Guobao Zhang, San Diego, CA (US); Carole Pissot Soldermann, Village-Neuf (FR); Werner Breitenstein, Basel (CH); Guido Bold, Gipf-Oberfrick (CH); Giorgio Caravatti, Bottmingen (CH); Pascal Furet, Thann (FR); Vito Guagnano, Basel (CH); Marc Lang, Mulhouse (FR); Paul William Manley, Basel (CH); Joseph Schoepfer, Riehen (CH); Carsten Spanka, Lorrach (DE)

(73) Assignees: Novartis AG, Basel (CH); IRM LLC, Hamilton (BM)

( * ) Notice: Subject to any disclaimer, the term of this patent is extended or adjusted under 35 U.S.C. 154(b) by 713 days.

(21) Appl. No.: 11/570,983

(22) PCT Filed: Jun. 23, 2005

(86) PCT No.: PCT/EP2005/006815
§ 371 (c)(1),
(2), (4) Date: Oct. 15, 2008

(87) PCT Pub. No.: WO2006/000420
PCT Pub. Date: Jan. 5, 2006

(65) Prior Publication Data
US 2009/0137804 A1 May 28, 2009

Related U.S. Application Data

(60) Provisional application No. 60/582,425, filed on Jun. 24, 2004.

(30) Foreign Application Priority Data

Jun. 16, 2005 (GB) .................................. 0512324.5

(51) Int. Cl.
*A01N 43/54* (2006.01)
*C07D 239/02* (2006.01)

(52) U.S. Cl.
USPC ........... 514/256; 544/242; 544/298; 544/299; 544/315; 544/319

(58) Field of Classification Search
USPC .......... 544/298, 299, 242, 315, 318; 514/256
See application file for complete search history.

(56) References Cited

U.S. PATENT DOCUMENTS

| | | | |
|---|---|---|---|
| 3,759,921 A | 9/1973 | Paget et al. | |
| 2003/0069284 A1* | 4/2003 | Keegan et al. | 514/345 |
| 2004/0014765 A1* | 1/2004 | Boyle et al. | 514/252.02 |
| 2004/0034038 A1 | 2/2004 | Li et al. | |
| 2004/0116388 A1 | 6/2004 | Armistead et al. | |
| 2008/0312248 A1 | 12/2008 | Bold et al. | |
| 2010/0120773 A1 | 5/2010 | Guagnano et al. | |
| 2012/0220600 A1 | 8/2012 | Aichholz et al. | |
| 2012/0245182 A1 | 9/2012 | Berghausen et al. | |
| 2012/0258940 A1 | 10/2012 | Caponigro et al. | |
| 2013/0012476 A1 | 1/2013 | Ding et al. | |
| 2013/0012704 A1 | 1/2013 | Ding et al. | |

FOREIGN PATENT DOCUMENTS

| | | |
|---|---|---|
| WO | 01/25220 A1 | 4/2001 |
| WO | WO 02/070494 | 9/2002 |
| WO | 03068228 A1 | 8/2003 |
| WO | 03/099771 A2 | 12/2003 |
| WO | WO 03/101444 | 12/2003 |
| WO | 2004/058713 A1 | 7/2004 |
| WO | 2004113274 A2 | 12/2004 |
| WO | 2005/030735 A1 | 4/2005 |
| WO | 2005/051366 A2 | 6/2005 |
| WO | 2005075425 A2 | 8/2005 |
| WO | 2005/121147 A1 | 12/2005 |
| WO | WO 2005/113548 | 12/2005 |

(Continued)

OTHER PUBLICATIONS

Vippagunta et al., "Crystalline Solids", Adv. Drug Del. Rev., 48 (2001) 3-26.*

(Continued)

*Primary Examiner* — Paul V. Ward
(74) *Attorney, Agent, or Firm* — Laura K. Madden

(57) ABSTRACT

The invention relates to compounds of formula (I)

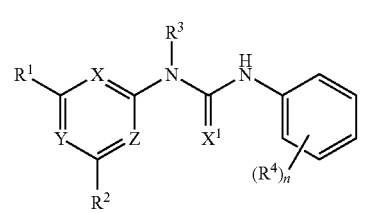

wherein the substituents $X^1$, $R^1$, $R^2$, $R^3$ and $R^4$ have the meaning as set forth and explained in the description of the invention, to processes for the preparation of these compounds, pharmaceutical compositions containing same, the use thereof optionally in combination with one or more other pharmaceutically active compounds for the therapy of a disease which responds to an inhibition of protein kinase activity, and a method for the treatment of such a disease.

43 Claims, No Drawings

(56) References Cited

FOREIGN PATENT DOCUMENTS

| WO | 2006/053227 A2 | 5/2006 |
|---|---|---|
| WO | 2006049941 A2 | 5/2006 |
| WO | 2006128129 A2 | 11/2006 |
| WO | 2006128172 A2 | 11/2006 |
| WO | 2007/024754 A1 | 3/2007 |

OTHER PUBLICATIONS

Traverso et al., J'nal of Med. Chem., "Synthesis of Pharmacological . . . ", vol. 5, p. 808-15, 1962.*
Modi et al; J.Indian Chem. Soc. vol. 71, pp. 697-700, 1994.
Desai et al; J.Indian Chem. Soc.; vol. 71, pp. 151-153, 1994.
Hurst et al; Aust.J.Chem; vol. 41 pp. 1221-1229, 1988.
Desai et al; J.Indian Chem. Soc; vol. 64, pp. 773-774 1987.
Traverso et al; Journal of Medicinal and Paharmaceutical Chemistry; vol. 5, pp. 808-815, 1962.
Maier et al, Bioorganic & Medicinal Chemistry Letters, 16, 3646-3650.
Ling, et al., Selenium-catalyzed carbonylation of substituted nitrobenzenes with aminomethylpyrimidines as co-reagents to synthesize N-phenyl-N'-methylpyrimidylurea derivatives, Journal of Molecular Catalysis A: Chemical, 2003 vol. 202 pp. 23-29.
Modi, et al., "Synthesis of 2-(2', 4'- Dihydroxy-1'-Phenyl)-4-Morpholino-6-Arylureido-S-Triazine Derivatives", Acta Ciencia Indica, 1994 vol. XXC No. 1 pp. 1-3.
Paget, et al., "Heterocyclic Substituted Ureas. III. Immunosuppressive and Antiviral 2-Pyrimidylureas", Journal of Medicinal Chemistry, 1969 vol. 12 No. 5 pp. 1097-1098.
Urbanski, et al., Potential Antimalarial Compounds. IX. Pyrimidine Derivatives of Urea and Guanidine, Journal of Medicinal Chemistry, 1967 vol. 10 No. 4 pp. 521-525.
Office Action dated Jul. 13, 2011, U.S. Appl. No. 12/158,873, filed Dec. 20, 2006, "Pyrimidinyl Aryl Urea Derivatives Being Fgf Inhibitors", Bold, Guido et al.
Office Action dated Jan. 27, 2011, U.S. Appl. No. 12/158,873, filed Dec. 20, 2006, "Pyrimidinyl Aryl Urea Derivatives Being Fgf Inhibitors", Bold, Guido et al.
Office Communication sent and received electronically on Apr. 12, 2013 in U.S. Appl. No. 13/516,093.
Kelarev et al; Chemistry of Heterocyclic Compounds, vol. 23, pp. 298-304, 1987.
Overberger et al; Journal of the American Chemical Society, vol. 76, pp. 93-96, 1954.
Maier et al, Bioorganic & Medicinal Chemistry Letters, 16, 3646-3650, (May 2006).

* cited by examiner

US 8,552,002 B2

COMPOUNDS AND COMPOSITIONS AS PROTEIN KINASE INHIBITORS

This application is the National Stage of Application No. PCT/EP2005/006815, filed on Jun. 23, 2005, which claims benefit under 35 U.S.C. §119(e) of U.S. Provisional Application No. 60/582,425, filed Jun. 24, 2004. The contents of both are incorporated herein by reference in their entirety.

The invention relates to novel compounds, formulations, methods and uses. More particularly it relates to compounds, which may be described as heteroaryl aryl ureas, useful for the treatment of protein kinase dependent diseases, or for the manufacture of pharmaceutical compositions for use in the treatment of said diseases. The invention further relates to methods of use of such compounds in the treatment of said diseases, pharmaceutical preparations comprising heteroaryl aryl ureas, and processes for the manufacture of heteroaryl aryl ureas. The invention relates to other subject matter as disclosed below.

BACKGROUND

Protein kinases (PKs) are enzymes which catalyze the phosphorylation of specific serine, threonine or tyrosine residues in cellular proteins. These post-translational modifications of substrate proteins act as molecular switch regulating cell proliferation, activation and/or differentiation. Aberrant or excessive PK activity has been observed in many disease states including benign and malignant proliferative disorders. In many cases, it has been possible to treat diseases in vitro and in many cases in vivo, such as proliferative disorders, by making use of PK inhibitors.

The kinases fall largely into two groups, those specific for phosphorylating serine and threonine, and those specific for phosphorylating tyrosine. Some kinases, referred to as "dual specificity" kinases, are able to phosphorylate tyrosine as well as serine/threonine residues.

Protein kinases can also be characterized by their location within the cell. Some kinases are transmembrane receptor proteins capable of binding ligands external to the cell membrane. Binding the ligands alters the receptor protein kinase's catalytic activity. Others are non-receptor proteins lacking a transmembrane domain and yet others are ecto-kinases that have a catalytic domain on the extracellular (ecto) portion of a transmembrane protein or which are secreted as soluble extracellular proteins.

Many kinases are involved in regulatory cascades where their substrates may include other kinases whose activities are regulated by their phosphorylation state. Thus, activity of a downstream effector is modulated by phosphorylation resulting from activation of the pathway.

Receptor protein tyrosine kinases (RPTKs) are a sub-class of transmembrane-spanning receptors endowed with intrinsic, ligand-stimulatable tyrosine kinase activity. RPTK activity is tightly controlled. When mutated or altered structurally, RPTKs can become potent oncoproteins, causing cellular transformation. In principle, for all RPTKs involved in cancer, oncogenic deregulation results from relief or perturbation of one or several of the autocontrol mechanisms that ensure the normal repression of catalytic domains. More than half of the known RPTKs have been repeatedly found in either mutated or overexpressed forms associated with human malignancies (including sporadic cases; Blume-Jensen et al., Nature 411: 355-365 (2001)).

RPTK over expression leads to constitutive kinase activation by increasing the concentration of dimers. Examples are Neu/ErbB2 and epidermal growth factor receptor (EGFR), which are often amplified in breast and lung carcinomas and the fibroblast growth factors (FGFR) associated with skeletal and proliferative disorders (Blume-Jensen et al., 2001).

Angiogenesis is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies et al., Cell Growth & Differentiation, 8, 3-10 (1997). On the other hand, unwanted angiogenesis is a hallmark of several diseases, such as retinopathies, psoriasis, rheumatoid arthritis, age-related macular degeneration (AMD), and cancer (solid tumors). Folkman, Nature Med., 1, 27-31 (1995). Protein kinases which have been shown to be involved in the angiogenic process include three members of the growth factor receptor tyrosine kinase family: VEGF-R2 (vascular endothelial growth factor receptor 2, also known as KDR (kinase insert domain receptor) and as FLK-1); FGF-R (fibroblast growth factor receptor); and TEK (also known as Tie-2).

TEK (also known as Tie-2) is a receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels.

The factor angiopoietin-2, on the other hand, appears to antagonize the action of angiopoietin-1 on TEK and disrupts angiogenesis. Maisonpierre et al., Science, 277, 55-60 (1997).

Administration of Ad-ExTek, a soluble adenoviral expressed extracellular domain of Tie-2, inhibited tumour metastasis when delivered at the time of surgical excision of primary tumours in a clinically relevant mouse model of tumor metastasis (Lin et al., Proc Natl Acad Sci USA 95, 8829-8834 (1998)). The inhibition of Tie-2 function by ExTek may be a consequence of sequestration of the angiopoietin ligand and/or heterodimerisation with the native Tie-2 receptor. This study demonstrates that disruption of Tie-2 signalling pathways, first, may be well tolerated in healthy organisms and, second, may provide therapeutic benefit.

The Philadelphia Chromosome is a hallmark for chronic myelogenous leukaemia (CML) and carries a hybrid gene that contains N-terminal exons of the bcr gene and the major C-terminal part (exons 2-11) of the c-abl gene. The gene product is a 210 kD protein (p210 Bcr-Abl). The Abl-part of the Bcr-Abl protein contains the abl-tyrosine kinase which is tightly regulated in the wild type c-abl, but constitutively activated in the Bcr-Abl fusion protein. This deregulated tyrosine kinase interacts with multiple cellular signalling pathways leading to transformation and deregulated proliferation of the cells (Lugo et al., Science 247, 1079 [1990]).

Mutant forms of the Bcr-Abl protein have also been identified. A detailed review of Bcr-Abl mutant forms has been published (Cowan-Jones et al, Mini Reviews in Medicinal Chemistry, 2004, 4 285-299).

EphB4 (also named HTK) and its ligand, ephrinB2 (HTKL) have critical roles in establishing and determining vascular networks. On the venous epithelium, EphB4 is expressed specifically, while, during early stages of vascular development, ephrinB2 is specifically and reciprocally expressed on arterial endothelial cells. Dysfunctional genes lead to embryonic lethality in mice, and the embryos show identical defects in forming capillary connections in case of either defect ephrinB2 and EphB4. Both are expressed at the first site of hematopoiesis and vascular development during embryogenesis. An essential role for proper hematopoietic, endothelial, hemangioblast and primitive mesoderm development was established. EphB4 deficiency results in an alteration in the mesodermal differentiation outcome of embryonic stem cells. Ectopic expression of EphB4 in mammary tissue results in disordered architecture, abnormal tissue function and a predisposition to malignancy (see e.g. N. Munarini et al., J. Cell. Sci. 115, 25-37 (2002)). From these and other data, it has been concluded that inadequate EphB4 expression may be involved in the formation of malignancies and thus that inhibition of EphB4 can be expected to be a tool to combat malignancies, e.g. cancer and the like.

c-Src (also known as p60 c-Src) is cytosolic, non-receptor tyrosine kinase. c-Src is involved in the transduction of mitogenic signals from a number of polypeptide growth factors such as epidermal growth factor (EGF) and platelet-derived growth factor (PDGF). c-Src is over expressed in mammary cancers, pancreatic cancers, neuroblastomas, and others. Mutant c-Src has been identified in human colon cancer. c-Src phosphorylates a number of proteins that are involved in regulating cross-talk between the extracellular matrix and the cytoplasmic actin cytoskeleton. Modulation cSrc activity could have implications in diseases relating to cell proliferation, differentiation and death. See Bjorge, J. D., et. al. (2000) Oncogene 19(49):5620-5635; Halpern, M. S., et. al. (1996) Proc. Natl. Acad. Sci. U.S.A. 93(2), 824-7; Belsches, A. P., et. al. (1997) Frontiers in Bioscience [Electronic Publication] 2:D501-D518; Zhan, X., et. al (2001) Chemical Reviews 101:2477-2496; Haskell, M. D., et. al. (2001) Chemical Reviews 101:2425-2440.

The fms-like tyrosine kinase 3 (FLT3) receptor tyrosine kinase is now recognized to be a critical mediator in the pathogenesis of myeloid and some lymphoid leukemias. Activation of FLT3 on leukemic cells by FLT3 ligand leads to receptor dimerization and signal transduction in pathways that promote cell growth and inhibit apoptosis (Blood, Vol. 98, No. 3, pp. 885-887 (2001)).

Use of tyrosine kinase inhibitors for AML therapy is hindered by the acquisition of mutations in the kinase catalytic domain, and in the case of BCR-ABL, these mutations confer resistance to imatinib.

FLT3 is widely expressed in AML and some cases of acute lymphocytic leukemia. Activating mutations in FLT3 confer a poor risk in patients with AML. Thus, FLT3 is a promising target for therapeutic intervention.

Platelet-derived growth factor receptor (PDGFR) tyrosine kinase is expressed in a number of tumours such as small-cell lung cancer, prostate cancer, and glioblastoma as well as in the stromal and vascular compartments of many tumors. Expression of both PDGF and PDGF receptors (PDGFRs) has been observed in pancreatic cancer (Ebert M et al., Int J Cancer, 62:529-535 (1995).

Fibroblast Growth Factors

Normal growth, as well as tissue repair and remodeling, require specific and delicate control of activating growth factors and their receptors. Fibroblast Growth Factors (FGFs) constitute a family of over twenty structurally related polypeptides that are developmentally regulated and expressed in a wide variety of tissues. FGFs stimulate proliferation, cell migration and differentiation and play a major role in skeletal and limb development, wound healing, tissue repair, hematopoiesis, angiogenesis, and tumorigenesis (reviewed in Ornitz, Novartis Found Svmp 232: 63-76; discussion 76-80, 272-82 (2001)).

The biological action of FGFs is mediated by specific cell surface receptors belonging to the RPTK family of protein kinases. These proteins consist of an extracellular ligand binding domain, a single transmembrane domain and an intracellular tyrosine kinase domain which undergoes phosphorylation upon binding of FGF. Four FGFRs have been identified to date: FGFR1 (also called Flg, fms-like gene, fit-2, bFGFR, N-bFGFR or Cek1), FGFR2 (also called Bek-Bacterial Expressed Kinase-, KGFR, Ksam, Ksaml and Cek3), FGFR3 (also called Cek2) and FGFR4. All mature FGFRs share a common structure consisting of an amino terminal signal peptide, three extracellular immunoglobulin-like domains (Ig domain I, Ig domain II, Ig domain III), with an acidic region between Ig domains (the "acidic box" domain), a transmembrane domain, and intracellular kinase domains (Ullrich and Schlessinger, Cell 61: 203, 1990; Johnson and Williams (1992) Adv. Cancer Res. 60: 1-41). The distinct FGFR isoforms have different binding affinities for the different FGF ligands, thus FGF8 (androgen-induced growth factor) and FGF9 (glial activating factor) appear to have increased selectivity for FGFR3 (Chellaiah et al. J Biol. Chem 1994; 269: 11620).

Another major class of cell surface binding sites includes binding sites for heparan sulfateproteoglycans (HSPG) that are required for high affinity interaction and activation of all members of the FGF family. Tissue-specific expression of heparan sulfate structural variants confer ligand-receptor specificity and activity of FGFs FGFR-Related Diseases Recent discoveries show that a growing number of skeletal abnormalities, including achondroplasia, the most common form of human dwarfism, result from mutations in FGFRs.

Specific point mutations in different domains of FGFR3 are associated with autosomal dominant human skeletal disorders including hypochondroplasia, severe achondroplasia with developmental delay and acanthosis nigricans (SADDAN) and thanatophoric dysplasia (TD) (Cappellen et al., *Nature Genetics,* 23: 18-20 (1999); Webster et al., *Trends Genetics* 13 (5): 178-182 (1997); Tavormina et al., *Am. J. Hum. Genet.,* 64: 722-731 (1999)). FGFR3 mutations have also been described in two craniosynostosis phenotypes: Muenke coronal craniosynostosis (Bellus et al., *Nature Genetics,* 14: 174-176 (1996); Muenke et al., *Am. J. Hum. Genet.,* 60:555-564 (1997)) and Crouzon syndrome with acanthosis nigricans (Meyers et al., *Nature Genetics,* 11: 462-464 (1995)). Crouzon syndrome is associated with specific point mutations in FGFR2 and both familial and sporadic forms of Pfeiffer syndrome are associated with mutations in FGFR1 and FGFR2 (Galvin et al., *PNAS USA,* 93: 7894-7899 (1996); Schell et al., *Hum Mol Gen,* 4: 323-328 (1995)). Mutations in FGFRs result in constitutive activation of the mutated receptors and increased receptor protein tyrosine kinase activity, rendering cells and tissue unable to differentiate.

Specifically, the achondroplasia mutation results in enhanced stability of the mutated receptor, dissociating receptor activation from down-regulation, leading to restrained chondrocyte maturation and bone growth inhibition (reviewed in Vajo et al., *Endocrine Reviews,* 21(1): 23-39 (2000)).

There is accumulating evidence for mutations activating FGFR3 in various types of cancer.

Constitutively activated FGFR3 in two common epithelial cancers, bladder and cervix, as well as in multiple myeloma, is the first evidence of an oncogenic role for FGFR3 in carcinomas. In addition, a very recent study reports the presence of FGFR3 activating mutations in a large proportion of benign skin tumors (Logie et al., Hum Mol Genet 2005). FGFR3 currently appears to be the most frequently mutated oncogene in bladder cancer where it is mutated in almost 50% of the total bladder cancer cases and in about 70% of cases having superficial bladder tumors (Cappellen, et al., Nature Genetics 1999, 23; 19-20; van Rhijn, et al., Cancer Research 2001, 61: 1265-1268; Billerey, et al, Am. J. Pathol. 2001, 158:1955-1959, WO 2004/085676). FGFR3 aberrant overexpression as a consequence of the chromosomal translocation t(4, 14) is reported in 10-25% of multiple myeloma cases (Chesi et al., Nature Genetics 1997, 16: 260-264; Richelda et al., Blood 1997, 90:4061-4070; Sibley et al., BJH 2002, 118: 514-520; Santra et al., Blood 2003, 101: 2374-2476). FGFR3 activating mutations are seen in 5-10% of multiple myelomas with t(4, 14) and are associated with tumor progression (Chesi et al., Nature Genetics 1997, 16: 260-264; Chesi et al., *Blood, 97* (3): 729-736 (2001); Intini, et al, BJH 2001, 114: 362-364).

In this context, the consequences of FGFR3 signaling appear to be cell type-specific. In chondrocytes, FGFR3 hyperactivation results in growth inhibition (reviewed in Omitz, 2001), whereas in the myeloma cell it contributes to tumor progression (Chesi et al., 2001).

The inhibition of FGFR3 activity has been found to represent a means for treating T cell mediated inflammatory or autoimmune diseases, as for example in treatment of T-cell mediated inflammatory or autoimmune diseases including but not limited to rheumatoid arthritis (RA), collagen II arthritis, multiple sclerosis (MS), systemic lupus erythematosus (SLE), psoriasis, juvenile onset diabetes, Sjogren's disease, thyroid disease, sarcoidosis, autoimmune uveitis, inflammatory bowel disease (Crohn's and ulcerative colitis), celiac disease and myasthenia gravis. See WO 2004/110487.

Disorders resulting from FGFR3 mutations are described also in WO 03/023004 and WO 02/102972.

Gene amplification and/or overexpression of FGFR1, FGFR2 and FGFR4 has been implicated in breast cancer (Penault-Llorca et al., Int J Cancer 1995; Theillet et al., Genes Chrom. Cancer 1993; Adnane et al., Oncogene 1991; Jaakola et al., Int J Cancer 1993; Yamada et al., Neuro Res 2002). Overexpression of FGFR1 and FGFR4 is also associated with pancreatic adenocarcinomas and astrocytomas (Kobrin et al., Cancer Research 1993; Yamanaka et al., Cancer Research 1993; Shah et al., Oncogene 2002; Yamaguchi et al., PNAS 1994; Yamada et al., Neuro Res 2002). Prostate cancer has also been related to FGFR1 overexpression (Giri et al., Clin Cancer Res 1999).

There is an unmet need for highly selective molecules capable of blocking aberrant constitutive receptor protein tyrosine kinase activity, in particular FGFR activity, thereby addressing the clinical manifestations associated with the above-mentioned mutations, and modulating various biological functions.

In view of the large number of protein kinase inhibitors and the multitude of proliferative and other PK-related diseases, there is an ever-existing need to provide novel classes of compounds that are useful as PK inhibitors and thus in the treatment of these Protein Tyrosine Kinase (PTK) related diseases. What is required are new classes of pharmaceutically advantageous PK inhibiting compounds.

Epidermal Growth Factor Family and Related Diseases

The epidermal growth factor receptor (EGF-R) and ErbB-2 kinase are protein tyrosine kinase receptors which, together with their family members ErbB-3 and ErbB-4, play a key role in signal transmission in a large number of mammalian cells, including human cells, especially epithelial cells, cells of the immune system and cells of the central and peripheral nervous system. For example, in various cell types, EGF-induced activation of receptor-associated protein tyrosine kinase is a prerequisite for cell division and hence for the proliferation of the cell population. Most importantly, overexpression of the EGF-R (HER-1) and/or ErbB-2 (HER-2) has been observed in substantial fractions of many human tumours. EGF-R, e.g., was found to be overexpressed in non small-cell lung cancers, squameous carcinoma (head and neck), breast, gastric, ovarian, colon and prostate cancers as well as in gliomas. ErbB-2 was found to be overexpressed in squameous carcinoma (head and neck), breast, gastric, and ovarian cancers as well as in gliomas.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention relates to compounds of Formula (I) and salts, esters, N-oxides or prodrugs thereof:

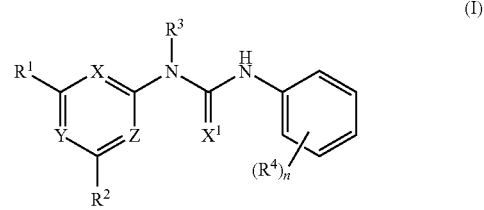

where
n is 0, 1, 2, 3, 4 or 5;
X, Y and Z are each independently selected from N or C—$R^5$, wherein at least two of X, Y and Z are N; and
$X^1$ is oxygen,
$R^1$, $R^2$, $R^3$ and $R^4$ if present, are each independently selected from an organic or inorganic moiety,
where the inorganic moiety is especially selected from halo, especially chloro, hydroxyl, cyano, azo (N=N=N), nitro; and
where the organic moiety is substituted or unsubstituted and may be attached via a linker, -$L^1$-, the organic moiety being especially selected from hydrogen; lower aliphatic (especially $C_1$, $C_2$, $C_3$ or $C_4$ aliphatic) e.g. lower alkyl, lower alkenyl, lower alkynyl; amino; guanidino; hydroxyguanidino; formamidino; isothioureido; ureido; mercapto; C(O)H or other acyl; acyloxy; substituted hydroxy; carboxy; sulfo; sulfamoyl; carbamoyl; a substituted or unsubstituted cyclic group, for example the cyclic group (whether substituted or unsubstituted) may be cycloalkyl, e.g. cyclohexyl, phenyl, pyrrole, imidazole, pyrazole, isoxazole, oxazole, thiazole, pyridazine, pyrimidine, pyrazine, pyridyl, indole, isoindole, indazole, purine, indolizidine, quinoline, isoquinoline, quinazoline, pteridine, quinolizidine, piperidyl, piperazinyl, pyrollidine, morpholinyl or thiomorpholinyl and, for example, substituted lower aliphatic or substituted hydroxy may be substituted by such substituted or unsubstituted cyclic groups.

and -L$^1$- having 1, 2, 3, 4 or 5 in-chain atoms (e.g. selected from C, N, O and S) and optionally being selected from (i) C$_1$, C$_2$, C$_3$ or C$_4$ alkyl, such an alkyl group optionally being interrupted and/or terminated by an —O—, —C(O)— or —NR$^a$— linkage; —O—; —S—; —C(O)—; cyclopropyl (regarded as having two in-chain atoms) and chemically appropriate combinations thereof; and —NR$^a$—, wherein R$^a$ is hydrogen, hydroxy, hydrocarbyloxy or hydrocarbyl, wherein hydrocarbyl is optionally interrupted by an —O— or —NH— linkage and may be, for example, selected from an aliphatic group (e.g. having 1 to 7 carbon atoms, for example 1, 2, 3, or 4), cycloalkyl, especially cyclohexyl, cycloalkenyl, especially cyclohexenyl, or another carbocyclic group, for example phenyl; where the hydrocarbyl moiety is substituted or unsubstituted;

each R$^4$ is the same or different and selected from an organic or inorganic moiety, for example, each R$^4$ is the same or different and selected from halogen; hydroxy; protected hydroxy for example trialkylsilylhydroxy; amino; amidino; guanidino; hydroxyguanidino; formamidino; isothioureido; ureido; mercapto; C(O)H or other acyl; acyloxy; carboxy; sulfo; sulfamoyl; carbamoyl; cyano; azo; nitro; C$_1$-C$_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other acyl, acyloxy, carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or more C$_1$-C$_7$ aliphatic groups.

In a particular embodiment, there is provided a compound of Formula (I), wherein:

n is 0, 1, 2, 3, 4 or 5;

X, Y and Z are each independently selected from N or C—R$^5$, wherein at least two of X, Y and Z are N; and R$^1$, R$^2$ and R$^5$ are each independently selected from H, R$^z$-L$^1$-; halogen; hydroxy; protected hydroxy for example trialkylsilylhydroxy; amino; amidino; guanidino; hydroxyguanidino; formamidino; isothioureido; ureido; mercapto; C(O)H or other acyl; acyloxy; carboxy; sulfo; sulfamoyl; carbamoyl; cyano; azo; nitro; C$_1$-C$_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other acyl, acyloxy, carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or, where possible, more C$_1$-C$_7$ aliphatic groups, wherein -L$^1$- has 1, 2, 3, 4 or 5 in-chain atoms and is selected from C$_1$, C$_2$, C$_3$ or C$_4$ aliphatic optionally interrupted and/or terminated by a linkage selected from the group consisting of —NR$^a$—; —O—; —S—; —C(O)—; cyclopropyl (regarded as having two in-chain atoms) and chemically appropriate combinations thereof; —NR$^a$—; —O—; —S—; —C(O)—; cyclopropyl (regarded as having two in-chain atoms) and chemically appropriate combinations thereof; and —NR$^a$—, wherein R$^a$ is hydrogen, hydroxy, hydrocarbyloxy or hydrocarbyl, wherein hydrocarbyl has from 1 to 15 carbon atoms, is optionally interrupted by an —O— or —NH— linkage and is unsubstituted or is substituted by hydroxy, halo, amino or mono- or di-(C$_1$-C$_4$) alkylamino, lower alkanoyl, trifluoromethyl, cyano, azo or nitro;

and R$^z$ is a moiety containing from 1 to 30 plural valent atoms selected from C, N, O, S and Si as well as monovalent atoms selected from H and halo;

R$^3$ is H or a moiety containing from 1 to 30 plural valent atoms selected from C, N, O S and Si as well as monovalent atoms selected from H and halo;

each R$^4$ is the same or different and selected from halogen; hydroxy; protected hydroxy for example trialkylsilylhydroxy; amino; amidino; guanidino; hydroxyguanidino; formamidino; isothioureido; ureido; mercapto; C(O)H or other acyl; acyloxy; carboxy; sulfo; sulfamoyl; carbamoyl; cyano; azo; nitro; C$_1$-C$_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other acyl, acyloxy, carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or, where possible, more C$_1$-C$_7$ aliphatic groups, or pharmaceutically acceptable salts, esters, N-oxides or prodrugs thereof.

Often, at least one of R$^1$, R$^2$ and R$^5$ is not H; in exemplary compounds a single one of R$^1$, R$^2$ and R$^5$ is not H. Normally R$^1$ is not H. The invention includes amongst others compounds in which at least one of R$^1$, R$^2$ and R$^5$ is R$^z$-L$^1$-. It includes a class of compounds in which a single one of R$^1$, R$^2$ and R$^5$ is R$^z$-L$^1$-, particularly R$^1$. The invention includes a class of compounds in which R$^2$ and R$^5$ are H and R$^1$ is not H, e.g. is R$^z$-L$^1$-.

Chemically appropriate combinations of —NR$^a$—; —O—; —S—; —C(O)—; cyclopropyl are combinations which form a chemically stable moiety, such as —NR$^a$C(O)—; —C(O)NR$^a$—; —C(O)O— and —OC(O)—, for example. In many classes of compounds, L$^1$ does not comprise cyclopropyl.

It has now been found that the above compounds, which may be described as belonging to the heteroaryl aryl urea class, show inhibition of a number of protein tyrosine kinases.

It is believed that certain compound of formula (I) lack novelty per se. In one embodiment, therefore, the invention provides compounds of formula (I) and salts, esters, N-oxides or prodrugs thereof excluding compounds of formula (I) in which:

(A) n is 0; R$^3$ is H; Y and Z are N; X is N, C—SO$_2$(NH) or C—NO$_2$ (or in a wider exclusionary embodiment any C—R$^5$ group); R$^2$ is H, SCH$_2$CH=CH$_2$ or SMe; and R$^1$ is of the formula NR'R" where R' and R" together with their adjoining nitrogen form morpholino or one of R' and R" is H and the other is phenyl, phenyl substituted by a single substituent selected from Me and Cl, or is —C(O)NHPh;

(B) n is 1; R$^4$ is methoxy; R$^3$ is H; X is CH; Y and Z are N; R$^1$ is NH$_2$; and R$^2$ is H or SMe;

(C) n is 1; R$^4$ is Cl; R$^3$ is ethyl; X, Y and Z are N; and one of R$^1$ and R$^2$ is H whilst the other is NEt$_2$; or (D) n is 2; one R$^4$ is meta-Cl and the other is para-methyl, R$^3$ is H; X, Y and Z are N; and one of R$^1$ and R$^2$ is H whilst the other is PhNH—, m-chloroPhNH—, p-chloroPhNH—, m-methylPhNH— or p-methylPhNH—.

In embodiments, there are additionally excluded (a) salts of the excluded compounds, (b) esters of excluded compounds, (c) N-oxides of excluded compounds, (d) prodrugs of excluded compounds, or (e) 1, 2, 3 or 4 of (a), (b), (c) and (d), e.g. all thereof.

Included in the invention is a method of treating a protein kinase-dependent disease in a warm-blooded animal, for example a human, comprising administering to the animal a therapeutically effective amount of a compound of Formula I or a salt, ester, N-oxide or prodrug thereof.

Also included is the use of a compound of Formula I or a salt, ester, N-oxide or prodrug thereof for the manufacture of a medicament for use in the treatment of a protein kinase-dependent disease.

As another aspect of the invention may be mentioned oral pharmaceutical formulations comprising compounds of Formula I or salts, esters, N-oxides or prodrugs thereof. Also to be mentioned as a further aspect are intravenous pharmaceutical formulations comprising compounds of Formula I or salts, esters, N-oxides or prodrugs thereof.

In embodiments of the aforesaid method, use and formulations, the compound is in the form of the compound of Formula (I) as such. In other embodiments, the compound is in the form of a salt, ester, N-oxide or prodrug thereof. Thus, in certain embodiments the compound is in the form of a salt whilst in others it is not.

The compounds of Formula (I) (or exemplary formula thereof), described below in more detail, especially show inhibition of protein kinases e.g. protein tyrosine kinases. As examples of kinases inhibited by the compounds of the disclosure may be mentioned FGFR1, FGFR2, FGFR3 and FGFR4. Another inhibited kinase is the receptor tyrosine kinase VEGF-R, in particular the VEGF receptor KDR (VEGF-R2). The disclosed compounds are appropriate for the inhibition of one or more of these and/or other protein tyrosine kinases and/or for the inhibition of mutants of these enzymes. In view of these activities, the compounds can be used for the treatment of diseases related to, especially, aberrant or excessive activity of such types of kinases, especially those mentioned.

The compounds of the disclosure can exist in different forms, such as free acids, free bases, esters and other prodrugs, salts and tautomers, for example, and the disclosure includes all variant forms of the compounds.

The extent of protection includes counterfeit or fraudulent products which contain or purport to contain a compound of the invention irrespective of whether they do in fact contain such a compound and irrespective of whether any such compound is contained in a therapeutically effective amount. Included in the scope of protection therefore are packages which include a description or instructions which indicate that the package contains a species or pharmaceutical formulation or composition of the invention and a product which is or comprises, or purports to be or comprise, such a formulation, composition or species.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Further aspects and embodiments of the disclosure are set forth in the following description and claims.

DETAILED DESCRIPTION

The present invention relates to compounds of Formula I as described above and salts, esters, N-oxides or prodrugs thereof. In an aspect, therefore, the invention provides products which are compounds of Formula I and salts, esters, N-oxides or prodrugs thereof.

In embodiments, the products do not include compounds which are believed to be included in the prior art and in which:

(A) n is 0; $R^3$ is H; Y and Z are N; X is N, C—$SO_2$(NH) or C—$NO_2$ (or in a wider exclusionary embodiment any C—$R^5$ group); $R^2$ is H, $SCH_2CH=CH_2$ or SMe; and $R^1$ is of the formula NR'R" where R' and R" together with their adjoining nitrogen form morpholino or one of R' and R" is H and the other is phenyl, phenyl substituted by a single substituent selected from Me and Cl, or is —C(O)NHPh;

(B) n is 1; $R^4$ is methoxy; $R^3$ is H; X is CH; Y and Z are N; $R^1$ is $NH_2$; and $R^2$ is H or SMe;

(C) n is 1; $R^4$ is Cl; $R^3$ is ethyl; X, Y and Z are N; and one of $R^1$ and $R^2$ is H whilst the other is $NEt_2$; or (D) n is 2; one $R^4$ is meta-Cl and the other is para-methyl, $R^3$ is H; X, Y and Z are N; and one of $R^1$ and $R^2$ is H whilst the other is PhNH—, m-chloroPhNH—, p-chloroPhNH—, m-methylPhNH— or p-methylPhNH—.

In another embodiment, 1, 2, 3 or 4 of excluded categories (A), (B), (C) and (D) is expanded to read as follows:

(A) n is 0; $R^3$ is H; Y and Z are N; X is N or C—$R^5$; $R^2$ is H or a substituent; and $R^1$ is of the formula NR'R" where R' and R" together with the nitrogen form a substituted or unsubstituted ring or R' and R" are each independently H or a substituent;

(B) n is 1; $R^4$ is a substituent; $R^3$ is H; Y and Z are N; X is CH (or in other embodiments is C—$R^5$); $R^2$ is H OR SMe (or in some excluded compounds S substituted by any substituent); and $R^1$ is $NH_2$ (or in a class of excluded compounds is substituted amino or—in some instances—any substituent)

(C) n is 1; $R^4$ is halo or alkyl (or in a class of embodiments is any substituent); $R^3$ is alkyl; X, Y and Z are N; and one of $R^1$ and $R^2$ is H whilst the other is a substituent; or (D) n is 2; each $R^4$ is independently selected from halo and alkyl (or in a class of embodiments is any substituent); $R^3$ is H; X, Y and Z are N; and one of $R^1$ and $R^2$ is H whilst the other is amino or substituted amino (or in an embodiment is any substituent).

In embodiments, there are additionally excluded (a) salts of the excluded compounds, (b) esters of excluded compounds, (c) N-oxides of excluded compounds, (d) prodrugs of excluded compounds, or (e) 1, 2, 3 or 4 of (a), (b), (c) and (d), e.g. all thereof.

Structural fragments and substituents of the compounds of Formula (I) will now be considered in turn:

The Left Hand Ring

By the "left hand ring" is meant the fragment:

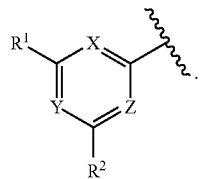

In a class of compounds, two of X, Y and Z are N, and in one sub-class X and Y are N while in another or X and Z are N; in an alternative class all of X, Y and Z are N. A particular class consists of compounds in which Y and Z are N, thus forming by way of example Fragment (A):

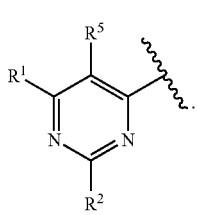

Fragment (A)

Substituent $R^5$

Considering now the left hand ring without restriction, i.e. without limitation to Fragment (A), the or each $R^5$ may independently be an $R^1$ group, for example as more particularly defined below, independently of the identity of $R^1$.

In some compounds the or each $R^5$ is independently H; hydroxy; halo; amino or mono- or di-alkylamino; cyano; azo or nitro; an aliphatic group having 1 to 7 carbon atoms and optionally interrupted by an —O— or —NH— linkage and/or linked to the left hand ring by a said linkage and/or substituted by hydroxy, halo, amino or mono- or di-alkylamino, cyano, azo or nitro; or acyl wherein the carbonyl moiety is substituted by a said aliphatic group; hydroxy, amino, mono- or dialkylamino, cyano, azo or nitro. Alkyl groups may have for example 1 to 7, e.g. 1, 2, 3 or 4 carbon atoms.

Often, $R^5$ is H, halo, hydroxy, amino, mono- or dialkylamino, alkyl (e.g. methyl), alkyl interrupted by an —O— or —NH— linkage and/or linked to the left hand ring by a said linkage (e.g. to form alkoxy, for example methoxy), trifluoromethyl, hydroxy, amino, mono- or dialkylamino; any alkyl moiety (interrupted or not) typically has 1, 2, 3 or 4 carbon atoms.

In a class of compounds, $R^5$ is H or halo, particularly H, F or Cl, for example is H or F. In a particular class of compounds, the or each $R^5$ is H.

The above description of $R^5$ applies of course to Fragment (A) as much as to other left hand ring structures.

Substituent $R^2$

Again considering the left hand ring without restriction, $R^2$ may be any moiety described above in relation to $R^5$ (e.g. may be any $R^1$ group as described more particularly below) and of course $R^2$ and $R^5$ may be the same or different.

In some compounds, $R^2$ and the or each $R^5$ are independently H; halo; an aliphatic group (e.g. having 1 to 7 carbon atoms, for example 1, 2, 3, or 4), the aliphatic group optionally being interrupted by an —O— or —NH— linkage and/or linked to the left hand ring by a said linkage and/or substituted by hydroxy, halo, amino or mono- or di-alkylamino, acyl wherein the carbonyl moiety is substituted by a said aliphatic group, trifluoromethyl, hydroxy, amino, mono- or di-alkylamino, cyano, azo or nitro.

Often, both $R^2$ and the or each $R^5$ are independently H, halo, alkyl, alkyl interrupted by an —O— or —NH— linkage and/or linked to the left hand ring by a said linkage, trifluoromethyl, hydroxy, amino, mono- or dialkylamino; any alkyl moiety (interrupted or not) typically has 1, 2, 3 or 4 carbon atoms.

In a class of compounds, both $R^2$ and the or each $R^5$ are independently H or halo, particularly H, F or Cl, for example are H or F. In a particular class of compounds, $R^2$ and the or each $R^5$ are H.

The above descriptions of $R^2$ and of $R^2$ and $R^5$ apply of course to Fragment (A) as much as to other left hand ring structures.

It will be understood from the aforegoing description that a particular left hand ring structure is Fragment (B):

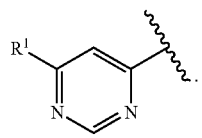

Fragment (B)

Substituent $R^1$

As previously described, $R^1$ is an organic or inorganic moiety.

As inorganic moieties may be mentioned halo, hydroxyl, amino, cyano, azo (N=N=N) and nitro. F and Cl are exemplary halogens.

The organic moiety, designated $R^z$, is substituted or unsubstituted and may be attached via a linker, -$L^1$-, the organic moiety being especially selected from hydrogen; lower aliphatic (especially $C_1$, $C_2$, $C_3$ or $C_4$ aliphatic) e.g. lower alkyl, lower alkenyl, lower alkynyl; amino; guanidino; hydroxyguanidino; formamidino; isothioureido; ureido; mercapto; carboxy; sulfo; sulfamoyl; carbamoyl; C(O)H or other acyl; acyloxy; substituted hydroxy; a substituted or unsubstituted cyclic group, for example the cyclic group (whether substituted or unsubstituted) may be cycloalkyl, e.g. cyclohexyl, phenyl, pyrrole, imidazole, pyrazole, isoxazole, oxazole, thiazole, pyridazine, pyrimidine, pyrazine, pyridyl, indole, isoindole, indazole, purine, indolizidine, quinoline, isoquinoline, quinazoline, pteridine, quinolizidine, piperidyl, piperazinyl, pyrollidine, morpholinyl or thiomorpholinyl and, for example, substituted lower aliphatic or substituted hydroxy may be substituted by such substituted or unsubstituted cyclic groups. See below for a description of particular classes of $R^z$ moiety.

Linker -$L^1$- has 1, 2, 3, 4 or 5 in-chain atoms and is selected from $C_1$, $C_2$, $C_3$ or $C_4$ aliphatic (notably linear aliphatic, and aliphatic particularly being alkyl) optionally interrupted and/or terminated by a linkage selected from the group consisting of —$NR^a$—; —O—; —S—; —C(O)—; cyclopropyl (regarded as having two in-chain atoms) and chemically appropriate combinations thereof; —$NR^a$—; —O—; —S—; —C(O)—; cyclopropyl (regarded as having two in-chain atoms) and chemically appropriate combinations thereof; and —$NR^a$— wherein $R^a$ is hydrogen, hydroxy, hydrocarbyloxy or hydrocarbyl, wherein hydrocarbyl has from 1 to 15 carbon atoms (e.g. 1 to 7), is optionally interrupted by an —O— or —NH— linkage and may be, for example, selected from an aliphatic group (e.g. having 1 to 7 carbon atoms, for example 1, 2, 3, or 4, aliphatic particularly being alkyl), cycloalkyl, especially cyclohexyl, cycloalkenyl, especially cyclohexenyl, or another carbocyclic group, for example phenyl; where the hydrocarbyl moiety is substituted or unsubstituted. Exemplary substituents are hydroxy, halo, amino or mono- or di-($C_1$-$C_4$)alkylamino, lower alkanoyl, trifluoromethyl, cyano, azo or nitro. $R^a$ is particularly H.

In a class of compounds, $R^1$ includes a linker $L^1$; in a sub-class, the linker is —$NR^a$—, alkyl terminated at the left hand ring by (i.e joined to the left hand ring by) —$NR^a$— alkyl terminated at its end remote from the left hand ring by —$NR^a$— or alkyl interrupted by —$NR^a$— wherein alkyl has 1, 2, 3 or 4 carbon atoms. In this class of compounds, $R^a$ is particularly H. A preferred linker is —NH—.

In other words, a common left hand ring structure is represented by Fragment (C):

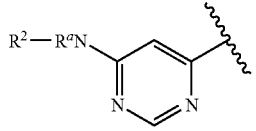

Fragment (C)

where $R^a$ is as described above and preferably H, and $R^z$ is a substituted or unsubstituted organic moiety as mentioned above and as further described below. Also to be mentioned are compounds in which $R^z$ is H, i.e. in which $R^1$ is amino when $R^a$ is also H, as well as variants in which $R^1$ is another substituted or unsubstituted basic group, for example amidino, guanidino; hydroxyguanidino; formamidino; isothioureido or ureido.

As previously described, therefore, $R^1$ may in certain compounds comprise a substituted or unsubstituted organic moiety, optionally joined to the left hand ring through a linker $L^1$. Thus, $R^1$ in such compounds may be represented as $R^z$-$L^1$-, where $R^z$ is a substituted or an unsubstituted organic moiety. This applies equally to left hand ring structures which do not correspond to fragment (C) as to those which do.

$R^z$ is commonly a moiety containing from 1 to 30 in-chain and/or in-ring atoms selected from C, N, O S and Si and in which one or more hydrogens are optionally replaced by halogen. Alternatively stated, such $R^z$ groups have from 1 to 30 plural valent atoms selected from C, N, O S and Si as well as monovalent atoms selected from H and halo, e.g. selected from H, F, Cl and Br, for example H, F and Cl. In some $R^z$ moieties there are from 1 to 25 plural valent atoms, e.g. 1 to 20, such as 1 to 16, for example.

Included are compounds in which $R^z$ contains one or a combination of moieties selected from categories 1), 2) and 3) below and optionally one or more moieties selected from category 4) below:

1) aliphatic moieties, in particular having from 1 to 7 carbon atoms, e.g. 1, 2, 3 or 4, particularly alkyl or alkenyl moieties, e.g. alkyl;
2) carbocyclic rings, which may be saturated or unsaturated (e.g. aromatic), particularly to be mentioned are bicyclic and monocyclic rings and especially monocyclic rings having 5 or 6 ring members;
3) heterocyclic rings, which may be saturated or unsaturated (e.g. aromatic), particularly to be mentioned are bicyclic and monocyclic rings and especially monocyclic rings having 5 or 6 ring members;
4) linking moieties selected from O, N, Si and C(O), wherein two or more linking moieties may be combined to form a larger linking group for example C(O)O, C(O)NH or OC(O)NH.

In these compounds, a plurality of moieties selected from 1), 2) and 3) may be linked together either directly or through a linking moiety 4). Of course, one compound may contain one or more linking moieties. Tri- or more valent linking moieties such as N and Si may serve to link together just two moieties selected from 1), 2) and 3), in which case the remaining valencies are suitably occupied by hydrogen; alternatively N or Si may link together three said moieties, or Si may link together four said moieties. Where $R^z$ contains a plurality of moieties selected from 1), 2) and 3), the moieties may be the same of different and may independently be selected from categories 1), 2) and 3).

Moieties 1), 2) and 3) may be substituted by one or more substituents selected from, in particular, hydroxy, amino, amidino, guanidino, hydroxyguanidino, formamidino, isothioureido, ureido, mercapto, C(O)H or other lower acyl, lower acyloxy, carboxy, sulfo, sulfamoyl, carbamoyl, cyano, azo, or nitro, which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or, where possible, more $C_1$-$C_7$ aliphatic groups. Often, but not always, $R^z$ has 0, 1, 2, 3, or 4 such substituents; sometimes there are a larger number of substituents as can happen, for example, when $R^z$ contains one or more perfluorinated alkyl or cyclic groups, e.g. $CF_3$, as well as other optional substituents.

Particular moieties 1), 2) and 3) to mention are straight chain and branched alkyl, 5- and 6-membered carbocyclic rings (notably phenyl and cyclohexyl), and 5- and 6-membered heterocyclic rings (notably 5-membered rings containing a single heteroatom, e.g. furan, thiophene, pyrrole; and 6-membered rings containing one or two heteroatoms, e.g. piperidine, piperazine, morpholine, pyridine, pyrimidine and pyrazine).

The invention includes compounds of Formula (I) wherein $R^1$ is of the formula $R^z$—$NR^a$—, as described above, and $R^z$ is selected from
(i) $C_1$-$C_7$ aliphatic moities,
(ii) $C_1$-$C_7$ aliphatic substituted by one or more halogens and/ or one or two functional groups selected from hydroxy, amino, amidino, guanidino, hydroxyguanidino, formamidino, isothioureido, ureido, mercapto, C(O)H or other lower acyl, lower acyloxy, carboxy, sulfo, sulfamoyl, carbamoyl, cyano, azo, or nitro, which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or, where possible, more $C_1$-$C_7$ aliphatic groups,
(iii) a group of the formula

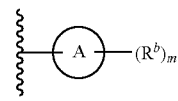

where:
ring A represents a mono- or bi-cyclic ring, particularly a 5- or 6-membered carbocyclic or heterocyclic ring;
m is 0, 1, 2; 3, 4 or 5, e.g. 0, 1 or 2;

the or each $R^b$ is independently selected from -$L^2$-$NR^cR^d$; -$L^2$-RING where RING is a mono- or bi-cyclic ring, particularly a 5- or 6-membered carbocyclic or heterocyclic ring, optionally substituted as defined below; halogen; hydroxy; protected hydroxy for example trialkylsilylhydroxy; amino; amidino; guanidino; hydroxyguanidino; formamidino; isothioureido; ureido; mercapto; C(O)H or other lower acyl; lower acyloxy; carboxy; sulfo; sulfamoyl; carbamoyl; cyano; azo; or nitro; and $C_1$-$C_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other lower acyl, lower acyloxy, carboxy, sulfo, sulfamoyl, carbamoyl, cyano, azo, or nitro; all of which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or, where possible, more $C_1$-$C_7$ aliphatic groups, wherein $L^2$ is a direct bond; a linkage selected from —O—; —S—; —C(O)—; —OC(O)—; —$NR^a$C(O)—; —C(O)—$NR^a$—; —OC(O)—$NR^a$—; cyclopropyl and —$NR^a$—; or is a $C_1$-$C_7$ aliphatic group optionally interrupted and/or terminated at a single end or at both ends by a said linkage ($R^a$ being as previously defined and typically H);

and wherein $R^c$ and $R^d$ are each independently selected from hydrogen, and $C_1$-$C_7$ aliphatic optionally substituted by one or more halogens, by an optionally substituted 5- or 6-membered heterocyclic or carbocyclic ring, and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other lower acyl, lower acyloxy, carboxy, sulfo, sulfamoyl, carbamoyl, cyano, azo, or nitro, which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or more $C_1$-$C_7$ aliphatic groups, or $R^c$ and $R^d$ together with their adjoining nitrogen form a 5- or 6-membered ring optionally substituted as described below, said optionally substituted rings independently of each other being substituted by 0, 1, 2, 3, 4 or 5 substituents selected from halogen; hydroxy; protected hydroxy for example trialkylsilylhydroxy; amino; amidino; guanidino; hydroxyguanidino; formamidino; isothioureido; ureido; mercapto; C(O)H or other lower acyl; lower acyloxy; carboxy; sulfo; sulfamoyl; carbamoyl; cyano; azo; nitro; $C_1$-$C_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other lower acyl; lower acyloxy carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or, where possible, more $C_1$-$C_7$ aliphatic groups (for example, therefore, a ring may be substituted by an alkoxy group, e.g. methoxy or ethoxy).

Still considering compounds wherein $R^1$ is of the formula $R^z$—$NR^a$— and $R^z$ is selected from categories (i), (ii) and (iii) above, aliphatic often has 1, 2, 3 or 4 carbon atoms and is often linear, but sometimes branched. In a class of compounds, aliphatic is alkyl, e.g. linear or branched alkyl having 1, 2, 3 or 4 carbon atoms; linear alkyl is more common, irrespective of the number of carbon atoms.

In a sub-class of those compounds wherein $R^1$ is of the formula $R^z$—$NR^a$—, $R^z$ is alkyl, e.g. linear or branched alkyl having 1, 2, 3 or 4 carbon atoms; linear alkyl being more common, irrespective of the number of carbon atoms. As already described, there also included compounds in which $R^z$ is H. This sub-class therefore comprises compounds in which $R^1$ is amino or mono- or di-alkylamino.

Turning now to those compounds in which $R^z$ is a category (iii) group, i.e. is of the formula

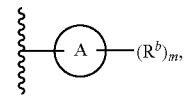

ring A is typically a 6-membered carbocyclic or heterocyclic ring, particularly phenyl, cyclohexyl or cyclohexenyl. Of these, phenyl is preferred. In other instances, ring A is a 5-membered carbocyclic or heterocyclic ring. Other exemplary residues forming ring A are pyridyl and pyrimidyl.

Integer m may be 0.

Integer m is often 1. Where m is greater than one, all the $R^b$ groups or all the $R^b$ groups except one are often halogen (notably F or Cl), methyl or trifluoromethyl. Also to be mentioned in this regard are hydroxy and amino. Often, a single $R^b$ group is selected from -$L^2$-$NR^cR^d$ and -$L^2$-RING and there are 0, 1 or 2 additional substituents which are not -$L^2$-$NR^cR^d$ or -$L^2$-RING but are, for example, halogen (notably F or Cl), lower alkyl (e.g. methyl), lower alkoxy (e.g. methoxy), hydroxy, amino or trifluoromethyl.

Accordingly, the invention includes compounds in which $R^z$ is, e.g. a 6-membered carbocyclic ring (notably phenyl) substituted by 1, 2, 3, 4 or 5 halogens, e.g. selected from F, Cl and Br; typically, such phenyl rings are mono- or di-substituted, e.g. are 2- and/or 4-substituted by F or 3-substituted by Cl. In some cases of plural substitution by halogen, all the halogens are the same. Thus, in a class of compounds $R^z$ is a monocyclic ring, particularly a 6-membered carbocyclic ring (notably phenyl), substituted solely by one or more halogens, particularly selected from F and Cl; sometimes the or each halogen is F but in some other cases the or each halogen is Cl.

In another class of compounds, $R^z$ is a monocyclic ring, particularly a 6-membered carbocyclic ring (notably phenyl), substituted by 1, 2, 3, 4 or 5 substituents, e.g. 1 or 2 substituents, selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. Certain such rings have 0, 1 or 2 substituents, e.g. 0 or 1.

In one class of compounds, $L^2$ is a direct bond, linear alkyl, linear alkyl terminated adjacent ring A by a said linkage, or is a said linkage. In a sub-class, any said linkage is —O— or —C(O)—, of which —O— may be particularly mentioned.

The invention includes a class of compounds in which ring A is a 6-membered ring, particularly phenyl, cyclohexyl or cyclohexenyl and has one or two substituents $R^b$ independently selected from -$L^2$-$NR^cR^d$ and -$L^2$-RING, as defined previously. In a sub-class, there is a single substituent at, in particular, the 3-position or 4-position selected from -$L^2$-$NR^cR^d$ and -$L^2$-RING such that the left hand ring has a structure corresponding to Fragments (D1), (D2), (E1) or (E2):

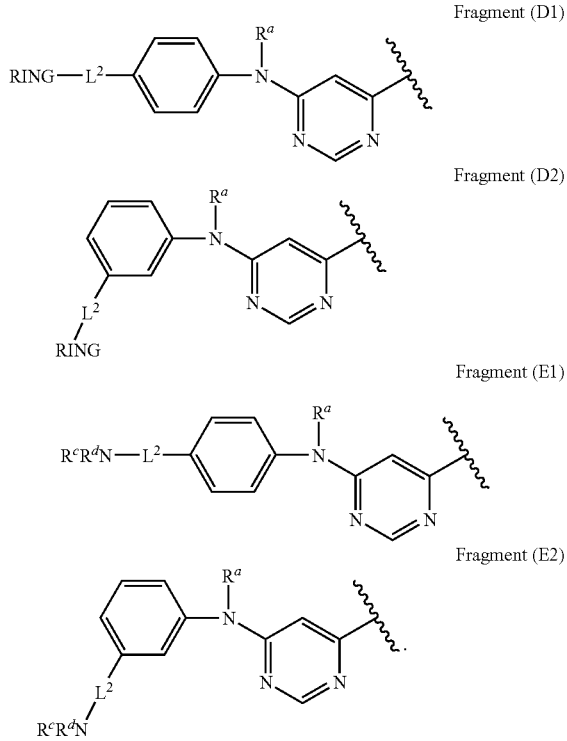

Fragment (D1)

Fragment (D2)

Fragment (E1)

Fragment (E2)

As previously described, $R^a$ is commonly H. Also as previously described, the phenyl ring may be replaced by cyclohexyl or cyclohexenyl, particularly cyclohexyl. It may alternatively be replaced by a 5- or 6-membered heterocycle, particularly pyridine.

In some embodiments, the phenyl ring of the above fragments (or other ring replacing phenyl) has 1, 2, 3 or 4 further substituents, for example selected from halogen (notably F or Cl), methyl, methoxy or trifluoromethyl, e.g. 1 or 2 such substituents. Also to be mentioned in this regard are hydroxy and amino.

$L^2$ is as previously described, that is a direct bond; a linkage selected from —O—; —S—; —C(O)—; —OC(O)—; —$NR^aC(O)$—; —C(O)—$NR^a$—; —OC(O)—$NR^a$—; cyclopropyl and —$NR^a$—; or $C_1$-$C_7$ aliphatic optionally interrupted and/or terminated at a single end or at both ends by a said linkage ($R^a$ being as previously defined and typically H). Any aliphatic moiety is often alkyl, e.g. alkyl or other aliphatic having 1, 2, 3 or 4 carbon atoms, as in the case of a sub-class of linkers $L^2$ in which aliphatic moieties are methyl, ethyl or n-propyl.

In particular fragments (D) and (E), $L^2$ is a direct bond, linear alkyl, linear alkyl terminated adjacent the phenyl ring in the above representations of the fragments by a said linkage, or is a said linkage; suitably but not necessarily any said linkage is —O— or —C(O)—, of which —O— may be particularly mentioned. Thus, the above fragments (D) and (E) may comprise sub-fragments -Ph-$NR^cR^d$, -Ph-RING, -Ph-O-alkyl-$NR^cR^d$, -Ph-O-alkyl-RING, -Ph-alkyl-$NR^cR^d$-Ph-alkyl-RING, and also to be mentioned are sub-fragments -Ph-O—$NR^cR^d$, -Ph-O-RING, -Ph-C(O)—$NR^cR^d$ and -Ph-C(O)—RING, where, in all these sub-fragments which contain alkyl, alkyl may be e.g. methyl, ethyl or n-propyl, or n-butyl.

Considering now in more detail fragments (D1) and (D2), these contain a moiety RING which is a cyclic moiety and in many cases a 5- or 6-membered carbocyclic or heterocyclic ring optionally substituted as defined previously. Exemplary rings are saturated, e.g. cyclopentane or cyclohexane. In particular compounds, RING is a 5- or 6-membered heterocycle, often containing one or two heteroatoms, typically selected from O and N; in a sub-class, the heterocycles contain one or two nitrogens and, where there is a single nitrogen, optionally an oxygen. Particular heterocycles include a nitrogen which is not a member of a double bond and these are more particularly saturated heterocycles. As heterocycles may be mentioned pyrrolidine, piperidine, piperazine and morpholine; in some compounds, RING is piperidine having its nitrogen at the 4-position relative to $L^2$. As already described, RING may be substituted and, in one class of compounds, is substituted by 0, 1, 2, 3, 4 or 5 substituents, e.g. selected from $C_1$-$C_7$ aliphatic groups, optionally substituted as described above, and less frequently $C_1$-$C_7$ aliphatic-oxy of which the aliphatic group is optionally substituted as described above. Any aliphatic group is often alkyl (straight chain or branched), e.g. alkyl or other aliphatic having 1, 2, 3 or 4 carbon atoms, as in the case of a sub-class of fragments (D1) and (D2) having substituents which are methyl, ethyl or n-propyl. Exemplary substituents on RING include straight chain or branched $C_1$, $C_2$, $C_3$ or $C_4$ alkyl such as, e.g., methyl, ethyl n-propyl, isopropyl or t-butyl, of which methyl may be particularly mentioned, halogen (notably F or Cl) and $C_1$, $C_2$, $C_3$ or $C_4$ alkoxy; also to be mentioned are hydroxy and amino. Alkyl moieties may be unsubstituted or substituted, e.g. by halogen (notably F or Cl) or in some cases by hydroxy or amino.

In some classes of RING moieties, there are 0, 1, 2, 3, 4 or 5 such substituents selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. Certain RING moieties have 0, 1 or 2 substituents, e.g. 0 or 1.

Considering now in more detail fragments (E1) and (E2), these contain a moiety $NR^cR^d$. $R^c$ and $R^d$ are as previously described. In one class of these fragments, $R^c$ and $R^d$ are the same or different (but more usually the same) and selected from $C_1$-$C_7$, e.g. $C_1$-$C_4$ aliphatic groups, optionally substituted as described above. As aliphatic $R^c$ and $R^d$ moieties may be mentioned alkyl, e.g having 1, 2, 3 or 4 carbon atoms, as in the case of a sub-class of fragments (E1) and (E2) having substituents which are methyl, ethyl or n-propyl. Alkyl or other aliphatic moieties may be substituted e.g. by amino or mono- or di ($C_1$-$C_4$) alkylamino, or e.g. by a 5- or 6-membered heterocyclic or carbocyclic ring optionally substituted as previously described, or be unsubstituted. Thus, particular $L^2NR^cR^d$ moieties are —$OCH_2NMe_2$, —$OCH_2NEt_2$, —$OCH_2CH_2NMe_2$, —$OCH_2CH_2NEt_2$, —$OCH_2CH_2CH_2NMe_2$, —$OCH_2CH_2CH_2NEt_2$, —$CH_2NMe_2$, —$CH_2NEt_2$, —$CH_2CH_2NMe_2$, —$CH_2CH_2NEt_2$, —$CH_2CH_2CH_2NMe_2$, and —$CH_2CH_2CH_2NEt_2$.

In another class of fragments (E1) and (E2), $R^c$ and $R^d$ together with the adjoining nitrogen form a heterocyclic moiety (normally a 5- or 6-membered heterocyclic ring), optionally substituted as previously described. In addition to the nitrogen of moiety $NR^cR^d$, the heterocyclic ring may contain at least one further heteroatom, and often exactly one further heteroatom, in either case typically selected from O and N; in a sub-class, the heterocycles contain altogether one or two nitrogens and, where there is a single nitrogen, optionally an oxygen. Particular heterocycles include a nitrogen which is not a member of a double bond and these are more particularly saturated heterocycles. As heterocycles may be mentioned pyrrolidine, piperidine, piperazine and morpholine; of these particular heterocycles are piperazine and morpholine. As already described, the heterocycle may be substituted and, in one class of compounds, is substituted by 0, 1, 2, 3, 4 or 5 substituents, e.g. selected from $C_1$-$C_7$ aliphatic groups, optionally substituted as described above, and less frequently $C_1$-$C_7$ aliphatic-oxy of which the aliphatic group is optionally substituted as described above. Any aliphatic group is often alkyl (straight chain or branched), e.g. alkyl or other aliphatic having 1, 2, 3 or 4 carbon atoms, as in the case of a sub-class of cyclic (E1) and (E2) fragments having substituents which are methyl, ethyl or n-propyl. Exemplary substituents on cyclic (E1) and (E2) fragments include straight chain or branched $C_1$, $C_2$, $C_3$ or $C_4$ alkyl such as, e.g., methyl, ethyl n-propyl, isopropyl or t-butyl, of which methyl may be particularly mentioned, halogen (notably F or Cl) and $C_1$, $C_2$, $C_3$ or $C_4$ alkoxy; also to be mentioned are hydroxy and amino. Alkyl moieties may be unsubstituted or substituted, e.g. by halogen (notably F or Cl) or in some cases by hydroxy or amino.

In some classes of cyclic (E1) and (E2) fragments (that is to say fragments in which $R^c$ and $R^d$ together with the adjoining nitrogen form a ring), there are 0, 1, 2, 3, 4 or 5 such substituents selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. Certain cyclic fragments have 0, 1 or 2 substituents, e.g. 0 or 1.

Particular $L^2NR^cR^d$ moieties are -Pip, -Morph, —OCH$_2$Pip, —OCH$_2$-Morph, —OCH$_2$CH$_2$Pip, —OCH$_2$CH$_2$-Morph, —OCH$_2$CH$_2$CH$_2$Pip, —OCH$_2$CH$_2$CH$_2$-Morph, —CH$_2$Pip, —CH$_2$-Morph, —CH$_2$CH$_2$Pip, —CH$_2$CH$_2$-Morph, —CH$_2$CH$_2$CH$_2$Pip, and —CH$_2$CH$_2$CH$_2$-Morph. Also to be mentioned are —C(O)Pip and —C(O)Morph. The abbreviation "Pip" stands for piperazine and "Morph" for morpholine, and these rings may be substituted as previously described. In particular piperazine is optionally N-substituted. Piperazine and morpholine may be substituted by a $C_1$-$C_7$ aliphatic group as mentioned in the previous paragraph, for example a straight chain or branched $C_1$, $C_2$, $C_3$ or $C_4$ moiety selected from alkyl and haloalkyl such as, e.g., methyl, trifluoromethyl, ethyl n-propyl, isopropyl or t-butyl, of which methyl and trifluoromethyl are exemplary. As described before, $R^a$ is in particular hydrogen.

Amongst the classes of compounds which are particularly to be mentioned are those in which the left hand ring has a structure corresponding to Fragment (D1) or (E1). Particularly exemplary are such compounds having a fragment (E1) in which $R^c$ and $R^d$ together with the adjoining nitrogen form a 5- or 6-membered heterocyclic ring as described above. These rings may be substituted as previously described. In particular they are optionally N-substituted by a $C_1$-$C_7$ aliphatic group as mentioned earlier, for example a straight chain or branched $C_1$, $C_2$, $C_3$ or $C_4$ moiety selected from alkyl and haloalkyl such as, e.g., methyl, trifluoromethyl, ethyl n-propyl, isopropyl or t-butyl, of which methyl and trifluoromethyl are exemplary. As described before, $R^a$ is in particular hydrogen.

It will be appreciated from the aforegoing that the invention includes compounds having a left hand ring having the structure of the following Fragment (F):

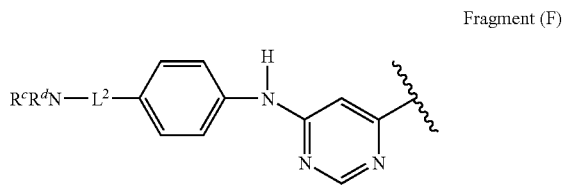

Fragment (F)

where $L^2NR^cR^d$ is in particular -Pip, -Morph, —OCH$_2$Pip, —OCH$_2$-Morph, —OCH$_2$CH$_2$Pip, —OCH$_2$CH$_2$-Morph, —OCH$_2$CH$_2$CH$_2$Pip, —OCH$_2$CH$_2$CH$_2$-Morph, —CH$_2$Pip, —CH$_2$-Morph, —CH$_2$CH$_2$Pip, —CH$_2$CH$_2$-Morph, —CH$_2$CH$_2$CH$_2$Pip, and —CH$_2$CH$_2$CH$_2$-Morph, or is —C(O)Pip or —C(O)Morph. "Pip" and "Morph" are as described in the last but one paragraph.

Substituent $R^3$

Substituent $R^3$ is as previously described in relation to Formula (I).

In embodiments, $R^3$ is selected from H, $R^b$ groups, and categories (i), (ii) and (iii) described above in relation to $R^z$, independently of the identity of $R^z$. In one class of embodiments, $R^3$ is H or a $C_1$-$C_7$ aliphatic group, for example straight chain or branched $C_1$-$C_4$ alkyl such as, e.g., methyl, ethyl or n-propyl, of which methyl is exemplary. In other compounds, $R^3$ is a $C_1$-$C_7$ aliphatic group (for example straight chain or branched $C_1$-$C_4$ alkyl such as, e.g., methyl, ethyl or n-propyl) substituted by a mono- or bi-cyclic ring, particularly a 5- or 6-membered saturated or unsaturated carbocyclic or heterocyclic ring, for example by phenyl, pyrrolidine, piperidine, piperazine, morpholine, thiophene, furan, pyrrole, pyridine, pyrazine or pyran. $R^3$ may therefore be straight chain alkyl (or other straight chain aliphatic group, for example in either case having up to 4 carbon atoms) substituted at its free end by such a mono- or bi-cyclic ring.

In one class of compounds $R^3$ is a category (iii) moiety, that is, a moiety having the structure:

$$\text{-}\!\!\!\!\!\!\!\text{-}\bigcirc\!\!\!\!\text{A}\!\!\!\!\!\text{-}(R^b)_m$$

as previously described. The identity of $R^3$ is independent of that of $R^z$, as already stated.

However, as particular compounds, may be mentioned those in which just one of $R^z$ and $R^3$ is a category (iii) moiety. In a subclass, one of $R^z$ and $R^3$ is a category (iii) moiety and the other is H; to be mentioned in this regard are compounds in which $R^3$ is a category (iii) moiety and $R^1$ is NH$_2$, or alternatively mono- or di-alkyl amino.

Where $R^3$ is a category (iii) moiety, it may have a structure corresponding to the category (iii) structures found in Fragments (D1), (D2), (E1), (E2) or (F), as previously described.

The Right Hand Ring

By the "right hand ring" is meant the fragment:

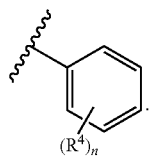

$(R^4)_n$

It has previously been mentioned that n is 0, 1, 2, 3, 4 or 5 and that each $R^4$ is the same or different and selected from an organic or inorganic moiety, for example, each $R^4$ is the same or different and selected from halogen; hydroxy; protected hydroxy for example trialkylsilylhydroxy; amino; amidino; guanidino; hydroxyguanidino; formamidino; isothioureido; ureido; mercapto; C(O)H or other acyl; acyloxy; carboxy; sulfo; sulfamoyl; carbamoyl; cyano; azo; nitro; $C_1$-$C_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other acyl, acyloxy, carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or, where possible, more $C_1$-$C_7$ aliphatic groups (for example, therefore, $R^4$ ring may be an alkoxy group, e.g. methoxy or ethoxy).

Integer n is more usually 1, 2, 3 or 4, e.g. 2, 3 or 4. In particular, there are often $R^4$ groups substituted at both ortho-positions and optionally at least one or two other positions, e.g. there may be a single further meta or para substituent.

$R^4$ is particularly selected from hydroxy, protected hydroxy, lower alkoxy, lower alkyl, trifluoromethyl and halo, notably F or Cl. $R^4$ may also be Br. Alkyl and the alkyl part of alkoxy may be branched or, more usually, straight chain, and often have 1, 2, 3, or 4 carbon atoms, as for example in the case of methyl, ethyl, methoxy and ethoxy. $R^4$ is especially selected from Cl, F, hydroxy, methyl, methoxy and trifluoromethyl, e.g. is selected from Cl, F, methyl, methoxy and trifluoromethyl, as in those compounds where $R^4$ is Cl, F, methyl or methoxy. In some of the compounds mentioned in this paragraph, chlorine is the sole halogen, in some others fluorine is the sole halogen. The reader is reminded that, where there are plural $R^4$ groups, they may be the same or different.

Included are compounds in which there is halogen selected from F and Cl at one or both ortho positions.

To be mentioned are right hand rings corresponding to Fragment (G):

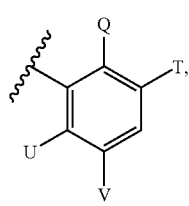

Fragment (G)

where:

Q is selected from F and Cl;

U is selected from H, F, Cl, methyl, trifluoromethyl and methoxy, and particularly Q and U are the same or different and both selected from F and Cl;

T and V are the same or different and selected from H, methyl, trifluoromethyl and methoxy, e.g. from H, methyl and methoxy.

In some Fragments (G), all of U, T and V are H. In other Fragments (G), Q and U are the same and selected from F and Cl.

A particular right hand ring is Fragment (H):

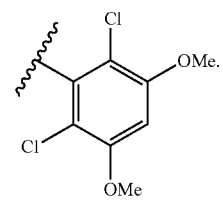

Fragment (H)

To be mentioned are right hand rings corresponding to Fragment (I):

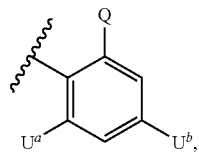

Fragment (I)

where:

Q is selected from F and Cl;

$U^a$ and $U^b$ are each independently selected from H, F, Cl, methyl, trifluoromethyl and methoxy; in some compounds $U^a$ and $U^b$ are the same.

In exemplary Fragment (I) structures, all of Q, $U^a$ and $U^b$ are the same and are fluorine or more particularly chlorine. In other exemplary structures, Q is F or, particularly, Cl whilst $U^a$ and $U^b$ are the same or different and selected from methyl, trifluoromethyl and methoxy; both $U^a$ and $U^b$ may be the same, e.g both may be methoxy.

The Compounds of Formula (I)

It has been described above how the compounds of formula (I) have the following variable domains:

left hand ring $R^3$ right hand ring.

Various particular moieties have been described for each of these variable domains and it will be appreciated that any combination of such moieties is permissible.

To be mentioned are compounds having the following combinations, amongst many others:

| Left hand ring | $R^3$ | Right hand ring |
|---|---|---|
| Fragment (A) | H, $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (B) | H, $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (C) | H, $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (C), $R^a$=H, Rz = category (i) or (ii) | H, $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (C), $R^a$=H, Rz = category (i) or (ii) | Category (iii) moiety, e.g. having a structure corresponding to the category (iii) structure of Fragment (D1) | n = 1, 2, 3, or 4. $R^4$ = selected from Cl, F, hydroxy, methyl, methoxy and trifluoromethyl. |
| Fragment (C), $R^a$=H, Rz = category (i) or (ii) | Category (iii) moiety, e.g. having a structure corresponding to the category (iii) structure of Fragment (D2) | n = 1, 2, 3, or 4. $R^4$ = selected from Cl, F, hydroxy, methyl, methoxy and trifluoromethyl. |
| Fragment (C), $R^a$=H, Rz = category (i) or (ii) | Category (iii) moiety, e.g. having a structure corresponding to the category (iii) structure of Fragment (E1). | n = 1, 2, 3, or 4. $R^4$ = selected from Cl, F, hydroxy, methyl, methoxy and trifluoromethyl. |
| Fragment (C), $R^a$=H, Rz = category (i) or (ii) | Category (iii) moiety, e.g. having a structure corresponding to the category (iii) structure of Fragment (E2). | n = 1, 2, 3, or 4. $R^4$ = selected from Cl, F, hydroxy, methyl, methoxy and trifluoromethyl. |
| Fragment (C), $R^a$=H, Rz = category (i) or (ii) | Category (iii) moiety, e.g. having a structure corresponding to the category (iii) structure of Fragment (F). | n = 1, 2, 3, or 4. $R^4$ = selected from Cl, F, hydroxy, methyl, methoxy and trifluoromethyl. |
| Fragment (C), $R^a$=H, $R^z$ = category (iii) | $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (D1) | $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (D2) | $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (E1) | $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (E2) | $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (F) | $C_1$-$C_4$ alkyl or $C_1$-$C_4$ alkyl substituted by an optionally substituted 5- or 6- membered ring | n = 1, 2, 3, or 4. $R^4$ = selected from Cl, F, hydroxy, methyl, methoxy and trifluoromethyl. |
| Fragment (C), $R^a$ typically = H, $R^z$ = category (iii) | H | n = 1, 2, 3, or 4. $R^4$ = selected from Cl, F, hydroxy, methyl, methoxy and trifluoromethyl. |
| Fragment (D1); $R^a$ typically = H, | H | n = 1, 2, 3, or 4. $R^4$ = selected from Cl, F, hydroxy, methyl, methoxy and trifluoromethyl. |

-continued

| Left hand ring | $R^3$ | Right hand ring |
|---|---|---|
| Fragment (D2); $R^a$ typically = H, | H | n = 1, 2, 3, or 4. $R^4$ = selected from Cl, F, hydroxy, methyl, methoxy and trifluoromethyl. |
| Fragment (E1); $R^a$ typically = H, | H | n = 1, 2, 3, or 4. $R^4$ = selected from Cl, F, hydroxy, methyl, methoxy and trifluoromethyl. |
| Fragment (E2); $R^a$ typically = H, | H | n = 1, 2, 3, or 4. $R^4$ = selected from Cl, F, hydroxy, methyl, methoxy and trifluoromethyl. |
| Fragment (F) | H | n = 1, 2, 3, or 4. $R^4$ = selected from Cl, F, hydroxy, methyl, methoxy and trifluoromethyl. |
| Fragment (A) | H, $C_1$-$C_4$ alkyl or $C_1$-$C_4$ alkyl substituted by an optionally substituted 5- or 6- membered ring | $R^4$ is Fragment (G), (H) or (I). |
| Fragment (B) | H, $C_1$-$C_4$ alkyl or $C_1$-$C_4$ alkyl substituted by an optionally substituted 5- or 6- membered ring | $R^4$ is Fragment (G), (H) or (I). |
| Fragment (C) | H, $C_1$-$C_4$ alkyl or $C_1$-$C_4$ alkyl substituted by an optionally substituted 5- or 6- membered ring | $R^4$ is Fragment (G), (H) or (I). |
| Fragment (C), $R^a$=H, Rz = category (i) or (ii) | H, $C_1$-$C_4$ alkyl or $C_1$-$C_4$ alkyl substituted by an optionally substituted 5- or 6- membered ring | $R^4$ is Fragment (G), (H) or (I). |
| Fragment (C), $R^a$=H, Rz = category (i) or (ii) | Category (iii) moiety, e.g. having a structure corresponding to the category (iii) structure of Fragment (D1) | $R^4$ is Fragment (G), (H) or (I). |
| Fragment (C), $R^a$=H, Rz = category (i) or (ii) | Category (iii) moiety, e.g. having a structure corresponding to the category (iii) structure of Fragment (D2) | $R^4$ is Fragment (G), (H) or (I). |
| Fragment (C), $R^a$=H, Rz = category (i) or (ii) | Category (iii) moiety, e.g. having a structure corresponding to the category (iii) structure of Fragment (E1). | $R^4$ is Fragment (G), (H) or (I). |
| Fragment (C), $R^a$=H, Rz = category (i) or (ii) | Category (iii) moiety, e.g. having a structure corresponding to the category (iii) structure of Fragment (E2). | $R^4$ is Fragment (G), (H) or (I). |
| Fragment (C), $R^a$=H, Rz = category (i) or (ii) | Category (iii) moiety, e.g. having a structure corresponding to the category (iii) structure of Fragment (F). | $R^4$ is Fragment (G), (H) or (I). |
| Fragment (C), $R^a$=H, $R^z$ = category (iii) | $C_1$-$C_4$ alkyl or $C_1$-$C_4$ alkyl substituted by an optionally substituted 5- or 6- membered ring | $R^4$ is Fragment (G), (H) or (I). |
| Fragment (D1) | $C_1$-$C_4$ alkyl or $C_1$-$C_4$ alkyl substituted by an optionally substituted 5- or 6- membered ring | $R^4$ is Fragment (G), (H) or (I). |
| Fragment (D2) | $C_1$-$C_4$ alkyl or $C_1$-$C_4$ alkyl substituted by an optionally substituted 5- or 6- membered ring | $R^4$ is Fragment (G), (H) or (I). |
| Fragment (E1) | $C_1$-$C_4$ alkyl or $C_1$-$C_4$ alkyl substituted by an optionally substituted 5- or 6- membered ring | $R^4$ is Fragment (G), (H) or (I). |
| Fragment (E2) | $C_1$-$C_4$ alkyl or $C_1$-$C_4$ alkyl substituted by an optionally substituted 5- or 6- membered ring | $R^4$ is Fragment (G), (H) or (I). |

-continued

| Left hand ring | R³ | Right hand ring |
|---|---|---|
| Fragment (F) | $C_1$-$C_4$ alkyl or $C_1$-$C_4$ alkyl substituted by an optionally substituted 5- or 6-membered ring | $R^4$ is Fragment (G), (H) or (I). |
| Fragment (C), $R^a$ typically = H, $R^z$ = category (iii) | H | $R^4$ is Fragment (G), (H) or (I). |
| Fragment (D1); $R^a$ typically = H, | H | $R^4$ is Fragment (G), (H) or (I). |
| Fragment (D2); $R^a$ typically = H, | H | $R^4$ is Fragment (G), (H) or (I). |
| Fragment (E1); $R^a$ typically = H, | H | $R^4$ is Fragment (G), (H) or (I). |
| Fragment (E2); $R^a$ typically = H, | H | $R^4$ is Fragment (G), (H) or (I). |
| Fragment (F) | H | $R^4$ is Fragment (G), (H) or (I). |

When $R^3$ is an optionally substituted ring, substituents are as described previously, e.g. methyl, ethyl, methoxy, trifluoromethyl, amino or hydroxy.

Each row of the above table provides support for an individual patent claim, presented by itself or with one or more other claims, each corresponding to a respective row of the table. The previous text provides support for claims dependent on such claims in describing sub-classes of the respective features or feature combinations of each row. For each row in the Table, a patent claim or claims may be written to protect individually a sub-class or sub-classes of the subject matter represented by the row.

It will be understood from the aforegoing that a sub-set of the Compounds of Formula (I) are of the following Formulae (II) and (III):

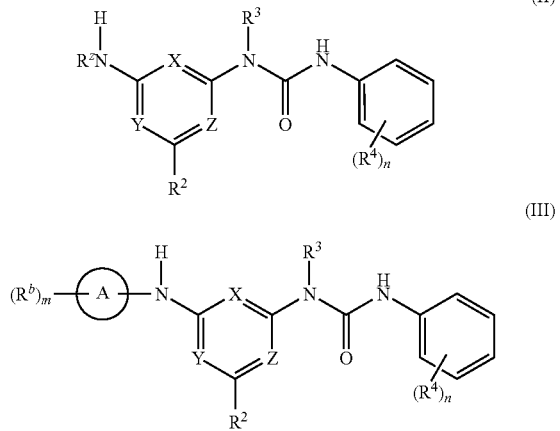

In Formulae (II) and (III), it is often the case that two of X, Y and Z are N and that $R^5$ and $R^2$ are H, e.g. in many compounds X is CH, Y and Z are N and $R^2$ is H. Alternatively, all of X, Y and Z are N and $R^2$ is H. Ring A is typically phenyl or a wholly or partially hydrogenated analogue thereof. Alternatively it may be a heterocycle, typically of six members, e.g. pyridine or pyrimidine. Integer m may be 0, 1 or 2, e.g. 1. In some cases there are one or more $R^b$ moieties which are F or Cl, as previously described, e.g. the only $R^b$ moieties may be one or two moieties selected from F and Cl.

Accordingly, Formulae (II) and (III) encompass the following sub-classes, amongst others:

1) Two of X, Y and Z are N, $R^5$ and $R^2$ are H, ring A is phenyl or a wholly or partially hydrogenated analogue thereof, m is 0, 1 or 2, e.g. 1;

2) Two of X, Y and Z are N, $R^5$ and $R^2$ are H, ring A is a heterocycle, typically of six members, e.g. pyridine or pyrimidine, m is 0, 1 or 2, e.g. 1;

3) All of X, Y and Z are N, $R^2$ is H, ring A is phenyl or a wholly or partially hydrogenated analogue thereof, m is 0, 1 or 2, e.g. 1;

4) All of X, Y and Z are N, $R^2$ is H, ring A is a heterocycle, typically of six members, e.g. pyridine or pyrimidine, m is 0, 1 or 2, e.g. 1;

5) X is CH, Y and Z are N, $R^2$ is H, ring A is phenyl or a wholly or partially hydrogenated analogue thereof, m is 0, 1 or 2, e.g. 1;

6) X is CH, Y and Z are N, $R^2$ is H, ring A is a heterocycle, typically of six members, e.g. pyridine or pyrimidine, m is 0, 1 or 2, e.g. 1.

In some instances of sub-classes 1), 2), 3) 4), 5) and 6) there are one or more $R^b$ moieties which are F or Cl, as previously described, e.g. the only $R^b$ moieties may be one or two moieties selected from F and Cl.

More commonly, ring A is substituted by one or two $R^b$ moieties (and normally a single $R^b$ moiety) comprising -$L^2$-RING or -$L^2$-$NR^cR^d$, and optionally other substituents (e.g. numbering 1, 2 or 3) selected from e.g. halogen; hydroxy; protected hydroxy for example trialkylsilylhydroxy; amino; amidino; guanidino; hydroxyguanidino; formamidino; isothioureido; ureido; mercapto; C(O)H or other lower acyl; lower acyloxy; carboxy; sulfo; sulfamoyl; carbamoyl; cyano; azo; nitro; which substituents are in turn optionally substituted on at least one heteroatom by one or, where possible, more $C_1$, $C_2$, $C_3$ or $C_4$ alkyl groups. Particular additional substituents on ring A are halogen, lower alkyl (e.g. methyl), lower alkoxy (e.g. methoxy), hydroxy, amino or trifluoromethyl.

Also to be mentioned therefore are compounds of the following formulae (IV), (V), (VI) and (VII):

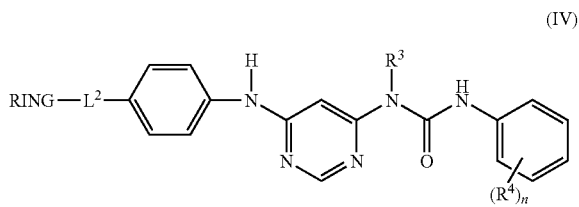

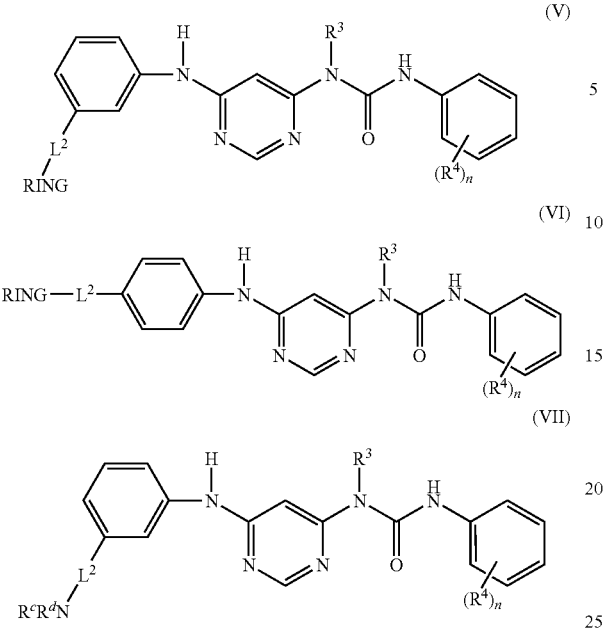

where
- $L^2NR^cR^d$ is in particular -Pip, -Morph, —OCH$_2$Pip, —OCH$_2$-Morph, —OCH$_2$CH$_2$Pip, —OCH$_2$CH$_2$-Morph, —OCH$_2$CH$_2$CH$_2$Pip, —OCH$_2$CH$_2$CH$_2$-Morph, —CH$_2$Pip, —CH$_2$-Morph, —CH$_2$CH$_2$Pip, —CH$_2$CH$_2$-Morph, —CH$_2$CH$_2$CH$_2$Pip, and —CH$_2$CH$_2$CH$_2$-Morph, or is —C(O)Pip or —C(O)Morph (or of course these heterocycles are replaced by another described herein, or in other embodiments R$^c$ and R$^d$ form a non-cyclic structure as previously described);
- $L^2$RING is in particular -RING, —OCH$_2$RING, —OCH$_2$CH$_2$RING, —OCH$_2$CH$_2$CH$_2$RING, —CH$_2$RING, —CH$_2$CH$_2$RING, —CH$_2$CH$_2$CH$_2$RING, or is —C(O)RING, where RING is in particular pyrrolidine, piperidine, piperazine or morpholine, or it may be another RING moiety disclosed herein;
- R$^3$ is as previously described and is particularly but not necessarily H;
- R$^4$ is as previously described and is particularly but not necessarily selected from Cl, F, hydroxy, methyl, methoxy and trifluoromethyl;
- n is 0, 1, 2, 3, 4 or 5, e.g. is 1, 2, 3, or 4.

In embodiments, RING or a heterocycle formed by $L^2NR^cR^d$ is substituted by 1, 2, 3, 4 or 5 substituents, e.g. 1 or 2 substituents, selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. N-alkyl substituted piperazine or piperadine are exemplary, as are RING moieties as a class substituted by one or two substituents or more, selected from alkyl and haloalkyl (e.g. trifluoromethyl). As an alternative to substitution, there may be no substitution.

Another embodiment comprises compounds of formula (XX):

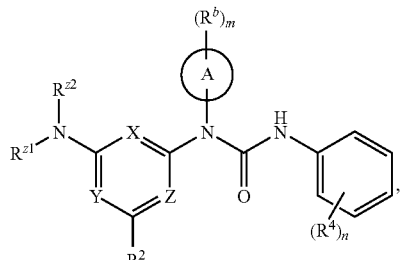

where $R^{z1}$ and $R^{z2}$ are selected from hydrogen and straight chain or branched alkyl having 1, 2, 3 or 4 carbon atoms, e.g. methyl or ethyl. In embodiments, one of $R^{z1}$ and $R^{z2}$ is hydrogen and more particularly both are hydrogen. It is often the case that X is CH, Y and Z are N and R$^2$ is H. Particular classes of compounds are of formulae (XXI), (XXII), (XXIII) and (XXIV):

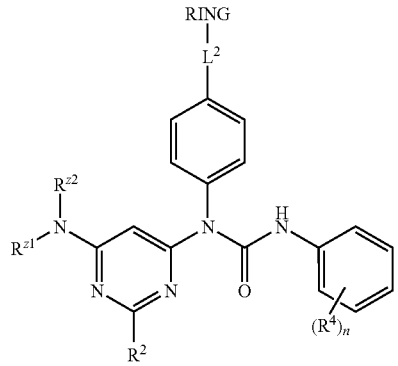

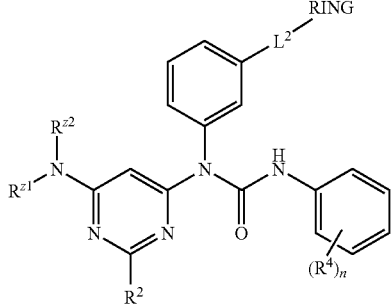

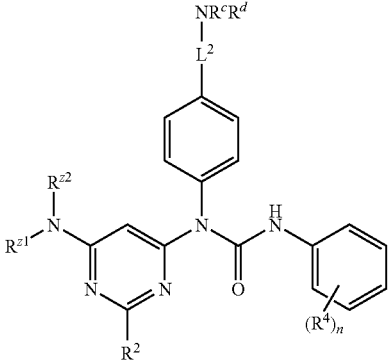

-continued

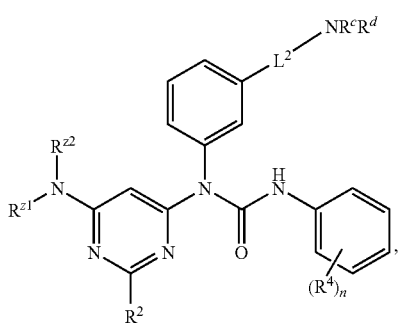
(XXIV)

where $R^{z1}$ and $R^{z2}$ are selected from hydrogen and straight chain or branched alkyl having 1, 2, 3 or 4 carbon atoms, e.g. methyl or ethyl, and $L^2NR^cR^d$, $L^2RING$, $R^3$ and $R^4$ are as described in relation to formulae (IV)-(VII).

The invention includes classes of compounds which correspond to Formulae (IV), (V), (VI), (VII), (XXI), (XXII), (XXIII) and (XXIV) in which the pyrimidine ring is replaced by a triazine ring One embodiment of the present invention relates to compounds to Formula (I*), which represent a subgroup of the compounds of Formula I, and salts, esters, N-oxides or prodrugs thereof:

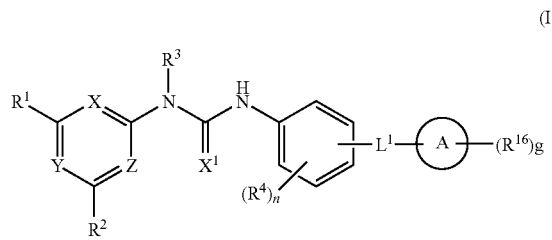
(I*)

in which compounds of Formula (I*) the radicals and symbols have the following meaning:
g is 0, 1, 2, 3, 4 or 5;
n is 0, 1, 2, 3 or 4;
X, Y and Z are each independently selected from N or C—$R^5$, wherein at least one of X, Y and Z is N;
$X^1$ is oxygen,
$L^1$ is a linker;
RING* A is a mono- or bicyclic ring; and
$R^1$, $R^2$, $R^3$, $R^{15}$ and $R^{16}$, if present, are each independently selected from an organic or inorganic moiety,
where the inorganic moiety is especially selected from halo, especially chloro, hydroxyl, cyano, azo (N=N=N), nitro; and
where the organic moiety is substituted or unsubstituted and may be attached via a linker, -$L^2$-, the organic moiety being especially selected from hydrogen; lower aliphatic (especially $C_1$, $C_2$, $C_3$ or $C_4$ aliphatic) e.g. lower alkyl, lower alkenyl, lower alkynyl; amino; guanidino; hydroxyguanidino; formamidino; isothioureido; ureido; mercapto; C(O)H or other acyl; acyloxy; substituted hydroxy; carboxy; sulfo; sulfamoyl; carbamoyl; a substituted or unsubstituted cyclic group, for example the cyclic group (whether substituted or unsubstituted) may be cycloalkyl, e.g. cyclohexyl, phenyl, pyrrole, imidazole, pyrazole, isoxazole, oxazole, thiazole, pyridazine, pyrimidine, pyrazine, pyridyl, indole, isoindole, indazole, purine, indolizidine, quinoline, isoquinoline, quinazoline, pteridine, quinolizidine, piperidyl, piperazinyl, pyrollidine, morpholinyl or thiomorpholinyl and, for example, substituted lower aliphatic or substituted hydroxy may be substituted by such substituted or unsubstituted cyclic groups, $L^1$ and $L^2$ each independently being selected from moieties having 1, 2, 3, 4 or 5 in-chain atoms (e.g. selected from C, N, O and S) and optionally being selected from (i) $C_1$, $C_2$, $C_3$ or $C_4$ alkyl, such an alkyl group optionally being interrupted and/or terminated by an —O—, —C(O)— or —$NR^a$— linkage; —O—; —S—; —C(O)—; cyclopropyl (regarded as having two in-chain atoms) and chemically appropriate combinations thereof; and —$NR^a$—, wherein $R^a$ is hydrogen, hydroxy, hydrocarbyloxy or hydrocarbyl, wherein hydrocarbyl is optionally interrupted by an —O— or —NH— linkage and may be, for example, selected from an aliphatic group (e.g. having 1 to 7 carbon atoms, for example 1, 2, 3, or 4), cycloalkyl, especially cyclohexyl, cycloalkenyl, especially cyclohexenyl, or another carbocyclic group, for example phenyl; where the hydrocarbyl moiety is substituted or unsubstituted;

each $R^4$ is the same or different and selected from an organic or inorganic moiety, for example, each $R^4$ is the same or different and selected from halogen; hydroxy; protected hydroxy for example trialkylsilylhydroxy; amino; amidino; guanidino; hydroxyguanidino; formamidino; isothioureido; ureido; mercapto; C(O)H or other acyl; acyloxy; carboxy; sulfo; sulfamoyl; carbamoyl; cyano; azo; nitro; $C_1$-$C_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other acyl, acyloxy, carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or more $C_1$-$C_7$ aliphatic groups.

The disclosure concerning pharmaceutical compositions, dosages, combinations, pharmacological assays etc provided for the compounds of Formula I apply to the compounds of Formula I* accordingly.

Chemically appropriate combinations of —$NR^a$—; —O—; —S—; —C(O)—; cyclopropyl are combinations which form a chemically stable moiety, such as —$NR^a$C(O)—; —C(O)$NR^a$—; —C(O)O— and —OC(O)—, for example. In many classes of compounds, $L^1$ does not comprise cyclopropyl.

$L^1$ is in particular selected from —$NR^a$CO— and —CON$R^a$—.

In another particular embodiment, there is provided a compound of Formula (II*):

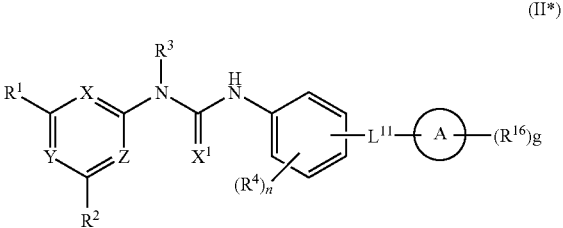
(II*)

wherein $L^{11}$ is selected from —NR$^a$CO— and —CONR$^a$— and the other symbols are as defined in relation to Formula (I*).

Often, at least one of $R^1$, $R^2$ and $R^{16}$ is not H; in exemplary compounds a single one of $R^1$, $R^2$ and $R^{16}$ is not H. Normally $R^1$ is not H. The invention includes amongst others compounds in which at least one of $R^1$, $R^2$ and $R^{16}$ is Rz*-L$^3$. It includes a class of compounds in which a single one of $R^1$, $R^2$ and $R^{16}$ is Rz*-L$^3$, particularly $R^1$. The invention includes a class of compounds in which $R^2$ and $R^{16}$ are H and $R^1$ is not H. e.g. is Rz*-L$^3$- where L$^3$ may be as hereinbefore defined for L$^1$.

In particular, the present invention pertains to compounds of formula I* wherein
(a) all of X, Y and Z are N,
(b) one of X, Y and Z is N,
(c) two or three of X and Y are N, or
(d) both of X and Z are N.

The compounds of Formula I* and II* are in particular useful to treat AML via inhibition of the tyrosine kinase domain of Flt-3. A further embodiment of the present invention is a method of treating acute myeloid leukemia (AML) which comprises administering a therapeutically effective amount of a claimed compound.

The Raf serine/threonine kinases are essential components of the Ras/Mitogen-Activated Protein Kinase (MAPK) signaling module that controls a complex transcriptional program in response to external cellular stimuli. Raf genes code for highly conserved serine-threonine-specific protein kinases which are known to bind to the ras oncogene. They are part of a signal transduction pathway believed to consist of receptor tyrosine kinases, p21 ras, Raf protein kinases, Mek1 (ERK activator or MAPKK) kinases and ERK (MAPK) kinases, which ultimately phosphorylate transcription factors. In this pathway Raf kinases are activated by Ras and phosphorylate and activate two isoforms of Mitogen-Activated Protein Kinase Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including transcription factors and in so doing set up their transcriptional program. Raf kinase participation in the Ras/MAPK pathway influences and regulates many cellular functions such as proliferation, differentiation, survival, oncogenic transformation and apoptosis.

Both the essential role and the position of Raf in many signaling pathways have been demonstrated from studies using deregulated and dominant inhibitory Raf mutants in mammalian cells as well as from studies employing biochemical and genetic techniques model organisms. In many cases, the activation of Raf by receptors that stimulate cellular tyrosine phosphorylation is dependent on the activity of Ras, indicating that Ras functions upstream of Raf. Upon activation, Raf-1 then phosphorylates and activates Mek1, resulting in the propagation of the signal to downstream effectors, such as MAPK (mitogen-activated protein kinase) (Crews et al. (1993) Cell 74:215). The Raf serine/threonine kinases are considered to be the primary Ras effectors involved in the proliferation of animal cells (Avruch et al. (1994) Trends Biochem. Sci. 19:279).

Raf kinase has three distinct isoforms, Raf-1 (c-Raf), A-Raf, and B-Raf, distinguished by their ability to interact with Ras, to activate MAPK kinase pathway, tissue distribution and sub-cellular localization (Marias et al., Biochem. J. 351: 289-305, 2000; Weber et. al., Oncogene 19:169-176, 2000; Pritchard et al., Mol. Cell. Biol. 15:6430-6442, 1995).

Recent studies have shown that B-Raf mutation in the skin nevi is a critical step in the initiation of melanocytic neoplasia (Pollock et. al., Nature Genetics 25: 1-2, 2002). Furthermore, most recent studies have emerged that activating mutation in the kinase domain of B-Raf occurs in .about. 66% of melanomas, 12% of colon carcinoma and 14% of liver cancer (Davies et. al., Nature 417:949-954, 2002) (Yuen et. al., Cancer Research 62:6451-6455, 2002) (Brose et. al., Cancer Research 62:6997-7000, 2002).

Inhibitors of Raf/MEK/ERK pathway at the level of Raf kinases can potentially be effective as therapeutic agents against tumors with over-expressed or mutated receptor tyrosine kinases, activated intracellular tyrosine kinases, tumors with aberrantly expressed Grb2 (an adapter protein that allows stimulation of Ras by the Sos exchange factor) as well as tumors harboring activating mutations of Raf itself. In early clinical trails an inhibitor of Raf-1 kinase, that also inhibits B-Raf, has shown promise as a therapeutic agent in cancer therapy (Crump, Current Pharmaceutical Design 8: 2243-2248, 2002; Sebastien et. al., Current Pharmaceutical Design 8: 2249-2253, 2002).

Disruption of Raf expression in cell lines through the application of RNA antisense technology has been shown to suppress both Ras and Raf-mediated tumorigenicity (Kolch et al., Nature 349:416-428, 1991; Monia et al., Nature Medicine 2(6):668-675, 1996).

As examples of kinases inhibited by the compounds of the disclosure may be mentioned c-Abl and Bcr-Abl, in particular, inhibition of Bcr-Abl may be mentioned. Another inhibited kinase is the receptor tyrosine kinase VEGF-R, in particular the VEGF receptor KDR (VEGF-R2). The compounds of the present invention also inhibit mutant forms of the Bcr-Abl kinases. The disclosed compounds are appropriate for the inhibition of one or more of these and/or other protein tyrosine kinases and/or the non-receptor tyrosine kinase Raf, and/or for the inhibition of mutants of these enzymes. In view of these activities, the compounds can be used for the treatment of diseases related to, especially, aberrant or excessive activity of such types of kinases, especially those mentioned.

For example, as inhibitors of VEGF-receptor tyrosine kinase activity, the compounds of the invention may primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, hemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, diabetes, endometriosis, chronic asthma, and especially neoplastic diseases (solid tumors, but also leukemias and other "liquid tumors", especially those expressing c-kit, KDR, Flt-1 or Flt-3), such as especially breast cancer, cancer of the colon, lung cancer (especially small-cell lung cancer), cancer of the prostate or Kaposi's sarcoma. A compound of Formula I*, II*, III*, IV*, V*, VI*, VII*, VIII* or IX* (or exemplary formula thereof) (or an N-oxide thereof) inhibits the growth of tumours and is especially suited to preventing the metastatic spread of tumors and the growth of micrometastases.

One class of target kinases of the compounds of the present invention are Bcr-Abl mutants. The mutants Glu255→Lysine, Glu255→Valine or the Thr3151→Isoleucine may be especially mentioned, most especially the Thr3151→Isoleucine mutant.

Other Bcr-Abl mutants include Met244→Val, Phe317→Leu, Leu248→Val, Met343→Thr, Gly250→Ala, Met351→Thr, Gly250→Glu, Glu355→Gly, Gln252→His, Phe358→Ala, Gln252→Arg, Phe359→Val, Tyr253→His, Val379→Ile, Tyr253→Phe, Phe382→Leu, Glu255→Lys, Leu387→Met, Glu255→Val, His396→Pro, Phe311→Ile, His396→Arg, Phe311→Leu, Ser417→Tyr, Thr315→Ile, Glu459→Lys and Phe486→Ser.

Structural fragments and substituents of the compounds of Formula (I*) will now be considered in turn:

The Left Hand Ring

By the "left hand ring" is meant the fragment:

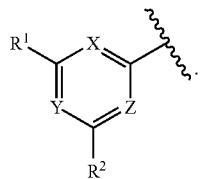

In a class of compounds, two of X, Y and Z are N, and in one sub-class X and Y are N while in another or X and Z are N; in an alternative class all of X, Y and Z are N. A particular class consists of compounds in which Y and Z are N, thus forming by way of example Fragment (A*):

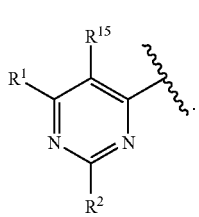

Fragment (A*)

Substituent $R^{15}$

Considering now the left hand ring without restriction, i.e. without limitation to Fragment (A*), the or each $R^{15}$ may independently be an $R^1$ group, for example as more particularly defined below, independently of the identity of $R^1$.

In some compounds the or each $R^{15}$ is independently H; hydroxy; halo; amino or mono- or di-alkylamino; cyano; azo or nitro; an aliphatic group having 1 to 7 carbon atoms and optionally interrupted by an —O— or —NH— linkage and/or linked to the left hand ring by a said linkage and/or substituted by hydroxy, halo, amino or mono- or di-alkylamino, cyano, azo or nitro; or acyl wherein the carbonyl moiety is substituted by a said aliphatic group; hydroxy, amino, mono- or dialkylamino, cyano, azo or nitro. Alkyl groups may have for example 1 to 7, e.g. 1, 2, 3 or 4 carbon atoms.

Often, $R^{15}$ is H, halo, hydroxy, amino, mono- or dialkylamino, alkyl (e.g. methyl), alkyl interrupted by an —O— or —NH— linkage and/or linked to the left hand ring by a said linkage (e.g. to form alkoxy, for example methoxy), trifluoromethyl, hydroxy, amino, mono- or dialkylamino; any alkyl moiety (interrupted or not) typically has 1, 2, 3 or 4 carbon atoms.

In a class of compounds, $R^{15}$ is H or halo, particularly H, F or Cl, for example is H or F. In a particular class of compounds, the or each $R^{15}$ is H.

The above description of $R^{15}$ applies of course to Fragment (A*) as much as to other left hand ring structures.

Substituent $R^2$

Again considering the left hand ring without restriction, $R^2$ may be any moiety described above in relation to $R^{15}$ (e.g. may be any $R^1$ group as described more particularly below) and of course $R^2$ and $R^{15}$ may be the same or different.

In some compounds, $R^2$ and the or each $R^{15}$ are independently H; halo; an aliphatic group (e.g. having 1 to 7 carbon atoms, for example 1, 2, 3, or 4), the aliphatic group optionally being interrupted by an —O— or —NH— linkage and/or linked to the left hand ring by a said linkage and/or substituted by hydroxy, halo, amino or mono- or di-alkylamino, acyl wherein the carbonyl moiety is substituted by a said aliphatic group, trifluoromethyl, hydroxy, amino, mono- or di-alkylamino, cyano, azo or nitro.

Often, both $R^2$ and the or each $R^{15}$ are independently H, halo, alkyl, alkyl interrupted by an —O— or —NH— linkage and/or linked to the left hand ring by a said linkage, trifluoromethyl, hydroxy, amino, mono- or dialkylamino; any alkyl moiety (interrupted or not) typically has 1, 2, 3 or 4 carbon atoms.

In a class of compounds, both $R^2$ and the or each $R^{15}$ are independently H or halo, particularly H, F or Cl, for example are H or F. In a particular class of compounds, $R^2$ and the or each $R^{15}$ are H.

The above descriptions of $R^2$ and of $R^2$ and $R^{15}$ apply of course to Fragment (A*) as much as to other left hand ring structures.

It will be understood from the aforegoing description that a particular left hand ring structure is Fragment (B*):

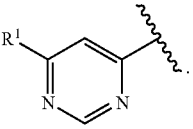

Fragment (B*)

Substituent $R^1$

As previously described, $R^1$ is an organic or inorganic moiety.

As inorganic moieties may be mentioned halo, hydroxyl, amino, cyano, azo (N=N=N) and nitro. F and Cl are exemplary halogens.

The organic moiety, designated Rz*, is substituted or unsubstituted and may be attached via a linker, -$L^3$-, the organic moiety being especially selected from hydrogen;

lower aliphatic (especially $C_1$, $C_2$, $C_3$ or $C_4$ aliphatic) e.g. lower alkyl, lower alkenyl, lower alkynyl, particularly lower and especially $C_1$, $C_2$, $C_3$ or $C_4$ alkyl;

substituted or unsubstituted functional groups selected from amino; guanidino; hydroxyguanidino; formamidino; isothioureido; ureido; mercapto; carboxy; sulfo; and hydroxy, exemplary substituents being a protecting group, a said lower aliphatic group, acyl particularly lower alkanoyl e.g. of which the alkyl part has 1, 2, 3 or 4 carbon atoms, carboxy, esterified carboxy (e.g. esterified by a said lower aliphatic group);

sulfamoyl; carbamoyl; C(O)H or other acyl; acyloxy; where acyl is particularly lower alkanoyl e.g. of which the alkyl part has 1, 2, 3 or 4 carbon atoms;

substituted or unsubstituted cyclic groups, for example the cyclic group (whether substituted or unsubstituted) may be cycloalkyl, e.g. cyclohexyl, phenyl, pyrrole, imidazole, pyrazole, isoxazole, oxazole, thiazole, pyridazine, pyrimidine, pyrazine, pyridyl, indole, isoindole, indazole, purine, indolizidine, quinoline, isoquinoline, quinazoline, pteridine, quinolizidine, piperidyl, piperazinyl, pyrollidine, morpholinyl or thiomorpholinyl and, for example, substituted lower aliphatic or substituted hydroxy may be substituted by such substituted or unsubstituted cyclic groups. See below for a description of particular classes of Rz* moiety.

Linker -$L^3$- has 1, 2, 3, 4 or 5 in-chain atoms and is selected from $C_1$, $C_2$, $C_3$ or $C_4$ aliphatic (notably linear aliphatic, and aliphatic particularly being alkyl) optionally interrupted and/or terminated by a linkage selected from the group consisting of —$NR^a$—; —O—; —S—; —C(O)—; cyclopropyl (regarded as having two in-chain atoms) and chemically appropriate combinations thereof; —$NR^a$—; —O—; —S—; —C(O)—; cyclopropyl (regarded as having two in-chain atoms) and chemically appropriate combinations thereof; and —$NR^a$—, wherein $R^a$ is hydrogen, hydroxy, hydrocarbyloxy or hydrocarbyl, wherein hydrocarbyl has from 1 to 15 carbon atoms (e.g. 1 to 7), is optionally interrupted by an —O— or —NH— linkage and may be, for example, selected from an aliphatic group (e.g. having 1 to 7 carbon atoms, for example 1, 2, 3, or 4, aliphatic particularly being alkyl), cycloalkyl, especially cyclohexyl, cycloalkenyl, especially cyclohexenyl, or another carbocyclic group, for example phenyl; where the hydrocarbyl moiety is substituted or unsubstituted. Exemplary substituents are hydroxy, halo, amino or mono- or di-($C_1$-$C_4$)alkylamino, lower alkanoyl, trifluoromethyl, cyano, azo or nitro. $R^a$ is particularly H.

In a class of compounds, $R^1$ includes a linker $L^3$; in a sub-class, the linker is —$NR^a$—, alkyl terminated at the left hand ring by (i.e joined to the left hand ring by) —$NR^a$—, alkyl terminated at its end remote from the left hand ring by —$NR^a$—, or alkyl interrupted by —$NR^a$— wherein alkyl has 1, 2, 3 or 4 carbon atoms. In this class of compounds, $R^a$ is particularly H. A preferred linker is —NH—.

In other words, a common left hand ring structure is represented by Fragment (C*):

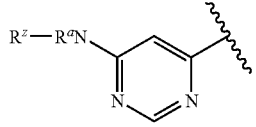

Fragment (C*)

where $R^a$ is as described above and preferably H, and Rz* is a substituted or unsubstituted organic moiety as mentioned above and as further described below. Also to be mentioned are compounds in which Rz* is H, i.e. in which $R^1$ is amino when $R^a$ is also H, as well as variants in which $R^1$ is another substituted or unsubstituted basic group, for example amidino, guanidino; hydroxyguanidino; formamidino; isothioureido or ureido.

As previously described, therefore, $R^1$ may in certain compounds comprise a substituted or unsubstituted organic moiety, optionally joined to the left hand ring through a linker $L^3$. Thus, $R^1$ in such compounds may be represented as Rz*-$L^3$, where Rz* is a substituted or an unsubstituted organic moiety. This applies equally to left hand ring structures which do not correspond to Fragment (C*) as to those which do.

Rz* is commonly a moiety containing from 1 to 30 in-chain and/or in-ring atoms selected from C, N, O S and Si and in which one or more hydrogens are optionally replaced by halogen. Alternatively stated, such Rz* groups have from 1 to 30 plural valent atoms selected from C, N, O, S and Si as well as monovalent atoms selected from H and halo, e.g. selected from H, F, Cl and Br, for example H, F and Cl. In some Rz* moieties there are from 1 to 25 plural valent atoms, e.g. 1 to 20, such as 1 to 16, for example.

Included are compounds in which Rz* contains one or a combination of moieties selected from categories 1), 2) and 3) below and optionally one or more moieties selected from category 4) below:

5) aliphatic moieties, in particular having from 1 to 7 carbon atoms, e.g. 1, 2, 3 or 4, particularly alkyl or alkenyl moieties, e.g. alkyl;
6) carbocyclic rings, which may be saturated or unsaturated (e.g. aromatic), particularly to be mentioned are bicyclic and monocyclic rings and especially monocyclic rings having 5 or 6 ring members;
7) heterocyclic rings, which may be saturated or unsaturated (e.g. aromatic), particularly to be mentioned are bicyclic and monocyclic rings and especially monocyclic rings having 5 or 6 ring members;
8) linking moieties selected from O, N, Si and C(O), wherein two or more linking moieties may be combined to form a larger linking group for example C(O)O, C(O) NH or OC(O)NH.

In these compounds, a plurality of moieties selected from 1), 2) and 3) may be linked together either directly or through a linking moiety 4). Of course, one compound may contain one or more linking moieties. Tri- or more valent linking moieties such as N and Si may serve to link together just two moieties selected from 1), 2) and 3), in which case the remaining valencies are suitably occupied by hydrogen; alternatively N or Si may link together three said moieties, or Si may link together four said moieties. Where Rz* contains a plurality of moieties selected from 1), 2) and 3), the moieties may be the same of different and may independently be selected from categories 1), 2) and 3).

Moieties 1), 2) and 3) may be substituted by one or more substituents selected from, in particular, hydroxy, amino, amidino, guanidino, hydroxyguanidino, formamidino, isothioureido, ureido, mercapto, C(O)H or other lower acyl, lower acyloxy, carboxy, sulfo, sulfamoyl, carbamoyl, cyano, azo, or nitro, which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or, where possible, more $C_1$-$C_7$ aliphatic groups. Often, but not always, Rz* has 0, 1, 2, 3, or 4 such substituents; sometimes there are a larger number of substituents as can happen, for example, when Rz* contains one or more perfluorinated alkyl or cyclic groups, e.g. $CF_3$, as well as other optional substituents.

Particular moieties 1), 2) and 3) to mention are straight chain and branched alkyl, 5- and 6-membered carbocyclic rings (notably phenyl and cyclohexyl), and 5- and 6-membered heterocyclic rings (notably 5-membered rings containing a single heteroatom, e.g. furan, thiophene, pyrrole; and 6-membered rings containing one or two heteroatoms, e.g. piperidine, piperazine, morpholine, pyridine, pyrimidine and pyrazine).

The invention includes compounds of Formula (I*) or (II*) wherein $R^1$ is of the formula Rz*-$NR^a$—, as described above, and Rz* is selected from
(i) -G-$R^x$ where G is a direct bond, C(=O) or C(=O)O and $R^x$ is selected from H and $C_1$-$C_7$ aliphatic moieties,
(II*) -G-$R^y$ where G is a direct bond, C(=O) or C(=O)O and $R^y$ is selected from $C_1$-$C_7$ aliphatic substituted by one or more halogens and/or one or two functional groups selected from hydroxy, amino, amidino, guanidino, hydroxyguanidino, formamidino, isothioureido, ureido, mercapto, C(O)H or other lower acyl, lower acyloxy, carboxy, sulfo, sulfamoyl, carbamoyl, cyano, azo, or nitro, which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or, where possible, more $C_1$-$C_7$ aliphatic groups, (iii) a group of the formula

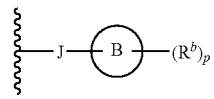

where:
J represents a direct bond, alkyl or alkyl terminated or interrupted by C(=O) or C(=O)O, where J has 1, 2, 3, 4 or 5 in-chain atoms;
ring B represents a mono- or bi-cyclic ring, particularly a 5- or 6-membered carbocyclic or heterocyclic ring;
p is 0, 1, 2; 3, 4 or 5, e.g. 0, 1 or 2;
the or each $R^b$ is independently selected from -$L^4$-$NR^cR^d$; -$L^4$-RING* where RING* is a mono- or bi-cyclic ring, particularly a 5- or 6-membered carbocyclic or heterocyclic ring, optionally substituted as defined below; halogen; hydroxy; protected hydroxy for example trialkylsilylhydroxy; amino; amidino; guanidino; hydroxyguanidino; formamidino; isothioureido; ureido; mercapto; C(O)H or other lower acyl; lower acyloxy; carboxy; sulfo; sulfamoyl; carbamoyl; cyano; azo; or nitro; and $C_1$-$C_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other lower acyl, lower acyloxy, carboxy, sulfo, sulfamoyl, carbamoyl, cyano, azo, or nitro; all of which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or, where possible, more $C_1$-$C_7$ aliphatic groups,
wherein $L^4$ is a direct bond; a linkage selected from —O—; —S—; —C(O)—; —OC(O)—; —$NR^a$C(O)—; —C(O)—$NR^a$—; —OC(O)—$NR^a$—; cyclopropyl and —$NR^a$—; or is a $C_1$-$C_7$ aliphatic group optionally interrupted and/or terminated at a single end or at both ends by a said linkage ($R^a$ being as previously defined and typically H);
and wherein $R^c$ and $R^d$ are each independently selected from hydrogen, and $C_1$-$C_7$ aliphatic optionally substituted by one or more halogens, by an optionally substituted 5- or 6-membered heterocyclic or carbocyclic ring, and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other lower acyl, lower acyloxy, carboxy, sulfo, sulfamoyl, carbamoyl, cyano, azo, or nitro, which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or more $C_1$-$C_7$ aliphatic groups,
or $R^c$ and $R^d$ together with their adjoining nitrogen form a 5- or 6-membered ring optionally substituted as described below,
said optionally substituted rings independently of each other being substituted by 0, 1, 2, 3, 4 or 5 substituents selected from halogen; hydroxy; protected hydroxy for example trialkylsilylhydroxy; amino; amidino; guanidino; hydroxyguanidino; formamidino; isothioureido; ureido; mercapto; C(O)H or other lower acyl; lower acyloxy; carboxy; sulfo; sulfamoyl; carbamoyl; cyano; azo; nitro; $C_1$-$C_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other lower acyl; lower acyloxy carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or, where possible, more $C_1$-$C_7$ aliphatic groups (for example, therefore, a ring may be substituted by an alkoxy group, e.g. methoxy or ethoxy).

Still considering compounds wherein $R^1$ is of the formula Rz*-$NR^a$— and Rz* is selected from categories (i), (ii) and (iii) above, aliphatic often has 1, 2, 3 or 4 carbon atoms and is often linear, but sometimes branched. In a class of compounds, aliphatic is alkyl, e.g. linear or branched alkyl having 1, 2, 3 or 4 carbon atoms; linear alkyl is more common, irrespective of the number of carbon atoms.

In a sub-class of the above category (i) compounds, -G- is a direct bond and $R^x$ is H or a said aliphatic group and more particularly $R^x$ is H or alkyl, e.g. linear or branched alkyl having 1, 2, 3 or 4 carbon atoms; linear alkyl being more common, irrespective of the number of carbon atoms. This sub-class therefore comprises compounds in which $R^1$ is amino or mono- or di-alkylamino. Included are members of this sub-class in which $R^x$ is not H but a said aliphatic group.

In another sub-class of category (i) compounds, -G- is C(=O) or C(=O)O and $R^x$ is H or a said aliphatic group and more particularly $R^x$ is H or alkyl, e.g. linear or branched alkyl having 1, 2, 3 or 4 carbon atoms, linear alkyl being more common, irrespective of the number of carbon atoms. Included are members of this sub-class in which $R^x$ is not H but a said aliphatic group. Methyl may be mentioned as an exemplary $R^x$ group. It will be understood that in some compounds of this sub-class -G- is C(=O) whereas in other compounds G is C(=O)O. As $R^1$ groups formed by this sub-class may be mentioned alkanoylamino, particularly acetylamino (—NHC(O)Me), and alkoxycarbonylamino, particularly methoxycarbonylamino (—NHC(O)OMe).

It will be appreciated from the preceding two paragraphs that the invention includes category (i) compounds in which $R^x$ is not H but a said aliphatic group as in the case of alkyl, e.g. linear or branched alkyl having 1, 2, 3 or 4 carbon atoms.

A particular genus of compounds are those in which $R^a$ is as previously defined, e.g. is selected from hydrogen and aliphatic groups, particularly alkyl groups (e.g. in either case having 1 to 7 carbon atoms, for example 1, 2, 3, or 4, and $R^1$ is selected from the group consisting of:
1) moieties falling within category (i) above, wherein -G- is a direct bond and $R^x$ is H or a said aliphatic group, and aliphatic often has 1, 2, 3 or 4 carbon atoms and is typically linear, but sometimes branched. In a sub-genus of these compounds, aliphatic is alkyl e.g. linear or branched alkyl having 1, 2, 3 or 4 carbon atoms; linear alkyl is more common, irrespective of the number of carbon atoms;

2) moieties of the formula Rz*-NR$^a$—, where Rz* is acyl; acyloxy; where acyl is particularly lower alkanoyl e.g. of which the alkyl part has 1, 2, 3 or 4 carbon atoms;

3) moieties falling within category (i) above, wherein -G- is C(=O) or C(=O)O and R$^x$ is H or a said aliphatic group and more particularly R$^x$ is H or alkyl e.g. linear or branched alkyl having 1, 2, 3 or 4 carbon atoms, linear alkyl being more common, irrespective of the number of carbon atoms. Included are members of this sub-class in which R$^x$ is not H but a said aliphatic group; methyl may be mentioned as an exemplary R$^x$ group;

4) $C_1$, $C_2$, $C_3$ or $C_4$ alkyl $C_1$, $C_2$, $C_3$ or $C_4$ haloalkyl (e.g. trifluoromethyl), halo (e.g. F or Cl), hydroxy, alkoxy (e.g. methoxy), cyano, azo (N=N=N) or nitro.

In many compounds of this genus, R$^a$ is H. Commonly, Rz* is as defined in sub-clause 1) or 3) of the preceding paragraph, e.g. is H; $C_1$, $C_2$, $C_3$ or $C_4$ alkyl; $C_1$, $C_2$, $C_3$ or $C_4$ alkanoyl; or alkoxycarbonyl of which the alkoxy part has 1, 2, 3 or 4 carbon atoms.

Particular compounds falling in category (ii) are those in which -G- is a direct bond. Also to be mentioned are category (ii) compounds in which -G- is C(=O) or C(=O)O.

Turning now to those compounds in which Rz* is a category (iii) group, i.e. is of the formula

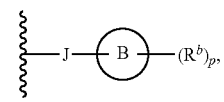

ring B is typically a 6-membered carbocyclic or heterocyclic ring, particularly phenyl, cyclohexyl or cyclohexenyl. Of these, phenyl is preferred. In other instances, ring B is a 5-membered carbocyclic or heterocyclic ring. Other exemplary residues forming ring B are pyridyl and pyrimidyl.

J is often a direct bond, thus forming Fragment H of the formula:

Fragment H

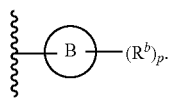

Integer p may be 0.

Integer p is often 1. Where p is greater than one, all the R$^b$ groups or all the R$^b$ groups except one are often halogen (notably F or Cl), methyl or trifluoromethyl. Also to be mentioned in this regard are hydroxy and amino. Often, a single R$^b$ group is selected from -L$^4$-NR$^c$R$^d$ and -L$^4$-RING* and there are 0, 1 or 2 additional substituents which are not -L$^4$-NR$^c$R$^d$ or -L$^4$-RING* but are, for example, halogen (notably F or Cl), lower alkyl (e.g. methyl), lower alkoxy (e.g. methoxy), hydroxy, amino or trifluoromethyl.

Accordingly, the invention includes compounds in which Rz* is, e.g. a 6-membered carbocyclic ring (notably phenyl) substituted by 1, 2, 3, 4 or 5 halogens, e.g. selected from F, Cl and Br; typically, such phenyl rings are mono- or di-substituted, e.g. are 2- and/or 4-substituted by F or 3-substituted by Cl. In some cases of plural substitution by halogen, all the halogens are the same. Thus, in a class of compounds Rz* is a monocyclic ring, particularly a 6-membered carbocyclic ring (notably phenyl), substituted solely by one or more halogens, particularly selected from F and Cl; sometimes the or each halogen is F but in some other cases the or each halogen is Cl.

In another class of compounds, Rz* is a monocyclic ring, particularly a 6-membered carbocyclic ring (notably phenyl), substituted by 1, 2, 3, 4 or 5 substituents, e.g. 1 or 2 substituents, selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. Certain such rings have 0, 1 or 2 substituents, e.g. 0 or 1.

In one class of compounds, L$^4$ is a direct bond, linear alkyl, linear alkyl terminated adjacent ring A by a said linkage, or is a said linkage. In a sub-class, any said linkage is —O—, —C(O)— or a direct bond, of which —O— and a direct bond may be particularly mentioned, for example —O—.

The invention includes a class of compounds in which ring A is a 6-membered ring, particularly phenyl, cyclohexyl or cyclohexenyl and has one or two substituents R$^b$ independently selected from -L$^4$-NR$^c$R$^d$ and -L$^4$-RING*, as defined previously. In a sub-class, there is a single substituent at, in particular, the 3-position or 4-position selected from -L$^4$-NR$^c$R$^d$ and -L$^4$-RING* such that the left hand ring has a structure corresponding to Fragments (D1), (D2), (E1) or (E2):

Fragment (D1)

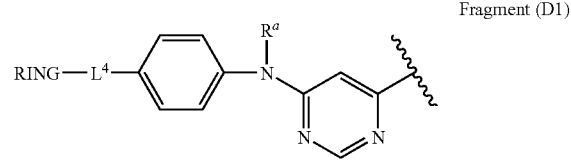

Fragment (D2)

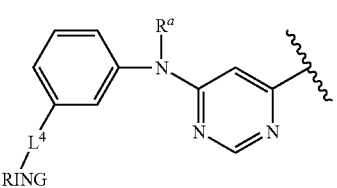

Fragment (E1)

Fragment (E2)

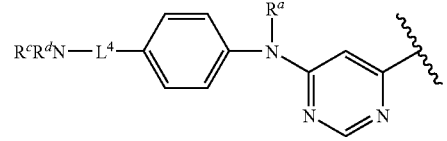

As previously described, R$^a$ is commonly H. Also as previously described, the phenyl ring may be replaced by cyclohexyl or cyclohexenyl, particularly cyclohexyl. It may alternatively be replaced by a 5- or 6-membered heterocycle, particularly pyridine.

In some embodiments, the phenyl ring of the above fragments (or other ring replacing phenyl) has 1, 2, 3 or 4 further substituents, for example selected from halogen (notably F or Cl), methyl, methoxy or trifluoromethyl, e.g. 1 or 2 such substituents. Also to be mentioned in this regard are hydroxy and amino.

$L^4$ is as previously described, that is a direct bond; a linkage selected from —O—; —S—; —C(O)—; —OC(O)—; —NR$^a$C(O)—; —C(O)—NR$^a$—; —OC(O)—NR$^a$—; cyclopropyl and —NR$^a$—; or $C_1$-$C_7$ aliphatic optionally interrupted and/or terminated at a single end or at both ends by a said linkage (R$^a$ being as previously defined and typically H). Any aliphatic moiety is often alkyl, e.g. alkyl or other aliphatic having 1, 2, 3 or 4 carbon atoms, as in the case of a sub-class of linkers $L^2$ in which aliphatic moieties are methyl, ethyl or n-propyl.

In particular fragments (D) and (E), $L^4$ is a direct bond, linear alkyl, linear alkyl terminated adjacent the phenyl ring in the above representations of the fragments by a said linkage, or is a said linkage; suitably but not necessarily any said linkage is —O— or —C(O)—, of which —O— may be particularly mentioned. Thus, the above fragments (D) and (E) may comprise sub-fragments -Ph-NR$^c$R$^d$, -Ph-RING*, -Ph-O-alkyl-NR$^c$R$^d$, -Ph-O-alkyl-RING*, -Ph-alkyl-NR$^c$R$^d$-Ph-alkyl-RING*, and also to be mentioned are sub-fragments -Ph-O—NR$^c$R$^d$-Ph-O-RING*, -Ph-C(O)—NR$^c$R$^d$ and -Ph-C(O)-RING*, where, in all these sub-fragments which contain alkyl, alkyl may be e.g. methyl, ethyl or n-propyl, or n-butyl.

In some embodiments $L^4$ is H, thus providing fragment (E3) and (E4):

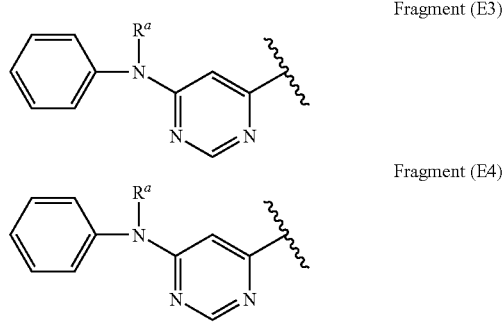

Fragment (E3)

Fragment (E4)

Considering now in more detail fragments (D1) and (D2), these contain a moiety RING* which is a cyclic moiety and in many cases a 5- or 6-membered carbocyclic or heterocyclic ring optionally substituted as defined previously. Exemplary rings are saturated, e.g. cyclopentane or cyclohexane. In particular compounds, RING* is a 5- or 6-membered heterocycle, often containing one or two heteroatoms, typically selected from O and N; in a sub-class, the heterocycles contain one or two nitrogens and, where there is a single nitrogen, optionally an oxygen. Particular heterocycles include a nitrogen which is not a member of a double bond and these are more particularly saturated heterocycles. As heterocycles may be mentioned pyrrolidine, piperidine, piperazine and morpholine; in some compounds, RING* is piperidine having its nitrogen at the 4-position relative to $L^2$. As already described, RING* may be substituted and, in one class of compounds, is substituted by 0, 1, 2, 3, 4 or 5 substituents, e.g. selected from $C_1$-$C_7$ aliphatic groups, optionally substituted as described above, and less frequently $C_1$-$C_7$ aliphatic-oxy. Any aliphatic group is often alkyl (straight chain or branched), e.g. alkyl or other aliphatic having 1, 2, 3 or 4 carbon atoms, as in the case of a sub-class of fragments (D1) and (D2) having substituents which are methyl, ethyl or n-propyl. Exemplary substituents on RING* include straight chain or branched $C_1$, $C_2$, $C_3$ or $C_4$ alkyl such as, e.g., methyl, ethyl n-propyl, isopropyl or t-butyl, of which methyl may be particularly mentioned, halogen (notably F or Cl) and $C_1$, $C_2$, $C_3$ or $C_4$ alkoxy; also to be mentioned are hydroxy and amino. Alkyl moieties may be unsubstituted or substituted, e.g. by halogen (notably F or Cl) or in some cases by hydroxy or amino.

In some classes of RING* moieties, there are 0, 1, 2, 3, 4 or 5 such substituents selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. Certain RING* moieties have 0, 1 or 2 substituents, e.g. 0 or 1.

Considering now in more detail fragments (E1) and (E2), these contain a moiety NR$^c$R$^d$. R$^c$ and R$^d$ are as previously described. In one class of these fragments, R$^c$ and R$^d$ are the same or different (but more usually the same) and selected from $C_1$-$C_7$, e.g. $C_1$-$C_4$ aliphatic groups, optionally substituted as described above. As aliphatic R$^c$ and R$^d$ moieties may be mentioned alkyl, e.g having 1, 2, 3 or 4 carbon atoms, as in the case of a sub-class of fragments (E1) and (E2) having substituents which are methyl, ethyl or n-propyl. Alkyl or other aliphatic moieties may be substituted e.g. by amino or mono- or di ($C_1$-$C_4$) alkylamino, or e.g. by a 5- or 6-membered heterocyclic or carbocyclic ring optionally substituted as previously described, or be unsubstituted. Thus, particular $L^4$NR$^c$R$^d$ moieties are —OCH$_2$NMe$_2$, —OCH$_2$NEt$_2$, —OCH$_2$CH$_2$NMe$_2$, —OCH$_2$CH$_2$NEt$_2$, —OCH$_2$CH$_2$CH$_2$NMe$_2$, —OCH$_2$CH$_2$CH$_2$NEt$_2$, —CH$_2$NMe$_2$, —CH$_2$NEt$_2$, —CH$_2$CH$_2$NMe$_2$, —CH$_2$CH$_2$NEt$_2$, —CH$_2$CH$_2$CH$_2$NMe$_2$, and —CH$_2$CH$_2$CH$_2$NEt$_2$.

In some compounds, R$^c$ and R$^d$ may each independently contain a carbonyl moiety. Where one of R$^c$ or R$^d$ contain a carbonyl moiety, the carbonyl moiety may form, for example, an amide bond with the nitrogen. Derivatives including an amide bond include moieties terminating in a carbocyclic acid residue or an ester, for example an alkyl ester, for example a methyl or ethyl ester. Typically compounds containing a carbonyl moiety are of the form of an ester.

Typically, when one of R$^c$ or R$^d$ contain a carbonyl moiety, the other of R$^c$ or R$^d$ is hydrogen.

In one class of fragments, $L^4$ is a direct bond and R$^c$ and R$^d$ are each independently selected from hydrogen, —C(O)-alkyl, —C(O)-alkyl where alkyl may be substituted or unsubstituted. Typically, alkyl is $C_1$, $C_2$, $C_3$ or $C_4$ alkyl such as, for example, methyl, ethyl, n-propyl, isopropyl or t-butyl, of which methyl may be particularly mentioned.

In another class of fragments (E1) and (E2), R$^c$ and R$^d$ together with the adjoining nitrogen form a heterocyclic moiety (normally a 5- or 6-membered heterocyclic ring), optionally substituted as previously described. In addition to the nitrogen of moiety NR$^c$R$^d$, the heterocyclic ring may contain at least one further heteroatom, and often exactly one further heteroatom, in either case typically selected from O and N; in a sub-class, the heterocycles contain altogether one or two nitrogens and, where there is a single nitrogen, optionally an oxygen. Particular heterocycles include a nitrogen which is not a member of a double bond and these are more particularly saturated heterocycles. As heterocycles may be mentioned pyrrolidine, piperidine, piperazine and morpholine; of these particular heterocycles are piperazine and morpholine. As already described, the heterocycle may be substituted and, in one class of compounds, is substituted by 0, 1, 2, 3, 4 or 5 substituents, e.g. selected from $C_1$-$C_7$ aliphatic groups, optionally substituted as described above, and less frequently $C_1$-$C_7$ aliphatic-oxy. Any aliphatic group is often alkyl (straight chain or branched), e.g. alkyl or other aliphatic having 1, 2, 3 or 4 carbon atoms, as in the case of a sub-class of cyclic (E1) and (E2) fragments having substituents which are methyl, ethyl or n-propyl. Exemplary substituents on cyclic (E1) and (E2) fragments include straight chain or branched $C_1$, $C_2$, $C_3$ or $C_4$ alkyl such as, e.g., methyl, ethyl n-propyl, isopropyl or t-butyl, of which methyl may be particularly mentioned, halogen (notably F or Cl) and $C_1$, $C_2$, $C_3$ or $C_4$ alkoxy; also to be mentioned are hydroxy and amino. Alkyl moieties may be unsubstituted or substituted, e.g. by halogen (notably F or Cl) or in some cases by hydroxy or amino.

In some classes of cyclic (E1) and (E2) fragments (that is to say fragments in which $R^c$ and $R^d$ together with the adjoining nitrogen form a ring), there are 0, 1, 2, 3, 4 or 5 such substituents selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. Certain cyclic fragments have 0, 1 or 2 substituents, e.g. 0 or 1.

Particular $L^4NR^cR^d$ moieties are -Pip, -Morph, —OCH$_2$Pip, —OCH$_2$-Morph, —OCH$_2$CH$_2$Pip, —OCH$_2$CH$_2$-Morph, —OCH$_2$CH$_2$CH$_2$Pip, —OCH$_2$CH$_2$CH$_2$-Morph, —CH$_2$Pip, —CH$_2$-Morph, —CH$_2$CH$_2$Pip, —CH$_2$CH$_2$-Morph, —CH$_2$CH$_2$CH$_2$Pip, and —CH$_2$CH$_2$CH$_2$-Morph. Also to be mentioned are —C(O)Pip and —C(O)Morph. The abbreviation "Pip" stands for piperazine and "Morph" for morpholine, and these rings may be substituted as previously described. In particular piperazine is optionally N-substituted. Piperazine and morpholine may be substituted by a $C_1$-$C_7$ aliphatic group as mentioned in the previous paragraph, for example a straight chain or branched $C_1$, $C_2$, $C_3$ or $C_4$ moiety selected from alkyl and haloalkyl such as, e.g., methyl, trifluoromethyl, ethyl n-propyl, isopropyl or t-butyl, of which methyl and trifluoromethyl are exemplary. As described before, $R^a$ is in particular hydrogen.

Amongst the classes of compounds which are particularly to be mentioned are those in which the left hand ring has a structure corresponding to Fragment (D1*) or (E1). Particularly exemplary are such compounds having a Fragment (E1*) in which $R^c$ and $R^d$ together with the adjoining nitrogen form a 5- or 6-membered heterocyclic ring as described above. These rings may be substituted as previously described. In particular they are optionally N-substituted by a $C_1$-$C_7$ aliphatic group as mentioned earlier, for example a straight chain or branched $C_1$, $C_2$, $C_3$ or $C_4$ moiety selected from alkyl and haloalkyl such as, e.g., methyl, trifluoromethyl, ethyl n-propyl, isopropyl or t-butyl, of which methyl and trifluoromethyl are exemplary. As described before, $R^a$ is in particular hydrogen.

It will be appreciated from the aforegoing that the invention includes compounds having a left hand ring having the structure of the following Fragment (F*):

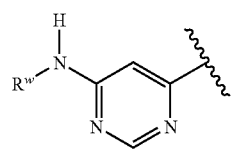

Fragment (F)

where $R^w$ is selected from the group consisting of:
(i) H; $C_1$, $C_2$, $C_3$ or $C_4$ alkyl; $C_1$, $C_2$, $C_3$ or $C_4$ alkanoyl; or alkoxycarbonyl of which the alkoxy part has 1, 2, 3 or 4 carbon atoms,
(ii) 4-phenyl or 4-phenyl substituted by -$L^4NR^cR^d$, where -$L^4NR^cR^d$ is as defined previously and in particular is:
 (a) -Pip, -Morph, —OCH$_2$Pip, —OCH$_2$-Morph, —OCH$_2$CH$_2$Pip, —OCH$_2$CH$_2$-Morph, —OCH$_2$CH$_2$CH$_2$Pip, —OCH$_2$CH$_2$CH$_2$-Morph, —CH$_2$Pip, —CH$_2$-Morph, —CH$_2$CH$_2$Pip, —CH$_2$CH$_2$-Morph, —CH$_2$CH$_2$CH$_2$Pip, or —CH$_2$CH$_2$CH$_2$-Morph, or is —C(O)Pip or —C(O)Morph, where "Pip" and "Morph" are as described in the last but one paragraph; or
 (b) —OCH$_2$NMe$_2$, —OCH$_2$NEt$_2$, —OCH$_2$CH$_2$NMe$_2$, —OCH$_2$CH$_2$NEt$_2$, —OCH$_2$CH$_2$CH$_2$NMe$_2$, —OCH$_2$CH$_2$CH$_2$NEt$_2$, —CH$_2$NMe$_2$, —CH$_2$NEt$_2$, —CH$_2$CH$_2$NMe$_2$, —CH$_2$CH$_2$NEt$_2$, —CH$_2$CH$_2$CH$_2$NMe$_2$, or —CH$_2$CH$_2$CH$_2$NEt$_2$.

In certain compounds, $R^w$ is H, formyl, acetyl or methoxycarbonyl.

In embodiments, the pyrimidine rings of Fragments (D1), (D2), (E1), (E2) and (F) are replaced by a pyridine or triazine ring.

Substituent $R^3$

Substituent $R^3$ is as previously described in relation to Formula (I*) or (II*).

In embodiments, $R^3$ is selected from H, $R^b$ groups, and categories (i), (ii) and (iii) described above in relation to Rz*, independently of the identity of Rz*. In one class of embodiments, $R^3$ is H or a $C_1$-$C_7$ aliphatic group, for example straight chain or branched $C_1$-$C_4$ alkyl such as, e.g., methyl, ethyl or n-propyl, of which methyl is exemplary. In other compounds, $R^3$ is a $C_1$-$C_7$ aliphatic group (for example straight chain or branched $C_1$-$C_4$ alkyl such as, e.g., methyl, ethyl or n-propyl) substituted by a mono- or bi-cyclic ring, particularly a 5- or 6-membered saturated or unsaturated carbocyclic or heterocyclic ring, for example by phenyl, pyrrolidine, piperidine, piperazine, morpholine, thiophene, furan, pyrrole, pyridine, pyrazine or pyran. $R^3$ may therefore be straight chain alkyl (or other straight chain aliphatic group, for example in either case having up to 4 carbon atoms) substituted at its free end by such a mono- or bi-cyclic ring.

In one class of compounds $R^3$ is a category (iii) moiety, that is, it is in particular a moiety having the structure of Fragment H:

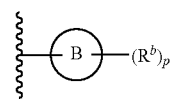

Fragment H as previously described. The identity of $R^3$ is independent of that of Rz*, as already stated.

However, as particular compounds, may be mentioned those in which just one of Rz* and $R^3$ is a category (iii)

moiety. In a subclass, one of Rz* and $R^3$ is a category (iii) moiety and the other is H; to be mentioned in this regard are compounds in which $R^3$ is a category (iii) moiety and $R^1$ is $NH_2$, or alternatively mono- or di-alkyl amino.

Where $R^3$ is a category (iii) moiety, it may have a structure corresponding to the category (iii) structures found in Fragments (D1), (D2), (E1), (E2) or (F), as previously described.

In many compounds $R^3$ is H; where it is not H it is often $C_1$, $C_2$, $C_3$ or $C_4$ alkyl (e.g. ethyl or methyl). It may also be, for example, such an alkyl group substituted, e.g. at a free end thereof, by a 5- or 6-membered heterocyclic ring; typically the ring is saturated, for example it may be selected from piperidine, piperizine, thiazolidine, morpholine and thiomorpholine The Right Hand Ring By the "right hand ring" is meant the Fragment (G*):

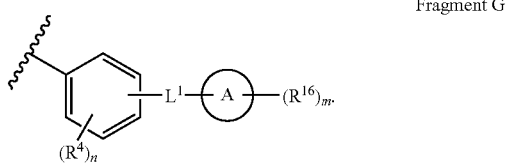

Fragment G

It has previously been mentioned that: n is 0, 1, 2, 3 or 4; m is m is 0, 1, 2, 3, 4 or 5; each $R^4$ is the same or different and selected from organic and inorganic moieties; $L^1$ is a linker; ring A is a mono- or bicyclic ring; and each $R^{16}$ is the same or different and selected from organic and inorganic moieties.

Integer m is normally 1. Typically, there is an $L^1$ group at the 3-position of the phenyl ring relative to $L^1$. Accordingly, preferred compounds are of Formula (III*):

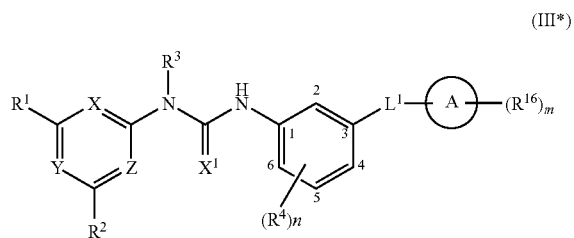

(III*)

In Formulae (I*) and (II*), $L^1$ is typically a linker $L^{11}$ selected from $—NR^aCO—$ and $—CONR^a—$, in which $R^a$ is as previously defined and is typically H or lower (e.g. 1, 2, 3 or 4C) alkyl particularly H. $L^1$ is more especially $—NR^aCO—$, e.g. $—NHCO—$, to form compounds of Formula (IV*):

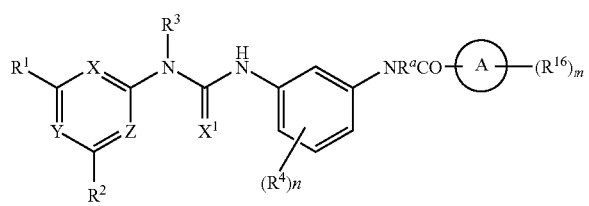

Integer n is often 0, 1, 2 or 3, e.g. 0, 1 or 2. In one class of compounds, n is 0; in another, n is 1.

In embodiments, each $R^4$ is the same or different and selected from halogen; hydroxy; protected hydroxy for example trialkylsilylhydroxy; amino; amidino; guanidino; hydroxyguanidino; formamidino; isothioureido; ureido; mercapto; C(O)H or other acyl; acyloxy; carboxy; sulfo; sulfamoyl; carbamoyl; cyano; azo; nitro; $C_1$-$C_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other acyl, acyloxy, carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or, where possible, more $C_1$-$C_7$ aliphatic groups (for example, therefore, $R^4$ may be an alkoxy group, e.g. methoxy or ethoxy).

$R^4$ is particularly selected from hydroxy, protected hydroxy, lower alkoxy, lower alkyl, trifluoromethyl and halo, notably F or Cl. $R^4$ may also be Br. Alkyl and the alkyl part of alkoxy may be branched or, more usually, straight chain, and often have 1, 2, 3, or 4 carbon atoms, as for example in the case of methyl, ethyl, methoxy and ethoxy. $R^4$ is especially selected from Cl, F, hydroxy, methyl, methoxy and trifluoromethyl, e.g. is selected from Cl, F, methyl, methoxy and trifluoromethyl, as in those compounds where $R^4$ is Cl, F, methyl or methoxy. In certain compounds. $R^4$ is methyl or methoxy, of which methyl may be mentioned in particular. In some of the compounds mentioned in this paragraph, chlorine is the sole halogen, in some others fluorine is the sole halogen. The reader is reminded that, where there are plural $R^4$ groups, they may be the same or different.

In a particular class of compounds, n is 1, i.e. there is a single $R^4$ group, such as methyl, methoxy or trifluoromethyl, for example.

Included are compounds in which there is an $R^4$ group at one or both ortho positions, relative to the urea moiety ($—NR^3C(O)NH—$). Also included in the invention are compounds in which there is a single $R^4$ group (e.g. methyl, methoxy or trifluoromethyl), which is at the 6-position relative to the urea moiety. Accordingly, there are included compounds of the formula (V*):

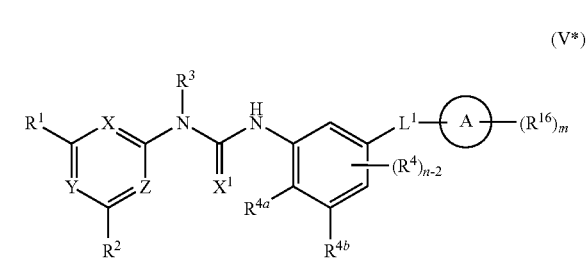

(V*)

where $R^{4a}$ and $R^{4b}$ are each independently selected from H, halo (especially F or Cl), alkyl, haloalkyl or alkoxy, wherein alkyl and the alkyl part of alkoxy are branched or straight chain and often have 1, 2, 3, or 4 carbon atoms; in embodiments, $R^{4a}$ and $R^{4b}$ may additionally be selected from hydroxy and amino. Typically $R^{4a}$ is H, alkyl, haloalkyl, or alkoxy, for example H, lower alkyl, lower haloalkyl or lower alkoxy, such as H, methyl, ethyl, trifluoromethyl, methoxy or ethoxy, for example. In a particular class of compounds $R^{4a}$ is H, methyl or methoxy or, in another class is trifluoromethyl. Typically, $R^{4b}$ is H or alkoxy, such as methoxy or ethoxy, for example.

Included are embodiments in which at least one of $R^{4a}$ or $R^{4b}$ is not H as well as embodiments in which both of $R^4$, or $R^{4b}$ are H. In one particular class of compounds, one of $R^{4a}$ or $R^{4b}$ is H and the other is not H.

Frequently, there is no $R^4$ group. For example, in particular compounds there is no $R^4$ group, and either (i) $R^{4a}$ is methyl or methoxy or, in some case, trifluoromethyl and $R^{4b}$ is H, or (ii) $R^{4a}$ is H and $R^{4b}$ is methoxy.

In embodiments, each $R^{16}$ is the same or different and selected from halogen; hydroxy; protected hydroxy for example trialkylsilylhydroxy; amino; amidino; guanidino; hydroxyguanidino; formamidino; isothioureido; ureido; mercapto; C(O)H or other acyl; acyloxy; carboxy; sulfo; sulfamoyl; carbamoyl; cyano; azo; nitro; $C_1$-$C_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other acyl, acyloxy, carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or, where possible, more $C_1$-$C_7$ aliphatic groups (for example, therefore, R16 may be an alkoxy group, e.g. methoxy or ethoxy).

Ring A and any substituents $R^{16}$ will for convenience be referred to subsequently as Fragment I:

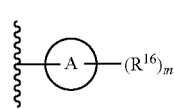

Fragment I

Fragment I may have any structure described herein for Fragment H, and may be the same as Fragment H, if present, or different. Thus, Ring A may be a mono- or bi-cyclic ring, particularly a 5- or 6-membered carbocyclic or heterocyclic ring, for example phenyl, cyclohexyl or cyclohexenyl. Of these, phenyl is preferred. In other instances, ring A is a 5-membered carbocyclic or heterocyclic ring. Other exemplary residues forming ring A are pyridyl and pyrimidyl.

Integer m is often 0, 1, 2 or 3, for example 0, 1 or 2, as in the case of compounds where m is 0 or 1. For example, where ring A is a 6-membered ring, there is often a substituent at the 3- or 4-position.

Interger m is often 1. Where m is greater than 1, all the $R^{16}$ groups except 1 are often halogen (notably F or Cl), methyl or trifluoromethyl. Also to be mentioned in this regard are hydroxyl and amino. Often a single $R^{16}$ group is selected from -$L^5$-$NR^cR^d$ and -$L^5$-RING* and there are 0, 1 or 2 additional substituents which are not -$L^5$-$NR^cR^d$ or -$L^5$-RING* but are, for example, halogen (notably F or Cl), lower alkyl (e.g. methyl), lower alkoxy (e.g. methoxy), hydroxyl, amino or trifluoromethyl.

Accordingly, the invention includes compounds in which $R^{16}$ is, e.g. a 6-membered carbocyclic ring (notably phenyl) substituted by 1, 2, 3, 4 or 5 halogens, e.g. selected from F, Cl and Br; typically, such phenyl rings are mono- or di-substituted, e.g. $R^2$ and/or 4-substituted by F or 3-substituted by Cl. In some cases of plural substitution by halogen, all the halogens are the same. Thus, in a class of compounds $R^{16}$ is a monocyclic ring, particularly a 6-membered carbocyclic ring (notably phenyl), substituted solely by one or more halogens, particularly selected from F and Cl; sometimes V or each halogen is F but in some other cases V or each halogen is Cl.

In another class of compounds, $R^{16}$ is a monocyclic ring, particularly a 6-membered carbocyclic ring (notably phenyl), substituted by 1, 2, 3, 4 or 5 substituents, e.g. 1 or 2 substituents, selected from alkyl alkoxy alkanoyl, alkanoyl oxy, halo alkyl, amino, mono- or di-alkyl amino, cyano, halogen, hydroxy or protected hydroxy, where alkyl or the alkyl part of alkoxy and alkanoyl (oxy) has 1, 2, 3 or 4 carbon atoms; exemplary substituents in this case are methyl, ethyl, methoxy, ethoxy, acetyl, trifluoromethyl, cyano, F, Cl and OH. Certain such rings have 0, 1 or 2 substituents, e.g. 0 or 1.

In one class of compounds, $L^5$ is a direct bond, linear alkyl, lineal alkyl terminated by a moiety RING*. In a sub-class, $L^5$ is —O— or —C(O)— or linear alkyl having 1, 2, 3, or 4, in-chain carbon atoms, or which —$CH_2$— may be particularly mentioned as may —C(O)—.

The invention includes a class of compounds in which ring A is a six-membered ring, particularly phenyl, cyclohexyl or cyclohexenyl and has 1 or 2 substituents $R^{16}$ independently selected from -$L^5$-$NR^cR^d$ and -$L^5$-RING*, as defined previously. In a sub-class, there is a single substituent at, in particular, the 3-position or 4-position selected from -$L^5$-$NR^cR^d$ and -$L^5$-RING* such that the right hand ring has a structure corresponding to fragments (J1), (J2), K1), (K2) or (JK):

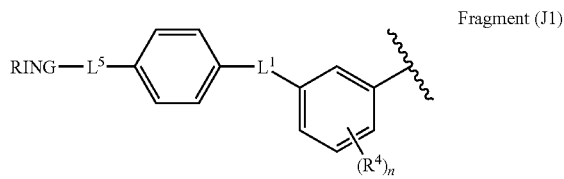

Fragment (J1)

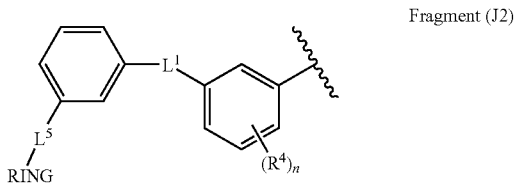

Fragment (J2)

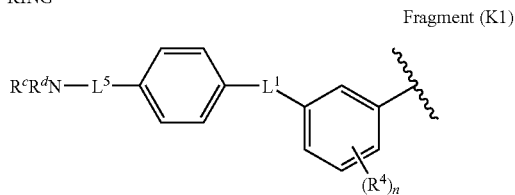

Fragment (K1)

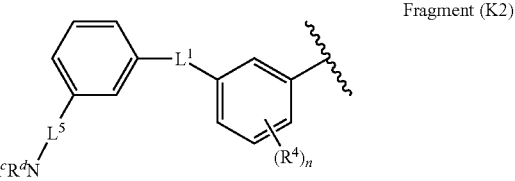

Fragment (K2)

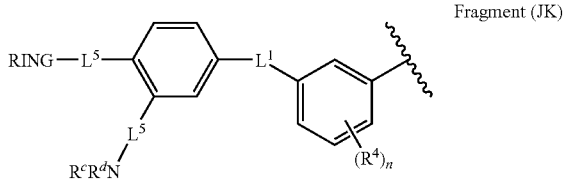

Fragment (JK)

In some embodiments, the phenyl ring of the above fragments (J1), (J2), K1), (K2) or (JK) (or other ring replacing phenyl, such as cyclohexyl, for example) has 1, 2, 3 or 4 further substituents, for example selected from halogen (notably F or Cl), methyl, methoxy or trifluoromethyl, e.g. 1 or 2 such substituents. Also to be mentioned in this regard are hydroxy and amino.

$L^5$ is as previously described, that is a direct bond; a linkage selected from —O—; —S—; —C(O)—; —OC(O)—; —NR$^a$C(O)—; —C(O)—NR$^a$—; —OC(O)—NR$^a$—; cyclopropyl and —NR$^a$—; or $C_1$-$C_7$ aliphatic optionally interrupted and/or terminated at a single end or at both ends by a said linkage (R$^a$ being as previously defined and typically H). Any aliphatic moiety is often alkyl, e.g. alkyl or other aliphatic having 1, 2, 3 or 4 carbon atoms, as in the case of a sub-class of linkers $L^2$ in which aliphatic moieties are methyl, ethyl or n-propyl.

In particular fragments (J) and (K), $L^2$ is a direct bond, linear alkyl, linear alkyl terminated adjacent the phenyl ring in the above representations of the fragments by a said linkage, or is a said linkage; suitably but not necessarily any said linkage is —O— or —C(O)—, of which —O— may be particularly mentioned. Thus, the above fragments (J) and (K) may comprise sub-fragments -Ph-NR$^c$R$^d$, -Ph-RING*, -Ph-O-alkyl-NR$^c$R$^d$, -Ph-O-alkyl-RING*, -Ph-alkyl-NR$^c$R$^d$-Ph-alkyl-RING*, and also to be mentioned are sub-fragments -Ph-O—NR$^c$R$^d$, -Ph-O-RING*, -Ph-C(O)—NR$^c$R$^d$ and -Ph-C(O)-RING*, where, in all these sub-fragments which contain alkyl, alkyl may be e.g. methyl, ethyl or n-propyl, or n-butyl.

In fragment (JK), the linker $L^5$ may be the same or different.

Considering now in more detail fragments (K1) and (K2), these contain a moiety RING* which is a cyclic moiety and in many cases a 5- or 6-membered carbocyclic or heterocyclic ring optionally substituted as defined previously. Exemplary rings are saturated, e.g. cyclopentane or cyclohexane. In particular compounds, RING* is a 5- or 6-membered heterocycle, often containing one or two heteroatoms, typically selected from O and N; in a sub-class, the heterocycles contain one or two nitrogens and, where there is a single nitrogen, optionally an oxygen. Particular heterocycles include a nitrogen which is not a member of a double bond and these are more particularly saturated heterocycles. As heterocycles may be mentioned pyrrolidine, piperidine, piperazine and morpholine; in some compounds, RING* is piperidine having its nitrogen at the 4-position relative to $L^2$. As already described, RING* may be substituted and, in one class of compounds, is substituted by 0, 1, 2, 3, 4 or 5 substituents, e.g. selected from $C_1$-$C_7$ aliphatic groups, optionally substituted as described above, and less frequently $C_1$-$C_7$ aliphatic-oxy. Any aliphatic group is often alkyl (straight chain or branched), e.g. alkyl or other aliphatic having 1, 2, 3 or 4 carbon atoms, as in the case of a sub-class of fragments (H1) and (H2) having substituents which are methyl, ethyl or n-propyl. Exemplary substituents on RING* include straight chain or branched $C_1$, $C_2$, $C_3$ or $C_4$ alkyl such as, e.g., methyl, ethyl n-propyl, isopropyl or t-butyl, of which methyl may be particularly mentioned, halogen (notably F or Cl) and $C_1$, $C_2$, $C_3$ or $C_4$ alkoxy; also to be mentioned are hydroxy and amino. Alkyl moieties may be unsubstituted or substituted, e.g. by halogen (notably F or Cl) or in some cases by hydroxy or amino.

In some classes of RING* moieties, there are 0, 1, 2, 3, 4 or 5 such substituents selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. Certain RING* moieties have 0, 1 or 2 substituents, e.g. 0 or 1.

Considering now in more detail fragments (J1) and (J2), these contain a moiety NR$^c$R$^d$. R$^c$ and R$^d$ are as previously described. In one class of these fragments, R$^c$ and R$^d$ are the same or different (but more usually the same) and selected from $C_1$-$C_7$, e.g. $C_1$-$C_4$ aliphatic groups, optionally substituted as described above. As aliphatic R$^c$ and R$^d$ moieties may be mentioned alkyl, e.g having 1, 2, 3 or 4 carbon atoms, as in the case of a sub-class of fragments (J1) and (J2) having substituents which are methyl, ethyl or n-propyl. Alkyl or other aliphatic moieties may be substituted e.g. by amino or mono- or di ($C_1$-$C_4$) alkylamino, or e.g. by a 5- or 6-membered heterocyclic or carbocyclic ring optionally substituted as previously described, or be unsubstituted. Thus, particular $L^2$NR$^c$R$^d$ moieties are —OCH$_2$NMe$_2$, —OCH$_2$NEt$_2$, —OCH$_2$CH$_2$NMe$_2$, —OCH$_2$CH$_2$NEt$_2$, —OCH$_2$CH$_2$CH$_2$NMe$_2$, —OCH$_2$CH$_2$CH$_2$NEt$_2$, —CH$_2$NMe$_2$, —CH$_2$NEt$_2$, —CH$_2$CH$_2$NMe$_2$, —CH$_2$CH$_2$NEt$_2$, —CH$_2$CH$_2$CH$_2$NMe$_2$, and —CH$_2$CH$_2$CH$_2$NEt$_2$.

In another class of fragments (J1) and (J2), R$^c$ and R$^d$ together with the adjoining nitrogen form a heterocyclic moiety (normally a 5- or 6-membered heterocyclic ring), optionally substituted as previously described. In addition to the nitrogen of moiety NR$^c$R$^d$, the heterocyclic ring may contain at least one further heteroatom, and often exactly one further heteroatom, in either case typically selected from O and N; in a sub-class, the heterocycles contain altogether one or two nitrogens and, where there is a single nitrogen, optionally an oxygen. Particular heterocycles include a nitrogen which is not a member of a double bond and these are more particularly saturated heterocycles. As heterocycles may be mentioned pyrrolidine, piperidine, piperazine and morpholine; of these particular heterocycles are piperazine and morpholine. As already described, the heterocycle may be substituted and, in one class of compounds, is substituted by 0, 1, 2, 3, 4 or 5 substituents, e.g. selected from $C_1$-$C_7$ aliphatic groups, optionally substituted as described above, and less frequently $C_1$-$C_7$ aliphatic-oxy. Any aliphatic group is often alkyl (straight chain or branched), e.g. alkyl or other aliphatic having 1, 2, 3 or 4 carbon atoms, as in the case of a sub-class of cyclic (K1) and (K2) fragments having substituents which are methyl, ethyl or n-propyl. Exemplary substituents on cyclic (K1) and (K2) fragments include straight chain or branched $C_1$, $C_2$, $C_3$ or $C_4$ alkyl such as, e.g., methyl, ethyl n-propyl, isopropyl or t-butyl, of which methyl may be particularly mentioned, halogen (notably F or Cl) and $C_1$, $C_2$, $C_3$ or $C_4$ alkoxy; also to be mentioned are hydroxy and amino. Alkyl moieties may be unsubstituted or substituted, e.g. by halogen (notably F or Cl) or in some cases by hydroxy or amino.

In some classes of cyclic (J1) and (J2) fragments (that is to say fragments in which R$^c$ and R$^d$ together with the adjoining nitrogen form a ring), there are 0, 1, 2, 3, 4 or 5 such substituents selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. Certain cyclic fragments have 0, 1 or 2 substituents, e.g. 0 or 1.

Particular $L^2$NR$^c$R$^d$ moieties are -Pip, -Morph, —OCH$_2$Pip, —OCH$_2$-Morph, —OCH$_2$CH$_2$Pip, —OCH$_2$CH$_2$-Morph, —OCH$_2$CH$_2$CH$_2$Pip, —OCH$_2$CH$_2$CH$_2$-Morph, —CH$_2$Pip, —CH$_2$-Morph, —CH₂CH₂Pip, —CH₂CH₂-Morph, —CH₂CH₂CH₂Pip, and —CH₂CH₂CH₂-Morph. Also to be mentioned are —C(O)Pip and —C(O)Morph. The abbreviation "Pip" stands for piperazine and "Morph" for morpholine, and these rings may be substituted as previously described. In particular piperazine is optionally N-substituted. Piperazine and morpholine may be substituted by a $C_1$-$C_7$ aliphatic group as mentioned in the previous paragraph, for example a straight chain or branched $C_1$, $C_2$, $C_3$ or $C_4$ moiety selected from alkyl and haloalkyl such as, e.g., methyl, trifluoromethyl, ethyl n-propyl, isopropyl or t-butyl, of which methyl and trifluoromethyl are exemplary. As described before, $R^a$ is in particular hydrogen.

Amongst the classes of compounds which are particularly to be mentioned are those in which the left hand ring has a structure corresponding to Fragment (J1) or (K1). Particularly exemplary are such compounds having a fragment (K1) in which $R^c$ and $R^d$ together with the adjoining nitrogen form a 5- or 6-membered heterocyclic ring as described above. These rings may be substituted as previously described. In particular they are optionally N-substituted by a $C_1$-$C_7$ aliphatic group as mentioned earlier, for example a straight chain or branched $C_1$, $C_2$, $C_3$ or $C_4$ moiety selected from alkyl and haloalkyl such as, e.g., methyl, trifluoromethyl, ethyl n-propyl, isopropyl or t-butyl, of which methyl and trifluoromethyl are exemplary. As described before, $R^a$ is in particular hydrogen.

To be mentioned are right hand rings corresponding to Fragment (L):

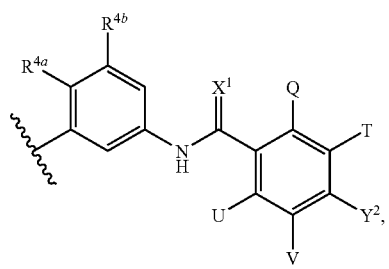

Fragment (L)

where:
$R^{4a}$ and $R^{4b}$ are as previously defined;
Q and U are the same or different and selected from H, F and Cl, e.g. are both H;
T and V are the same or different and selected from H, methyl, trifluoromethyl and methoxy, e.g. from H and trifluoromethyl, as in the case where one of T and V is H and the other is trifluoromethyl;
$Y^2$ is selected from H, $C_1$, $C_2$, $C_3$ or $C_4$ alkyl (e.g. methyl or ethyl), which may be unsubstituted or substituted, for example at a free end thereof, by a 5 or 6 membered heterocyclic ring optionally substituted by 1C, 2C, 3C or 4C alkyl; typically the optionally substituted ring is saturated and may be selected from, for example, piperidine, 4-($C_1$-$C_4$)alkylpiperidine, piperazine, 4-($C_1$-$C_4$)alkylpiperazine, thiazolidine, morpholine or thiomorpholine.

A particular right hand ring is Fragment (M):

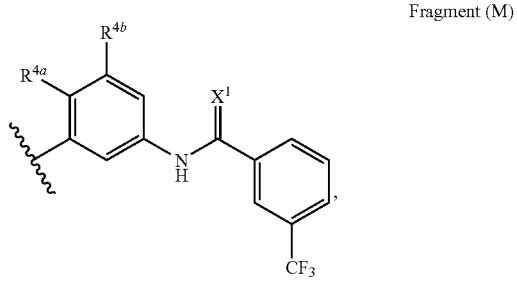

Fragment (M)

where $R^{4a}$ and $R^{4b}$ are as previously defined.

To be mentioned are right hand rings corresponding to Fragment (N):

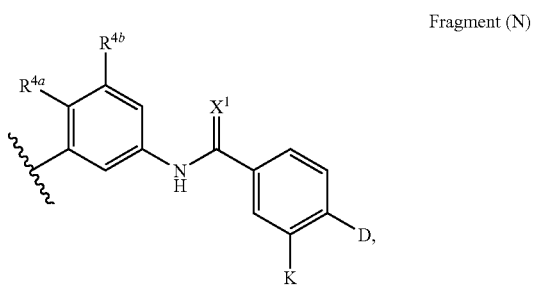

Fragment (N)

where:
$R^{4a}$ and $R^{4b}$ are as previously defined;
K is selected from H, methyl, trifluoromethyl and methoxy, and in particular is H or trifluoromethyl; and
D is selected from 1C, 2C, 3C and 4C alkyl and 1C, 2C, 3C or 4C alkyl substituted by piperidine, 4-($C_1$-$C_4$)alkylpiperidine, piperazine, 4-($C_1$-$C_4$)alkylpiperazine, thiazolidine, morpholine or thiomorpholine. A particular D group is 4-methylpiperazine; for example in many compounds D is 4-methylpiperazine and K is H or trifluoromethyl.

In fragments L and N, alkyl is particularly linear alkyl and in many cases is methyl.

Any formula disclosed herein may have its illustrated right hand ring replaced by a right hand ring of formula L, M or N. The Compounds of Formula (I*)

It has been described above how the compounds of formula (I*) have the following variable domains:
left hand ring
$R^3$
right hand ring.

Various particular moieties have been described for each of these variable domains and it will be appreciated that any combination of such moieties is permissible.

To be mentioned are compounds having the following combinations, amongst many others:

| Left hand ring | $R^3$ | Right hand ring |
|---|---|---|
| Fragment (A*) | H, $C_1$-$C_4$ alkyl or $C_1$-$C_4$ alkyl substituted by an optionally substituted 5- or 6-membered ring | n = 1, 2, 3, or 4. $R^4$ = selected from Cl, F, hydroxy, methyl, methoxy, trifluoromethyl, and alkyl |

-continued

| Left hand ring | R³ | Right hand ring |
|---|---|---|
| | | substituted by an optionally substituted 5- or 6-membered ring |
| Fragment (B*) | H, C₁-C₄ alkyl or C₁-C₄ alkyl substituted by an optionally substituted 5- or 6-membered ring | n = 1, 2, 3, or 4. R⁴ = selected from Cl, F, hydroxy, methyl, methoxy, trifluoromethyl, and alkyl substituted by an optionally substituted 5- or 6-membered ring |
| Fragment (C*) | H, C₁-C₄ alkyl or C₁-C₄ alkyl substituted by an optionally substituted 5- or 6-membered ring | n = 1, 2, 3, or 4. R⁴ = selected from Cl, F, hydroxy, methyl, methoxy, trifluoromethyl, and alkyl substituted by an optionally substituted 5- or 6-membered ring |
| Fragment (C*), Rᵃ=H, Rz* = category (i) or (ii) | H, C₁-C₄ alkyl or C₁-C₄ alkyl substituted by an optionally substituted 5- or 6-membered ring | n = 1, 2, 3, or 4. R⁴ = selected from Cl, F, hydroxy, methyl, methoxy, trifluoromethyl, and alkyl substituted by an optionally substituted 5- or 6-membered ring |
| Fragment (C*), Rᵃ=H, Rz* = category (i) or (ii) | Category (iii) moiety, e.g. having a structure corresponding to the category (iii) structure of Fragment (D1*) | n = 1, 2, 3, or 4. R⁴ = selected from Cl, F, hydroxy, methyl, methoxy, trifluoromethyl, and alkyl substituted by an optionally substituted 5- or 6-membered ring |
| Fragment (C*), Rᵃ=H, Rz* = category (i) or (ii) | Category (iii) moiety, e.g. having a structure corresponding to the category (iii) structure of Fragment (D2*) | n = 1, 2, 3, or 4. R⁴ = selected from Cl, F, hydroxy, methyl, methoxy, trifluoromethyl, and alkyl substituted by an optionally substituted 5- or 6-membered ring |
| Fragment (C*), Rᵃ=H, Rz* = category (i) or (ii) | Category (iii) moiety, e.g. having a structure corresponding to the category (iii) structure of Fragment (E1*). | n = 1, 2, 3, or 4. R⁴ = selected from Cl, F, hydroxy, methyl, methoxy, trifluoromethyl, and alkyl substituted by an optionally substituted 5- or 6-membered ring |
| Fragment (C*), Rᵃ=H, Rz* = category (i) or (ii) | Category (iii) moiety, e.g. having a structure corresponding to the category (iii) structure of Fragment (E2*). | n = 1, 2, 3, or 4. R⁴ = selected from Cl, F, hydroxy, methyl, methoxy, trifluoromethyl, and alkyl substituted by an optionally substituted 5- or 6-membered ring |
| Fragment (C*), Rᵃ=H, Rz* = category (i) or (ii) | Category (iii) moiety, e.g. having a structure corresponding to the category (iii) structure of Fragment (E3). | n = 1, 2, 3, or 4. R⁴ = selected from Cl, F, hydroxy, methyl, methoxy, trifluoromethyl, and alkyl substituted by an optionally substituted 5- or 6-membered ring |
| Fragment (C*), Rᵃ=H, Rz* = category (i) or (ii) | Category (iii) moiety, e.g. having a structure corresponding to the category (iii) structure of Fragment (E4). | n = 1, 2, 3, or 4. R⁴ = selected from Cl, F, hydroxy, methyl, methoxy, trifluoromethyl, and alkyl substituted by an optionally substituted 5- or 6-membered ring |
| Fragment (C*), Rᵃ=H, Rz* = category (i) or (ii) | Category (iii) moiety, e.g. having a structure corresponding to the category (iii) structure of Fragment (F*). | n = 1, 2, 3, or 4. R⁴ = selected from Cl, F, hydroxy, methyl, methoxy, trifluoromethyl, and alkyl substituted by an optionally substituted 5- or 6-membered ring |

| Left hand ring | $R^3$ | Right hand ring |
| --- | --- | --- |
| Fragment (C*), $R^a$=H, Rz* = category (iii) | $C_1$-$C_4$ alkyl or $C_1$-$C_4$ alkyl substituted by an optionally substituted 5- or 6-membered ring | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (D1*) | $C_1$-$C_4$ alkyl or $C_1$-$C_4$ alkyl substituted by an optionally substituted 5- or 6-membered ring | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (D2*) | $C_1$-$C_4$ alkyl or $C_1$-$C_4$ alkyl substituted by an optionally substituted 5- or 6-membered ring | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (E1*) | $C_1$-$C_4$ alkyl or $C_1$-$C_4$ alkyl substituted by an optionally substituted 5- or 6-membered ring | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (E2*) | $C_1$-$C_4$ alkyl or $C_1$-$C_4$ alkyl substituted by an optionally substituted 5- or 6-membered ring | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (E3) | $C_1$-$C_4$ alkyl or $C_1$-$C_4$ alkyl substituted by an optionally substituted 5- or 6-membered ring | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (E4) | $C_1$-$C_4$ alkyl or $C_1$-$C_4$ alkyl substituted by an optionally substituted 5- or 6-membered ring | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (F*) | $C_1$-$C_4$ alkyl or $C_1$-$C_4$ alkyl substituted by an optionally substituted 5- or 6-membered ring | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (C*), $R^a$ typically = H, Rz* = category (iii) | H | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (D1*); $R^a$ typically = H, | H | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (D2*); $R^a$ typically = H, | H | n = 1, 2, 3, or 4. $R^4$ = selected from Cl, F, hydroxy, methyl, methoxy, trifluoromethyl, and alkyl substituted by an optionally substituted 5- or 6-membered ring |

-continued

| Left hand ring | R³ | Right hand ring |
|---|---|---|
| Fragment (E1*); $R^a$ typically = H, | H | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (E2*); $R^a$ typically = H, | H | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (F*) | H | n = 1, 2, 3, or 4. $R^4$ = selected from Cl, F, hydroxy, methyl, methoxy, trifluoromethyl, and alkyl substituted by an optionally substituted 5- or 6-membered ring |
| Fragment (A*) | H, $C_1$-$C_4$ alkyl or $C_1$-$C_4$ alkyl substituted by an optionally substituted 5- or 6-membered ring | $R^4$ is Fragment (L), (M) or (N). |
| Fragment (B*) | H, $C_1$-$C_4$ alkyl or $C_1$-$C_4$ alkyl substituted by an optionally substituted 5- or 6-membered ring | $R^4$ is Fragment (L), (M) or (N). |
| Fragment (C*) | H, $C_1$-$C_4$ alkyl or $C_1$-$C_4$ alkyl substituted by an optionally substituted 5- or 6-membered ring | $R^4$ is Fragment (L), (M) or (N). |
| Fragment (C*), $R^a$=H, Rz* = category (i) or (ii) | H, $C_1$-$C_4$ alkyl or $C_1$-$C_4$ alkyl substituted by an optionally substituted 5- or 6-membered ring | $R^4$ is Fragment (L), (M) or (N). |
| Fragment (C*), $R^a$=H, Rz* = category (i) or (ii) | Category (iii) moiety, e.g. having a structure corresponding to the category (iii) structure of Fragment (D1*) | $R^4$ is Fragment (L), (M) or (N). |
| Fragment (C*), $R^a$=H, Rz* = category (i) or (ii) | Category (iii) moiety, e.g. having a structure corresponding to the category (iii) structure of Fragment (D2*) | $R^4$ is Fragment (L), (M) or (N). |
| Fragment (C*), $R^a$=H, Rz* = category (i) or (ii) | Category (iii) moiety, e.g. having a structure corresponding to the category (iii) structure of Fragment (E1*). | $R^4$ is Fragment (L), (M) or (N). |
| Fragment (C*), $R^a$=H, Rz* = category (i) or (ii) | Category (iii) moiety, e.g. having a structure corresponding to the category (iii) structure of Fragment (E2*). | $R^4$ is Fragment (L), (M) or (N). |
| Fragment (C*), $R^a$=H, Rz* = category (i) or (ii) | Category (iii) moiety, e.g. having a structure corresponding to the category (iii) structure of Fragment (E3). | $R^4$ is Fragment (L), (M) or (N). |

-continued

| Left hand ring | $R^3$ | Right hand ring |
|---|---|---|
| Fragment (C*), $R^a$=H, Rz* = category (i) or (ii) | Category (iii) moiety, e.g. having a structure corresponding to the category (iii) structure of Fragment (E4). | $R^4$ is Fragment (L), (M) or (N). |
| Fragment (C*), $R^a$=H, Rz* = category (i) or (ii) | Category (iii) moiety, e.g. having a structure corresponding to the category (iii) structure of Fragment (F*). | $R^4$ is Fragment (L), (M) or (N). |
| Fragment (C*), $R^a$=H, Rz* = category (iii) | $C_1$-$C_4$ alkyl or $C_1$-$C_4$ alkyl substituted by an optionally substituted 5- or 6-membered ring | $R^4$ is Fragment (L), (M) or (N). |
| Fragment (D1*) | $C_1$-$C_4$ alkyl or $C_1$-$C_4$ alkyl substituted by an optionally substituted 5- or 6-membered ring | $R^4$ is Fragment (L), (M) or (N). |
| Fragment (D2*) | $C_1$-$C_4$ alkyl or $C_1$-$C_4$ alkyl substituted by an optionally substituted 5- or 6-membered ring | $R^4$ is Fragment (L), (M) or (N). |
| Fragment (E1*) | $C_1$-$C_4$ alkyl or $C_1$-$C_4$ alkyl substituted by an optionally substituted 5- or 6-membered ring | $R^4$ is Fragment (L), (M) or (N). |
| Fragment (E2*) | $C_1$-$C_4$ alkyl or $C_1$-$C_4$ alkyl substituted by an optionally substituted 5- or 6-membered ring | $R^4$ is Fragment (L), (M) or (N). |
| Fragment (E3) | $C_1$-$C_4$ alkyl or $C_1$-$C_4$ alkyl substituted by an optionally substituted 5- or 6-membered ring | $R^4$ is Fragment (L), (M) or (N). |
| Fragment (E4) | $C_1$-$C_4$ alkyl or $C_1$-$C_4$ alkyl substituted by an optionally substituted 5- or 6-membered ring | $R^4$ is Fragment (L), (M) or (N). |
| Fragment (F*) | $C_1$-$C_{44}$ alkyl or $C_1$-$C_4$ alkyl substituted by an optionally substituted 5- or 6-membered ring | $R^4$ is Fragment (L), (M) or (N). |
| Fragment (C*), $R^a$ typically = H, Rz* = category (iii) | H | $R^4$ is Fragment (L), (M) or (N). |
| Fragment (D1*); $R^a$ typically = H, | H | $R^4$ is Fragment (L), (M) or (N). |
| Fragment (D2*); $R^a$ typically = H, | H | $R^4$ is Fragment (L), (M) or (N). |
| Fragment (E1*); $R^a$ typically = H, | H | $R^4$ is Fragment (L), (M) or (N). |
| Fragment (E2*); $R^a$ typically = H, | H | $R^4$ is Fragment (L), (M) or (N). |
| Fragment (E3); $R^a$ typically = H, | H | $R^4$ is Fragment (L), (M) or(N). |
| Fragment (E4); $R^a$ typically = H, | H | $R^4$ is Fragment (L), (M) or (N). |
| Fragment (F*) | H | $R^4$ is Fragment (L), (M) or (N). |

When R³ is an optionally substituted ring, substituents are as described previously, e.g. methyl, ethyl, methoxy, trifluoromethyl, amino or hydroxy.

Each row of the above table provides support for an individual patent claim, presented by itself or with one or more other claims, each corresponding to a respective row of the table. The previous text provides support for claims dependent on such claims in describing sub-classes of the respective features or feature combinations of each row. For each row in the Table, a patent claim or claims may be written to protect individually a sub-class or sub-classes of the subject matter represented by the row.

It will be understood from the aforegoing that a sub-set of the Compounds of Formula (I*) are of the following Formulae (VI*) and (VII*):

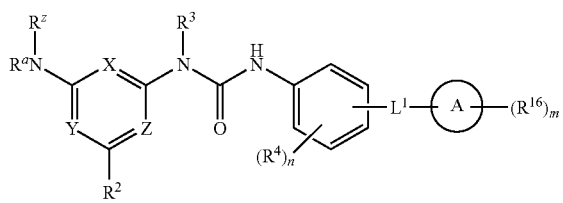
(VI*)

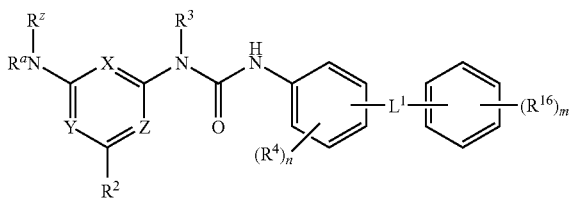
(VII*)

In Formulae (VI*) and (VII*), it is often the case that two of X, Y and Z are N and that R³ and R² are H, e.g. in many compounds X is CH, Y and Z are N and R² is H. Alternatively, all of X, Y and Z are N and R² is H. Ring A is typically phenyl or a wholly or partially hydrogenated analogue thereof. Alternatively it may be a heterocycle, typically of six members, e.g. pyridine or pyrimidine. Integer m may be 0, 1 or 2, e.g. 1. In some cases there are one or more $R^b$ moieties which are F or Cl, as previously described, e.g. the only $R^b$ moieties may be one or two moieties selected from F and Cl.

Accordingly, Formulae (VI*) and (VII*) encompass the following sub-classes, amongst others:
1) One of X, Y and Z are N, $R^{15}$ and R² are H, ring A is phenyl or a wholly or partially hydrogenated analogue thereof, m is 0, 1 or 2, e.g. 1;
2) One of X, Y and Z are N, $R^{15}$ and R² are H, ring A is a heterocycle, typically of six members, e.g. pyridine or pyrimidine, m is 0, 1 or 2, e.g. 1;
3) Two of X, Y and Z are N, $R^{15}$ and R² are H, ring A is phenyl or a wholly or partially hydrogenated analogue thereof, m is 0, 1 or 2, e.g. 1;
4) Two of X, Y and Z are N, $R^{15}$ and R² are H, ring A is a heterocycle, typically of six members, e.g. pyridine or pyrimidine, m is 0, 1 or 2, e.g. 1;
5) All of X, Y and Z are N, R² is H, ring A is phenyl or a wholly or partially hydrogenated analogue thereof, m is 0, 1 or 2, e.g. 1;
6) All of X, Y and Z are N, R² is H, ring A is a heterocycle, typically of six members, e.g. pyridine or pyrimidine, m is 0, 1 or 2, e.g. 1;
7) X is CH, Y and Z are N, R² is H, ring A is phenyl or a wholly or partially hydrogenated analogue thereof, m is 0, 1 or 2, e.g. 1;
8) X is CH, Y and Z are N, R² is H, ring A is a heterocycle, typically of six members, e.g. pyridine or pyrimidine, m is 0, 1 or 2, e.g. 1.

In some instances of sub-classes 1), 2), 3) 4), 5) and 6) there are one or more $R^b$ moieties which are F or Cl, as previously described, e.g. the only $R^b$ moieties may be one or two moieties selected from F and Cl.

More commonly, ring A is substituted by one or two $R^b$ moieties (and normally a single $R^b$ moiety) comprising -L²-RING* or -L²-NR$^c$R$^d$, and optionally other substituents (e.g. numbering 1, 2 or 3) selected from e.g. halogen; hydroxy; protected hydroxy for example trialkylsilylhydroxy; amino; amidino; guanidino; hydroxyguanidino; formamidino; isothioureido; ureido; mercapto; C(O)H or other lower acyl; lower acyloxy; carboxy; sulfo; sulfamoyl; carbamoyl; cyano; azo; nitro; which substituents are in turn optionally substituted on at least one heteroatom by one or, where possible, more $C_1$, $C_2$, $C_3$ or $C_4$ alkyl groups. Particular additional substituents on ring A are halogen, lower alkyl (e.g. methyl), lower alkoxy (e.g. methoxy), hydroxy, amino or trifluoromethyl.

Also to be mentioned therefore are compounds of the following formulae (VIII*), (IX*), (X*) and (XI*):

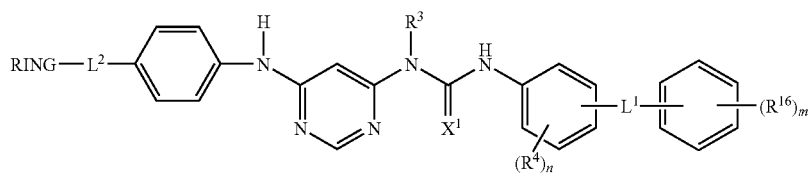
(VIII*)

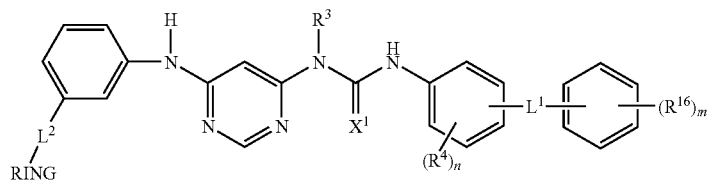
(IX*)

-continued

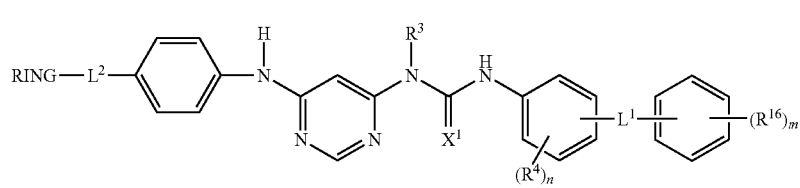
(X*)

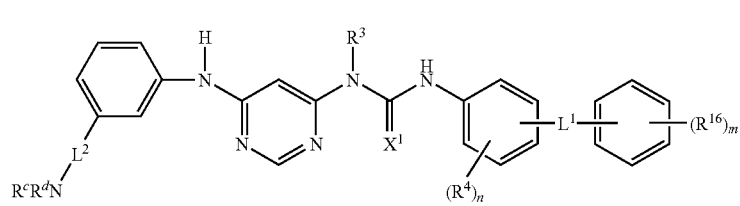
(XI*)

where
- $L^2NR^cR^d$ is in particular -Pip, -Morph, —OCH$_2$Pip, —OCH$_2$-Morph, —OCH$_2$CH$_2$Pip, —OCH$_2$CH$_2$-Morph, —OCH$_2$CH$_2$CH$_2$Pip, —OCH$_2$CH$_2$CH$_2$-Morph, —CH$_2$Pip, —CH$_2$-Morph, —CH$_2$CH$_2$Pip, —CH$_2$CH$_2$-Morph, —CH$_2$CH$_2$CH$_2$Pip, and —CH$_2$CH$_2$CH$_2$-Morph, or is —C(O)Pip or —C(O)Morph (or of course these heterocycles are replaced by another described herein, or in other embodiments $R^c$ and $R^d$ form a non-cyclic structure as previously described);
- $L^2$RING* is in particular -RING*, —OCH$_2$RING*, —OCH$_2$CH$_2$RING*, —OCH$_2$CH$_2$CH$_2$RING*, —CH$_2$RING*, —CH$_2$CH$_2$RING*, —CH$_2$CH$_2$CH$_2$RING*, or is —C(O)RING*, where RING* is in particular pyrrolidine, piperidine, piperazine or morpholine, or it may be another RING* moiety disclosed herein;
- $R^3$ is as previously described and is particularly but not necessarily H;
- $R^4$ is as previously described and is particularly but not necessarily selected from Cl, F, hydroxy, methyl, methoxy and trifluoromethyl;
- $L^1$ is in particular —NR$^a$CO— and —CONR$^a$—;
- $R^{16}$ is as previously described but is in particular substituted alkyl, where the substitutents are in particular fluorine and piperizine,
- m is 0, 1, 2, 3, 4 or 5, e.g. is 1 or 2;
- n is 0, 1, 2, 3, 4 or 5, e.g. is 1, 2, 3, or 4.

In embodiments, RING* or a heterocycle formed by $L^2NR^cR^d$ is substituted by 1, 2, 3, 4 or 5 substituents, e.g. 1 or 2 substituents, selected from alkyl, alkoxy, alkanoyl, alkanoyloxy, haloalkyl, amino, mono- or di-alkylamino, cyano, halogen, hydroxy or protected hydroxy, wherein alkyl or the alkyl part of alkoxy and alkanoyl(oxy) has 1, 2, 3 or 4 carbon atoms; exemplary substituents in this case are methyl, ethyl, methoxy, ethoxy, acetyl, trifluoromethyl, cyano, F, Cl and OH. N-alkyl substituted piperazine or piperadine are exemplary, as are RING* moieties as a class substituted by one or two substituents or more, selected from alkyl and haloalkyl (e.g. trifluoromethyl). As an alternative to substitution, there may be no substitution.

Another embodiment comprises compounds of formula (XXI*):

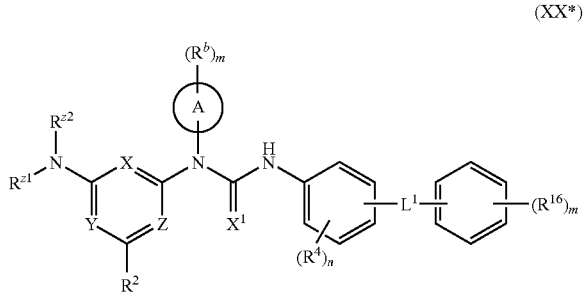
(XX*)

where Rz*$^1$ and Rz*$^2$ are selected from hydrogen and straight chain or branched alkyl having 1, 2, 3 or 4 carbon atoms, e.g. methyl or ethyl. In embodiments, one of Rz*$^1$ and Rz*$^2$ is hydrogen and more particularly both are hydrogen. It is often the case that X is CH, Y and Z are N and $R^2$ is H. Particular classes of compounds are of formulae (XXI*), (XXII*), (XXIII*) and (XXIV*):

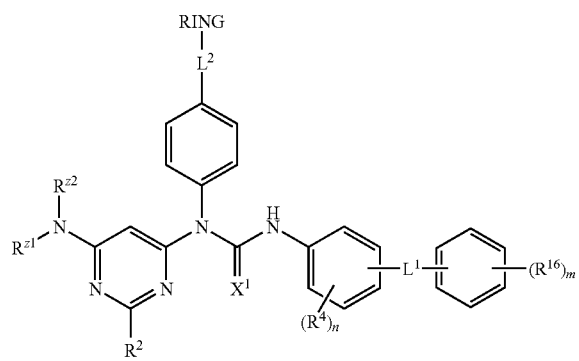
(XXI*)

(XXII*)

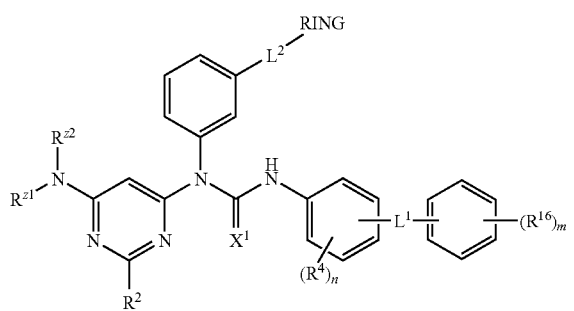

(XXIII*)

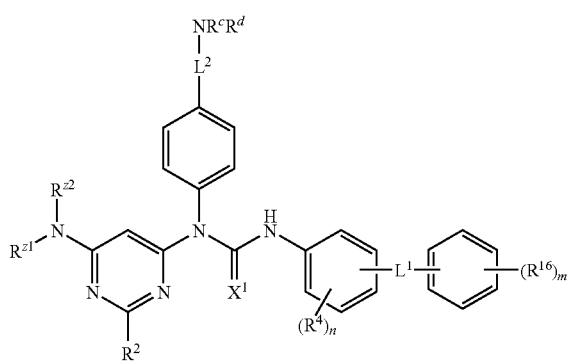

(XXIV*)

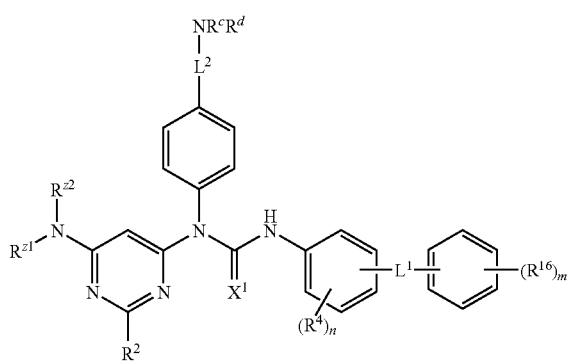

where $Rz^{*1}$ and $Rz^{*2}$ are selected from hydrogen and straight chain or branched alkyl having 1, 2, 3 or 4 carbon atoms, e.g. methyl or ethyl, and $L^2NR^cR^d$, $L^2RING^*$, $R^3$ and $R^4$ are as described in relation to formulae (IV*)-(VII*).

The invention includes classes of compounds which correspond to Formulae (IV*), (V*), (VI*), (VII*), (XXI*), (XXII*), (XXIII*) and (XXIV*) in which the pyrimidine ring is replaced by a triazine ring Substituents The following definitions apply to the compounds of the invention as appropriate and expedient and if not mentioned otherwise.

"Substituted", wherever used for a moiety, means that one or more hydrogen atoms in the respective moiety, especially up to 5, more especially 1, 2 or 3 of the hydrogen atoms are replaced independently of each other by the corresponding number of substituents which preferably are independently selected from the group consisting of lower alkyl, for example methyl, ethyl or propyl, halo-lower alkyl, for example trifluoromethyl, $C_6$-$C_{16}$-aryl, especially phenyl pyridine.

$C_6$-$C_{16}$-aryl is unsubstituted or substituted by one or more, especially 1, 2 or 3 moieties selected from, for example, lower alkyl, halogen, carboxy, lower alkoxycarbonyl, hydroxy, etherified or esterified hydroxy, lower alkoxy, phenyl-lower alkoxy, lower alkanoyloxy, lower alkanoyl, amino, mono- or di-substituted amino, halo, halo-lower alkyl, e.g. trifluoromethyl, sulfo, sulfamoyl, carbamoyl, N-mono substituted or N,N-disubstituted carbamoyl, N-lower alkyl-carbamoyl, N-(hydroxy-lower alkyl)-carbamoyl, such as N-(2-hydroxyethyl)-carbamoyl, cyano, cyano-lower alkyl and nitro;

Substituents also include hydroxy, $C_3$-$C_{10}$-cycloalkyl, especially cyclopropyl or cyclohexyl, hydroxy-$C_3$-$C_8$-cycloalkyl, such as hydroxy-cyclohexyl, heterocyclyl with 5 or 6 ring atoms and 1 to 3 ring heteroatoms selected from O, N and S, especially piperidinyl, especially piperidin-1-yl, piperazinyl, especially piperazin-1-yl, morpholinyl, especially morpholin-1-yl, hydroxy, lower alkoxy, for example methoxy, halo-lower alkoxy, especially 2,2,2-trifluoroethoxy, phenyl-lower alkoxy, amino-lower alkoxy, such as 2-eminoethoxy; lower alkanoyloxy, hydroxy-lower alkyl, such as hydroxymethyl or 2-hydroxyethyl, amino, mono- or di-substituted amino, carbamoyl-lower alkoxy, N-lower alkylcarbamoyl-lower alkoxy or N,N-di-lower alkylcarbamoyl-lower alkoxy, amidino, ureido, mercapto, N-hydroxy-amidino, guanidino, amidino-lower alkyl, such as 2-amidinoethyl, N-hydroxyamidino-lower alkyl, such as N-hydroxy-amidino-methyl or -2-ethyl, halogen, for example fluoro, chloro, bromo or iodo, carboxy, esterified carboxy, lower alkoxycarbonyl, phenyl-, naphthyl- or fluorenyl-lower alkoxycarbonyl, such as benzyloxycarbonyl, benzoyl, lower alkanoyl, sulfo, lower alkanesulfonyl, for example methanesulfonyl ($CH_3$—$S(O)_2$—), lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, halogen-lower alkylmercapto, halogen-lower alkylsulfonyl, such as especially trifluoromethanesulfonyl, dihydroxybora (—$B(OH)_2$), phosphono (—$P(=O)(OH)_2$), hydroxy-lower alkoxy phosphoryl or di-lower alkoxyphosphoryl, carbamoyl, mono- or di-lower alkylcarbamoyl, mono- or di-(hydroxy-lower alkyl)-carbamoyl, sulfamoyl, mono- or di-lower alkylaminosulfonyl, nitro, cyano-lower alkyl, such as cyanomethyl, and cyano, lower alkenyl, lower alkynyl.

It goes without saying that substituents are only at positions where they are chemically possible, the person skilled in the art being able to decide (either experimentally or theoretically) without inappropriate effort which substitutions are possible and which are not. For example, amino or hydroxy groups with free hydrogen may be unstable if bound to carbon atoms with unsaturated (e.g. olefinic) bonds. Additionally, it will of course be understood that the substituents as listed above may themselves be substituted by any substituent, subject to the aforementioned restriction to appropriate substitutions as recognised by the skilled man.

Other Definitions

The general terms used hereinbefore and hereinafter preferably have within the context of this disclosure the following meanings, unless otherwise indicated:

The prefix "lower" denotes a radical having up to and including a maximum of 7 in-chain atoms, especially up to and including a maximum of 4 in-chain atoms. Particular classes of alkyl and aliphatic comprise 1, 2, 3 or 4 carbon atoms. The radicals in question being either linear or branched with single or multiple branching.

Lower alkyl is preferably alkyl with from and including 1 up to and including 7 carbon atoms, preferably 1, 2, 3 or 4 carbon atoms, and is linear or branched; for example, lower alkyl is butyl, such as n-butyl, sec-butyl, isobutyl, tert-butyl, propyl, such as n-propyl or isopropyl, ethyl or methyl. Exemplary lower alkyl is methyl, propyl or tert-butyl.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. Radicals having any unsaturation are present in cis-, trans- or (cis, trans) form. The compounds may thus be present as mixtures of isomers or as pure isomers, preferably as enantiomer-pure diastereomers.

The invention relates also to possible tautomers of the disclosed compounds.

In view of the close relationship between the heteroaryl aryl ureas in free form and in the form of their salts, including those salts that can be used as intermediates, for example in the purification or identification of the novel compounds, tautomers or tautomeric mixtures and their salts, any reference hereinbefore and hereinafter to these compounds, is to be understood as referring also to the corresponding tautomers of these compounds, or salts of any of these, as appropriate and expedient and if not mentioned otherwise.

Tautomers can, e.g., be present in cases where amino or hydroxy, each with a least one bound hydrogen, are bound to carbon atoms that are bound to adjacent atoms by double bonds (e.g. keto-enol or imine-enamine tautomerism).

Where "a compound . . . , a tautomer thereof; or a salt thereof" or the like is mentioned, this means "a compound . . . , a tautomer thereof, or a salt of the compound or the tautomer".

By acyl is meant an organic radical corresponding to the residue of, for example, an organic acid from which the hydroxyl group has been removed, i.e., a radical having the formula R—C(O)—, where R may in particular be aliphatic or substituted aliphatic, or it may for example be a substituted or unsubstituted mono- or bi-cyclic ring. Thus, R may be selected from lower $C_1$-$C_6$ alkyl, $C_3$-$C_7$ cycloalkyl, phenyl, benzyl or phenethyl group. Amongst others. Exemplary acyl is alkyl-carbonyl. Examples of acyl groups, include, but are not limited to, formyl, acetyl, propionyl and butyryl. Lower acyl is for example formyl or lower alkylcarbonyl, in particular acetyl.

Aliphatic may have up to 20, e.g up to 12, carbon atoms and is linear or branched one or more times; preferred is lower aliphatic, especially $C_1$-$C_4$-aliphatic. Aliphatic moieties may be alkyl, alkenyl or alkynyl; alkenyl and alkynyl may contain one or more, e.g. one or two, unsaturated carbon-carbon bonds.

Alkyl may have up to 20, e.g up to 12, carbon atoms and is linear or branched one or more times; preferred is lower alkyl, especially $C_1$-$C_4$-alkyl, in particular methyl, ethyl or i-propyl or t-butyl. Where alkyl may be substituted by one or more substituents independently selected from those mentioned above under the title "Substituents". Unsubstituted alkyl, preferably lower alkyl, is especially preferred. The term alkyl also encompasses cycloalkyl as defined further below:

Alkyl may be optionally interrupted by one or more in-chain heteroatoms, for example —O—, thus forming, for example, an ether linkage.

Cycloalkyl is preferably $C_3$-$C_{10}$-cycloalkyl, especially cyclopropyl, dimethylcyclopropyl, cyclobutyl, cyclopentyl, cyclohexyl or cycloheptyl, cycloalkyl being unsubstituted or substituted by one or more, especially 1, 2 or 3, substituents independently selected from the group consisting of the substituents defined above under the title "Substituents".

Alkenyl may have one or more double bonds and preferably has 2 to 20, more preferably up to 12, carbon atoms; it is linear or branched one or more times (as far as possible in view of the number of carbon atoms). Preferred is $C_2$-$C_7$-alkenyl, especially $C_3$ or $C_4$-alkenyl, such as allyl or crotyl. Alkenyl can be unsubstituted or substituted, especially by one or more, more especially up to three, of the substituents mentioned above under "the title "Substituents". Substituents such as amino or hydroxy (with free dissociable hydrogen) preferably are not bound to carbon atoms that participate at a double bond, and also other substituents that are not sufficiently stable are preferably excluded. Unsubstituted alkenyl, in particular $C_2$-$C_7$-alkenyl, is preferred.

Alkynyl is preferably a moiety with one or more triple bonds and preferably has 2 to 20, more preferably up to 12, carbon atoms; it is linear of branched one or more times (as far as possible in view of the number of carbon atoms). Preferred is $C_2$-$C_7$-alkynyl, especially $C_3$ or $C_4$-alkynyl, such as ethinyl or propin-2-yl. Alkynyl can be unsubstituted or substituted, especially by one or more, more especially up to three, of the substituents mentioned above under the title "Substituents". Substituents such as amino or hydroxy (with free dissociable hydrogen) preferably are not bound to carbon atoms that participate at a triple bond, and also other substituents that are not sufficiently stable are preferably excluded. Unsubstituted alkynyl, in particular $C_2$-$C_7$-alkynyl, is preferred.

An aryl group is an aromatic radical and may be heterocyclic or carbocyclic. Preferably, aryl is carbocyclic and is bound to the molecule via a bond located at an aromatic ring carbon atom of the radical (or optionally bound via a linking group, such as —O— or —$CH_2$—). Preferably aryl has a ring system of not more than 16 carbon atoms and is preferably mono- bi- or tri-cyclic and may be fully or partially substituted, for example substituted by at least two substituents. Preferably, aryl is selected from phenyl, naphthyl, indenyl, azulenyl and anthryl, and is preferably in each case unsubstituted or lower alkyl, especially methyl, ethyl or n-propyl, halo (especially fluoro, chloro, bromo or iodo), halo-lower alkyl (especially trifluoromethyl), hydroxy, lower alkoxy (especially methoxy), halo-lower alkoxy (especially 2,2,2-trifluoroethoxy), amino-lower alkoxy (especially 2-amino-ethoxy), lower alkyl (especially methyl or ethyl) carbamoyl, N-(hydroxy-lower alkyl)-carbamoyl (especially N-(2-hydroxy-ethyl)-carbamoyl) and/or sulfamoyl-substituted aryl, especially a corresponding substituted or unsubstituted phenyl. Also, heterocyclic groups can be mentioned here, as defined below.

Any carbocyclic group especially comprises 3, 4, 5, 6 or 7 in ring carbon atoms and may be aromatic (aryl) or non aromatic. Where the carbocycle is non-aromatic, it may be saturated or unsaturated. Especially preferred carbocycles are phenyl, cyclohexyl and cyclopentyl.

Heterocyclyl (or heterocyclic group) is preferably a heterocyclic radical that is unsaturated, saturated or partially saturated and is preferably a monocyclic or in a broader aspect of the invention bicyclic or tricyclic ring; has 3 to 24, more preferably 4 to 16 ring atoms. Heterocycles may contain one or more, preferably one to four, especially one or two ring-forming heteroatoms selected from the group consisting of nitrogen, oxygen and sulfur, the ring preferably having 4 to 12, especially 5 to 7 ring atoms. Heterocycles may be unsubstituted or substituted by one or more, especially 1 to 3, substituents independently selected from the group consisting of the substituents defined above under the tile "Substituents". Heterocycle especially is a radical selected from the group consisting of oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, pyranyol, thiazolyl, isothiazolyl, dithiazolyl, oxazolyl, isoxazolyl, pyridyl, pyrazinyl, pyrimidinyl, piperidyl, especially piperidin-1-yl, piperazinyl, especially piperazin-1-yl, pyridazinyl, morpholinyl, especially morpholino, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, each of these radicals being unsubstituted or substituted by one to two radicals selected from the group consisting of lower alkyl, especially methyl or tert-butyl, lower alkoxy, especially methoxy, and halo, especially bromo or chloro. Unsubstituted heterocyclyl, especially piperidyl, piperazinyl, thiomorpholino or morpholino, is preferred.

Any heterocyclic group especially comprises five or six in-chain atoms of which at least one is a heteroatom selected from N, O or S. Especially preferred heterocycles are pyridine, pyrrolidine, piperidine and morpholine.

Mono- or disubstituted amino may be an amino group substituted by one or more of the substituents as listed under the heading "Substituents" and may form a secondary or tertiary amine group and/or is especially an amino and having the formula $NR^k_2$, $NR^kOH$, $NR^kCOR^k$ (e.g. NHCO-alkyl), $NR^kCOOR^k$ (e.g $NR^kCOO$-alkyl), $NR^kC(NR^k)H$ (e.g. NHC(NH)H), $NR^kC(NR^k)NR^kOH$ (e.g. NHC(NH)NHOH), $NR^kC(NR^k)NR^kCN$, (e.g. NHC(NH)NHCN), $NR^kC(NR^k)NR^k\text{-}COR^k$, (e.g. NHC(NH)NHCOR$^k$), $NR^kC(NR^k)NR^kR^2$ (e.g. NHC(NH)NHR$^k$), $N(COOR^k)C(NH_2)\text{=}NCOOR^k$, (e.g. $N(COOR^k)C(NH_2)\text{=}NCOOR^k$), where each $R^k$ is independently selected from the substituents as listed under the heading "Substituents" and may especially be selected from hydrogen, hydroxy, alkyl, substituted alkyl, lower alkyl, such as methyl; hydroxy-lower alkyl, such as 2-hydroxyethyl; halo-lower alkyl, lower alkoxy lower alkyl, such as methoxy ethyl; alkenyl, substituted alkenyl, alkynyl, substituted alkynyl, aryl, cycloalkyl, substituted cycloalkyl, heteroaryl, heterocyclyl, lower alkanoyl, such as acetyl; benzoyl; substituted benzoyl, phenyl, phenyl-lower alkyl, such as benzyl or 2-phenylethyl.

Any $R^k$ group may be substituted by the substituents as defined under the heading "Substituents" and the substituents may be selected from, preferably one or two of, nitro, amino, halogen, hydroxy, cyano, carboxy, lower alkoxycarbonyl, lower alkanoyl, and carbamoyl; and phenyl-lower alkoxycarbonyl.

As such, exemplary substituted amino groups are N-lower alkylamino, such as N-methylamino, N,N-di-lower alkylamino, N-lower alkylaminoamino-lower alkyl, such as aminomethyl or 2-aminoethyl, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, benzoylamino, phenyl-lower alkoxycarbonylamino, carbamoyl or aminocarbonylamino, amino-lower alkyl-oxyphenyl-amino, sulfamoylphenylamino, [N-(hydroxy-lower alkyl)-carbamoyl]-phenylamino. An example of a substituted amino is an amino substituted by a 4-substituted cyclohexyl, for example cyclohexan-4-ol.

Disubstituted amino may also be lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazine, N-methoxycarbonylpiperazino, N-mono substituted or N,N-disubstituted carbamoyl, N-lower alkyl-carbamoyl or N-(hydroxy-lower alkyl)-carbamoyl, such as N-(2-hydroxyethyl)-carbamoyl. It is also contemplated that an alkanoylamino extends to a carbamate, such as carbamic acid methyl ester.

Halogen (halo) is especially fluorine, chlorine, bromine, or iodine, especially fluorine, chlorine, or bromine most especially chlorine or fluorine.

Etherified hydroxy is especially $C_8$-$C_{20}$alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic hetero-aryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is alkylcarbonyl, especially lower alkanoyl, e.g. acetyl. The alkyl part of the alkanoyl group may be substituted to form a moiety $R^{10}$.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

Salts are especially the pharmaceutically acceptable salts of compounds of Formula (I) (or exemplary formula thereof), especially if they are forming salt-forming groups.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or poly-acid addition salts may be formed.

Compounds having acidic groups, a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxy-ethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

Such salts are formed, for example, as acid addition salts, preferably with organic or inorganic acids, from compounds of Formula (I) (or an exemplary formula thereof) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of Formula (I) (or an exemplary formula thereof) may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of Formula (I) (or exemplary formulae thereof) and N-oxides thereof have valuable pharmacological properties, as described hereinbefore and hereinafter.

Biology

The efficacy of the compounds of the invention as inhibitors of Bcr-Abl, EGF-R, VEGF-R2 (KDR) and FGFR3 (KDR) receptor tyrosine kinase activity can be demonstrated as follows:

Test for Activity Against Bcr-Abl:

The murine myeloid progenitor cell line 32Dcl3 transfected with the p210 Bcr-Abl expression vector pGDp210Bcr/Abl (32D-bcr/abl) was obtained from J. Griffin (Dana Faber Cancer Institute, Boston, Mass., USA). The cells express the fusion Bcr-Abl protein with a constitutively active abl kinase and proliferate growth factor independent. The cells are expanded in RPMI 1640 (AMIMED), 10% fetal calf serum, 2 mM glutamine (Gibco) ("complete medium"), and a working stock is prepared by freezing aliquots of $2 \times 10^6$ cells per vial in freezing medium (95% FCS, 5% DMSO (SIGMA)). After thawing, the cells are used during maximally 10-12 passages for the experiments. The antibody anti-abl SH3 domain cat. # 06-466 from Upstate Biotechnology is used for the ELISA. For detection of bcr-abl phosphorylation, the anti-phosphotyrosine antibody Ab PY20, labelled with alkaline phosphatase (PY10(AP)) from ZYMED (cat. # 03-7722) is used. As comparison and reference compound, (N-{5-[4-(4-methyl-piperazino-methyl)-benzoylamido]-2-methylphenyl}-4-(3-pyridyl)-2-pyrimidine-amine, in the form of the methane sulfonate (monomesylate) salt (STI571) (marketed as Gleevec® or Glivec®, Novartis), is used. A stock solution of 10 mM is prepared in DMSO and stored at −20° C. For the cellular assays, the stock solution is diluted in complete medium in two steps (1:100 and 1:10) to yield a starting concentration of 10 μmM followed by preparation of serial threefold dilutions in complete medium. No solubility problems are encountered using this procedure. The test compounds are treated analogously. For the assay, 200'000 32D-bcr/abl cells in 50 μl are seeded per well in 96 well round bottom tissue culture plates. 50 μl per well of serial threefold dilutions of the test compound are added to the cells in triplicates. The final concentration of the test compound range e.g. from 5 μM down to 0.01 μM. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 μl lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium orthovanadate, 1 mM phenylmethyl sulfonylfluoride, 50 μg/ml aprotinin and 80 μg/ml leupeptin) and either used immediately for the ELISA or stored frozen at −20° C. until usage. The anti-abl SH3 domain antibody is coated at 200 ng in 50 μl PBS per well to black ELISA plates (Packard HTRF-96 black plates; 6005207) overnight at 4° C. After washing 3× with 200 μl/well PBS containing 0.05% Tween 20 (PBST) and 0.5% TopBlock (Juro, Cat. # TB 232010), residual protein binding sites are blocked with 200 μl/well PBST, 3% TopBlock for 4 h at room temperature, followed by incubation with 50 μl lysates of untreated or test compound-treated cells (20 μg total protein per well) for 3-4 h at 4° C. After 3× washing, 50 μl/well PY20(AP) (Zymed) diluted to 0.5 μg/ml in blocking buffer is added and incubated overnight (4 !C). For all incubation steps, the plates are covered with plate sealers (Costar, cat. #3095). Finally, the plates are washed another three times with washing buffer and once with deionized water before addition of 90 μl/well of the AP substrate CPDStar RTU with Emerald II. The plates now sealed with Packard Top Seal™-A plate sealers (cat. # 6005185) are incubated for 45 min at room temperature in the dark and luminescence is quantified by measuring counts per second (CPS) with a Packard Top Count Microplate Scintillation Counter (Top Count). For the final optimized version of the ELISA, 50 μl of the lysates of the cells grown, treated and lysed in 96 well tissue culture plates, are transferred directly from these plates to the ELISA plates that are precoated with 50 ng/well of the rabbit polyclonal ant-abl-SH3 domain AB 06-466 from Upstate. The concentration of the anti-phosphotyrosine AB PY20 (AP) can be reduced to 0.2 μg/ml. Washing, blocking and incubation with the luminescent substrate are as above. The quantification is achieved as follows: The difference between the ELISA readout (CPS) obtained for with the lysates of the untreated 32D-bcr/abl cells and the readout for the assay background (all components, but without cell lysate) is calculated and taken as 100% reflecting the constitutively phosphorylated bcr-abl protein present in these cells. The activity of the compound in the bcr-abl kinase activity is expressed as percent reduction of the bcr-abl phosphorylation. The values for the $IC_{50}$ are determined from the dose response curves by graphical inter- or extrapolation. The compounds of the invention here preferably show $IC_{50}$ values in the range from 15 nM to 500 μM, most preferably 15 nM to 200 μM.

For cellular assays, compounds are dissolved in DMSO and diluted with complete medium to yield a starting concentration of 10 μM followed by preparation of serial 3-fold dilutions in complete medium. 32D or Ba/F3 cells expressing either 'wt'-Bcr-Abl or Bcr-Abl mutants (e.g. T-315-I) were seeded at 200'000 cells in 50 μL complete medium are seeded per well in 96 well round bottom tissue culture plates. 50 μL per well of serial 3-fold dilutions of the test compound are added to the cells in triplicates. Untreated cells are used as control. The compound is incubated together with the cells for 90 min at 37° C., 5% $CO_2$, followed by centrifugation of the tissue culture plates at 1300 rpm (Beckmann GPR centrifuge) and removal of the supernatants by careful aspiration taking care not to remove any of the pelleted cells. The cell pellets are lysed by addition of 150 μL lysis buffer (50 mM Tris/HCl, pH 7.4, 150 mM sodium chloride, 5 mM EDTA, 1 mM EGTA, 1% NP-40, 2 mM sodium ortho-vanadate, 1 mM PMSF, 50 μg/mL aprotinin and 80 μg/mL leupeptin) and either used immediately for the ELISA or stored frozen in the plates at −20° C. until usage.

The rabbit polyclonal anti-abl-SH3 domain Ab 06-466 from Upstate was coated at 50 ng in 50 μl PBS per well to black ELISA plates (Packard HTRF-96 black plates; 6005207) over night at 4° C. After washing 3 times with 200 μL/well PBS containing 0.05% Tween20 (PBST) and 0.5% TopBlock (Juro), residual protein binding sites are blocked with 200 μL/well PBST, 3% TopBlock for 4 h at room temperature followed by incubation with 50 L lysates of untreated or compound-treated cells (20 μg total protein per well) for 3-4 h at 4° C. After 3 washings, 50 μL/well anti-phosphotyrosine Ab PY20(AP) labeled with alkaline phosphatase (Zymed) diluted to 0.2 μg/mL in blocking buffer is added and incubated over night (4° C.). For all incubation steps the plates are covered with plate sealers (Costar). Finally, the plates are washed another three times with washing buffer and once with deionized water before addition of 90 μL/well of the AP-substrate CDPStar RTU with Emerald II. The plates, now sealed with Packard TopSeal™-A plate sealers, are incubated for 45 min at room temperature in the dark and luminescence is quantified by measuring counts per second (CPS) with a Packard Top Count Microplate Scintillation Counter (Top Count).

The difference between the ELISA-readout (CPS) obtained for with the lysates of the untreated 32D-Bcr/Abl cells and the readout for the assay-background (all components, but without cell lysate) is calculated and taken as 100% reflecting the constitutively phosphorylated Bcr-Abl protein present in these cells. The activity of the compound on the Bcr-Abl kinase activity is expressed as percent reduction of the Bcr-Abl phosphorylation. The values for the $IC_{50}$ (and $IC_{90}$) are determined from the dose response curves by graphical extrapolation.

The compounds of the invention here preferably show $IC_{50}$ values below 500 nM for inhibition of autophosphorylation and inhibition of IL-3 independent proliferation of Bcr-Abl mutants in Ba/F3 transfected cells, in particular T315I.

The 32D cl3 cells were obtained from the American Type Culture Collection (ATCC CRL11346) and the Ba/F3 cells from the German Collection of Microorganisms and Cell Cultures (DSMZ, Braunschweig and DSMZ No. ACC 300)

Palacios et al., *Nature,* 309: 1984, 126, PubMed ID 6201749.

Palacios et al., *Cell,* 41: 1985, 727, PubMed ID 3924409

The Ba/F3.p210 cells and the murine hematopoietic 32D cl3cells, (32D p210 cells) were obtained by transfecting the IL-3-dependent murine hematopoietic Ba/F3 cell line with a pGD vector containing p210BCR-ABL (B2A2) cDNA Daley and Baltimore, 1988; Sattler et al., 1996; Okuda et al., 1996.

Daley, G. Q., Baltimore, D. (1988) Transformation of an interleukin 3-dependent hematopoietic cell line by the chronic myeloid leukemia-specific p210 BCR-ABL protein. *PNAS* 85, 9312-9316

Sattler M, Salgia R, Okuda K, Uemura N, Durstin M A, Pisick E, et al. (1996) The proto-oncogene product p120CBL and the adaptor proteins CRKL and c-CRK link c-ABL, p190BCR-ABL and p210BCR-ABL to the phosphatidylinositol-3' kinase pathway. *Oncogene* 12, 839-46.

Okuda K, Golub T R, Gilliland D G, Griffin J D. (1996) p210BCR-ABL, p190BCR-ABL, and TEL/ABL activate similar signal transduction pathways in hematopoietic cell lines. *Oncogene* 13, 1147-52.

Test for Activity Against c-KIT

The baculovirus donor vector pFbacG01 GIBCO is used to generate a recombinant baculovirus that expresses the amino acid region amino acids 544-976 of the cytoplasmic kinase domains of human c-Kit. The coding sequences for the cytoplasmic domain of c-Kit is amplified by PCR from a human uterus c-DNA library (Clontech). The amplified DNA fragment and the pFbacG01 vector are made compatible for ligation by digestion with BamH1 and EcoRI. Ligation of these DNA fragments results in the baculovirus donor plasmid c-Kit. The production of the viruses, the expression of proteins in Sf9 cells and the purification of the GST-fused proteins are performed as follows:

Production of virus: Transfer vector pFbacG01-c-Kit containing the c-Kit kinase domain is transfected into the DH10Bac cell line (GIBCO) and the transfected cells are plated on selective agar plates. Colonies without insertion of the fusion sequence into the viral genome (carried by the bacteria) are blue. Single white colonies are picked and viral DNA (bacmid) is isolated from the bacteria by standard plasmid purification procedures. Sf9 cells or Sf21 cells American Type Culture Collection are then transfected in 25 $cm^2$ flasks with the viral DNA using Cellfectin reagent.

Determination of small scale protein expression in Sf9 cells: Virus containing media is collected from the transfected cell culture and used for infection to increase its titer. Virus containing media obtained after two rounds of infection is used for large-scale protein expression. For large-scale protein expression 100 cm² round tissue culture plates are seeded with 5×10⁷ cells/plate and infected with 1 mL of virus-containing media (approx. 5 MOIs). After 3 days the cells are scraped off the plate and centrifuged at 500 rpm for 5 min. Cell pellets from 10-20,100 cm² plates, are resuspended in 50 mL of ice-cold lysis buffer (25 mM Tris-HCl, pH 7.5, 2 mM EDTA, 1% NP-40, 1 mM DTT, 1 mM PMSF). The cells are stirred on ice for 15 min and then centrifuged at 5000 rpms for 20 min.

Purification of GST-tagged protein: The centrifuged cell lysate is loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged protein is eluted by 10 applications (1 mL each) of 25 mM Tris-HCl, pH 7.5, 10 mM reduced-glutathione, 100 mM NaCl, 1 mM DTT, 10% Glycerol and stored at −70° C.

Kinase assay: Tyrosine protein kinase assays with purified GST-c-Kit are carried out in a final volume of 30 µL containing 200-1800 ng of enzyme protein (depending on the specific activity), 20 mM Tris-HCl, pH 7.6, 3 mM $MnCl_2$, 3 mM $MgCl_2$, 1 mM DTT, 10 µM $Na_3VO_4$, 5 µg/mL poly(Glu,Tyr) 4:1, 1% DMSO, 1.0 µM ATP and 0.1 µCi [$\gamma^{33}$ P] ATP. The activity is assayed in the presence or absence of inhibitors, by measuring the incorporation of $^{33}$P from [$\gamma^{33}$P] ATP into the poly(Glu,Tyr) 4:1 substrate. The assay (30 µL) is carried out in 96-well plates at ambient temperature for 20 min under conditions described below and terminated by the addition of 20 µL of 125 mM EDTA. Subsequently, 40 µL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed 4× on a shaker with 1.0% $H_3PO_4$ and once with ethanol. Membranes are counted after drying at ambient temperature, mounting in Packard TopCount 96-well frame, and addition of 10 µL/well of Microscint™ (Packard). $IC_{50}$ values are calculated by linear regression analysis of the percentage inhibition of each compound in duplicate, at four concentrations (usually 0.01, 0.1, 1 and 10 µM). One unit of protein kinase activity is defined as 1 nmole of $^{33}$P ATP transferred from [$\gamma^{33}$P] ATP to the substrate protein per minute per mg of protein at 37° C.

Test for Activity Against EphB4

The efficacy of compounds of the formula I as inhibitors or Ephrin B4 receptor (EphB4) kinases can be demonstrated as follows:

Generation of Bac-to-Bac™ (Invitrogen Life Technologies, Basel, Switzerland) GST-fusion expression vectors: Entire cytoplasmatic coding regions of the EphB-class are amplified by PCR from cDNA libraries derived from human placenta or brain, respectively. Recombinant baculovirus are generated that express the amino acid region 566-987 of the human EphB4 receptor (SwissProt Database, Accession No. P54760). GST sequence is cloned into pFastBac1® vector (Invitrogen Life Technologies, Basel, Switzerland) and PCR amplified. cDNAs encoding EphB4-receptor domains, respectively are cloned in frame 3'prime to the GST sequence into this modified FastBac1 vector to generate pBac-to-Bac™ donor vectors. Single colonies arising from the transformation are inoculated to give overnight cultures for small scale plasmid preparation. Restriction enzyme analysis of plasmid DNA reveals several clones to contain inserts of the expected size. By automated sequencing the inserts and approximately 50 bp of the flanking vector sequences are confirmed on both strands.

Production of viruses: Viruses for each of the kinases are made according to the protocol supplied by GIBCO if not stated otherwise. In brief, transfer vectors containing the kinase domains are transfected into the DH10Bac cell line (GIBCO) and plated on selective agar plates. Colonies without insertion of the fusion sequence into the viral genome (carried by the bacteria) are blue. Single white colonies are picked and viral DNA (bacmid) isolated from the bacteria by standard plasmid purification procedures. Sf9 cells or Sf21 cells are then transfected in 25 cm² flasks with the viral DNA using Cellfectin reagent according to the protocol.

Purification of GST-tagged kinases: The centrifuged cell lysate is loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged proteins are then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Protein kinase assays: The activities of protein kinases are assayed in the presence or absence of inhibitors, by measuring the incorporation of $^{33}$P from [$\gamma^{33}$P]ATP into a polymer of glutamic acid and tyrosine (poly(Glu,Tyr)) as a substrate. The kinase assays with purified GST-EphB (30 ng) are carried out for 15-30 min at ambient temperature in a final volume of 30 µL containing 20 mM Tris.HCl, pH 7.5, 10 mM $MgCl_2$, 3-50 mM $MnCl_2$, 0.01 mM $Na_3VO_4$, 1% DMSO, 1 mM DTT, 3 µg/mL poly(Glu,Tyr) 4:1 (Sigma; St. Louis, Mo., USA) and 2.0-3.0 µM ATP ($\gamma$-[$^{33}$P]-ATP 0.1 µCi). The assay is terminated by the addition of 20 µL of 125 mM EDTA. Subsequently, 40 µl of the reaction mixture are transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µl 0.5% $H_3PO_4$. Membranes are removed and washed 4× on a shaker with 1.0% $H_3PO_4$, once with ethanol. Membranes are counted after drying at ambient temperature, mounting in Packard TopCount96-well frame, and addition of 10 µL/well of Microscint™ (Packard). $IC_{50}$ values are calculated by linear regression analysis of the percentage inhibition of each compound in duplicate, at four concentrations (usually 0.01, 0.1, 1 and 10 µM). One unit of protein kinase activity is defined as 1 nmole of $^{33}$P ATP transferred from [$\gamma^{33}$P] ATP to the substrate protein per minute per mg of protein at 37° C.

Test for Activity Against EGF-R:

The inhibition of EGF-R tyrosine kinase activity can be demonstrated using known methods, for example using the recombinant intracellular domain of the EGF-receptor [EGF-R ICD; see, for example, E. McGlynn et al., Europ. J. Biochem. 207, 265-275 (1992)]. Compared with the control without inhibitor, the compounds of formula I inhibit the enzyme activity by 50% ($IC_{50}$), for example in a concentration of from 0.0005 to 0.5 µM, especially from 0.001 to 0.1 µM.

As well as or instead of inhibiting EGF-R tyrosine kinase activity, the compounds of formula I also inhibit other members of this family of receptors, like ErbB-2. The inhibitory activity ($IC_{50}$) is approximately in the range of 0.001 to 0.5

µM. The inhibition of ErbB-2 tyrosine kinase (HER-2) can be determined, for example, analogously to the method used for EGF-R protein tyrosine kinase [see C. House et al., Europ. J. Biochem. 140, 363-367 (1984)]. The ErbB-2 kinase can be isolated, and its activity determined, by means of protocols known per se, for example in accordance with T. Akiyama et al., Science 232, 1644 (1986).

Test for Activity Against VEGF-R2 (KDR):

The inhibition of VEGF-induced receptor autophosphorylation can be confirmed with a further in vitro experiments in cells such as transfected CHO cells, which permanently express human VEGF-R2 receptor (KDR), are seeded in complete culture medium (with 10% fetal calf serum =FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/ml. After a further five minutes incubation at 37° C., the cells are washed twice with ice-cold PBS (phosphate-buffered saline) and immediately lysed in 100 µl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the VEGF-R2 phosphorylation: a monoclonal antibody to VEGF-R2 (for example Mab 1495.12.14; prepared by H. Towbin, Novartis or comparable monoclonal antibody) is immobilized on black ELISA plates (OptiPlate™ HTRF-96 from Packard). The plates are then washed and the remaining free protein-binding sites are saturated with 3% TopBlock® (Juro, Cat. # TB232010) in phosphate buffered saline with Tween 20® (polyoxyethylen(20)sorbitane monolaurate, ICI/Uniquema) (PBST). The cell lysates (20 µg protein per well) are then incubated in these plates overnight at 4° C. together with an antiphosphotyrosine antibody coupled with alkaline phosphatase (PY20:AP from Zymed). The (plates are washed again and the) binding of the antiphosphotyrosine antibody to the captured phosphorylated receptor is then demonstrated using a luminescent AP substrate (CDP-Star, ready to use, with Emerald II; Applied Biosystems). The luminescence is measured in a Packard Top Count Microplate Scintillation Counter. The difference between the signal of the positive control (stimulated with VEGF) and that of the negative control (not stimulated with VEGF) corresponds to VEGF-induced VEGF-R2 phosphorylation (=100%). The activity of the tested substances is calculated as percent inhibition of VEGF-induced VEGF-R2 phosphorylation, wherein the concentration of substance that induces half the maximum inhibition is defined as the $IC_{50}$ (inhibitory dose for 50% inhibition).

Test for Activity Against Recombinant Protein Kinases Ret (Ret-Men2A), Tie-2 (Tek) and FGFR3-K650E:

Cloning and expression of recombinant protein kinases: (Ret); The Baculovirus donor vector pFB-GSTX3 was used to generate a recombinant Baculovirus that expresses the amino acid region 658-1072 of the intra-cytoplasmic kinase domain of human Ret-Men2A which corresponds to the wild type kinase domain of Ret. The coding sequence for the cytoplasmic domain of Ret was amplified by PCR from the plasmid pBABEpuro RET-Men2A which was received from Dr. James Fagin, College of Medicine, University of Cincinnati (Novartis collaboration). The amplified DNA fragments and the pFB-GSTX3 vector were made compatible for ligation by digestion with SalI and KpnI. Ligation of these DNA fragments resulted in the baculovirus donor plasmid pFB-GX3-Ret(-Men2A).

(Tie-2/Tek): The baculovirus donor vector pFbacG01 was used to generate a recombinant baculovirus that expressed the amino acid region amino acids 773-1124 of the cytoplasmic kinase domain of human Tek, N-terminally fused to GST (Provided by Dr. Marmé, Institute of Molecular Medicine, Freiburg, Germany based on a Research Collaboration). Tek was recloned into the pFbacG01 transfer vector by EcoRI excision and ligation into EcoRI digested pFbacG01 (FBG-Tie2/Tek).

(FGFR-3-K650E): The baculovirus donor vector pFast-BacGST2 was used to generate a recombinant baculovirus that expressed the amino acid (aa) region amino acids 411-806 of the cytoplasmic domain of human FGFR-3, N-terminally fused to GST (Provided by Dr. Jim Griffin, Dana Farber Cancer Institute, Boston, USA based on a Research Collaboration). DNA encoding amino acids 411-806 was amplified by PCR, inserted into the pFastBac-GT2 vector to yield pFB-GT2-FGFR3-wt. This plasmid was in turn used to generate a vector encoding FGFR3(411-806) with a mutation at K650 using the Stratagene XL-Site directed Mutagenesis Kit to produce pFB-GT2-FGFR3-K650E. The production of the viruses, the expression of proteins in Sf9 cells and the purification of the GST-fused proteins were performed as described in the following sections.

Production of virus: Transfer vectors containing the kinase domains were transfected into the DH10Bac cell line (GIBCO) and plated on selective agar plates. Colonies without insertion of the fusion sequence into the viral genome (carried by the bacteria) are blue. Single white colonies were picked and viral DNA (bacmid) isolated from the bacteria by standard plasmid purification procedures. Sf9 cells or Sf21 cells were then transfected in 25 $cm^2$ flasks with the viral DNA using Cellfectin reagent.

Determination of small scale protein expression in Sf9 cells: Virus containing media was collected from the transfected cell culture and used for infection to increase its titer. Virus containing media obtained after two rounds of infection was used for large-scale protein expression. For large-scale protein expression 100 $cm^2$ round tissue culture plates were seeded with $5\times10^7$ cells/plate and infected with 1 mL of virus-containing media (approx. 5 MOIs). After 3 days the cells were scraped off the plate and centrifuged at 500 rpm for 5 min. Cell pellets from 10-20, 100 $cm^2$ plates, were resuspended in 50 mL of ice-cold lysis buffer (25 mMTris-HCl, pH7.5, 2 mMEDTA, 1% NP-40, 1 mM DTT, 1 mMP MSF). The cells were stirred on ice for 15 min and then centrifuged at 5000 rpms for 20 min.

Purification of GST-tagged proteins: The centrifuged cell lysate was loaded onto a 2 mL glutathione-sepharose column and washed three times with 10 mL of 25 mM Tris-HCl, pH 7.5, 2 mM EDTA, 1 mM DTT, 200 mM NaCl. The GST-tagged proteins were then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Measure of enzyme activity: Tyrosine protein kinase assays with either purified GST-Ret, GST-Tek or GST-FGFR-3-K650E were carried out in a final volume of 30 µL with final concentrations of the following components: Ret included 15 ng of GST-Ret, 20 mM Tris-HCl, pH 7.5, 1 mM $MnCl_2$, 10 mM $MgCl_2$, 1 mM DTT, 3 µg/mL poly(Glu,Tyr) 4:1, 1% DMSO and 2.0 µM ATP ($\gamma$-[$^{33}$P]-ATP 0.1 µCi). Tek included 150 ng of GST-Tek, 20 mM Tris-HCl, pH 7.5, 3 mM $MnCl_2$, 3 mM $MgCl_2$, 1 mM DTT, 0.01 mM $Na_3VO_4$, 250 µg/mL PEG 20'000, 10 µg/mL poly(Glu,Tyr) 4:1, 1% DMSO and 4.0 µM ATP (γ-[$^{33}$P]-ATP 0.1 µCi). FGFR-3-K650E included 10 ng of GST-FGFR-3-K650E, 20 mM Tris-HCl, pH 7.5, 3 mM MnCl$_2$, 3 mM MgCl$_2$, 1 mM DTT, 0.01 mM PEG 20'000, 10 µg/mL poly(Glu,Tyr) 4:1, 1% DMSO and 4.0 µM ATP (γ-[$^{33}$P]-ATP 0.1 µCi). The activity was assayed in the presence or absence of inhibitors, by measuring the incorporation of $^{33}$P from [γ$^{33}$P] ATP into poly(Glu,Tyr) 4:1. The assay was carried out in 96-well plates at ambient temperature for 30 min under conditions described below and terminated by the addition of 50 µL of 125 mM EDTA. Subsequently, 60 µL of the reaction mixture were transferred onto Immobilon-PVDF membrane (Millipore) previously soaked for 5 min with methanol, rinsed with water, then soaked for 5 min with 0.5% H$_3$PO$_4$ and mounted on vacuum manifold with disconnected vacuum source. After spotting all samples, vacuum was connected and each well rinsed with 200 µL 0.5% H$_3$PO$_4$. Membranes were removed and washed 4× on a shaker with 1.0% H$_3$PO$_4$, once with ethanol. Membranes were counted after drying at ambient temperature, mounting in Packard TopCount 96-well frame, and addition of 10 µL/well of Microscint™ (Packard). IC50 values were calculated by linear regression analysis of the percentage inhibition of each compound in duplicate, at four concentrations (usually 0.01, 0.1, 1 and 10 µM). One unit of protein kinase activity is defined as 1 nmole of $^{33}$P ATP transferred from [γ$^{33}$P] ATP to the substrate protein per minute per mg of protein at 37° C.

On the basis of the inhibitory studies hereinbefore described, a compound of Formula (I) or (I*) (or exemplary formula thereof) according to the invention shows therapeutic efficacy especially against disorders dependent on protein kinase, especially proliferative diseases.

The heteroaryl aryl ureas useful according to the invention, especially compounds of Formula (I) (or exemplary formula thereof), that inhibit the protein kinase activities mentioned, especially tyrosine protein kinases mentioned above and below, can therefore be used in the treatment of protein kinase dependent diseases. Protein kinase dependent diseases are especially proliferative diseases, preferably benign or especially malignant tumours (for example carcinoma of the kidneys, liver, adrenal glands, bladder, breast, stomach, ovaries, colon, rectum, prostate, pancreas, lungs, vagina or thyroid, sarcoma, glioblastomas and numerous tumours of the neck and head, as well as leukemias). They are able to bring about the regression of tumours and to prevent the formation of tumour metastases and the growth of (also micro)metastases. In addition they can be used in epidermal hyperproliferation (e.g. psoriasis), in prostate hyperplasia, and in the treatment of neoplasias, especially of epithelial character, for example mammary carcinoma. It is also possible to use the compounds of Formula (I) (or exemplary formula thereof) in the treatment of diseases of the immune system insofar as several or, especially, individual tyrosine protein kinases are involved; furthermore, the compounds of Formula (I) (or exemplary formula thereof) can be used also in the treatment of diseases of the central or peripheral nervous system where signal transmission by at least one tyrosine protein kinase, especially selected from those mentioned specifically, is involved.

The expression of FGFR1 (also known as "Flg"), FGFR2 (also known as "Bek") and the like belonging to a fibroblast growth factor receptor family is reported to be found in various cancers such as brain tumors, lung cancer, breast cancer, gastric cancer, head and neck cancer, and prostatic cancer (Proc. Natl. Acad. Sci. USA, 87: 5710-5714 (1990); Oncogene. 1997 Aug. 14; 15 (7): 817-26; Cancer Res. 1994 Jan. 15; 54 (2): 523-30; Cancer Res. 1992 Feb. 1; 52 (3): 571-7). In particular, it is reported for gastric cancer that overexpression of FGFR2 correlates with poor prognosis mainly in poorly differentiated cancers such as scirrhus gastric cancers (Clin Cancer Res. 1996 Aug.; 2 (8): 1373-81; J Cancer Res Clin Oncol. 2001 April; 127 (4): 207-16; Int Rev Cytol. 2001; 204: 49-95.). Further diseases associated with FGFR1 and FGFR4 are diabetes and obesity.

Diseases related to FGFR1, FGFR2, FGFR3 and FGFR4 are described previously herein under the heading "BACKGROUND", and as inhibitors of these kinases the compounds of the invention may find application in treating those diseases.

As inhibitors of VEGF-receptor tyrosine kinase activity, the compounds of the invention may primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, diabetes, endometriosis, chronic asthma, and especially neoplastic diseases (solid tumors, but also leukemias and other "liquid tumors", especially those expressing KDR), such as especially breast cancer, cancer of the colon, lung cancer (especially small-cell lung cancer), cancer of the prostate or Kaposi's sarcoma. A compound of Formula (I) (or exemplary formula thereof) (or an N-oxide thereof) inhibits the growth of tumours and is especially suited to preventing the metastatic spread of tumors and the growth of micrometastases.

Vascular endothelial growth factor receptor-2 (VEGF-R2; KDR) is selectively expressed on the primary vascular endothelium and is essential for normal vascular development. In order to grow beyond minimal size, tumors must generate new vascular supply. Angiogenesis, or the sprouting of new blood vessels, is a central process in the growth of solid tumors. For many cancers, the extent of vascularization of a tumor is a negative prognostic indicator signifying aggressive disease and increased potential for metastasis. Recent efforts to understand the molecular basis of tumor-associated angiogenesis have identified several potential therapeutic targets, including the receptor tyrosine kinases for the angiogenic factor vascular endothelial growth factor (VEGF) (see Zeng et al., J. Biol. Chem. 276(35), 32714-32719 (2001)). The heteroaryl aryl ureas according to the present invention, especially the compounds of Formula (I) (or exemplary formula thereof) for use as KDR inhibitors are thus especially appropriate for the therapy of diseases related to VEGF receptor tyrosine kinase overexpression. Among these diseases, especially retinopathies, age-related macula degeneration, psoriasis, haemangioblastoma, haemangioma, arteriosclerosis, inflammatory diseases, such as rheumatoid or rheumatic inflammatory diseases, especially arthritis, such as rheumatoid arthritis, or other chronic inflammatory disorders, such as chronic asthma, arterial or post-transplantational atherosclerosis, endometriosis, and especially neoplastic diseases, for example so-called solid tumors (especially cancers of the gastrointestinal tract, the pancreas, breast, stomach, cervix, bladder, kidney, prostate, ovaries, endometrium, lung, brain, melanoma, Kaposi's sarcoma, squamous cell carcinoma of head and neck, malignant pleural mesothelioma, lymphoma or multiple myeloma) and liquid tumors (e.g. leukemias) are especially important.

In particular, the present invention pertains to the use of a compound of Formula I for the manufacture of a medicament for the treatment of a proliferative disorder, a skeletal disorder, a cancer, a solid tumour, especially an epithelial cancer, a T cell mediated inflammatory or autoimmune disease.

In chronic myelogeous leukemia (CML), a reciprocally balanced chromosomal translocation in hematopoietic stem cells (HSCs) produces the BCR-ABL hybrid gene. The latter encodes the oncogenic Bcr-Abl fusion protein. Whereas ABL encodes a tightly regulated protein tyrosine kinase, which plays a fundamental role in regulating cell proliferation, adherence and apoptosis, the BCR-ABL fusion gene encodes as constitutively activated kinase, which trans-forms HSCs to produce a phenotype exhibiting deregulated clonal proliferation, reduced capacity to adhere to the bone marrow stroma and a reduces apoptotic response to mutagenic stimuli, which enable it to accumulate progressively more malignant transformations. The resulting granulocytes fail to develop into mature lymphocytes and are released into the circulation, leading to a deficiency in the mature cells and increased susceptibility to infection. ATP-competitive inhibitors of Bcr-Abl have been described which prevent the kinase from activating mitogenic and anti-apoptotic pathways (e.g. P-3 kinase and STAT5), leading to the death of the BCR-ABL phenotype cells and thereby providing an effective therapy against CML. The heteroaryl aryl ureas useful according to the present invention, especially the compounds of the Formula (I) (or exemplary formula thereof) are thus especially appropriate for the therapy of diseases related to its overexpression, especially leukemias, such as leukemias, e.g. CML or ALL.

Compounds of the Formula I*, II*, III*, IV*, V*, VI*, VII*, VIII* or IX* (or exemplary formula thereof), in view of their activity as PDGF receptor inhibitors, are also especially appropriate in the treatment of proliferate diseases, especially small lung cancer, atherosclerosis, thrombosis, psoriasis, scleroderma or fibrosis.

There are also experiments to demonstrate the antitumor activity of compounds of the Formula (I) (or exemplary formula thereof) in vivo: The in vivo antitumor activity is tested, for example, using breast carcinoma cell lines, such as the human estrogen dependent breast carcinoma MCF-7 (ATCC: HTB22) or ZR-75-1 (ATCC: CRL1500), or the estrogen-independent breast carcinomas MDA-MB468 (ATCC: HTB132) or MDA-MB231 (ATCC: HTB26); colon carcinoma cell lines, such as the colon-carcinoma Colo 205 (ATCC: CCL222); glioblastoma cell lines, such as the glioblastomas U-87MG (ATCC: HTB14) or U-373MG (ATCC: HTB17); lung carcinoma cell lines, such as the "small cell lung carcinomas" NCI-H69 (ATCC: HTB119) or NCI-H209 (ATCC: HTB172), or the lung carcinoma NCI-H596 (ATCC: HTB178); skin tumor cell lines, such as the melanomas Hs294T (ATCC: HTB140) or A375 (ATCC: CRL1619); tumor cell lines from the genitourinary systems, such as the ovarial carcinoma NIH-Ovcar3 (ATCC: HTB161), as well as the prostate carzinomas DU145 (ATCC: HTB81) or PC-3 (ATCC: CRL1435), or the bladder carcinoma T24 (ATCC: HTB4); epithelial carcinomas, such as the epithelial carcinoma KB31; or (especially with regard to leukemias) K562 cells (American Type Culture Collection, Mannassas, Va.) or human CFU-G cells (CFU-G stands for granulocyte colony forming unit, and it represents an early but committed granulocyte forming precursor cell that circulates in the blood stream or bone marrow) each of which is transplanted into female or male Balb/c nude mice. Other cell lines include leukemic cell lines such as K-562, SUPB15, MEG01, Ku812F, MOLM-13, BaF3, CEM/0, JURKAT/0 or U87MG.

Tumors are obtained after subcutaneous injection of the respective cells (minimum $2\times10^6$ cells in 100 ml phosphate buffered physiological saline) into the carrier mice (e.g. 4-8 mice per cell line). The resulting tumors are passed serially through at least three subsequent transplantations before treatment is started. Tumor fragments (about 25 mg each) are injected s.c. into the left flank of the animals using a 13-gauge Trocar needle under Forene narcosis (Abbott, Switzerland) for implantation. Mice transplanted with estrogen-dependent tumor are, in addition, supplied with an estrogen pellet (1.0 cm of a tube with a quality appropriate for medical purposes, Dow Chemicals, with 5 mg estradiole, Sigma). The treatment is started routinely (that is at low or intermediate tumor burden), as soon as the tumor has reached an average size of 100 $mm^3$. Tumor growth is determined once, twice or thrice weekly (depending on tumor growth of the cell line) and 24 h after the last treatment by measurement of the perpendicular diameter. In case of tumors, tumor volumes are determined according to the Formula L×D×p/6 (see Evans, B. D., Smith, I. E., Shorthouse, A. J. and Millar, J. J., Brit. J. Cancer, 45: 466-468, 1982). The antitumor activity is expressed as T/C % (average increase of the tumor volume of treated animals divided by the average increase of tumor volume in control animals multiplied by 100). Tumor regression (%) represents the smallest mean tumor volume compared to the mean tumor volume at the beginning of the treatment. Each animal in which the tumor reaches a diameter of more than 1.5 to 2 $cm^3$ is sacrificed. Leukemia burden is assessed by examining both peripheral white blood count and weight of spleen and thymus in animals tumored with leukemia cell lines.

An exemplary (though not limiting) schedule for administration of a heteroaryl aryl urea, especially of Formula (I) (or exemplary formula thereof), or a salt thereof, is daily administration, with preferably 1 to 3 daily dosages for a longer time, possibly until the disease is cured or, if only palliative treatment is achieved, for as long as required; alternatively, treatment e.g. for 5 days, and/or administration at days 1, 4 and 9, with eventual repetition after a certain time without treatment is possible. Alternatively, treatment several times a day (e.g. 2 to 5 times) or treatment by continuous administration (e.g. infusion), e.g. at the time points indicated in the last sentence, are possible. Generally, administration is orally or parenterally, preferably orally. The test compounds are preferably diluted in water or in sterile 0.9% saline.

All human tumor cell lines are obtained from the American Type Culture Collection (ATCC, Rockville, Md., USA) if not indicated otherwise and are cultivated in the suggested media with the corresponding additives (ATCC culture conditions), if not mentioned otherwise. The c-sis- and v-sis-transformed BALB/c 3T3 cells are obtained from Dr. C. Stiles (Dana Farber Cancer Institute, Boston, Mass., USA). They are cultured in "Dulbecco's modified Eagle's medium" (DMEM), that is supplemented with 10% calf serum and Hygromycin B in a concentration of 0.2 mg/ml or G418 in a concentration of 0.5 mg/ml. BALB/c AMuLV A.6R.1 cells (ATCC) are kept in DMEM, supplemented with 10% fetal calf serum.

The pharmacological activity of a heteroaryl aryl urea of the Formula (I) (or exemplary formula thereof) may, for example, be demonstrated in a clinical study or in a test procedure as essentially described hereinafter.

Suitable clinical studies are, for example, open label non-randomized, dose escalation studies in patients with one of the tumor diseases mentioned above. The beneficial effects on proliferative diseases can be determined directly through the results of these studies or by changes in the study design which are known as such to a person skilled in the art. The efficacy of the treatment can be determined in such studies, e.g., in case of tumors after 18 or 24 weeks by radiologic evaluation of the tumors every 6 weeks, in case of a leukemia e.g. by determination of the count of aberrant white blood cells, and by staining mononuclear cells and/or by means of determining minimum residual disease (MRD) e.g. by FACS-LPC MRD or PCR.

Alternatively, a placebo-controlled, double blind study can be used in order to prove the benefits of the heteroaryl aryl ureas useful according to the invention, especially the compounds of the Formula (I) (or exemplary formula thereof) mentioned herein.

In a further embodiment, the present invention provides compounds of Formula I** representing a sub-group of the compounds of Formula I,

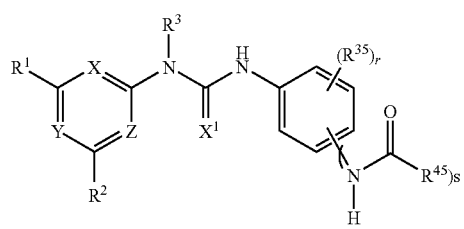

(I**)

in which
r is selected from 0, 1 and 2;
s is selected from 0 and 1;
$X^1$ is selected from O or S;
X is $CR_6$;
Y and Z are both nitrogen;
$R_1$ is selected from $-X5NR_7R_8$, $-X5NR_7X5NR_7R_8$, $-X5NR_7X5C(O)OR_8$, $-X5OR_7$, $-X5R_7$ and $-X5S(O)_{0-2}R_7$; wherein X5 is a bond or $C_{1-4}$alkylene optionally substituted by 1 to 2 $C_{1-6}$alkyl radicals; $R_7$ is selected from hydrogen, $C_{1-6}$alkyl, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; and $R_8$ is selected from hydrogen and $C_{1-6}$alkyl; or $R_7$ and $R_8$ together with the nitrogen to which $R_7$ and $R_8$ are both attached form heteroaryl or heterocycloalkyl;
wherein any aryl, heteroaryl, cycloalkyl and heterocycloalkyl of $R_7$ or the combination of $R_7$ and $R_8$ can be optionally substituted with 1 to 3 radicals independently selected from halo, nitro, cyano, hydroxy, $C_{1-6}$alkyl, $C_{1-6}$alkoxy, halo-substituted-alkyl, halo-substituted-alkoxy, $-X5NR_9R_{10}$, $-X5OR_9$, $-X5NR_9S(O)_2R_{10}$, $-X5NR_9S(O)R_{10}$, $-X5NR_9SR_{10}$, $-X5C(O)NR_9R_{10}$, $-X5NR_9C(O)NR_9R_{10}$, $-X5NR_9C(O)R_{10}$, $-X5NR_9X5NR_9R_{10}$, $-X5NR_9X5OR_9$, $-X5NR_9C(=NR_9)NR_9R_{10}$, $-X5S(O)_{0-2}R_{11}$, $-X5NR_9C(O)R_{10}$, $-X5NR_9C(O)R_{11}$, $-X5R_{11}$, $-X5C(O)OR_{10}$, $-X5S(O)_2NR_9R_{10}$, $-X5S(O)NR_9R_{10}$ and $-X5SNR_9R_{10}$; wherein X5 is a bond or $C_{1-4}$alkylene; $R_9$ and $R_{10}$ are independently selected from hydrogen and $C_{1-4}$alkyl; and $R_{11}$ is $C_{3-10}$heterocycloalkyl optionally substituted with 1 to 3 radicals selected from $C_{1-4}$alkyl, $-X5NR_9X5NR_9R_9$, $X5NR_9X5OR_9$ and $-X5OR_9$;
$R_3$ is selected from hydrogen, $C_{1-4}$alkyl, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; wherein any alkyl, aryl, heteroaryl, cycloalkyl or heterocycloalkyl of $R_3$ is optionally substituted by 1-3 radicals selected from halo, $C_{1-4}$alkyl, $-X5S(O)_{0-2}NR_9R_{10}$ and $-X5OR_9$; wherein X5, $R_9$ and $R_{10}$ are as described above;
$R_{45}$ is selected from $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; wherein any aryl, heteroaryl, cycloalkyl or heterocycloalkyl of $R_{45}$ is optionally substituted with 1 to 3 radicals selected from halo, hydroxy, $C_{1-4}$alkyl, $C_{1-4}$alkoxy, halo-substituted-$C_{1-4}$alkyl, halo-substituted-$C_{1-4}$alkoxy and $C_{3-8}$heterocyclo$C_{0-4}$alkyl; wherein any heterocycloalkyl substituent of $R_4$ is optionally substituted by 1 to 3 $C_{1-4}$alkyl radicals;
$R_2$, $R_6$ and $R_{35}$ are independently selected from halo, hydroxy, $C_{1-4}$alkyl, $C_{1-4}$alkoxy, halo-substituted-$C_{1-4}$alkyl and halo-substituted-$C_{1-4}$alkoxy; and the N-oxide derivatives, prodrug derivatives, protected derivatives, individual isomers and mixture of isomers thereof; and the pharmaceutically acceptable salts and solvates (e.g. hydrates) of such compounds.

For the definition of the compound of Formula I**, the following definitions apply:

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from $-O-$, $-N=$, $-NR-$, $-C(O)-$, $-S-$, $-S(O)-$ or $-S(O)_2-$, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

"Mutant forms of BCR-Abl" means single or multiple amino acid changes from the wild-type sequence. Over 22 mutations have been reported to date with the most common being G250E, E255V, T315I, F317L and M351T.

"Treat", "treating" and "treatment" refer to a method of alleviating or abating a disease and/or its attendant symptoms.

The fusion protein BCR-Abl is a result of a reciprocal translocation that fuses the Abl proto-oncogene with the Bcr gene. BCR-Abl is then capable of transforming B-cells through the increase of mitogenic activity. This increase results in a reduction of sensitivity to apoptosis, as well as altering the adhesion and homing of CML progenitor cells. The present invention provides compounds of Formula I**, compositions and methods for the treatment of kinase related disease, particularly Abl, BCR-Abl, BMX, FGFR35, Lck, JNK1, JNK2, CSK, RAF, MKK6 and P38kinase related diseases. For example, leukemia and other proliferation disorders related to BCR-Abl can be treated through the inhibition of wild type and mutant forms of BCR-Abl.

With reference to compounds of Formula I**, preferably r is selected from 0, 1 and 2;
s is selected from 0 and 1;
$X_1$ is selected from O or S;
$R_1$ is selected from —X5NR$_7$R$_8$, —X5NR$_7$X5NR$_7$R$_8$, —X5NR$_7$X5C(O)OR$_8$; wherein X5 is a bond or $C_{1-4}$alkylene optionally substituted by 1 to 2 $C_{1-6}$alkyl radicals; $R_7$ is selected from hydrogen, $C_{1-6}$alkyl, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; and $R_8$ is selected from hydrogen and $C_{1-6}$alkyl; or $R_7$ and $R_8$ together with the nitrogen to which $R_7$ and $R_8$ are both attached form heteroaryl or heterocycloalkyl;
wherein any aryl, heteroaryl, cycloalkyl and heterocycloalkyl of $R_7$ or the combination of $R_7$ and $R_8$ can be optionally substituted with 1 to 3 radicals independently selected from halo, $C_{1-6}$alkyl, $C_{1-6}$alkoxy, halo-substituted-alkyl, —X5NR$_9$R$_{10}$, —X5C(O)NR$_9$R$_{10}$, —X5NR$_9$C(O)R$_{10}$, —X5S(O)$_{0-2}$R$_{11}$—X5R$_{11}$; $R_9$ and $R_{10}$ are independently selected from hydrogen and $C_{1-4}$alkyl; and $R_{11}$ is $C_{3-10}$heterocycloalkyl optionally substituted with 1 to 3 $C_{1-4}$alkyl radicals;
$R_3$ is selected from hydrogen, $C_{1-4}$alkyl, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; wherein any alkyl, aryl, heteroaryl, cycloalkyl or heterocycloalkyl of $R_3$ is optionally substituted by 1-3 radicals selected from halo, $C_{1-4}$alkyl, —X5S(O)$_{0-2}$NR$_9$R$_{10}$ and —X5OR$_9$; wherein X5, $R_9$ and $R_{10}$ are as described above;
$R_{45}$ is selected from $C_{6-10}$aryl-$C_{0-4}$alkyl optionally substituted with 1 to 3 radicals selected from halo-substituted-$C_{1-4}$alkyl and $C_{3-8}$heterocycloC$_{0-4}$alkyl; wherein any heterocycloalkyl substituent of R45 is optionally substituted by 1 to 3 $C_{1-4}$alkyl radicals;
$R_{35}$, $R_2$ and $R_6$ are independently selected from halo, $C_{1-4}$alkyl, $C_{1-4}$alkoxy, and halo-substituted-$C_{1-4}$alkyl.

In another embodiment, the present invention provides a compound of Formula I**, wherein
$R_1$ represents NR$_7$R$_8$, in which:
$R_7$ is selected from hydrogen, methyl, isopropyl, carboxyethyl, amino-propyl, tetrahydrofuran-2-ylmethyl, diisopropyl-amino-ethyl, benzo[1,3]dioxol-5-yl, phenyl, furanyl-methyl, benzyl, 1-phenyl-ethyl, pyridinyl, phenethyl, morpholino-propyl, 3-(2-oxo-pyrrolidin-1-yl)-propyl, cycloheptyl, morpholino-ethyl, cyclopropyl, pyridinyl-ethyl; wherein any phenyl, benzyl, pyridinyl, phenethyl, morpholino, cyclopropyl, cycloheptyl, pyridinyl, furanyl and benzodioxolyl is optionally substituted by 1 to 2 radicals selected from methyl, dimethyl-amino, methyl-carbonyl-amino, morpholino, morpholino-methyl, morpholino-sulfonyl, methyl-piperazinyl, trifluoro-methyl, halo, methoxy, methyl-amino-carbonyl, amino-carbonyl, methyl-carbonyl-amino,
$R_8$ is hydrogen or $R_7$ and $R_8$ together with the nitrogen atom to which $R_7$ and $R_8$ are attached form morpholino, $X_1$ is oxygen and the other radicals and symbols have the same meanings as provided for a compound of formula I** above.

In a further embodiment with respect to a compound of formula I**, $R_3$ is selected from hydrogen, methyl, 2-methoxy-1-methyl-ethyl, pyridinyl-methyl, pyridinyl-ethyl, morpholino, pyrrolidinyl-ethyl, phenethyl, morpholino-ethyl, morpholino-propyl, 3-(2-oxo-pyrrolidin-1-yl)-propyl, cycloheptyl, 3-(tetrahydro-furan-2-yl)-methyl, pyrrolidinyl-ethyl and pyrazinyl-methyl; wherein any alkyl, aryl, heteroaryl, cycloalkyl or heterocycloalkyl of R3 is optionally substituted by 1-3 radicals selected from fluoro, methyl and amino-sulfonyl.

In another embodiment with respect to a compound of formula I**, s and r are both 1; $R_{35}$ is selected from methyl, methoxy and fluoro; and $R_{45}$ is selected from phenyl optionally substituted by trifluoromethyl, piperazinyl-methyl; wherein any piperazinyl substituent of R45 is optionally substituted by methyl.

In another embodiment, r is 0; s is selected from 1 or 2; and $R_{35}$ is selected from methoxy and trifluoromethyl.

Preferred compounds of formula I** are selected from: N-[4-Methyl-3-(3-methyl-3-{6-[(tetrahydro-furan-2-ylmethyl)-amino]-pyrimidin-4-yl}-ureido)-phenyl]-3-trifluoromethyl-benzamide; N-(3-{3-[6-(Benzo[1,3]dioxol-5-ylamino)-pyrimidin-4-yl]-3-methyl-ureido}-4-methyl-phenyl)-3-trifluoromethyl-benzamide; N-(3-{3-[6-(3-Dimethylamino-phenylamino)-pyrimidin-4-yl]-3-methyl-ureido}-4-methyl-phenyl)-3-trifluoromethyl-benzamide; N-(3-{3-[6-(3-Acetylamino-phenylamino)-pyrimidin-4-yl]-3-methyl-ureido}-4-methyl-phenyl)-3-trifluoromethyl-benzamide; N-(4-Methyl-3-{3-methyl-3-[6-(4-morpholin-4-yl-phenylamino)-pyrimidin-4-yl]-ureido}-phenyl)-3-trifluoromethyl-benzamide; N-[4-Methyl-3-(3-methyl-3-{6-[4-(4-methyl-piperazin-1-yl)-phenylamino]-pyrimidin-4-yl}-ureido)-phenyl]-3-trifluoromethyl-benzamide; N-{3-[3-(6-Amino-pyrimidin-4-yl)-3-(2-morpholin-4-yl-ethyl)-ureido]-4-methyl-phenyl}-3-trifluoromethyl-benzamide; N-(3-{3-(6-Amino-pyrimidin-4-yl)-3-[3-(2-oxo-pyrrolidin-1-yl)-propyl]-ureido}-4-methyl-phenyl)-3-trifluoromethyl-benzamide; N-(4-Fluoro-3-{3-[6-(4-trifluoromethyl-phenylamino)-pyrimidin-4-yl]-ureido}-phenyl)-4-(4-methyl-piperazin-1-ylmethyl)-benzamide; N-(3-{3-[6-(4-Chloro-benzylamino)-pyrimidin-4-yl]-3-methyl-ureido}-4-methyl-phenyl)-3-trifluoromethyl-benzamide; N-{4-Methyl-3-[3-methyl-3-(6-phenethylamino-pyrimidin-4-yl)-ureido]-phenyl}-3-trifluoromethyl-benzamide; N-(3-{3-[6-(4-Methoxy-benzylamino)-pyrimidin-4-yl]-3-methyl-ureido}-4-methyl-phenyl)-3-trifluoromethyl-benzamide; N-[4-Methyl-3-(3-methyl-3-{6-[3-(2-oxo-pyrrolidin-1-yl)-propylamino]-pyrimidin-4-yl}-ureido)-phenyl]-3-trifluoromethyl-benzamide; N-{4-Methyl-3-[3-methyl-3-(6-methylamino-pyrimidin-4-yl)-ureido]-phenyl}-3-trifluoromethyl-benzamide; N-(4-Methyl-3-{3-methyl-3-[6-(1-phenyl-ethylamino)-pyrimidin-4-yl]-ureido}-phenyl)-3-trifluoromethyl-benzamide; N-(4-Methyl-3-{3-methyl-3-[6-(3-morpholin-4-yl-propylamino)-pyrimidin-4-yl]-ureido}-phenyl)-3-trifluoromethyl-benzamide; N-{3-[3-(6-Cyclopentylamino-pyrimidin-4-yl)-3-methyl-ureido]-4-methyl-phenyl}-3-trifluoromethyl-benzamide; N-(3-{3-[6-(2-Diisopropylamino-ethylamino)-pyrimidin-4-yl]-3-methyl-ureido}-4-methyl-phenyl)-3-trifluoromethyl-benzamide; N-(4-Methyl-3-{3-methyl-3-[6-(2-pyridin-2-yl-ethylamino)-pyrimidin-4-yl]-ureido}-phenyl)-3-trifluoromethyl-benzamide; N-{3-[3-(6-Isopropylamino-pyrimidin-4-yl)-3-methyl-ureido]-4-methyl-phenyl}-3-trifluoromethyl-benzamide; N-[3-(3-{6-[(Furan-2- ylmethyl)-amino]-pyrimidin-4-yl}-3-methyl-ureido)-4-methyl-phenyl]-3-trifluoromethyl-benzamide; N-{3-[3-(6-Amino-pyrimidin-4-yl)-3-methyl-ureido]-4-methyl-phenyl}-3-trifluoromethyl-benzamide; N-(3-{3-[6-(2-Amino-ethylamino)-pyrimidin-4-yl]-3-methyl-ureido}-4-methyl-phenyl)-3-trifluoromethyl-benzamide; N-[3-(3-{6-[2-(4-Fluoro-phenyl)-ethylamino]-pyrimidin-4-yl}-3-methyl-ureido)-4-methyl-phenyl]-3-trifluoromethyl-benzamide; N-(3-{3-[6-(4-Fluoro-benzylamino)-pyrimidin-4-yl]-3-methyl-ureido}-4-methyl-phenyl)-3-trifluoromethyl-benzamide; 3-(6-{1-Methyl-3-[2-methyl-5-(3-trifluoromethyl-benzoylamino)-phenyl]-ureido}-pyrimidin-4-ylamino)-propionic acid; N-(3-{3-[6-(3-Amino-propylamino)-pyrimidin-4-yl]-3-methyl-ureido}-4-methyl-phenyl)-3-trifluoromethyl-benzamide; N-[3-(3-{6-[2-(4-Methoxy-phenyl)-ethylamino]-pyrimidin-4-yl}-3-methyl-ureido)-4-methyl-phenyl]-3-trifluoromethyl-benzamide; N-(3-{3-[6-(6-Methoxy-pyridin-3-ylamino)-pyrimidin-4-yl]-3-methyl-ureido}-4-methyl-phenyl)-3-trifluoromethyl-benzamide; N-(4-Methyl-3-{3-methyl-3-[6-(2-trifluoromethyl-benzylamino)-pyrimidin-4-yl]-ureido}-phenyl)-3-trifluoromethyl-benzamide; N-[3-(3-{6-[(Benzo[1,3]dioxol-5-ylmethyl)-amino]-pyrimidin-4-yl}-3-methyl-ureido)-4-methyl-phenyl]-3-trifluoromethyl-benzamide; N-{4-Methyl-3-[3-methyl-3-(6-morpholin-4-yl-pyrimidin-4-yl)-ureido]-phenyl}-3-trifluoromethyl-benzamide; N-(4-Methyl-3-{3-methyl-3-[6-(2-morpholin-4-yl-ethylamino)-pyrimidin-4-yl]-ureido}-phenyl)-3-trifluoromethyl-benzamide; N-(4-Methyl-3-{3-methyl-3-[6-((3-methyl-amino-carbonyl-phenyl)-amino)-pyrimidin-4-yl]-ureido}-phenyl)-3-trifluoromethyl-benzamide; N-{3-[3-(6-Cyclopropylamino-pyrimidin-4-yl)-3-methyl-ureido]-4-methyl-phenyl}-3-trifluoromethyl-benzamide; N-(4-Methyl-3-{3-methyl-3-[6-((4-amino-carbonyl-phenyl)-amino)-pyrimidin-4-yl]-ureido}-phenyl)-3-trifluoromethyl-benzamide; N-(3-{3-[6-(4-Acetylamino-phenylamino)-pyrimidin-4-yl]-3-methyl-ureido}-4-methyl-phenyl)-3-trifluoromethyl-benzamide; N-[4-Methyl-3-(3-methyl-3-{6-[4-(4-methyl-piperazin-1-ylmethyl)-phenylamino]-pyrimidin-4-yl}-ureido)-phenyl]-3-trifluoromethyl-benzamide; N-(4-Methyl-3-{3-methyl-3-[6-(3-morpholin-4-ylmethyl-phenylamino)-pyrimidin-4-yl]-ureido}-phenyl)-3-trifluoromethyl-benzamide; N-[4-Methyl-3-(3-methyl-3-{6-[3-(morpholine-4-sulfonyl)-phenylamino]-pyrimidin-4-yl}-ureido)-phenyl]-3-trifluoromethyl-benzamide; N-{3-[3-(6-Amino-pyrimidin-4-yl)-3-cyclopentyl-ureido]-4-methyl-phenyl}-3-trifluoromethyl-benzamide; N-{3-[3-(6-Amino-pyrimidin-4-yl)-3-(tetrahydro-furan-2-ylmethyl)-ureido]-4-methyl-phenyl}-3-trifluoromethyl-benzamide; N-{3-[3-(6-Amino-pyrimidin-4-yl)-3-(2-pyrrolidin-1-yl-ethyl)-ureido]-4-methyl-phenyl}-3-trifluoromethyl-benzamide; N-{3-[3-(6-Amino-pyrimidin-4-yl)-3-(5-methyl-pyrazin-2-ylmethyl)-ureido]-4-methyl-phenyl}-3-trifluoromethyl-benzamide; N-{3-[3-(6-Amino-pyrimidin-4-yl)-3-(2-methoxy-1-methyl-ethyl)-ureido]-4-methyl-phenyl}-3-trifluoromethyl-benzamide; N-{3-[3-(6-Amino-pyrimidin-4-yl)-3-pyridin-2-ylmethyl-ureido]-4-methyl-phenyl}-3-trifluoromethyl-benzamide; N-{3-[3-(6-Amino-pyrimidin-4-yl)-3-(2-pyridin-2-yl-ethyl)-ureido]-4-methyl-phenyl}-3-trifluoromethyl-benzamide; N-{3-[3-(6-Amino-pyrimidin-4-yl)-3-morpholin-4-yl-ureido]-4-methyl-phenyl}-3-trifluoromethyl-benzamide; N-(3-{3-(6-Amino-pyrimidin-4-yl)-3-[2-(1-methyl-pyrrolidin-2-yl)-ethyl]-ureido}-4-methyl-phenyl)-3-trifluoromethyl-benzamide; N-(3-{3-(6-Amino-pyrimidin-4-yl)-3-[2-(4-sulfamoyl-phenyl)-ethyl]-ureido}-4-methyl-phenyl)-3-trifluoromethyl-benzamide; N-{3-[3-(6-Amino-pyrimidin-4-yl)-3-(3-morpholin-4-yl-propyl)-ureido]-4-methyl-phenyl}-3-trifluoromethyl-benzamide; N-(3-{3-(6-Amino-pyrimidin-4-yl)-3-[2-(2-fluoro-phenyl)-ethyl]-ureido}-4-methyl-phenyl)-3-trifluoromethyl-benzamide; N-{3-[3-[6-(2,6-Dimethyl-pyridin-3-ylamino)-pyrimidin-4-yl]-3-(2-morpholin-4-yl-ethyl)-ureido]-4-methyl-phenyl}-3-trifluoromethyl-benzamide; N-{3-[3-[6-(4,6-Dimethyl-pyridin-3-ylamino)-pyrimidin-4-yl]-3-(2-morpholin-4-yl-ethyl)-ureido]-4-methyl-phenyl}-3-trifluoromethyl-benzamide; N-{3-[3-(6-Amino-5-methyl-pyrimidin-4-yl)-3-(2-morpholin-4-yl-ethyl)-ureido]-4-methyl-phenyl}-3-trifluoromethyl-benzamide; N-{3-[3-(6-Amino-2-methyl-pyrimidin-4-yl)-3-(2-morpholin-4-yl-ethyl)-ureido]-4-methyl-phenyl}-3-trifluoromethyl-benzamide; 1-(6-Amino-pyrimidin-4-yl)-3-(2,4-dimethoxy-phenyl)-1-(2-morpholin-4-yl-ethyl)-urea; 1-(6-Amino-pyrimidin-4-yl)-3-(2,5-dimethoxy-phenyl)-1-(2-morpholin-4-yl-ethyl)-urea; 1-(6-Amino-pyrimidin-4-yl)-3-(3,4-dimethoxy-phenyl)-1-(2-morpholin-4-yl-ethyl)-urea; 1-(6-Amino-pyrimidin-4-yl)-3-(3,5-dimethoxy-phenyl)-1-(2-morpholin-4-yl-ethyl)-urea; 1-(6-Amino-pyrimidin-4-yl)-3-(3,5-bis-trifluoromethyl-phenyl)-1-(2-morpholin-4-yl-ethyl)-urea; and 1-(6-Amino-pyrimidin-4-yl)-3-(3,5-bis-trifluoromethyl-phenyl)-1-(2-morpholin-4-yl-ethyl)-thiourea.

Further preferred compounds of Formula I** are detailed in the Examples and Table I, infra.

Compounds of Formula I inhibit abl kinase, especially v-abl kinase. The compounds of Formula I also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of Formula I** can inhibit PDGF receptor (PDGFR) activity and are, therefore, suitable for the treatment of tumor diseases, such as gliomas, sarcomas, prostate tumors, and tumors of the colon, breast, and ovary.

Compounds of Formula I can be used not only as a tumor-inhibiting substance, for example in small cell lung cancer, but also as an agent to treat non-malignant proliferative disorders, such as atherosclerosis, thrombosis, psoriasis, scleroderma and fibrosis, as well as for the protection of stem cells, for example to combat the hemotoxic effect of chemotherapeutic agents, such as 5-fluoruracil, and in asthma. Compounds of Formula I can especially be used for the treatment of diseases, which respond to an inhibition of the PDGF receptor kinase.

Compounds of Formula I** show useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchioalveolar lavage fluids.

Compounds of Formula I** are also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the compounds of the present invention, and also by investigating its effect on the thickening of the vascular intima following mechanical injury in vivo.

The compounds of Formula I** also inhibit cellular processes involving stem-cell factor (SCF, also known as the c-kit ligand or steel factor), such as inhibiting SCF receptor (kit) autophosphorylation and SCF-stimulated activation of MAPK kinase (mitogen-activated protein kinase). MO7e cells are a human promegakaryocytic leukemia cell line, which depends on SCF for proliferation. Compounds of the invention can inhibit the autophosphorylation of SCF receptors.

The trk family of neurotrophin receptors (trkA, trkB, trkC) promotes the survival, growth and differentiation of the neuronal and non-neuronal tissues. The TrkB protein is expressed in neuroendocrine-type cells in the small intestine and colon, in the alpha cells of the pancreas, in the monocytes and macrophages of the lymph nodes and of the spleen, and in the granular layers of the epidermis (Shibayama and Koizumi, 1996). Expression of the TrkB protein has been associated with an unfavorable progression of Wilms tumors and of neuroblastomas. TkrB is, moreover, expressed in cancerous prostate cells but not in normal cells. The signaling pathway downstream of the trk receptors involves the cascade of MAPK activation through the Shc, activated Ras, ERK-1 and ERK-2 genes, and the PLC-gammal transduction pathway (Sugimoto et al., 2001).

The kinase, c-Src transmits oncogenic signals of many receptors. For example, over-expression of EGFR or HER3/neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

The Tec family kinase, Bmx, a non-receptor protein-tyrosine kinase, controls the proliferation of mammary epithelial cancer cells.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3, and one mutation, TDII FGFR35, has a constitutive tyrosine kinase activity which activates the transcription factor Stat1, leading to expression of a cell-cycle inhibitor, growth arrest and abnormal bone development (Su et al., Nature, 1997, 386, 288-292). FGFR35 is also often expressed in multiple myeloma-type cancers.

The activity of serum and glucocorticoid-regulated kinase (SGK), is correlated to perturbed ion-channel activities, in particular, those of sodium and/or potassium channels and compounds of the invention can be useful for treating hypertension.

Lin et al (1997) J. Clin. Invest. 100, 8: 2072-2078 and P. Lin (1998) PNAS 95, 8829-8834, have shown an inhibition of tumor growth and vascularization and also a decrease in lung metastases during adenoviral infections or during injections of the extracellular domain of Tie-2 (Tek) in breast tumor and melanoma xenograft models. Tie2 inhibitors can be used in situations where neovascularization takes place inappropriately (i.e. in diabetic retinopathy, chronic inflammation, psoriasis, Kaposi's sarcoma, chronic neovascularization due to macular degeneration, rheumatoid arthritis, infantile haemangioma and cancers).

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis.

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases. As a result of the importance of JNK activation associated with liver disease or episodes of hepatic ischemia, compounds of the invention may also be useful to treat various hepatic disorders. A role for JNK in cardiovascular disease such as myocardial infarction or congestive heart failure has also been reported as it has been shown JNK mediates hypertrophic responses to various forms of cardiac stress. It has been demonstrated that the JNK cascade also plays a role in T-cell activation, including activation of the IL-2 promoter.

Thus, inhibitors of JNK may have therapeutic value in altering pathologic immune responses. A role for JNK activation in various cancers has also been established, suggesting the potential use of JNK inhibitors in cancer. For example, constitutively activated JNK is associated with HTLV-1 mediated tumorigenesis [Oncogene 13:135-42 (1996)]. JNK may play a role in Kaposi's sarcoma (KS). Other proliferative effects of other cytokines implicated in KS proliferation, such as vascular endothelial growth factor (VEGF), IL-6 and TNF☐, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [Blood 92:2450-60 (1998)].

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. For example, expression of the c-raf protein is believed to play a role in abnormal cell proliferation since it has been reported that 60% of all lung carcinoma cell lines express unusually high levels of c-raf mRNA and protein. Further examples of abnormal proliferative conditions are hyper-proliferative disorders such as cancers, tumors, hyperplasia, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

The stress activated protein kinases (SAPKs) are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Therefore, agents that inhibit SAPK activity in a cell prevent DNA repair and sensitize the cell to agents that induce DNA damage or inhibit DNA synthesis and induce apoptosis of a cell or that inhibit cell proliferation.

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I** or a pharmaceutically acceptable salt thereof. For any of the above uses, the required dosage will vary depending on the mode of administration, the particular condition to be treated and the effect desired.

In general, compounds of Formula I** will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of Formula I** can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of Formula I** can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G. FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of Formula I** as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The present invention also includes processes for the preparation of compounds of Formula I**. In the reactions described herein, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Detailed examples of the synthesis of a compound of Formula I can be found in the Examples, infra. The examples include solid phase synthesis of compounds of Formula I.

A compound of Formula (I) (or exemplary formula thereof) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of Formula (I) (or exemplary formula thereof) can besides or in addition be administered especially for tumor therapy, such as leukaemia therapy, in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Therapeutic agents for possible combination are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, and an inhibitor of the interaction of an SH2 domain with a phosphorylated protein. A specific example of a combination agent is (N-{5-[4-(4-methyl-piperazino-methyl)-benzoylamido]-2-methylphenyl}-4-(3-pyridyl)-2-pyrimidine-amine (Glivec®/Gleevec®).

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

In general, the invention relates also to the use of a compound of Formula (I) (or exemplary formula thereof) or a N-oxide thereof for the inhibition of tyrosine kinase activity, either in vitro or in vivo.

With the groups of preferred compounds of Formula (I) (or exemplary formula thereof) and N-oxides thereof, definitions of substituents from the general definitions mentioned hereinbefore may reasonably be used, for example, to replace more general definitions with more specific definitions or especially with definitions characterized as being preferred.

Especially, the invention relates to the use of a compound of Formula (I) (or exemplary formula thereof) or of a N-oxide or a possible tautomer thereof or of a pharmaceutically acceptable salt of such a compound for the preparation of a pharmaceutical composition for the treatment of a disease which responds to an inhibition of protein kinase activity, wherein the disease is a neoplastic disease.

More particularly, the invention relates to the use of a compound of the Formula (I) (or exemplary formula thereof) or of a N-oxide or a possible tautomer thereof; or of a pharmaceutically acceptable salt of such a compound for the preparation of a pharmaceutical composition for the treatment of leukaemia which responds to an inhibition of the Abl, Abl-Bcr, including mutant forms thereof, and VEGF-R2 tyrosine kinase activity.

Particular active products are compounds named in the examples and salts, esters, N-oxides or prodrugs thereof.

In addition, the invention provides a method for the treatment of a disease which responds to an inhibition of protein kinase activity, which comprises administering a compound of Formula (I) (or exemplary formula thereof) or a N-oxide or a pharmaceutically acceptable salt thereof, wherein the radicals and symbols have the meanings as defined above, in a quantity effective against said disease, to a warm-blooded animal requiring such treatment.

A compound of the invention may be prepared by processes that, though not applied hitherto for the new compounds of the present invention, are known per se,
where the compounds and intermediates may also be present with functional groups in protected form if necessary and/or in the form of salts, provided a salt-forming group is present and the reaction in salt form is possible;
any protecting groups in a protected derivative of a compound of the Formula (I) (or exemplary formula thereof) are removed;
and, if so desired, an obtainable compound of Formula (I) (or exemplary formula thereof) is converted into another compound of Formula (I) (or exemplary formula thereof) or a N-oxide thereof, a free compound of Formula (I) (or exemplary formula thereof) is converted into a salt, an obtainable salt of a compound of Formula (I) (or exemplary formula thereof) is converted into the free compound or another salt, and/or a mixture of isomeric compounds of Formula (I) (or exemplary formula thereof) is separated into the individual isomers.

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

Protecting Groups

If one or more other functional groups, for example carboxy, hydroxy, amino, or mercapto, are or need to be protected in a compound of Formula (I) (or exemplary formula thereof) II, because they should not take part in the reaction, these are such groups as are usually used in the synthesis of amides, in particular peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis as cited hereinbefore, and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, "Protective Groups in Organic Synthesis", Wiley, New York.

Pharmaceutical Preparations, Methods, and Uses

The present invention relates also to pharmaceutical compositions that comprise a compound of Formula (I) (or exemplary formula thereof) or a N-oxide thereof as active ingredient and that can be used especially in the treatment of the aforementioned diseases.

The pharmacologically acceptable compounds of the present invention may be used, for example, for the preparation of pharmaceutical compositions that comprise a pharmaceutically effective amount of a compound of the Formula (I) (or exemplary formula thereof), or a pharmaceutically acceptable salt thereof, as active ingredient together or in admixture with a significant amount of one or more inorganic or organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, e.g. lymphocytes), for the treatment or, in a broader aspect of the invention, prevention of (=prophylaxis against) a disease that responds to inhibition of tyrosin protein kinase activity, especially one of the diseases mentioned above as being preferred for use of a compound of Formula (I) (or exemplary formula thereof), comprising an amount of a novel compound of Formula (I) (or exemplary formula thereof), or a pharmaceutically acceptable salt thereof, which is effective for said inhibition, together with at least one pharmaceutically acceptable carrier.

Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of Formula (I) (or exemplary formula thereof), a tautomer, a N-oxide or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, to a process for the preparation thereof (especially in the form of compositions for the treatment of tumors) and to a method of treating tumor diseases, especially those mentioned hereinabove.

The invention relates also to processes and to the use of compounds of Formula (I) (or exemplary formula thereof) or N-oxides thereof for the preparation of pharmaceutical preparations which comprise compounds of Formula (I) (or exemplary formula thereof) or N-oxides thereof as active component (active ingredient).

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, sprays, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents or solubilizers, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls A G, Germany), but especially vegetable oils, such as cottonseed oil, almond oil, olive oil, castor oil, sesame oil, soybean oil and more especially groundnut oil.

Injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or dragée coatings or the capsule casings, for example for identification purposes or to indicate different doses of active ingredient.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations.

Pharmaceutical compositions for oral administration also include hard capsules consisting of gelatin, and also soft, sealed capsules consisting of gelatin and a plasticizer. The hard capsules may contain the active ingredient in the form of granules, for example in admixture with fillers, binders, and/or glidants, and optionally stabilizers. In soft capsules, the active ingredient is preferably dissolved or suspended in suitable liquid excipients, to which stabilizers and detergents may also be added.

Pharmaceutical compositions suitable for rectal administration are, for example, suppositories that consist of a combination of the active ingredient and a suppository base.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

The invention relates likewise to a process or a method for the treatment of one of the pathological conditions mentioned hereinabove, especially a disease which responds to an inhibition of a tyrosine kinase, especially a corresponding neoplastic disease. The compounds of Formula (I) (or exemplary formula thereof) or N-oxides thereof can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

The invention also provides for a method of treating a protein kinase dependent disease, comprising administering to a warm-blooded animal, for example a human, one or more cytostatic or cytotoxic compounds e.g. Glivec® in combination with a compound of the invention, whether at the same time, or a separate time. The term "the same time" is taken to mean in quick succession or immediately after one another.

The present invention relates especially also to the use of a compound of Formula (I) (or exemplary formula thereof) or N-oxides thereof, or a pharmaceutically acceptable salt thereof, especially a compound of Formula (I) (or exemplary formula thereof) which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of a protein kinase, especially a neoplastic disease, more especially leukaemia which responds to an inhibition of the Abl tyrosine kinase.

The preferred dose quantity, composition, and preparation of pharmaceutical formulations (medicines) which are to be used in each case are described above.

A compound of the Formula (I) (or exemplary formula thereof) may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be Formulated as disclosed in U.S. Pat. No. 4,659,516 or it can be administered, e.g., in the form as it is marketed, e.g. under the trademark FASLODEX™.

The term "topoisomerase I inhibitors" as used herein includes, but is not limited to topotecan, irinotecan, 9-nitrocamptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal Formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTINR.P.™. Vincristine sulfate can be administered, e.g., in the form as it is marketed, e.g. under the trademark FARMISTIN™.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enzyme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cisplatin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, the Platelet-derived Growth Factor (PDGF), Bcr-Abl, c-Kit, Flt-3, the Insulin-like Growth Factor I Receptor (IGF-IR) and the Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958, WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™, described by M. S. O'Reilly et al, Cell 88, 1997, 277-285;

compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266, EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but are not limited to, compounds inhibiting the c-Src protein tyrosine kinase activity as defined below and to SH2 interaction inhibitors such as those disclosed in WO97/07131 and WO97/08193; compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d] pyrimidines. Preferably, the term relates to those compounds disclosed in WO 96/10028, WO 97/28161, WO97/32879 and WO97/49706; compounds which decreases the activity of the protein kinase C are especially those staurosporine derivatives disclosed in EP 0 296 110 (pharmaceutical preparation described in WO 00/48571) which compounds are protein kinase C inhibitors; further specific compounds that decrease protein kinase activity and which may also be used in combination with the compounds of the present invention are Imatinib (Gleevec®/Glivec®), PKC412, Iressa™ (ZD1839), PKI166, PTK787, ZD6474, GW2016, CHIR-200131, CEP-7055/CEP-5214, CP-547632, KRN-633 and SU5416;

anti-angiogenic compounds having another mechanism of action than decreasing the protein kinase activity include, but are not limited to e.g. thalidomide (THALOMID), celecoxib (Celebrex) and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be Formulated, e.g. as disclosed in U.S. Pat. No. 5,843,901.

The term "anti-androgens" as used herein includes, but is not limited to bicalutamide (CASODEX™), which can be Formulated, e.g. as disclosed in U.S. Pat. No. 4,636,505.

The term "bengamides" relates to bengamides and derivatives thereof having aniproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

For the treatment of acute myeloid leukemia (AML), compounds of Formula (I) (or exemplary formula thereof) can be used in combination with standard leukemia therapies, especially in combination with therapies used for the treatment of AML. In particular, compounds of Formula (I) (or exemplary formula thereof) can be administered in combination with e.g. farnesyltransferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the Formula (I) (or exemplary formula thereof), can be prepared and administered as described in the art such as in the documents cited above.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the H⁺ form, depending on the type of reaction and/or reactants at reduced, normal, or elevated temperature, for example in the range from −100° C. to about 190° C., preferably from about −80° C. to about 150° C., for example at −80 to −60° C., at room temperature, at −20 to 40° C. or at the boiling point of the solvent used, under atmospheric pressure or in a closed vessel, where appropriate under pressure, and/or in an inert atmosphere, for example under argon or nitrogen.

It should be emphasized that reactions analogous to the conversions mentioned in this chapter may also take place at the level of appropriate intermediates.

Detailed Description of the Process

The heteroaryl aryl ureas of the present invention may be prepared according to methods known in the art.

According to a general exemplary process, compounds of having the structure of general formula (I), may be prepared by reacting a heteroaryl amine of general Formula (VIII) with an aryl isocyanate of general Formula (IX):

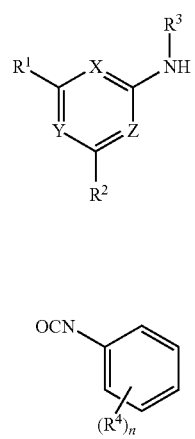

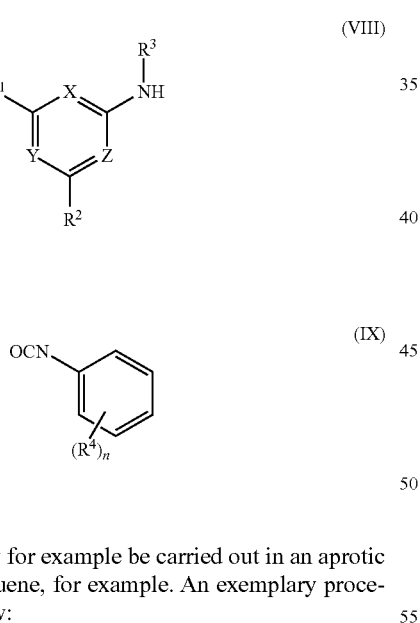

The reaction may for example be carried out in an aprotic solvent, such as toluene, for example. An exemplary procedure is shown below:

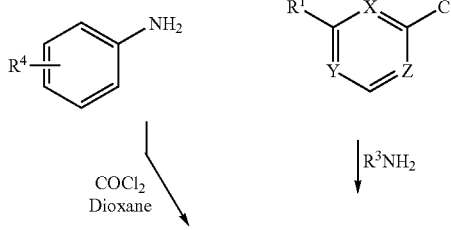

A preferred embodiment is as follows:

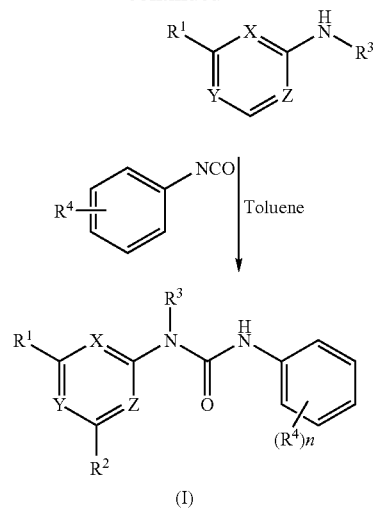

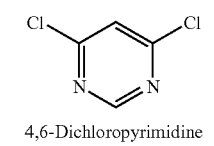

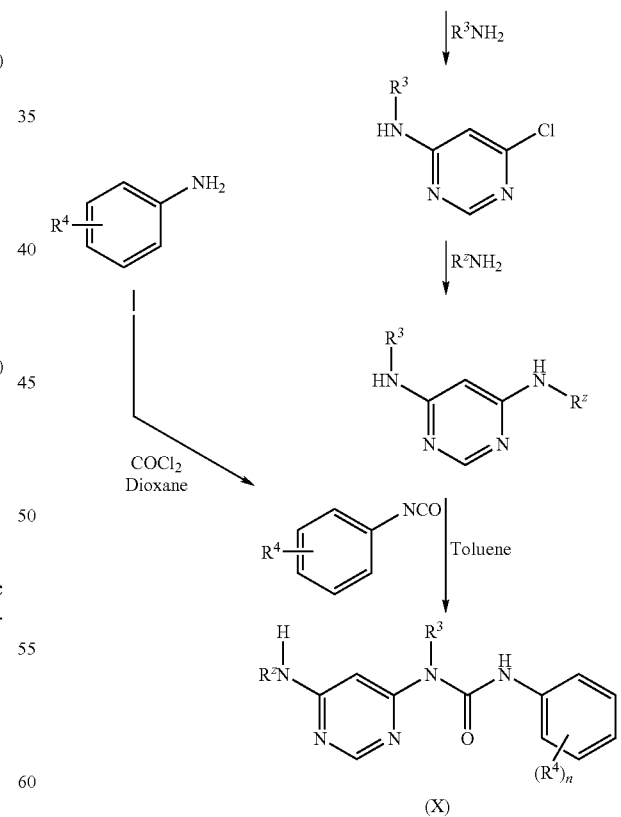

According to a general exemplary process, compounds of having the structure of general formula (I*), may be prepared by reacting a heteroaryl amine of general Formula (VIIIp) with an aryl isocyanate of general Formula (IXp):

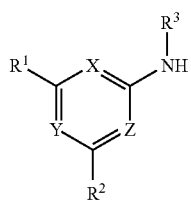
(VIIIp)
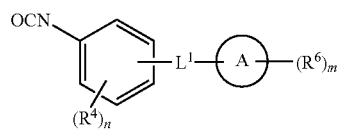
(IXp)
The reaction may for example be carried out in an aprotic solvent, such as toluene, for example. An exemplary procedure is shown below:
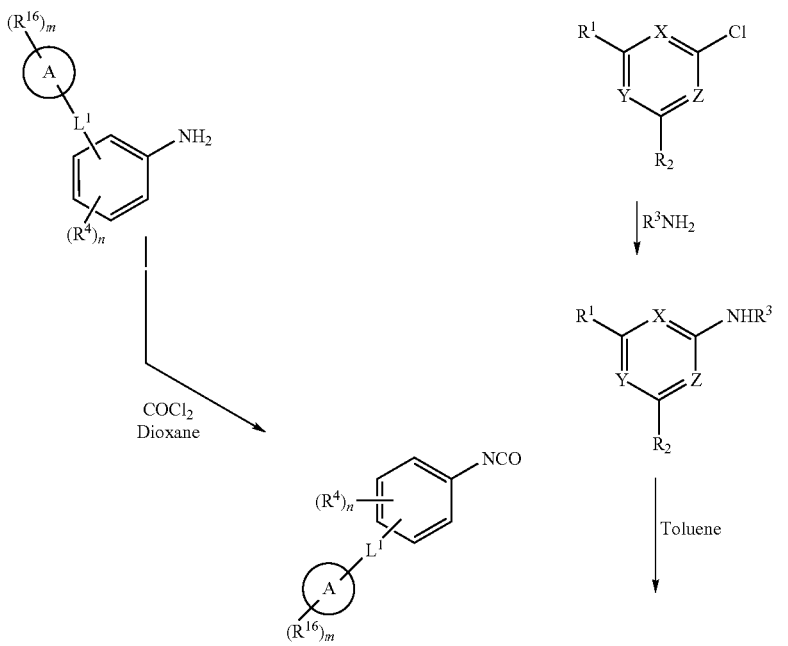
(I)
A preferred embodiment is as follows:
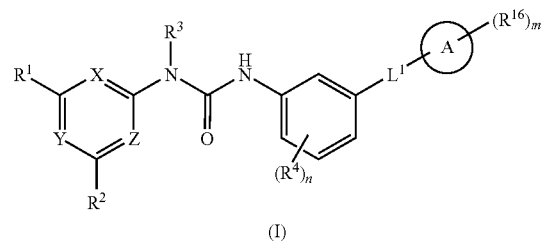
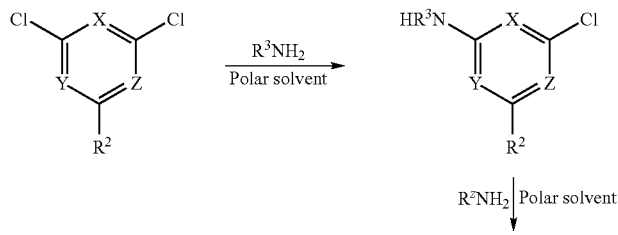

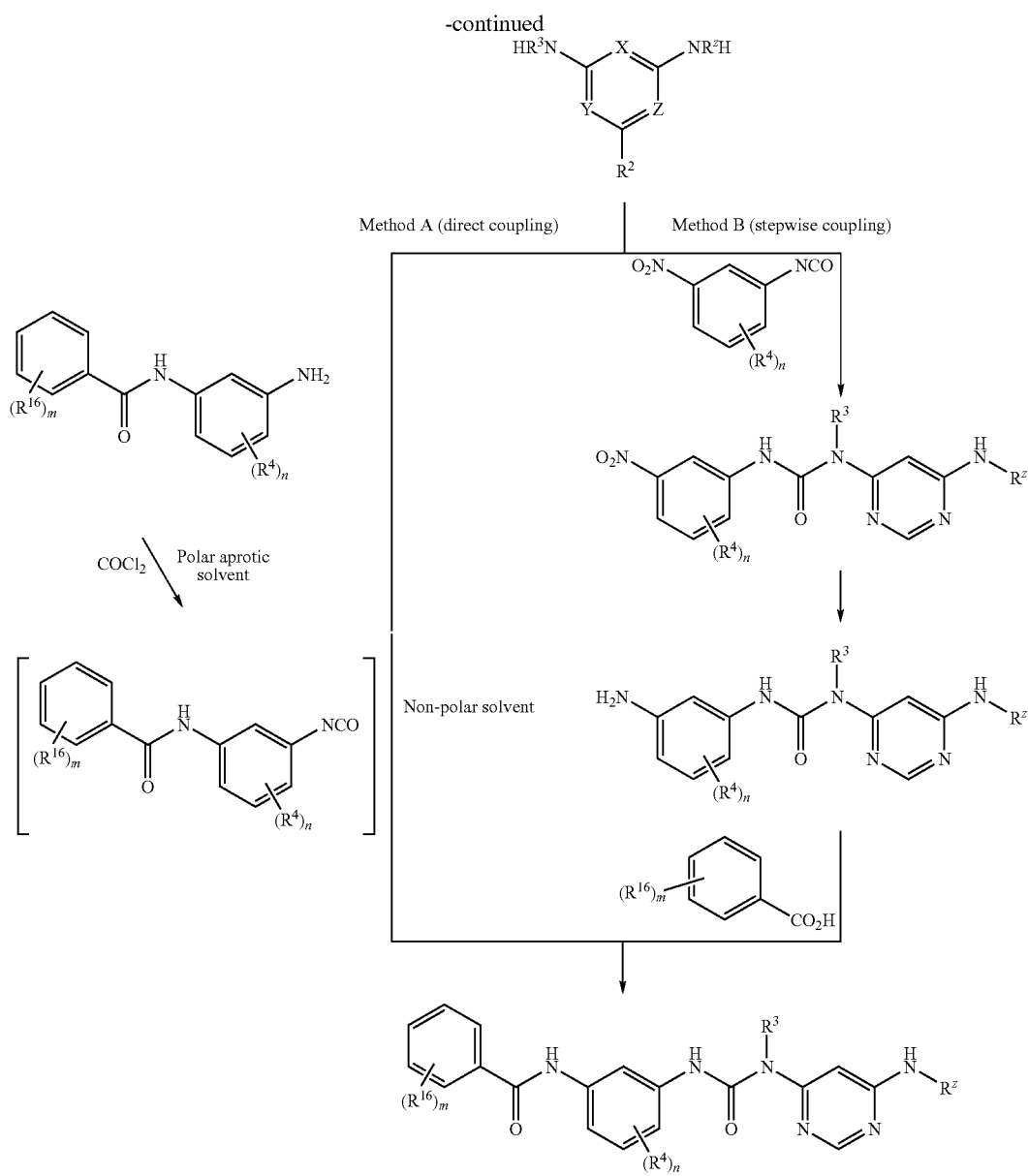

Additional Process Steps

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of Formula (I) (or exemplary formula thereof) with a salt-forming group may be prepared in a manner known per se. Acid addition salts of compounds of Formula (I) (or exemplary formula thereof) may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of Formula (I) (or exemplary formula thereof) itself. Enantiomers may be separated through the formation of diastereomeric salts, for example by salt formation with an enantiomer-pure chiral acid, or by means of chromatography, for example by HPLC, using chromatographic substrates with chiral ligands.

A compound of the invention, where hydrogen is present, can be converted to the respective compound wherein $R^3$ or $R^z$ is lower alkyl by reaction e.g. with a diazo lower alkyl compound, especially diazomethane, in an inert solvent, preferably in the presence of a noble metal catalyst, especially in dispersed form, e.g. copper, or a noble metal salt, e.g. copper (I)-chloride or copper(II)-sulfate. Also reaction with lower alkylhalogenides is possible, or with other leaving group carrying lower alkanes, e.g. lower alkyl alcohols esterified by a strong organic sulfonic acid, such as a lower alkanesulfonic acid (optionally substituted by halogen, such as fluoro), an aromatic sulfonic acid, for example unsubstituted or substituted benzenesulfonic acid, the substituents preferably being selected from lower alkyl such as methyl, halogen, such as bromo, and/or nitro, e.g. esterified by methanesulfonic acid, or p-toluene sulfonic acid. The alkylation takes place under usual conditions for alkylation of amides, especially in aqueous solution and/or in the presence of polar solvents, typically alcohols, for example methanol, ethanol, isopropanol, or ethylene glycol, or dipolar aprotic solvents, e.g. tetrahydrofuran, dioxane, or dimethylformamide, where applicable in the presence of acidic or basic catalysts, generally at temperatures from about 0° C. to the boiling temperature of the corresponding reaction mixture, preferably between 20° C. and reflux temperature, if necessary under increased pressure, e.g. in a sealed tube, and/or under inert gas, typically nitrogen or argon.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described hereinabove as preferred, particularly as especially preferred, primarily preferred, and/or preferred above all.

In the preferred embodiment, a compound of Formula (I) (or exemplary formula thereof) is prepared according to or in analogy to the processes and process steps defined in the Examples.

The compounds of Formula (I) (or exemplary formula thereof), including their salts, are also obtainable in the form of hydrates, or their crystals can include for example the solvent used for crystallization (present as solvates).

EXAMPLES

The following Examples serve to illustrate the invention without limiting the scope thereof.

Temperatures are measured in degrees Celsius. Unless otherwise indicated, the reactions take place at room temperature under $N_2$-atmosphere.

The $R_f$ values which indicate the ratio of the distance moved by each substance to the distance moved by the eluent front are determined on silica gel thin-layer plates (Merck, Darmstadt, Germany) by thin-layer chromatography using the respective named solvent systems.

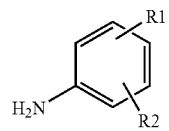

Most respective anilines are described in WO 03/099771 or can be prepared analogously to the therein exemplified derivatives. All others are described elsewhere.

General Synthesis Scheme:

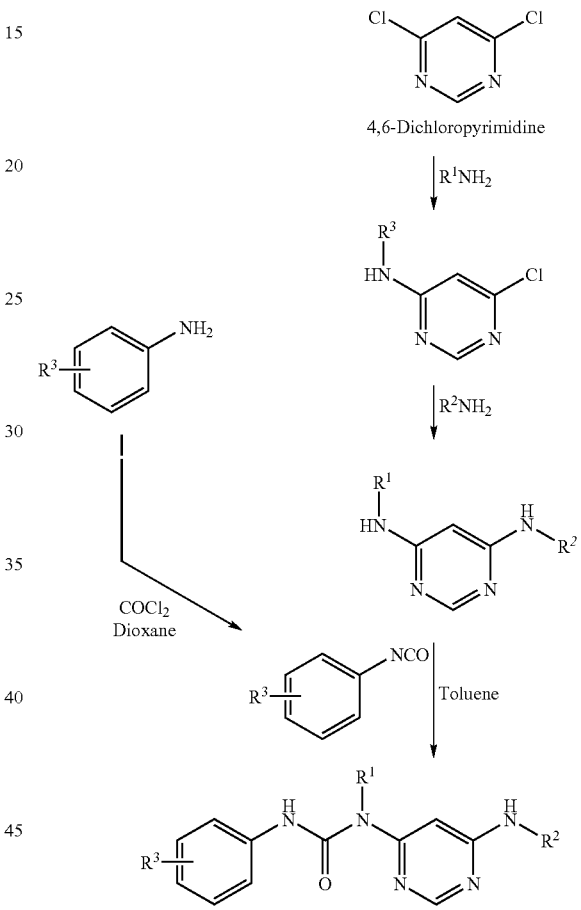

HPLC Conditions

Gradient A: Performed on a Waters system equipped with a CTC Analytics HTS PAL autosampler, 515 pumps, and a 996 DAD detector operating at 210 nm. Column: CC70/3 Nucleosil 100-3 $C_{18}$ (3μ, 70×3 mm, Macherey-Nagel, order # 721791.30), temperature: 45° C., flow: 1.2 mL min$^{-1}$. Eluents: A: Water+0.2% $H_3PO_4$ (85%, (Merck 100552)+2% Me$_4$NOH, (10%, Merck 108123), B: Acetonitrile+20% water+0.1% $H_3PO_4$ (85%)+1% Me$_4$NOH (10%). Gradient: 0% B to 95% B within 6.6 min., then 95% B 4.4 min.

Gradient B: Linear gradient 20-100% $CH_3CN$ (0.1% TFA) and $H_2O$ (0.1% TFA) in 7 min+2 min 100% $CH_3CN$ (0.1% TFA); detection at 215 nm, flow rate 1 mL/min at 30° C. Column: Nucleosil 100-3 C18 (125×4.0 mm).

Gradient C: Column: (50×4.6 mm) packed with reversed-phase material C18-Nucleosil (Interchrom UP3ODB-5QS, Optisphere 3 μM ODB). Detection by UV absorption at 215 nm. The retention times ($t_R$) are given in minutes. Flow rate:

2 ml/min. Gradient: 20%→100% a) in b) for 14 min+5 min 100% a). a): Acetonitrile+0.1% TFA; b): water+0.1% TFA.

Gradient D: Column: (50×4.6 mm) packed with reversed-phase material C18-Nucleosil (Interchrom UP3ODB-5QS, Optisphere 3 μM ODB). Detection by UV absorption at 215 nm. The retention times ($t_R$) are given in minutes. Flow rate: 2 ml/min. Gradient: 15%→100% a) in b) for 2.25 min+1.25 min 100% a). a): Acetonitrile+0.1% TFA; b): water+0.1% TFA.

Gradient E: Column: (50×4.6 mm) packed with reversed-phase material C18-Nucleosil (Interchrom UP3ODB-5QS, Optisphere 3 μM ODB). Detection by UV absorption at 215 nm. The retention times ($t_R$) are given in minutes. Flow rate: 2 ml/min. Gradient: 5%→60% a) in b) for 9 min+7 min 60% a). a): Acetonitrile+0.1% TFA; b): water+0.1% TFA.

Gradient F: Column: (125×4 mm) packed with Nucleosil 100-5 C18 AB. Detection by UV absorption at 215 nm. The retention times ($t_R$) are given in minutes. Flow rate: 1.5 ml/min. Linear gradient: 5%-100% CH$_3$CN (0.1% TFA) and H$_2$O (0.1% TFA) in 5 min, then 100% CH$_3$CN (0.1% TFA) for 1 min.

Gradient G: Column: (125×4 mm) packed with Nucleosil 100-5 C18 AB. Detection by UV absorption at 215 nm. The retention times ($t_R$) are given in minutes. Flow rate: 1.5 ml/min. Linear gradient: 10%-100% CH$_3$CN (0.1% TFA) and H$_2$O (0.1% TFA) in 5 min, then 100% CH$_3$CN (0.1% TFA) for 1 min.

Gradient H: Column: (125×4 mm) packed with Nucleosil 100-5 C18 AB. Detection by UV absorption at 215 nm. The retention times ($t_R$) are given in minutes. Flow rate: 1.5 ml/min. Linear gradient: 30%-100% CH$_3$CN (0.1% TFA) and H$_2$O (0.1% TFA) in 5 min, then 100% CH$_3$CN (0.1% TFA) for 1 min.

Gradient I: Column: (250×4 mm) packed with Nucleosil 100-5 C18 AB. Detection by UV absorption at 215 nm. The retention times ($t_R$) are given in minutes. Flow rate: 2 ml/min. Linear gradient: 2%-100% CH$_3$CN (0.1% TFA) and H$_2$O (0.1% TFA) in 10 min, then 100% CH$_3$CN (0.1% TFA) for 3 min.

Gradient J: Linear gradient 20-100% CH$_3$CN in 5 min+1.5 min 100% CH$_3$CN (0.1% TFA); detection at 215 nm, flow rate 1 ml/min at 30° C. Column: Nucleosil 100-3 C18 (70×4.0 mm).

Abbreviations

| | |
|---|---|
| Ac = | Acetyl |
| AcCN = | Acetonitrile |
| Anal. elemental analysis (for indicated atoms, difference between calculated and measured value ≤0.4%) | |
| Brine = | saturated aqueous solution of sodium chloride |
| conc. | concentrated |
| d | day(s) |
| DCM = | Dichloromethane |
| DIPE | diisopropyl-ether |
| DIPEA = | N,N-Diisopropylethylamine |
| DMAP | dimethylaminopyridine |
| DMEU | 1,3-dimethyl-2-imidazolidinone |
| DMF | dimethyl formamide |
| DMSO = | Dimethylsulfoxide |
| EE = | Ethyl acetate |
| ESI-MS = | Electro-spray ionization mass spectroscopy |
| Ether | diethylether |
| EtOAc | ethyl acetate |
| EtOH = | Ethanol |
| Et$_3$N | triethylamine |
| Ex. | Example |
| h | hour(s) |
| HATU = | O-(7-Azobenzotriazol-1-yl)-1,1,3,3-tetramethyluronium hexafluorophosphate |
| HPLC = | High performance liquid chromatography |
| Hx = | Hexanes |
| L | liter(s) |
| Me | methyl |
| MeOH = | Methanol |
| min | minute(s) |
| m.p. = | Melting point |
| MPLC | medium pressure liquid chromatography |
| Combi Flash system: normal phase SiO$_2$ | |
| Gilson system: reversed phase Nucleosil C18 (H$_2$O/CH$_3$CN + TFA), generally product obtained as free base after neutralization with NaHCO$_3$ | |
| MS | mass spectrum |
| NEt$_3$ | triethylamine |
| NMP = | N-methyl-pyrrolidinone |
| NMR = | Nuclear magnetic resonance spectroscopy |
| Pd(PhCN)$_2$Cl$_2$ = | Bis(benzonitrile)palladium (II) chloride |
| R$_f$= | Retention factor (TLC) |
| RT = | Room temperature |
| sat. | saturated |
| TBME = | tert.-Butyl methyl ether |
| TFA = | Trifluoroacetic acid |
| THF = | Tetrahydrofuran |
| TLC = | Thin layer chromatography |
| $t_R$ = | Retention time (HPLC) |
| triphosgene | bis(trichloromethyl) carbonate |

PREPARATIONS

Preparation 1

2,6-Dichloro-3-methoxyisocyanate

To a solution of 2,6-dichloro-3-methoxyaniline (0.25 g, 1.30 mmol, 1.0 eq.) in dioxane (7.5 ml) is added a 20% phosgene solution in toluene (0.69 ml, 1.30 mmol, 1.0 eq.) via a hypodermic syringe. The light brown reaction mixture is stirred under nitrogen at room temperature over night. The obtained clear solution is high vacuum evaporated using a rotary evaporator at 45° C. bath temperature to afford a brown oil that solidifies upon standing: 400 MHz $^1$H-NMR (CDCl$_3$) δ: 3.90 (s, 3H, OMe), 6.72 (d, 1H, Ar—H4), 7.27 (d, 1H, Ar—H5).

2,6-Dichloro-3-methoxyaniline

To a solution of 2,4-dichloro-3-aminophenol hydrochloride (GLSynthesis, 7.70 g, 35.9 mmol, 1.0 eq.) in acetone (75 ml) is added powdered potassium hydroxide 85% (9.48 g, 143.6 mmol, 4.0 eq.) in small portions. Then, dimethyl sulfate (5.13 ml, 53.9 mmol, 1.5 eq.) is added at such a rate that the internal temperature does not rise above 30° C. After 1 h stirring at room temperature water (50 ml) is added and stirring is continued for another hour. The solvent is evaporated and the residue is distributed between ethyl acetate (150 ml) and water (100 ml). The organic layer is isolated, dried over Na$_2$SO$_4$ and evaporated to give a yellow oil. Kugelrohr distillation affords the desired product as a colorless oil: b.p. 150° C./0.3 mbar, HPLC: $t_R$=5.61 min (purity: 90%, gradient A), 400 MHz $^1$H-NMR (CDCl$_3$) δ: 3.87 (s, 3H, OMe), 4.49 (br s, 2H, NH$_2$), 6.30 (d, 1H, Ar—H4), 7.11 (d, 1H, Ar—H5).

Preparation 2

2,6-Dichloro-3,5-dimethoxyaniline

To a solution of N-(2-chloro-3,5-dimethoxy-phenyl)-acetamide (6.72 g, 25.4 mmol) in ethanol (400 ml) is added 3M KOH (134 ml). Then, the reaction mixture is refluxed for 90 h. After cooling water (270 ml) is added dropwise with vigorous stirring. The precipitate formed is filtered off, washed (1×EtOH/water 1:1, 50 ml, 1× water, 100 ml), and vacuum dried at 50° C. overnight. The title compound was obtained as colorless crystals: HPLC: $t_R$=5.43 min (purity: >99%, gradient A), ESI-MS: 221.9/223.9/225.8 [MH]$^+$, 400 MHz $^1$H-NMR (CDCl$_3$) δ: 3.89 (s, 6H, 2× OMe), 4.56 (br s, 2H, NH$_2$), 6.03 (s, 1H, Ar—H4).

N-(2-chloro-3,5-dimethoxy-phenyl)-acetamide

Sulfurylchloride (26.9 ml, 325 mmol, 1.93 eq.) is added (in 7 min) to a cold (0° C.) suspension of N-(3,5-dimethoxyphenyl)-acetamide (32.9 g, 169 mmol) in AcCN (500 ml), under an inert atmosphere. The resulting yellowish is allowed to stir 30 min and quenched by dropwise addition of a saturated aqueous solution of sodium bicarbonate (250 ml). The resulting precipitate is collected by vacuum filtration, washed with water (300 ml) and dried to afford 20 g of the desired product (batch 1). The filtrate is diluted with a saturated aqueous solution of sodium bicarbonate (300 ml) and extracted with EE (2×300 ml). The organic phase is washed with water and brine, dried (sodium sulphate), filtered and concentrated. The residue is purified by silica gel column chromatography (EE/Hx, 1:1→2:1) to provide 8.8 g of product (batch 2). Batch 1 and 2 are combined and stirred in hexane. The solid is collected by filtration, washed with hexane and dried to afford 25.8 g of the title compound as a white solid. ESI-MS: 264.0/266.0 [MH]$^+$.

Preparation 3

N-(3-Amino-4-methyl-phenyl)-3-trifluoromethyl-benzamide

A suspension of N-(4-methyl-3-nitro-phenyl)-3-trifluoromethyl-benzamide (9.91 g, 30.6 mmol) and 10% palladium on charcoal (990 mg) in ethanol (180 ml) is hydrogenated at atmospheric pressure and room temperature. After 2 h the reaction is complete, the catalyst is removed by filtration through Celite, and the filtrate is evaporated to dryness. Recrystallization of the crude product from ethyl acetate/hexanes followed by vacuum drying at 45° C. overnight affords the title compound as fluffy light grey needles: HPLC: $t_R$=5.38 min (purity: >99%, gradient A), ESI-MS: 295.3 [MH]$^+$ N-(4-methyl-3-nitro-phenyl)-3-trifluoromethyl-benzamide To a solution of 4-methyl-3-nitroaniline (5 g, 32.2 mmol, 1.0 eq.) and triethylamine (5.38 ml, 38.6 mmol, 1.2 eq.) in dichloromethane (100 ml) is added a solution of 3-trifluoromethylbenzoyl chloride 33.8 mmol, 1.05 eq.) within 30 min. The suspension formed is stirred for 1 h at room temperature. Then, the reaction mixture is diluted with dichloromethane (800 ml) and extracted with water (100 ml), 2M aqueous Na$_2$CO$_3$ (100 ml), 2M HCl (100 ml), water (100 ml). The organic layer is dried over Na$_2$SO$_4$, evaporated to a volume of about 100 ml and diluted with hexanes (100 ml). The precipitate is filtered off, washed with hexanes/dichloromethane 1:1 and hexanes. Vacuum drying over night at room temperatures gives light yellow fine needles: HPLC: $t_R$=6.72 min (purity: >99%, gradient A), ESI-MS: 325.2 [MH]$^+$ Preparation 4

4-(4-Methyl-piperazin-1-ylmethyl)-3-trifluoromethyl-benzoic acid

To a solution of ethyl 4-(4-methyl-piperazin-1-ylmethyl)-3-trifluoromethyl-benzoate (7.23 g, 21.1 mmol, 1.0 eq.) in ethanol (40 ml) is added 1M NaOH (30.6 ml, 30.6 mmol, 1.4 eq.). After stirring for 2 h at room temperature a clear pale yellow solution is obtained. The mixture is evaporated to a volume of 30 ml. Then, the solution is adjusted to pH 7 by addition of 1M HCl and the solvent is stripped off. The residue is taken up three times in toluene (70 ml) and evaporated. The crude material is dissolved in ethanol/THF 1:9 (150 ml), filtered, evaporated, triturated with ethyl acetate, and vacuum dried at 60° C. over night to afford a beige powder: HPLC: $t_R$=3.61 min (purity: >99%, gradient A), ESI-MS: 303.3 [MH]$^+$ Ethyl 4-(4-methyl-piperazin-1-ylmethyl)-3-trifluoromethyl-benzoate To a solution of N-methylpiperazine (5.8 g, 57.9 mmol, 1.0 eq.) in tetrahydrofuran (225 ml) containing anhydrous finely ground potassium carbonate (10.4 g, 75.2 mmol, 1.3 eq.) is added a solution of ethyl 4-bromomethyl-3-trifluoromethyl-benzoate (18.0 g, 57.9 mmol, 1.0 eq.) in tetrahydrofuran with vigorous mechanical stirring within 20 min. Stirring is continued at room temperature for 20 h. The obtained suspension is filtered, and the filtrate is evaporated to give a brown oil. The crude product is purified by medium pressure chromatography (290 g silica gel, gradient: TBME to EtOH/TBME 1:4 within 30 min, then 25% NH$_3$/EtOH/TBME 1:19:80 for 60 min). The fractions containing the title compound are pooled and evaporated to afford a yellow oil: HPLC: $t_R$=4.75 min (purity: >99%, gradient A), ESI-MS: 331.4 [MH]$^+$.

Ethyl 4-bromomethyl-3-trifluoromethyl-benzoate

A mixture of ethyl 4-methyl-3-trifluoromethylbenzoate (25.19 g, 108.5 mmol, 1.0 eq.), N-bromosuccinimide (19.94 g, 112.02 mmol, 1.03 eq.) and benzoyl peroxide (0.21 g, 0.83 mmol, 0.75 mol %) is heated to reflux and illuminated by a 100 W daylight lamp for 7 h. After cooling to room temperature the formed succinimide is filtered off. The filtrate is evaporated to dryness giving a yellow oil. Flash chromatography (TBME/hexanes) gives a colorless oil that solidifies upon standing: HPLC: $t_R$=7.17 min (purity: 97%, gradient A), TLC: $R_f$=0.30 (TBME/hexanes 1:9).

Ethyl 4-methyl-3-trifluoromethylbenzoate

A solution of commercially available 4-methyl-3-trifluoromethylbenzoic acid (24.5 g, 120 mmol) and conc. sulfuric acid (6.5 ml) in dry ethanol (245 ml) is refluxed for 23 h. After reaching room temperature the solvent is evaporated and the residue is neutralized by addition of saturated aqueous NaHCO$_3$ solution. The mixture is extracted with ethyl acetate (3×40 ml). The organic extracts are combined, dried over Na$_2$SO$_4$ and evaporated to dryness to afford a pale yellow oil: HPLC: $t_R$=7.15 min (purity: >96%, gradient A), ESI-MS: 233.3 [MH]$^+$.

Example 1

3-(2,6-Dichloro-3-methoxy-phenyl)-1-methyl-1-{6-[4-(4-methyl-piperazin-1-yl)-phenylamino]-pyrimidin-4-yl}-urea

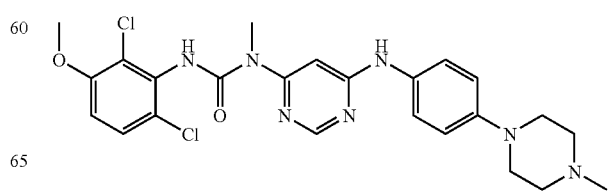

To a solution of 2,6-dichloro-3-methoxyphenylisocyanate (preparation 1, 52.3 mg, 0.24 mmol, 1.2 eq.) in toluene (2.5 ml) is added N-methyl-N'-[4-(4-methyl-piperazin-1-yl)-phenyl]-pyrimidine-4,6-diamine (59.7 mg, 0.2 mmol, 1.0 eq.). The obtained suspension is stirred under argon at 110° C. for 17 h. After cooling the crude product is filtered off und purified by flash chromatography (100% DCM to 5% MeOH in DCM within 35 min). Fractions containing the product are pooled and evaporated to dryness. The residue is triturated with ether (2 ml) and treated with ultra sound until a homogeneous suspension is obtained. The precipitate is filtered off and vacuum dried at 60° C. over night to afford the title compound as a colorless powder: m.p. 161.5-163° C., HPLC: $t_R$=5.07 min (purity: >99%, gradient A), ESI-MS: 516.6/518.5/520.4 [MH]+.

N-Methyl-N'-[4-(4-methyl-piperazin-1-yl)-phenyl]-pyrimidine-4,6-diamine

A solution of (6-chloro-pyrimidin-4-yl)-methyl-amine (1.65 g, 11.5 mmol, 1.1 eq.) and commercially available 4-(4-methylpiperazin-1-yl)-aniline (2.0 g, 10.5 mmol, 1.0 eq.) in a mixture of water (4 ml) and glacial acetic acid (16 ml) is heated to 100° C. internal temperature for 16 h. After cooling the solvent is evaporated.

The residue is taken up in methanol (50 ml) and made alkaline by addition of 25% NH$_3$ in water. To this silica gel (11 g) is added and the solvent is evaporated. The silica adsorbed crude product is purified by medium pressure liquid chromatography (A: TBME; B: MeOH—NH$_3$ 99:1; gradient: 5% B->25% B in 180 min). The fractions containing the product are pooled and evaporated to dryness. The residue is triturated with ether. The product is filtered off, washed with ether, and vacuum dried at 50° C. over night to give the title compound as pale yellow powder: $t_R$=3.04 min (purity: 97%, gradient A), ESI-MS: 299.3 [MH]+.

(6-chloro-pyrimidin-4-yl)-methyl-amine

This material was prepared by a modified procedure published in the literature (*J. Appl. Chem.* 1955, 5, 358): To a suspension of commercially available 4,6-dichloropyrimidine (20 g, 131.6 mmol, 1.0 eq.) in isopropanol (60 ml) is added 33% methylamine in ethanol (40.1 ml, 328.9 mmol, 2.5 eq.) at such a rate that the internal temperature does not rise above 50° C. After completion of the addition the reaction mixture was stirred for 1 h at room temperature. Then, water (50 ml) is added and the suspension formed is chilled in an ice bath to 5° C. The precipitated product is filtered off, washed with cold isopropanol/water 2:1 (45 ml) and water. The collected material is vacuum dried over night at 45° C. to afford the title compound as colorless powder: $t_R$=3.57 min (purity: >99%, gradient A), ESI-MS: 144.3/146.2 [MH]+.

Example 2

3-(2,6-Dichloro-3,5-dimethoxy-phenyl)-1-methyl-1-{6-[4-(4-methyl-piperazin-1-yl)-phenylamino]-pyrimidin-4-yl}-urea

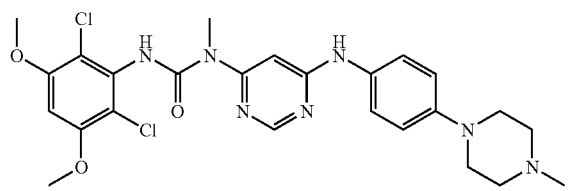

To a solution of 2,6-dichloro-3,5-dimethoxyaniline (preparation 2, 74 mg, 0.34 mmol, 1.25 eq.) in dioxane is added 20% phosgene solution in toluene (191 μl, 0.36 mmol, 1.35 eq.) under argon. The reaction mixture is stirred for further 6 h at room temperature under argon. Then, the solvent is evaporated and the colorless crystalline residue is taken up in dry toluene (2.5 ml). After the addition of N-methyl-N'-[4-(4-methyl-piperazin-1-yl)-phenyl]-pyrimidine-4,6-diamine (see example 1, 80 mg, 0.27 mmol, 1.0 eq.) the suspension is stirred at 70° C. for 36 h under argon. After cooling the precipitate is filtered off, washed with toluene, methanol/ether 1:1, and ether to give a beige powder. The crude product is purified by flash chromatography (1% MeOH in DCM to 16% MeOH in DCM within 30 min). The fractions containing the product are pooled, evaporated, and triturated with ether. The precipitate is filtered off, washed (1× cold methanol/ether 1:1, 1× ether), and vacuum dried at 45° C. over night to afford the title compound as colorless powder: m.p. 221° C. (dec.), ESI-MS: 546.1/548.0/550.0 [MH]+.

By following the procedures of Examples 1 and 2 but using the appropriate starting materials, examples 3—may be prepared:

Example 3

3-(2,6-Dichloro-3,5-dimethoxy-phenyl)-1-methyl-1-{6-[3-(4-methyl-piperazin-1-yl)-phenylamino]-pyrimidin-4-yl}-urea

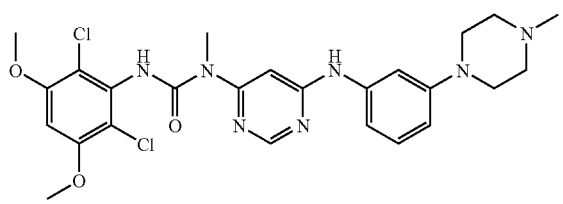

Colorless powder, m.p. 157-160° C., ESI-MS: 546.1/547.8/549.9 [MH]+.

Example 4

1-(2,6-Dichloro-phenyl)-3-{6-[4-(4-methyl-piperazin-1-yl)-phenylamino]-pyrimidin-4-yl}-urea

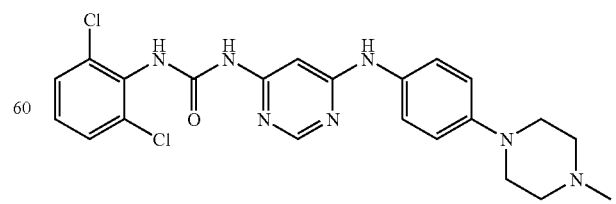

Colorless powder, HPLC: $t_R$=3.84 min (purity: >99%, gradient B), ESI-MS: 472/474/476 [MH]+.

Example 5

1-(2,6-Dichloro-phenyl)-3-{6-[3-(4-methyl-piperazin-1-yl)-phenylamino]-pyrimidin-4-yl}-urea

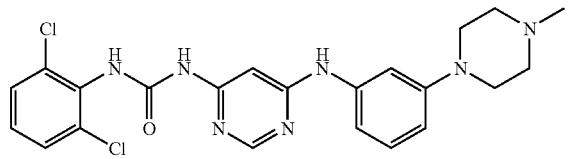 [SMILES: CN1CCN(c2cccc(Nc3cc(NC(=O)Nc4c(Cl)cccc4Cl)ncn3)c2)CC1]

Beige powder, m.p. 209-212° C., TLC: $R_f$=0.36 (DCM/MeOH/25% NH$_3$ 350:50:1), ESI-MS: 472/474/476 [MH]$^+$.

Example 6

1-(2-Chloro-6-methyl-Phenyl)-3-{6-[4-(4-methyl-piperazin-1-yl)-phenyl-amino]-pyrimidin-4-yl}-urea

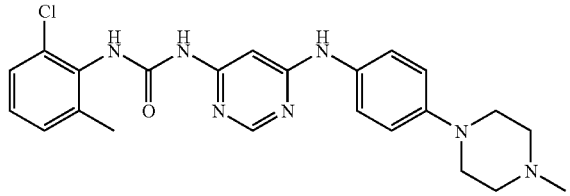 [SMILES: Cc1cccc(Cl)c1NC(=O)Nc1cc(Nc2ccc(N3CCN(C)CC3)cc2)ncn1]

Colorless powder, TLC: $R_f$=0.41 (DCM/MeOH/25% NH$_3$ 350:50:1), HPLC: $t_R$=10.39 min (purity: 98%, Gradient C), ESI-MS: 452/454 [MH]$^+$.

Example 7

1-(2-Chloro-6-methyl-phenyl)-3-{6-[3-(4-methyl-piperazin-1-yl)-phenyl-amino]-pyrimidin-4-yl}-urea

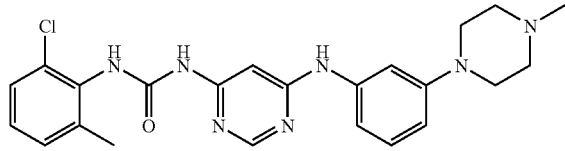 [SMILES: Cc1cccc(Cl)c1NC(=O)Nc1cc(Nc2cccc(N3CCN(C)CC3)c2)ncn1]

Colorless powder, TLC: $R_f$=0.29 (DCM/MeOH/25% NH$_3$ 350:50:1), HPLC: $t_R$=7.91 min (purity: 99%, Gradient C), ESI-MS: 452/454 [MH]$^+$.

Example 8

1-(3-Methoxy-phenyl)-3-{6-[4-(4-methyl-piperazin-1-yl)-phenylamino]-py-rimidin-4-yl}-urea

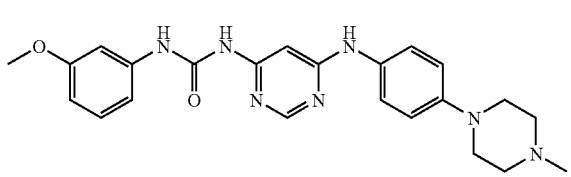

Beige powder, HPLC: $t_R$=4.52 min (purity: >99%, gradient A), ESI-MS: 434.4 [MH]$^+$.

Example 9

1-(3-Methoxy-phenyl)-3-{6-[3-(4-methyl-piperazin-1-yl)-phenylamino]-py-rimidin-4-yl}-urea

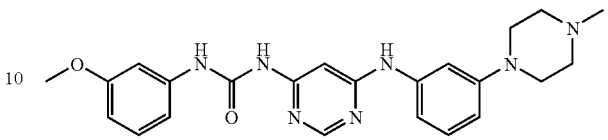

Colorless powder, TLC: $R_f$=0.20 (TBME/MeOH/NH$_3$ 90:9:1), HPLC: $t_R$=4.67 min (purity: >99%, gradient A), ESI-MS: 434.4 [MH]$^+$.

Example 10

1-(3,5-Dichloro-phenyl)-3-{6-[4-(4-methyl-piperazin-1-yl)-phenylamino]-pyrimidin-4-yl}-urea

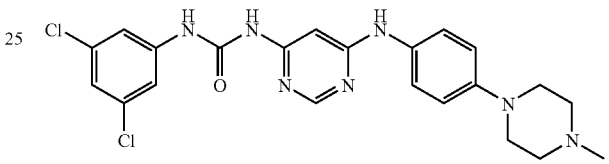

Colorless powder, HPLC: $t_R$=5.62 min (purity: >99%, gradient A), ESI-MS: 472.3/474.2 [MH]$^+$.

Example 11

1-(3,5-Dichloro-phenyl)-3-{6-[3-(4-methyl-piperazin-1-yl)-phenylamino]-pyrimidin-4-yl}-urea

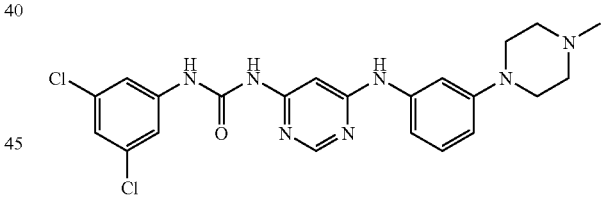

Colorless powder, HPLC: $t_R$=5.71 min (purity: >99%, gradient A), ESI-MS: 472.4/474.2 [MH]$^+$.

Example 12

1-(2,5-Dimethoxy-phenyl)-3-{6-[4-(4-methyl-piperazin-1-yl)-phenyl-amino]-pyrimidin-4-yl}-urea

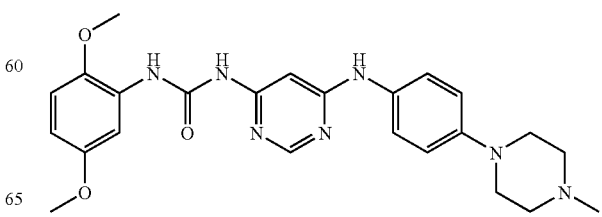

Colorless powder, TLC: Rf=0.44 (TBME/MeOH/NH3 80:18:2), HPLC: $t_R$=4.76 min (purity: 90%, gradient A), ESI-MS: 464.4 [MH]⁺.

Example 13

1-(2,5-Dimethoxy-phenyl)-3-{6-[3-(4-methyl-piperazin-1-yl)-phenyl-amino]-pyrimidin-4-yl}-urea

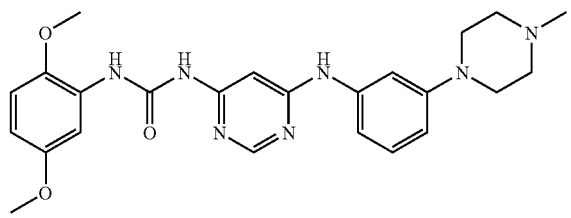 [SMILES: COc1ccc(OC)c(NC(=O)Nc2cc(Nc3cccc(N4CCN(C)CC4)c3)ncn2)c1]

Colorless powder, TLC: $R_f$=0.27 (TBME/MeOH/NH₃ 80:18:2), HPLC: $t_R$=4.90 min (purity: >99%, gradient A), ESI-MS: 464.4 [MH]⁺.

Example 14

1-{6-[4-(4-Methyl-piperazin-1-yl)-phenylamino]-pyrimidin-4-yl}-3-(3,4,5-trimethoxy-phenyl)-urea

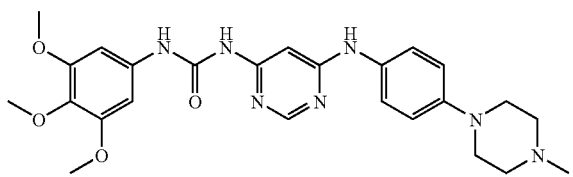

Colorless powder, TLC: Rf=0.30 (TBME/MeOH/NH3 80:18:2), HPLC: $t_R$=4.36 min (purity: >99%, gradient A), ESI-MS: 494.5 [MH]⁺.

Example 15

1-{6-[3-(4-Methyl-piperazin-1-yl)-phenylamino]-pyrimidin-4-yl}-3-(3,4,5-trimethoxy-phenyl)-urea

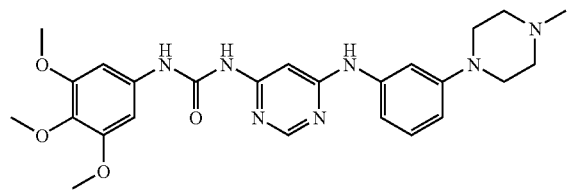

Colorless powder, HPLC: $t_R$=4.72 min (purity: >99%, gradient A), ESI-MS: 494.5 [MH]⁺.

Example 16

1-(2,4-Dimethoxy-phenyl)-3-{6-[4-(4-methyl-piperazin-1-yl)-phenyl-amino]-pyrimidin-4-yl}-urea

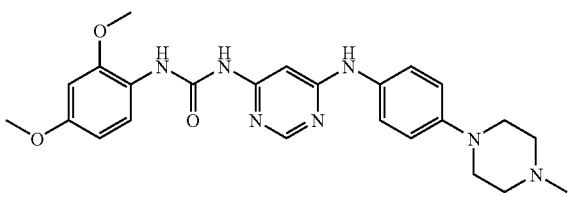

Colorless powder, TLC: Rf=0.24 (TBME/MeOH/NH3 80:18:2), HPLC: $t_R$=4.60 min (purity: >99%, gradient A), ESI-MS: 464.4 [MH]⁺.

Example 17

1-(2,4-Dimethoxy-phenyl)-3-{6-[3-(4-methyl-piperazin-1-yl)-phenyl-amino]-pyrimidin-4-yl}-urea

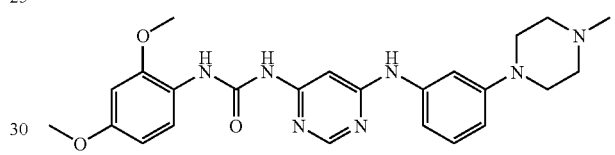

Colorless powder, HPLC: $t_R$=4.75 min (purity: >95%, gradient A), ESI-MS: 464.4 [MH]⁺.

Example 18

1-(3,5-Dimethoxy-phenyl)-3-{6-[4-(4-methyl-piperazin-1-yl)-phenyl-amino]-pyrimidin-4-yl}-urea

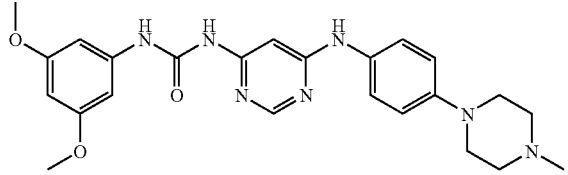 [SMILES: COc1cc(NC(=O)Nc2cc(Nc3ccc(N4CCN(C)CC4)cc3)ncn2)cc(OC)c1]

Colorless powder, TLC: Rf=0.19 (TBME/MeOH/NH3 80:18:2), HPLC: $t_R$=4.66 min (purity: >99%, gradient A), ESI-MS: 464.4 [MH]⁺.

Example 19

1-(3,5-Dimethoxy-phenyl)-3-{6-[3-(4-methyl-piperazin-1-yl)-phenyl-amino]-pyrimidin-4-yl}-urea

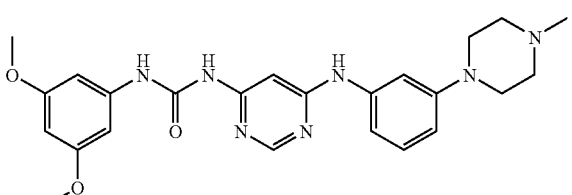

Colorless powder, HPLC: $t_R$=4.78 min (purity: >99%, gradient A), ESI-MS: 464.4 [MH]⁺.

Example 20

1-(3,5-Bis-trifluoromethyl-phenyl)-3-{6-[4-(4-methyl-piperazin-1-yl)-phenylamino]-pyrimidin-4-yl}-urea

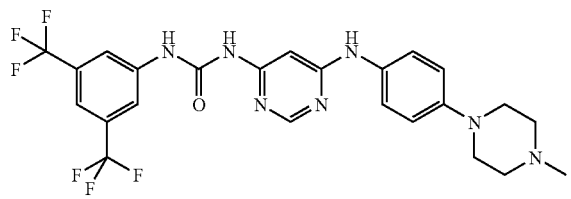 [SMILES: CN1CCN(c2ccc(Nc3cc(NC(=O)Nc4cc(C(F)(F)F)cc(C(F)(F)F)c4)ncn3)cc2)CC1]

Colorless powder, HPLC: $t_R$=5.86 min (purity: >99%, gradient A), ESI-MS: 540.4 [MH]$^+$.

Example 21

1-(3,5-Bis-trifluoromethyl-phenyl)-3-{6-[3-(4-methyl-piperazin-1-yl)-phenylamino]-pyrimidin-4-yl}-urea

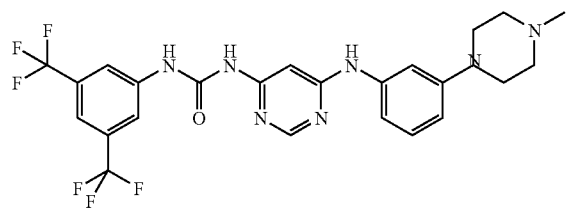

Colorless powder, HPLC: $t_R$=5.98 min (purity: >99%, gradient A), ESI-MS: 540.3 [MH]$^+$.

Example 22

1-(3,5-Dimethyl-phenyl)-3-{6-[4-(4-methyl-piperazin-1-yl)-phenyl-amino]-pyrimidin-4-yl}-urea

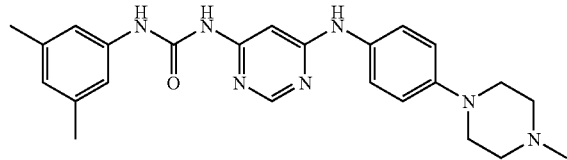

Colorless powder, TLC: $R_f$=0.69 (TBME/MeOH/NH3 80:18:2), HPLC: $t_R$=4.05 min (purity: >99%, gradient A), ESI-MS: 432.4 [MH]$^+$.

Example 23

1-(3,5-Dimethyl-Phenyl)-3-{6-[3-(4-methyl-piperazin-1-yl)-phenyl-amino]-pyrimidin-4-yl}-urea

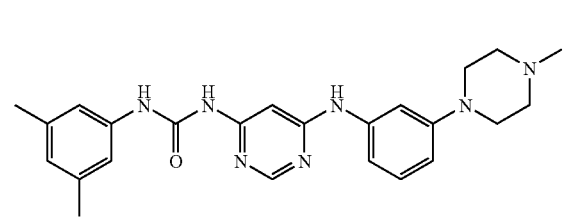

Colorless powder, TLC: $R_f$=0.31 (TBME/MeOH/NH3 90:9:1), HPLC: $t_R$=5.33 min (purity: >99%, gradient A), ESI-MS: 432.4 [MH]$^+$.

Example 24

1-(3-Chloro-4-methoxy-phenyl)-3-{6-[4-(4-methyl-piperazin-1-yl)-phenyl-amino]-pyrimidin-4-yl}-urea

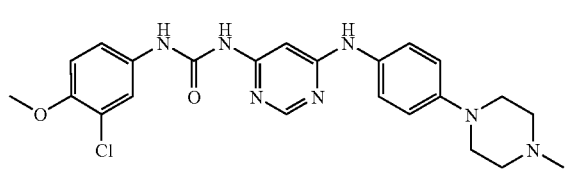

Colorless powder, TLC: $R_f$=0.17 (TBME/MeOH/NH3 80:18:2), HPLC: $t_R$=4.79 min (purity: >99%, gradient A), ESI-MS: 468.3/470.4 [MH]$^+$.

Example 25

1-(3-Chloro-4-methoxy-phenyl)-3-{6-[3-(4-methyl-piperazin-1-yl)-phenyl-amino]-pyrimidin-4-yl}-urea

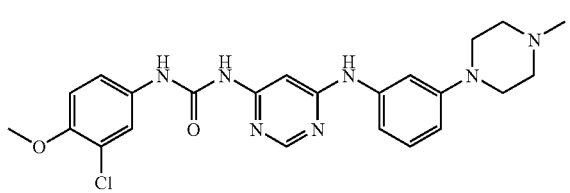

Colorless powder, TLC: $R_f$=0.57 (TBME/MeOH/NH3 90:9:1), HPLC: $t_R$=4.96 min (purity: >99%, gradient A), ESI-MS: 468.3/470.3 [MH]$^+$.

Example 26

1-(5-Methoxy-2-methyl-phenyl)-3-{6-[4-(4-methyl-piperazin-1-yl)-phenyl-amino]-pyrimidin-4-yl}-urea

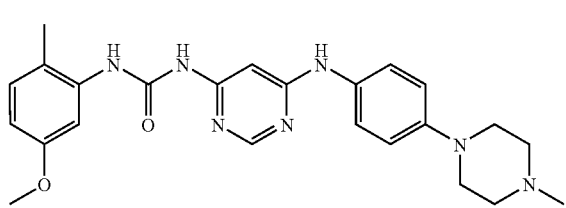 [SMILES: COc1ccc(C)c(NC(=O)Nc2cc(Nc3ccc(N4CCN(C)CC4)cc3)ncn2)c1]

Light grey powder, HPLC: $t_R$=4.87 min (purity: >99%, gradient A), ESI-MS: 448.4 [MH]$^+$.

Example 27

1-(5-Methoxy-2-methyl-phenyl)-3-{6-[3-(4-methyl-piperazin-1-yl)-phenyl-amino]-pyrimidin-4-yl}-urea

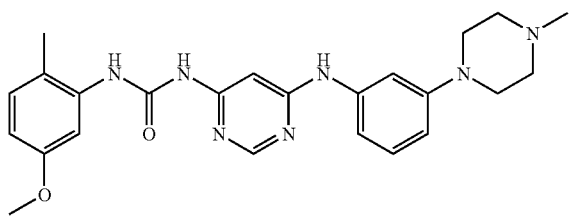 [SMILES: COc1ccc(C)c(NC(=O)Nc2cc(Nc3cccc(N4CCN(C)CC4)c3)ncn2)c1]

Colorless powder, TLC: Rf=0.63 (TBME/MeOH/NH3 80:18:2), HPLC: $t_R$=4.95 min (purity: >99%, gradient A), ESI-MS: 448.5 [MH]$^+$.

Example 28

1-(2-Chloro-5-methoxy-phenyl)-3-{6-[4-(4-methyl-piperazin-1-yl)-phenyl-amino]-pyrimidin-4-yl}-urea

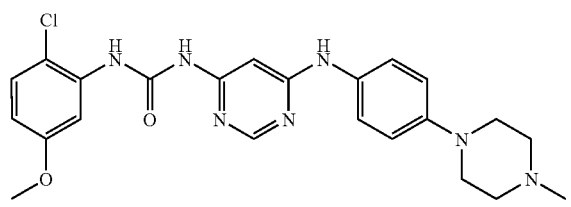 [SMILES: COc1ccc(Cl)c(NC(=O)Nc2cc(Nc3ccc(N4CCN(C)CC4)cc3)ncn2)c1]

Colorless powder, HPLC: $t_R$=5.35 min (purity: >99%, gradient A), ESI-MS: 468.3/470.4 [MH]$^+$.

Example 29

1-(2-Chloro-5-methoxy-phenyl)-3-{6-[3-(4-methyl-piperazin-1-yl)-phenyl-amino]-pyrimidin-4-yl}-urea

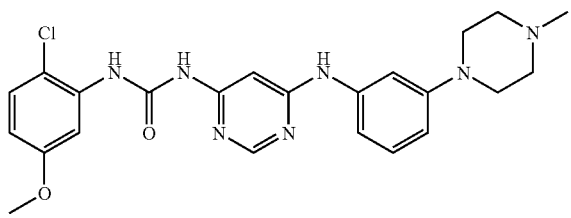

Colorless powder, HPLC: $t_R$=5.33 min (purity: >99%, gradient A), ESI-MS: 468.4/470.5 [MH]$^+$.

Example 30

1-(3,4-Dimethoxy-phenyl)-3-{6-[4-(4-methyl-piperazin-1-yl)-phenyl-amino]-pyrimidin-4-yl}-urea

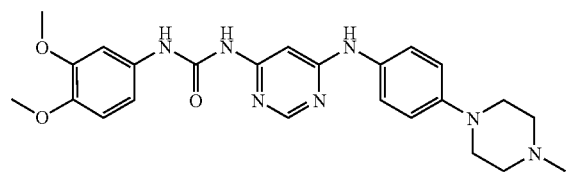

Pale yellow powder, TLC: R$_f$=0.32 (TBME/MeOH/NH3 80:18:2), HPLC: $t_R$=5.34 min (purity: 98%, gradient A), ESI-MS: 464.4 [MH]$^+$.

Example 31

1-(3,4-Dimethoxy-Phenyl)-3-{6-[3-(4-methyl-piperazin-1-yl)-phenyl-amino]-pyrimidin-4-yl}-urea

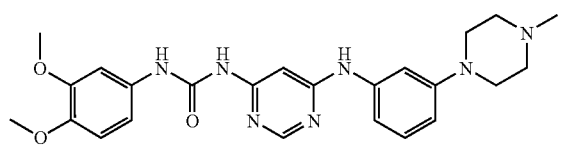

Colorless powder, TLC: R$_f$=0.36 (TBME/MeOH/NH3 80:18:2), HPLC: $t_R$=4.62 min (purity: 98%, gradient A), ESI-MS: 464.4 [MH]$^+$.

Example 32

1-(4-Fluoro-3-methoxy-phenyl)-3-{6-[4-(4-methyl-piperazin-1-yl)-phenyl-amino]-pyrimidin-4-yl}-urea

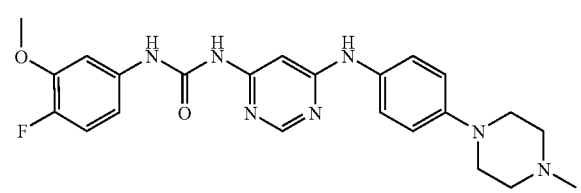

Colorless powder, TLC: R$_f$=0.63 (TBME/MeOH/NH3 70:27:3), HPLC: $t_R$=4.58 min (purity: >99%, gradient A), ESI-MS: 452.4 [MH]$^+$.

Example 33

1-(4-Fluoro-3-methoxy-phenyl)-3-{6-[3-(4-methyl-piperazin-1-yl)-phenyl-amino]-pyrimidin-4-yl}-urea

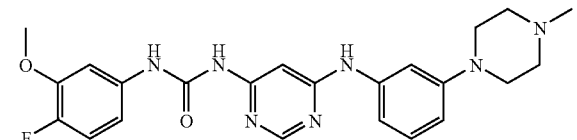

Pale yellow powder, TLC: R$_f$=0.31 (TBME/MeOH/NH3 80:18:2), HPLC: $t_R$=4.91 min (purity: >99%, gradient A), ESI-MS: 452.4 [MH]$^+$.

Example 34

1-(4,5-Dimethoxy-2-methyl-phenyl)-3-{6-[4-(4-methyl-piperazin-1-yl)-phenyl-amino]-pyrimidin-4-yl}-urea

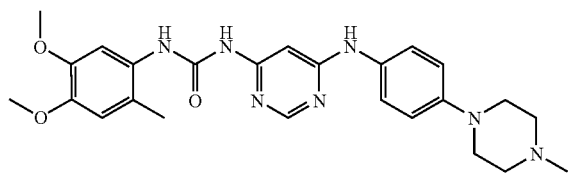

Colorless powder, TLC: R$_f$=0.27 (TBME/MeOH/NH3 70:27:3), HPLC: t$_R$=4.62 min (purity: >99%, gradient A), ESI-MS: 478.4 [MH]$^+$.

Example 35

1-(4,5-Dimethoxy-2-methyl-phenyl)-3-{6-[3-(4-methyl-piperazin-1-yl)-

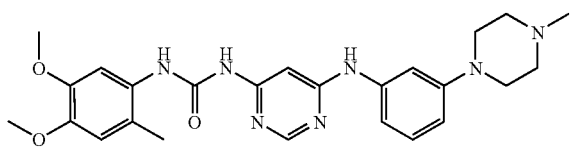

Pale yellow powder, TLC: R$_f$=0.32 (TBME/MeOH/NH3 80:18:2), HPLC: t$_R$=4.77 min (purity: >99%, gradient A), ESI-MS: 478.4 [MH]$^+$.

Example 36

1-(2,6-Dichloro-3-methoxy-phenyl)-3-{6-[4-(4-methyl-piperazin-1-yl)-phenyl-amino]-pyrimidin-4-yl}-urea

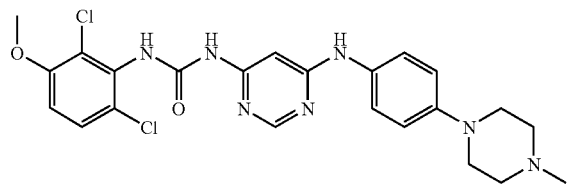

Colorless powder, TLC: R$_f$=0.30 (DCM/MeOH 80:20), HPLC: t$_R$=4.83 min (purity: >100%, gradient A), ESI-MS: 502.6/504.4/506.4 [MH]$^+$.

Example 37

1-(2,6-Dichloro-3-methoxy-phenyl)-3-{6-[3-(2-morpholin-4-yl-ethoxy)-phenylamino]-pyrimidin-4-yl}-urea

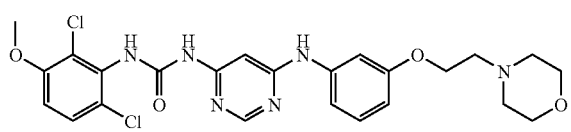 [SMILES: COc1ccc(Cl)c(NC(=O)Nc2cc(Nc3cccc(OCCN4CCOCC4)c3)ncn2)c1Cl]

Pale yellow powder, TLC: R$_f$=0.63 (DCM/MeOH 80:20), HPLC: t$_R$=4.84 min (purity: 89%, gradient A), ESI-MS: 533.6/535.5/537.5 [MH]$^+$.

Example 38

1-(2-Chloro-3,5-dimethoxy-phenyl)-3-(6-methylamino-pyrimidin-4-yl)-urea

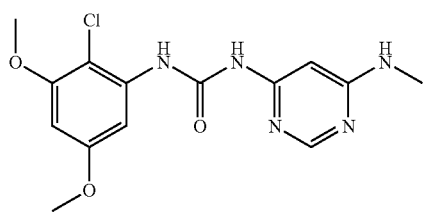 [SMILES: CNc1cc(NC(=O)Nc2cc(OC)cc(OC)c2Cl)ncn1]

Colorless powder, TLC: R$_f$=0.47 (TBME/MeOH/NH3 90:9:1), HPLC: t$_R$=5.21 min (purity: >100%, gradient A), ESI-MS: 338.3/340.4 [MH]$^+$.

Example 39

1-(2-Chloro-3,5-dimethoxy-phenyl)-3-(6-phenylamino-pyrimidin-4-yl)-urea

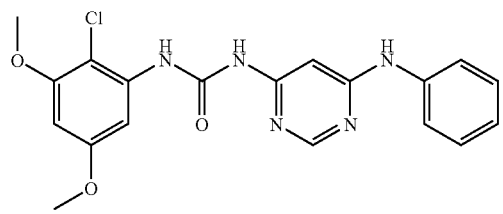

Colorless powder, HPLC: t$_R$=6.60 min (purity: >99%, gradient A), ESI-MS: 400.4/402.4 [MH]$^+$.

Example 40

1-(2-Chloro-3,5-dimethoxy-phenyl)-3-{6-[4-(4-methyl-Piperazin-1-yl)-phenyl-amino]-pyrimidin-4-yl}-urea

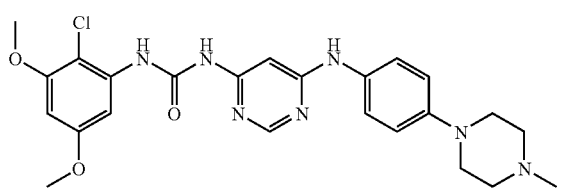 [SMILES: COc1cc(NC(=O)Nc2cc(Nc3ccc(N4CCN(C)CC4)cc3)ncn2)c(Cl)c(OC)c1]

Colorless powder, TLC: R$_f$=0.52 (TBME/MeOH/NH3 80:18:2), HPLC: t$_R$=5.27 min (purity: >99%, gradient A), ESI-MS: 498.4/500.2 [MH]$^+$.

Example 41

1-(2-Chloro-3,5-dimethoxy-2-methyl-phenyl)-3-{6-[3-(4-methyl-piperazin-1-yl)-phenyl-amino]-pyrimidin-4-yl}-urea

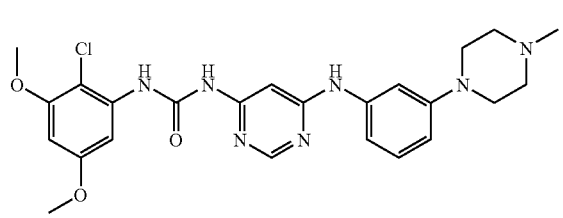 [SMILES: COc1cc(NC(=O)Nc2cc(Nc3cccc(N4CCN(C)CC4)c3)ncn2)c(Cl)c(OC)c1]

Colorless powder, TLC: $R_f$=0.47 (TBME/MeOH/NH3 80:18:2), HPLC: $t_R$=5.29 min (purity: >99%, gradient A), ESI-MS: 498.4/500.3 [MH]$^+$.

Example 42

1-(2-Chloro-3,5-dimethoxy-phenyl)-3-{6-[4-(2-diethylamino-ethoxy)-phenylamino]-pyrimidin-4-yl}-urea

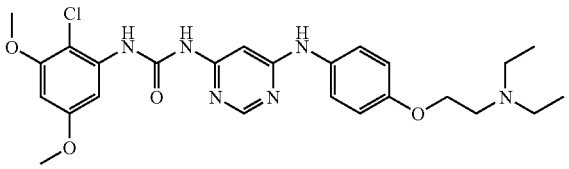 [SMILES: CCN(CC)CCOc1ccc(Nc2cc(NC(=O)Nc3cc(OC)cc(OC)c3Cl)ncn2)cc1]

Colorless powder, TLC: $R_f$=0.60 (TBME/MeOH/NH3 80:18:2), HPLC: $t_R$=5.49 min (purity: >99%, gradient A), ESI-MS: 515.5/517.4 [MH]$^+$.

Example 43

1-(2-Chloro-3,5-dimethoxy-phenyl)-3-{6-[3-(2-dimethylamino-ethoxy)-phenylamino]-pyrimidin-4-yl}-urea

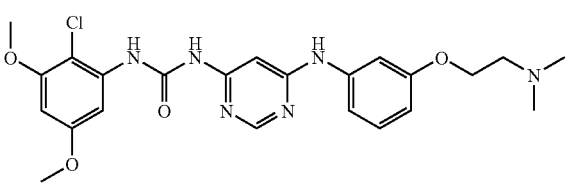

Colorless powder, TLC: $R_f$=0.20 (TBME/MeOH 30:70), HPLC: $t_R$=5.38 min (purity: >99%, gradient A), ESI-MS: 487.4/489.4 [MH]$^+$.

Example 44

1-(2-Chloro-3,5-dimethoxy-phenyl)-3-{6-[4-(2-morpholin-4-yl-ethoxy)-phenylamino]-pyrimidin-4-yl}-urea

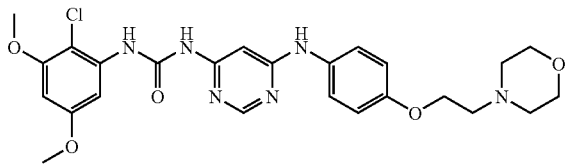 [SMILES: COc1cc(NC(=O)Nc2cc(Nc3ccc(OCCN4CCOCC4)cc3)ncn2)c(Cl)c(OC)c1]

Colorless powder, HPLC: $t_R$=5.30 min (purity: 96%, gradient A), ESI-MS: 529.4/531.3 [MH]$^+$.

Example 45

1-(2-Chloro-3,5-dimethoxy-phenyl)-3-{6-[3-(2-morpholin-4-yl-ethoxy)-phenylamino]-pyrimidin-4-yl}-urea

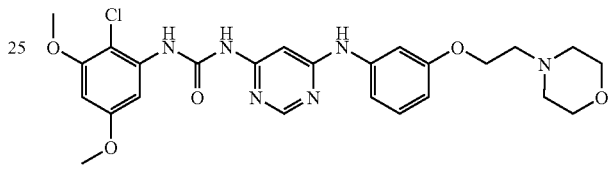

Colorless powder, TLC: $R_f$=0.40 (TBME/MeOH 75:25), HPLC: $t_R$=5.29 min (purity: >99%, gradient A), ESI-MS: 529.4/531.4 [MH]$^+$.

Example 46

3-(2,3-Dimethoxy-phenyl)-1-ethyl-1-{6-[4-(4-methyl-piperazin-1-yl)-phenylamino]-pyrimidin-4-yl}-urea

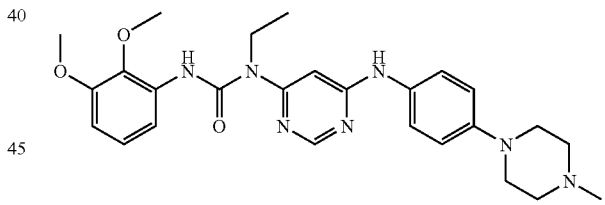

Colorless powder, TLC: $R_f$=0.57 (DCM/MeOH 85:15), HPLC: $t_R$=5.29 min (purity: 98%, gradient A), ESI-MS: 492.2 [MH]$^+$.

Example 47

3-(3,5-Dimethoxy-phenyl)-1-methyl-1-{6-[4-(4-methyl-piperazin-1-yl)-phenylamino]-pyrimidin-4-yl}-urea

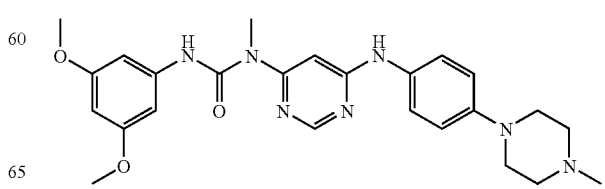

Pale yellow powder, TLC: R$_f$=0.38 (TBME/MeOH/NH3 80:18:2), HPLC: t$_R$=5.13 min (purity: 95%, gradient A), ESI-MS: 478.5 [MH]$^+$.

Example 48

3-(3,5-Dimethoxy-phenyl)-1-methyl-1-{6-[3-(4-methyl-piperazin-1-yl)-phenylamino]-pyrimidin-4-yl}-urea

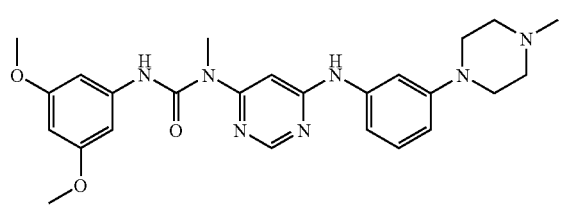 [SMILES: COc1cc(NC(=O)N(C)c2cc(Nc3cccc(N4CCN(C)CC4)c3)ncn2)cc(OC)c1]

Colorless powder, TLC: R$_f$=0.48 (TBME/MeOH/NH3 80:18:2), HPLC: t$_R$=5.21 min (purity: 95%, gradient A), ESI-MS: 478.4 [MH]$^+$.

Example 49

3-(2-Chloro-3,5-dimethoxy-phenyl)-1-methyl-1-(6-phenylamino-pyrimidin-4-yl)-urea

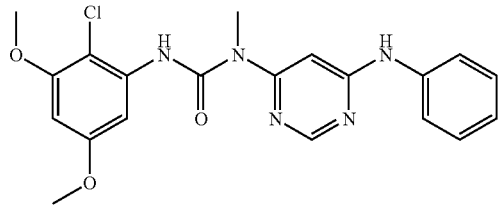 [SMILES: COc1cc(NC(=O)N(C)c2cc(Nc3ccccc3)ncn2)c(Cl)c(OC)c1]

Colorless powder, HPLC: t$_R$=7.38 min (purity: 96%, gradient A), ESI-MS: 414.5/416.4 [MH]$^+$.

Example 50

3-(2-Chloro-3,5-dimethoxy-phenyl)-1-methyl-1-{6-[4-(4-methyl-piperazin-1-yl)-phenylamino]-pyrimidin-4-yl}-urea

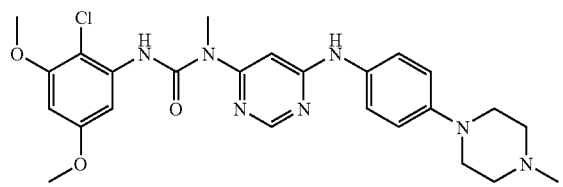

Colorless powder, HPLC: t$_R$=5.65 min (purity: 95%, gradient A), ESI-MS: 512.4/514.3 [MH]$^+$.

Example 51

3-(2-Chloro-3,5-dimethoxy-phenyl)-1-methyl-1-{6-[3-(4-methyl-piperazin-1-yl)-phenylamino]-pyrimidin-4-yl}-urea

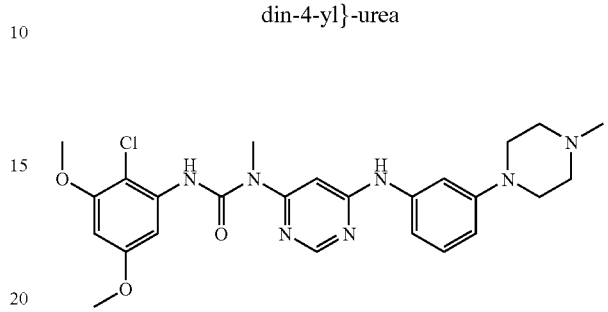

Colorless powder, TLC: R$_f$=0.53 (TBME/MeOH/NH3 80:18:2), HPLC: t$_R$=5.63 min (purity: >99%, gradient A), ESI-MS: 512.5/514.4 [MH]$^+$.

Example 52

3-(2-Chloro-3,5-dimethoxy-phenyl)-1-methyl-1-{6-[4-(4-methyl-piperazine-1-carbonyl)-phenylamino]-pyrimidin-4-yl}-urea

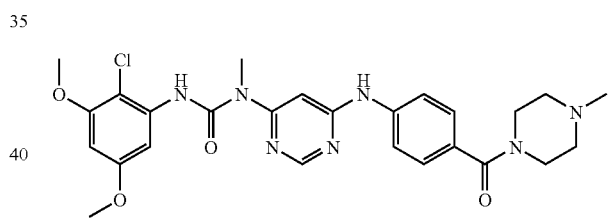

Colorless powder, TLC: R$_f$=0.45 (DCM/MeOH 80:20), HPLC: t$_R$=5.33 min (purity: 90%, gradient A), ESI-MS: 540.5/542.4 [MH]$^+$.

Example 53

3-(2-Chloro-3,5-dimethoxy-Phenyl)-1-{6-[4-(2-diethylamino-ethoxy)-phenylamino]-pyrimidin-4-yl}-1-methyl-urea

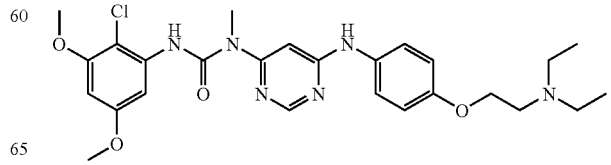

Colorless powder, TLC: R_f=0.22 (TBME/MeOH 75:25), HPLC: t_R=5.74 min (purity: >99%, gradient A), ESI-MS: 529.4/531.3 [MH]+.

Example 54

3-(2-Chloro-3,5-dimethoxy-phenyl)-1-{6-[3-(2-dimethylamino-ethoxy)-phenylamino]-pyrimidin-4-yl}-1-methyl-urea

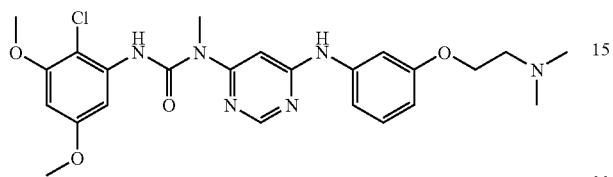

Colorless powder, TLC: R_f=0.34 (TBME/MeOH/NH3 80:18:2), HPLC: t_R=5.57 min (purity: >99%, gradient A), ESI-MS: 501.4/503.3 [MH]+.

Example 55

3-(2-Chloro-3,5-dimethoxy-phenyl)-1-ethyl-1-{6-[4-(4-methyl-piperazin-1-yl)-phenylamino]-pyrimidin-4-yl}-urea

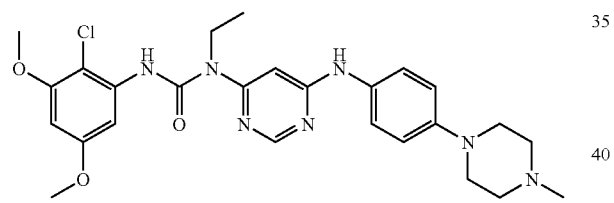

Colorless powder, TLC: R_f=0.26 (DCM/MeOH 90:10), HPLC: t_R=5.69 min (purity: >100%, gradient A), ESI-MS: 526.5/528.4 [MH]+.

Example 56

3-(2-Chloro-3,5-dimethoxy-phenyl)-1-{6-[4-(4-methyl-piperazin-1-yl)-phenylamino]-pyrimidin-4-yl}-1-thiophen-2-ylmethyl-urea

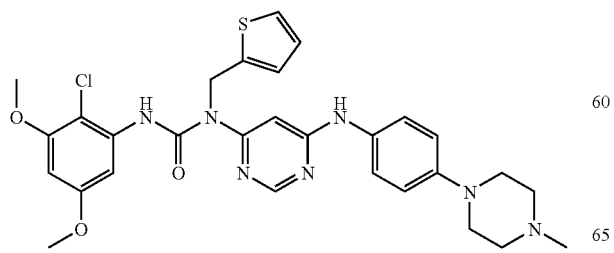

Colorless powder, TLC: R_f=0.36 (DCM/MeOH 90:10), HPLC: t_R=6.10 min (purity: >100%, gradient A), ESI-MS: 594.5/596.4 [MH]+.

Example 57

3-(2-Chloro-3,5-dimethoxy-phenyl)-1-[2-(4-methyl-piperazin-1-yl)-ethyl]-1-(6-phenylamino-pyrimidin-4-yl)-urea

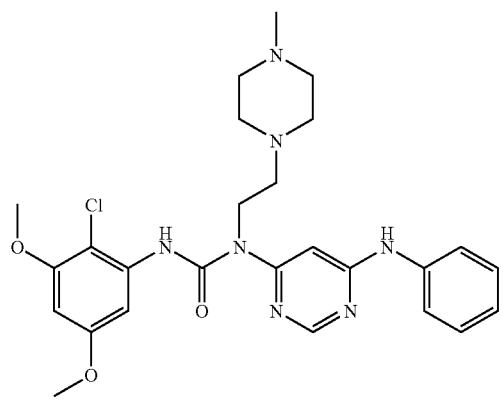 [SMILES: COc1cc(NC(=O)N(CCN2CCN(C)CC2)c2cc(Nc3ccccc3)ncn2)c(Cl)c(OC)c1]

Colorless powder, TLC: R_f=0.15 (TBME/MeOH 50:50), HPLC: t_R=5.82 min (purity: >100%, gradient A), ESI-MS: 526.5/528.4 [MH]+.

Example 58

3-(2-Chloro-3,5-dimethoxy-phenyl)-1-(6-phenylamino-pyrimidin-4-yl)-1-(2-pyridin-2-yl-ethyl)-urea

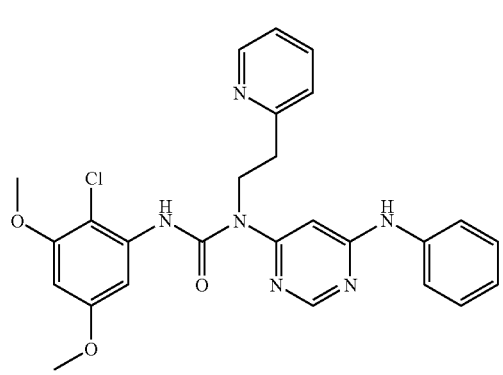 [SMILES: COc1cc(NC(=O)N(CCc2ccccn2)c2cc(Nc3ccccc3)ncn2)c(Cl)c(OC)c1]

Colorless powder, HPLC: t_R=7.30 min (purity: 95%, gradient A), ESI-MS: 505.4/507.4 [MH]+.

Example 59

3-(2,6-Dichloro-3-methoxy-phenyl)-1-ethyl-1-{6-[4-(4-methyl-piperazin-1-yl)-phenylamino]-pyrimidin-4-yl}-urea

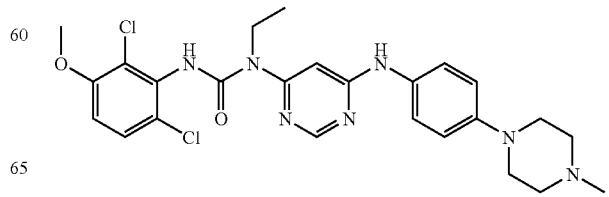

Yellow foam, TLC: $R_f$=0.26 (TBME/MeOH 40:60), HPLC: $t_R$=5.37 min (purity: 96%, gradient A), ESI-MS: 530.1/532.0/534.0 [MH]$^+$.

Example 60

3-(2,6-Dichloro-3-methoxy-phenyl)-1-methyl-1-{6-[3-(4-methyl-piperazin-1-yl)-phenylamino]-pyrimidin-4-yl}-urea

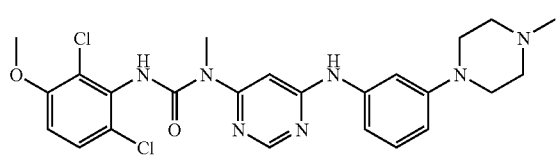

Colorless powder, TLC: $R_f$=0.15 (TBME/MeOH 60:40), HPLC: $t_R$=5.31 min (purity: 97%, gradient A), ESI-MS: 516.1/518.0/520.1 [MH]$^+$.

Example 61

3-(2,6-Dichloro-3-methoxy-phenyl)-1-methyl-1-{6-[4-(4-methyl-piperazine-1-carbonyl)-phenylamino]-pyrimidin-4-yl}-urea

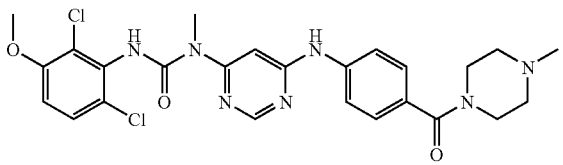

Colorless powder, TLC: $R_f$=0.67 (DCM/MeOH 80:20), HPLC: $t_R$=5.11 min (purity: 91%, gradient A), ESI-MS: 544.4/546.3/548.4 [MH]$^+$.

Example 62

3-(2,6-Dichloro-3-methoxy-phenyl)-1-methyl-1-{6-[4-(4-methyl-piperazin-1-ylmethyl)-phenylamino]-pyrimidin-4-yl}-urea

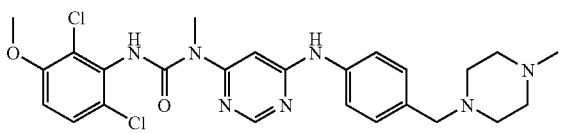

Beige powder, HPLC: $t_R$=5.14 min (purity: 93%, gradient A), ESI-MS: 529.2/531.0/533.1 [MH]$^+$.

Example 63

3-(2,6-Dichloro-3-methoxy-phenyl)-1-(6-methoxy-pyridin-3-ylmethyl)-1-{6-[4-(4-methyl-piperazin-1-yl)-phenylamino]-pyrimidin-4-yl}-urea

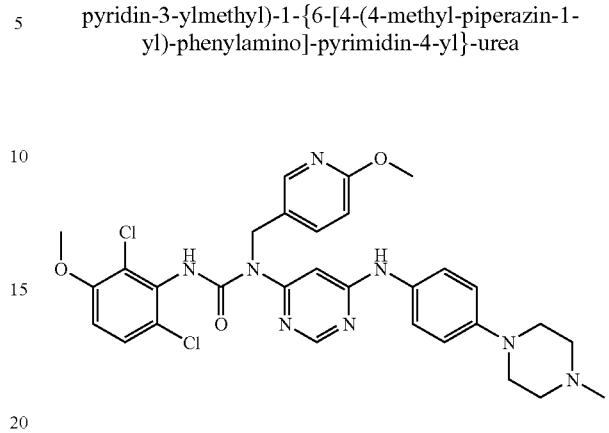

Colorless powder, TLC: $R_f$=0.56 (DCM/MeOH 80:20), HPLC: $t_R$=5.69 min (purity: >99%, gradient A), ESI-MS: 623.0/625.5/627.3 [MH]$^+$.

Example 64

3-(2,6-Dichloro-3,5-dimethoxy-phenyl)-1-ethyl-1-{6-[4-(4-methyl-piperazine-1-carbonyl)-phenylamino]-pyrimidin-4-yl}-urea

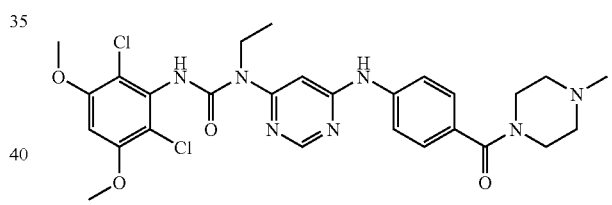

Colorless powder, TLC: $R_f$=0.44 (DCM/MeOH 85:15), HPLC: $t_R$=5.23 min (purity: >99%, gradient A), ESI-MS: 588.5/590.1/592.2 [MH]$^+$.

Example 65

1-(2-Chloro-6-methyl-phenyl)-3-(6-isopropylamino-pyrimidin-4-yl)-urea

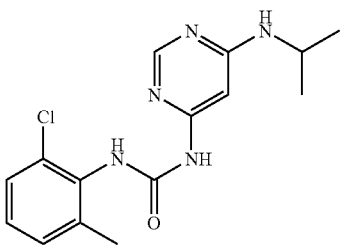 [SMILES: Cc1cccc(Cl)c1NC(=O)Nc1cc(NC(C)C)ncn1]

Beige powder, m.p. 233-233° C., TLC: $R_f$=0.55 (DCM/MeOH/25% NH$_3$ 350:50:1), ESI-MS: 319/321 [MH]$^+$.

Example 66

(2,6-dichloro-phenyl)-carbamic acid 4-{6-[3-(2,6-dichloro-phenyl)-ureido]-pyrimidin-4-ylamino}-cyclohexylester

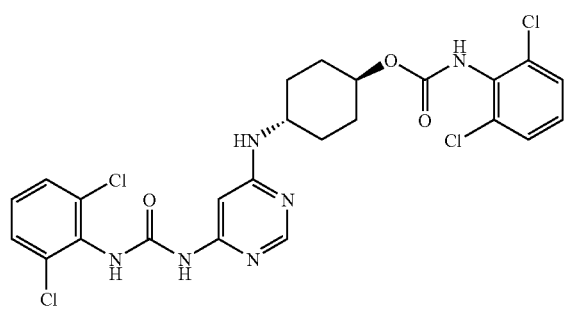 [SMILES: O=C(Nc1cc(N[C@H]2CC[C@H](OC(=O)Nc3c(Cl)cccc3Cl)CC2)ncn1)Nc1c(Cl)cccc1Cl]

Colorless powder, m.p. 222-224° C., ESI-MS: 582/584/586 [MH]$^+$.

Example 67

1-(6-Isopropylamino-pyrimidin-4-yl)-3-(2,4,6-trichloro-phenyl)-urea

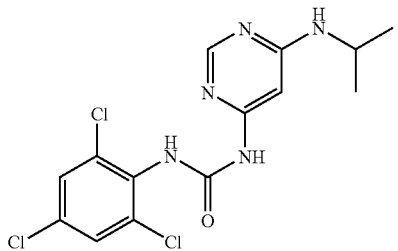 [SMILES: CC(C)Nc1cc(NC(=O)Nc2c(Cl)cc(Cl)cc2Cl)ncn1]

Colorless powder, m.p. 218-220° C., HPLC: $t_R$=9.92 min (purity: 100%, gradient C).

Example 68

1-(2,6-Dichloro-phenyl)-3-(6-isopropylamino-pyrimidin-4-yl)-urea

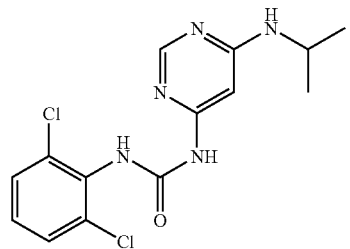 [SMILES: CC(C)Nc1cc(NC(=O)Nc2c(Cl)cccc2Cl)ncn1]

Colorless powder, m.p. 203-204° C., ESI-MS: 340/342/586 [MH]$^+$.

Example 69

1-{6-[4-(1-Methyl-piperidin-4-ylmethoxy)-phenylamino]-pyrimidin-4-yl}-3-(2,4,6-trichloro-phenyl)-urea

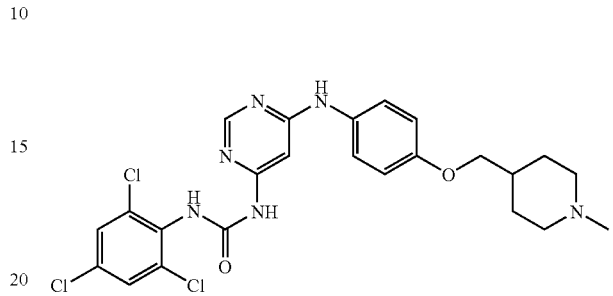

Slightly yellow powder, m.p. 189-191° C., ESI-MS: 535/537/539 [MH]$^+$.

Example 70

1-(2-Chloro-6-methyl-phenyl)-3-{6-[4-(1-methyl-piperidin-4-ylmethoxy)-phenylamino]-pyrimidin-4-yl}-urea

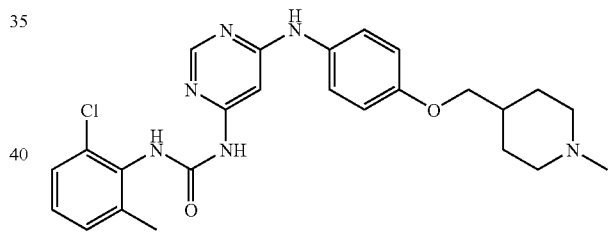

Slightly yellow powder, m.p. 178-180° C., ESI-MS: 481/483 [MH]$^+$.

Example 71

1-(2,6-Dichloro-phenyl)-3-{6-[4-(1-methyl-piperidin-4-ylmethoxy)-phenylamino]-pyrimidin-4-yl}-urea

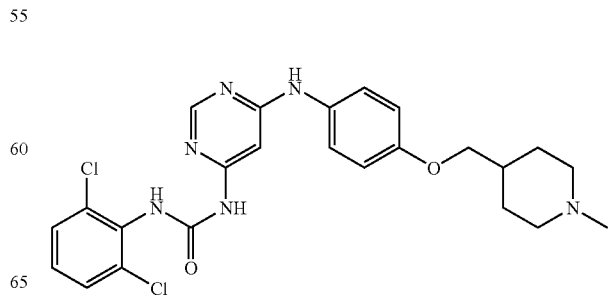

Colorless powder, m.p. 183-185° C., ESI-MS: 501/503 [MH]+.

Example 72

1-(2,5-Dichloro-Phenyl)-3-{6-[4-(4-methyl-piperazin-1-yl)-phenylamino]-pyrimidin-4-yl}-urea

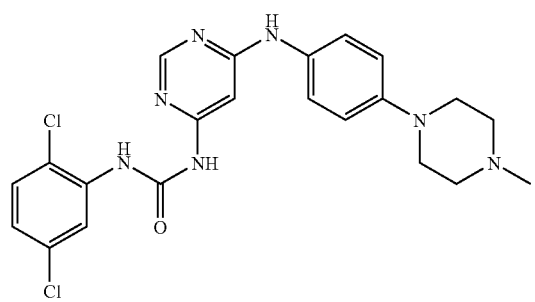 [SMILES: CN1CCN(c2ccc(Nc3cc(NC(=O)Nc4cc(Cl)ccc4Cl)ncn3)cc2)CC1]

Colorless powder, m.p. 223-225° C., ESI-MS: 472/474 [MH]+.

Example 73

1-{6-[4-(4-Methyl-piperazin-1-yl)-phenylamino]-pyrimidin-4-yl}-3-(2,4,6-trichloro-phenyl)-urea

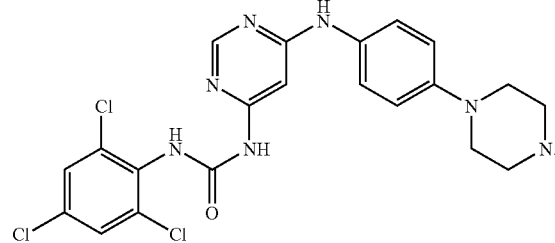

Colorless powder, m.p. 209-211° C., ESI-MS: 506/508/510 [MH]+.

Example 74

1-{6-[4-(4-Methyl-piperazin-1-yl)-phenylamino]-pyrimidin-4-yl}-3-(2,4,5-trichloro-phenyl)-urea

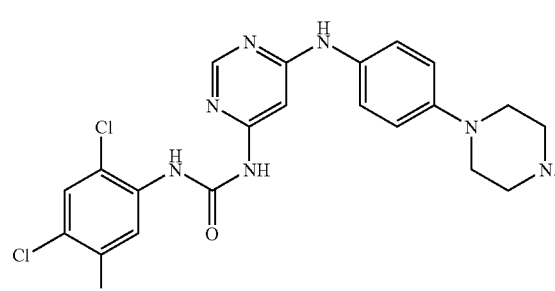

Colorless powder, m.p. 252-254° C., ESI-MS: 506/508/510 [MH]+.

Example 75

1-(3,4-Dichloro-phenyl)-3-{6-[4-(4-methyl-piperazin-1-yl)-phenylamino]-pyrimidin-4-yl}-urea

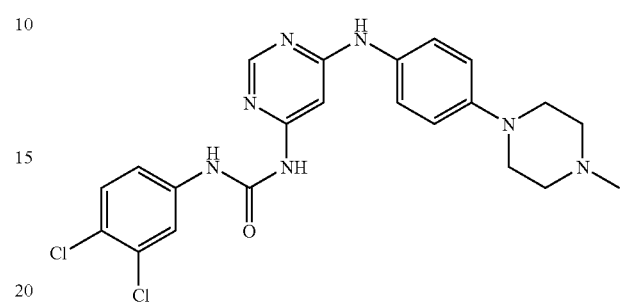

Colorless powder, m.p. 260-262° C., ESI-MS: 472/474 [MH]+.

Example 76

1-(6-Amino-pyrimidin-4-yl}-3-(2,3-dichloro-phenyl)-1-[4-(4-methyl-piperazin-1-yl)-phenyl]-urea

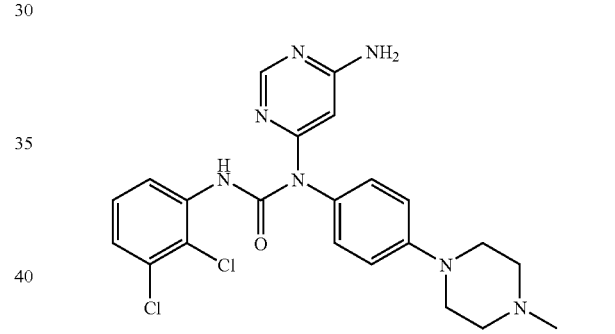

Colorless powder, m.p. 280-282° C., ESI-MS: 472/474 [MH]+.

Example 77

1-(2,3-Dichloro-Phenyl)-3-{6-[4-(4-methyl-piperazin-1-yl)-phenylamino]-pyrimidin-4-yl}-urea

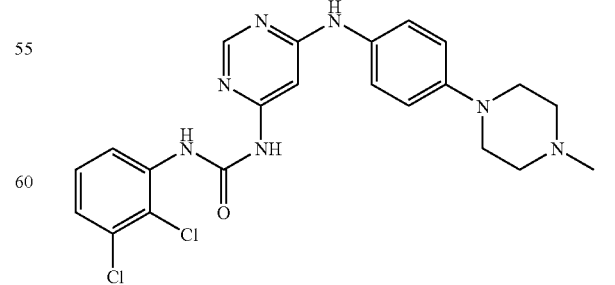

Colorless powder, m.p. 279-281° C., ESI-MS: 472/474 [MH]+.

Example 78

1-(5-Chloro-2-methoxy-phenyl)-3-{6-[4-(4-methyl-piperazin-1-yl)-phenylamino]-pyrimidin-4-yl}-urea

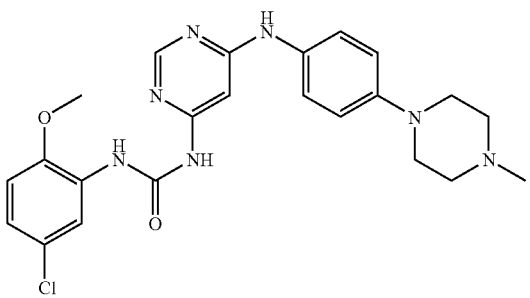 [SMILES: COc1ccc(Cl)cc1NC(=O)Nc1cc(Nc2ccc(N3CCN(C)CC3)cc2)ncn1]

Colorless resin, TLC: R$_f$=0.41 (DCM/MeOH/25% NH$_3$ 350:50:1), HPLC: t$_R$=13.25 min (purity: 100%, gradient E), ESI-MS: 468/470 [MH]$^+$.

Example 79

1-(2-Chloro-6-methyl-phenyl)-3-{6-[3-(1-methyl-piperidin-4-ylmethoxy)-phenylamino]-pyrimidin-4-yl}-urea

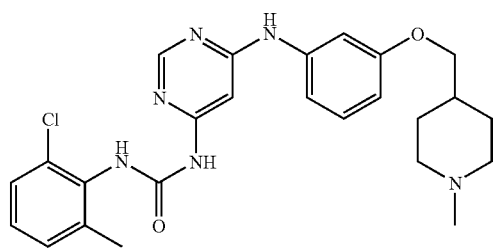 [SMILES: Cc1cccc(Cl)c1NC(=O)Nc1cc(Nc2cccc(OCC3CCN(C)CC3)c2)ncn1]

Colorless powder, m.p. 200-204° C., ESI-MS: 481/483 [MH]$^+$.

Example 80

1-(2,6-Dichloro-Phenyl)-3-{6-[3-(1-methyl-piperidin-4-ylmethoxy)-phenylamino]-pyrimidin-4-yl}-urea

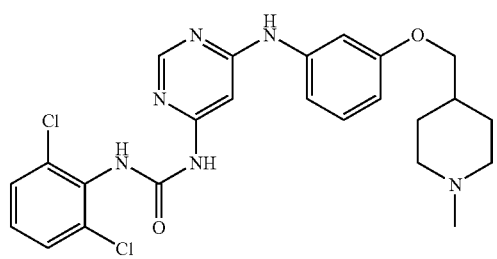 [SMILES: CN1CCC(COc2cccc(Nc3cc(NC(=O)Nc4c(Cl)cccc4Cl)ncn3)c2)CC1]

Colorless powder, m.p. 198-200° C., ESI-MS: 501/503 [MH]$^+$.

Example 81

1-{6-[3-(1-Methyl-piperidin-4-ylmethoxy)-phenylamino]-pyrimidin-4-yl}-3-(2,4,6-trichloro-phenyl)-urea

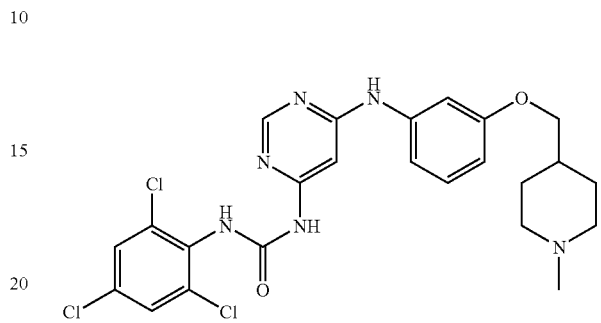

Colorless powder, m.p. 222-225° C., ESI-MS: 535/537/539 [MH]$^+$.

Example 82

1-(2-Chloro-6-methyl-phenyl)-3-{6-[4-(4-methyl-piperazin-1-ylmethyl)-phenylamino]-pyrimidin-4-yl}-urea

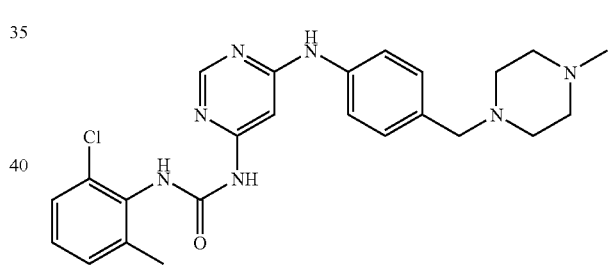

Colorless powder, m.p. 199-201° C., ESI-MS: 466/468 [MH]$^+$.

Example 83

1-(2,6-Dichloro-Phenyl)-3-{6-[4-(4-methyl-piperazin-1-ylmethyl)-phenylamino]-pyrimidin-4-yl}-urea

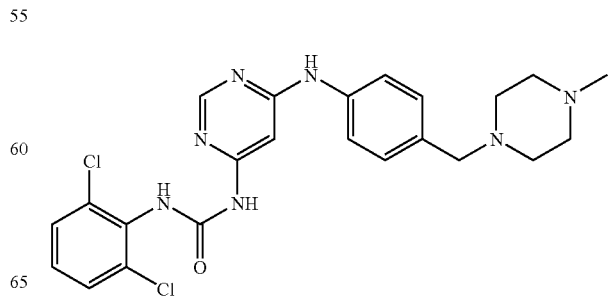

Colorless powder, m.p. 199-201° C., ESI-MS: 466/468 [MH]+.

Example 84

1-{6-[4-(4-Methyl-piperazin-1-ylmethyl)-phenylamino]-pyrimidin-4-yl}-3-(2,4,6-trichloro-phenyl)-urea

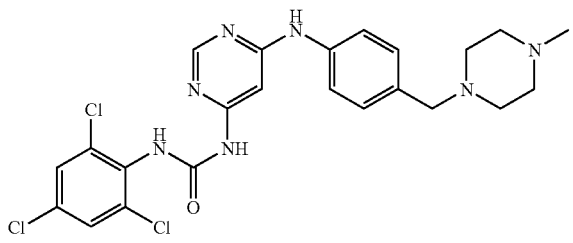 [SMILES: CN1CCN(Cc2ccc(Nc3cc(NC(=O)Nc4c(Cl)cc(Cl)cc4Cl)ncn3)cc2)CC1]

Yellowish powder, m.p. 194-196° C., ESI-MS: 520/522/524 [MH]+.

Example 85

1-{6-[4-(4-Methyl-piperazin-1-carbonyl)-phenylamino]-pyrimidin-4-yl}-3-(2,4,6-trichloro-phenyl)-urea

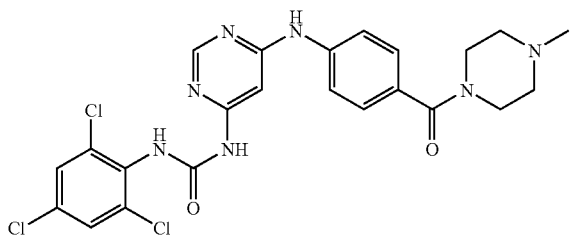 [SMILES: CN1CCN(C(=O)c2ccc(Nc3cc(NC(=O)Nc4c(Cl)cc(Cl)cc4Cl)ncn3)cc2)CC1]

Amorphous material, m.p. 165-175° C., TLC: $R_f$=0.61 (DCM/MeOH/25% NH$_3$ 150:50:1), HPLC: $t_R$=8.63 min (purity: 98.8%, gradient C), ESI-MS: 534/536/538 [MH]+.

Example 86

1-{6-[3-(4-Methyl-piperazin-1-yl)-phenylamino]-pyrimidin-4-yl}-3-(2,4,6-trichloro-phenyl)-urea

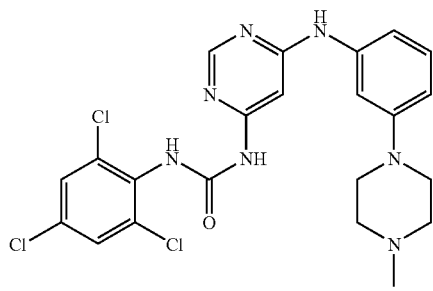 [SMILES: CN1CCN(c2cccc(Nc3cc(NC(=O)Nc4c(Cl)cc(Cl)cc4Cl)ncn3)c2)CC1]

Yellowish amorphous material, m.p. 138-142° C., TLC: $R_f$=0.41 (DCM/MeOH/25% NH$_3$ 350:50:1), HPLC: $t_R$=8.92 min (purity: 99%, gradient C), ESI-MS: 506/508/510 [MH]+.

Example 87

1-{6-[(trans)-4-(tert-Butyl-dimethyl-silanyloxy)-cyclohexylamino]-pyrimidin-4-yl}-3-(2,4,6-trichloro-phenyl)-urea

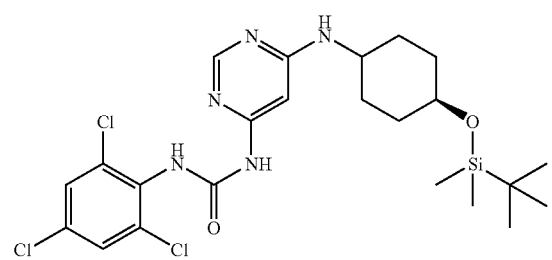

Colorless powder, m.p. 198-199° C., ESI-MS: 570/572/574 [MH]+.

Example 88

1-[6-((trans)-4-Hydroxy-cyclohexylamino)-pyrimidin-4-yl]-3-(2,4,6-trichloro-phenyl)-urea

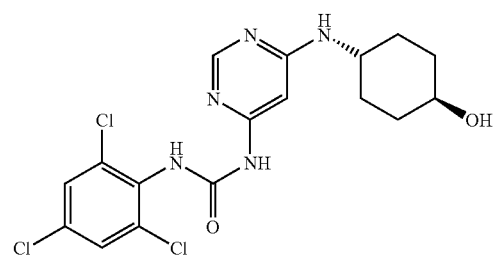

Colorless powder, m.p. 171-173° C., ESI-MS: 430/432/434 [MH]+.

Example 89

1-{6-[(trans)-4-(tert-Butyl-dimethyl-silanyloxy)-cyclohexylamino]-pyrimidin-4-yl}-3-(2-chloro-6-methyl-phenyl)-urea

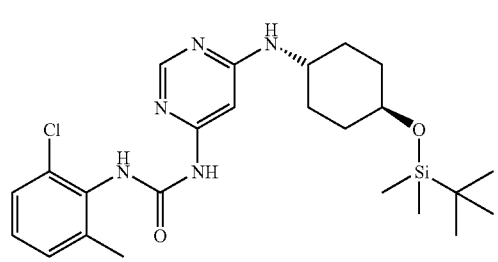

Beige powder, m.p. 218-220° C., TLC: $R_f$=0.74 (ethyl acetate/methanol 95:5), HPLC: $t_R$=13.92 min (purity: 93.9%, gradient C), ESI-MS: 490/492 [MH]⁺.

Example 90

1-(2-Chloro-6-methyl-phenyl)-3-[6-((trans)-4-hydroxy-cyclohexylamino)-pyrimidin-4-yl]-urea

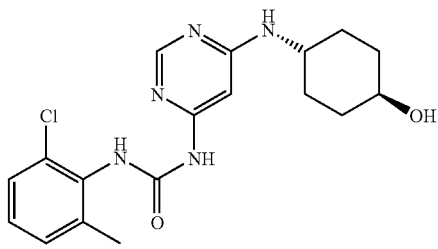

Colorless powder, m.p. 149-152° C., TLC: $R_f$=0.22 (ethyl acetate/methanol 95:5), HPLC: $t_R$=7.77 min (purity: 95.2%, gradient C), ESI-MS: 376/378 [MH]⁺.

Example 91

1-{6-[(trans)-4-(tert-Butyl-dimethyl-silanyloxy)-cyclohexylamino]-pyrimidin-4-yl}3-(2,6-dichloro-phenyl)-urea

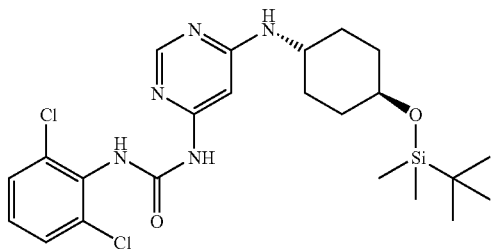

Colorless powder, m.p. 211-212° C., HPLC: $t_R$=2.63 min (purity: 97.9%, gradient D), ESI-MS: 510/512 [MH]⁺.

Example 92

1-(2,6-Dichloro-phenyl)-3-[6-((trans)-4-hydroxy-cyclohexylamino)-pyrimidin-4-yl]-urea

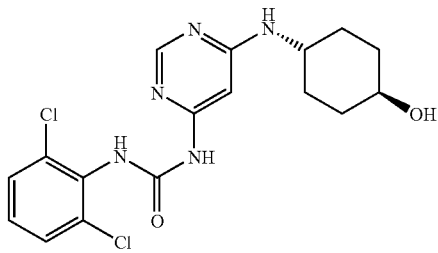

Amorphous material, TLC: $R_f$=0.28 (ethyl acetate/methanol 95:5), HPLC: $t_R$=13.54 min (purity: 100%, gradient C), ESI-MS: 396/398 [MH]⁺.

Example 93

1-(2-Chloro-phenyl)-3-{6-[4-(4-methyl-piperazin-1-yl)-phenylamino]-pyrimidin-4-yl}-urea

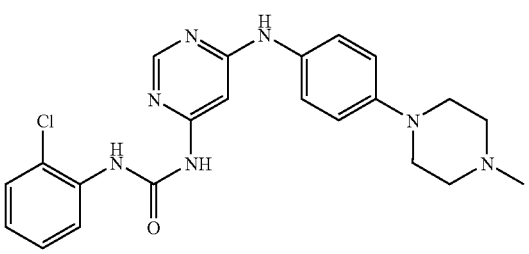 [SMILES: CN1CCN(c2ccc(Nc3cc(NC(=O)Nc4ccccc4Cl)ncn3)cc2)CC1]

Beige powder, HPLC: $t_R$=4.17 min (purity: 100%, gradient B), ESI-MS: 438/440 [MH]⁺.

Example 94

1-(2-Bromo-phenyl)-3-{6-[4-(4-methyl-piperazin-1-yl)-phenylamino]-pyrimidin-4-yl}-urea

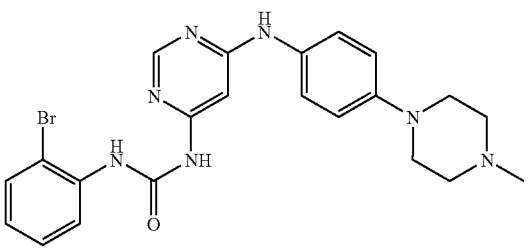 [SMILES: CN1CCN(c2ccc(Nc3cc(NC(=O)Nc4ccccc4Br)ncn3)cc2)CC1]

Colorless powder, HPLC: $t_R$=4.23 min (purity: 100%, gradient B), ESI-MS: 482/484 [MH]⁺.

Example 95

1-(6-Amino-pyrimidin-4-yl}-3-(2-chloro-phenyl)-1-[4-(3-diethylamino-propoxy)-phenyl]-urea

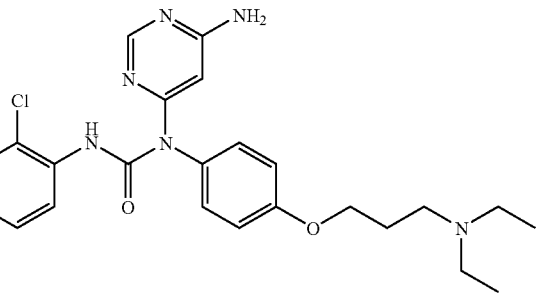

Colorless powder, HPLC: $t_R$=4.42 min (purity: 100%, gradient B), ESI-MS: 469/471 [MH]⁺.

Example 96

1-(2,6-Dichloro-phenyl)-3-{6-[4-(2-morpholin-4-yl-ethoxy)-phenylamino]-pyrimidin-4-yl}-urea

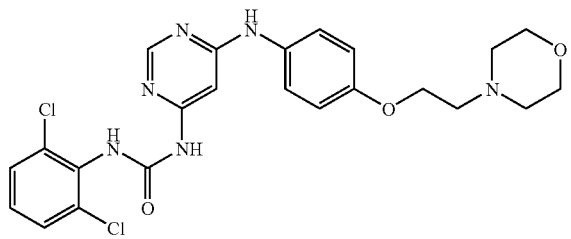 [SMILES: O=C(Nc1cc(Nc2ccc(OCCN3CCOCC3)cc2)ncn1)Nc1c(Cl)cccc1Cl]

Beige powder, HPLC: $t_R$=3.93 min (purity: 100%, gradient B), ESI-MS: 503/505 [MH]⁺.

Example 97

1-(2-Bromo-phenyl)-3-{6-[4-(2-morpholin-4-yl-ethoxy)-phenylamino]-pyrimidin-4-yl}-urea

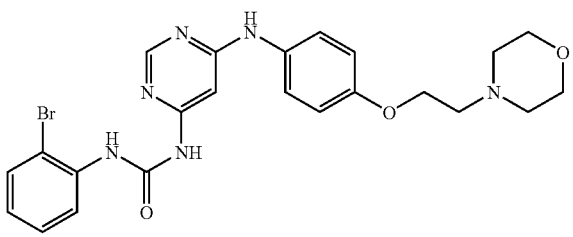 [SMILES: O=C(Nc1cc(Nc2ccc(OCCN3CCOCC3)cc2)ncn1)Nc1ccccc1Br]

White powder, HPLC: $t_R$=4.29 min (purity: 100%, gradient B), ESI-MS: 513/515 [MH]⁺.

Example 98

1-(2,6-Dichloro-phenyl)-3-{6-[4-(3-morpholin-4-yl-propoxy)-phenylamino]-pyrimidin-4-yl}-urea

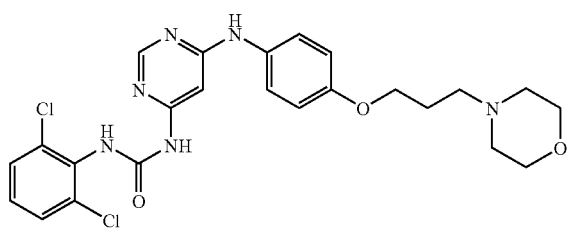 [SMILES: O=C(Nc1cc(Nc2ccc(OCCCN3CCOCC3)cc2)ncn1)Nc1c(Cl)cccc1Cl]

Colorless powder, HPLC: $t_R$=4.05 min (purity: 100%, gradient B), ESI-MS: 517/519 [MH]⁺.

Example 99

1-(2-Bromo-phenyl)-3-{6-[4-(3-morpholin-4-yl-propoxy)-phenylamino]-pyrimidin-4-yl}-urea

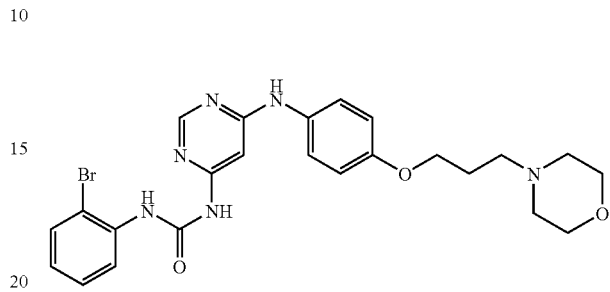

Colorless powder, HPLC: $t_R$=4.42 min (purity: 100%, gradient B), ESI-MS: 527/529 [MH]⁺.

Example 100

1-(2,6-Dichloro-Phenyl)-3-{6-[4-(2-diethylamino-ethoxy)-phenylamino]-pyrimidin-4-yl}-urea

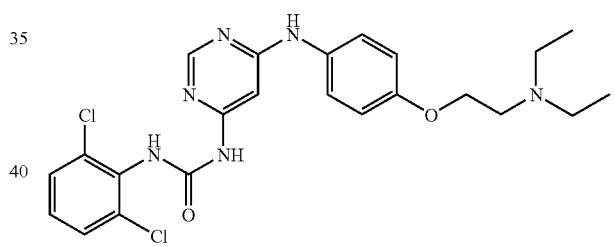

Colorless powder, HPLC: $t_R$=4.12 min (purity: 100%, gradient B), ESI-MS: 489/491 [MH]⁺.

Example 101

1-(2-Bromo-phenyl)-3-{6-[4-(2-diethylamino-ethoxy)-phenylamino]-pyrimidin-4-yl}-urea

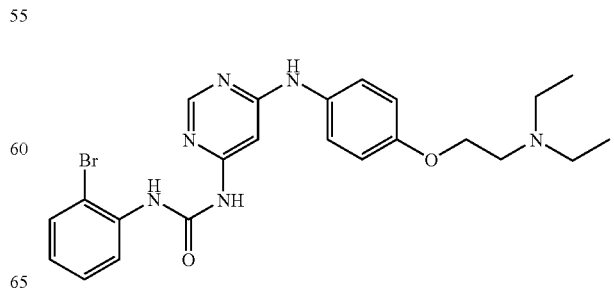

Colorless powder, HPLC: $t_R$=4.55 min (purity: 100%, gradient B), ESI-MS: 499/501 [MH]$^+$.

Example 102

1-(2-Chloro-phenyl)-3-{6-[4-(3-diethylamino-propoxy)-phenylamino]-pyrimidin-4-yl}-urea

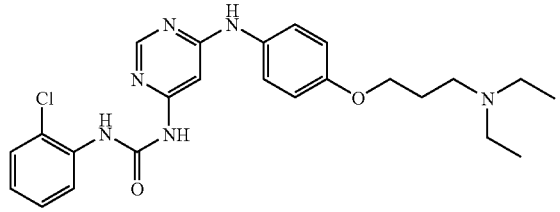 [SMILES: CCN(CC)CCCOc1ccc(Nc2cc(NC(=O)Nc3ccccc3Cl)ncn2)cc1]

Colorless powder, HPLC: $t_R$=4.58 min (purity: 100%, gradient B), ESI-MS: 469/471 [MH]$^+$.

Example 103

1-(2,6-Dichloro-phenyl)-3-{6-[4-(3-diethylamino-propoxy)-phenylamino]-pyrimidin-4-yl}-urea

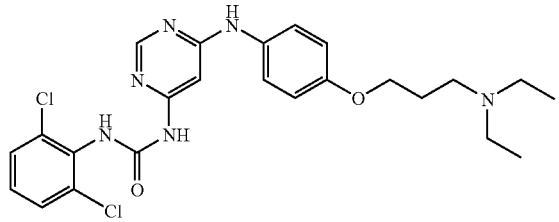 [SMILES: CCN(CC)CCCOc1ccc(Nc2cc(NC(=O)Nc3c(Cl)cccc3Cl)ncn2)cc1]

Colorless powder, HPLC: $t_R$=4.26 min (purity: 100%, gradient B), ESI-MS: 503/505 [MH]$^+$.

Example 104

1-(2-Bromo-phenyl)-3-{6-[4-(3-diethylamino-propoxy)-phenylamino]-pyrimidin-4-yl}-urea

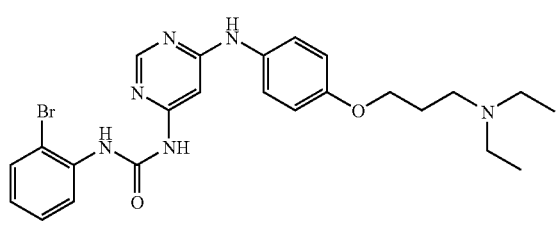 [SMILES: CCN(CC)CCCOc1ccc(Nc2cc(NC(=O)Nc3ccccc3Br)ncn2)cc1]

Colorless powder, HPLC: $t_R$=4.62 min (purity: 100%, gradient B), ESI-MS: 513/515 [MH]$^+$.

Example 105

1-[6-(4-Diethylamino-phenylamino)-pyrimidin-4-yl]-3-(2,6-difluoro-phenyl)-urea

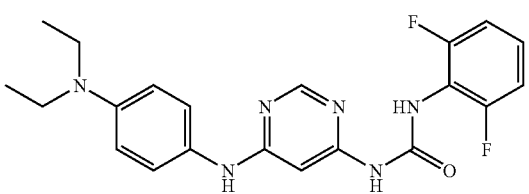 [SMILES: CCN(CC)c1ccc(Nc2cc(NC(=O)Nc3c(F)cccc3F)ncn2)cc1]

A.
N-(4-Diethylamino-phenyl)-pyrimidine-4,6-diamine

A mixture of 6-chloro-pyrimidin-4-ylamine (0.65 g, 5 mmol), 4-amino-N,N-diethylaniline (0.82 mL, 5 mmol), 2-propanol (5 mL) and HCl conc. (0.225 mL, ~2.5 mmol) is shaken for 36 h at 90° C. After cooling to room temperature, the reaction mixture is distributed between half-saturated K$_2$CO$_3$-solution and ethyl acetate. The precipitate thus formed is filtered off, washed with H$_2$O and ethyl acetate and dried in vacuo to afford the title compound. Greyish solid, HPLC: $t_R$=2.37 min (gradient F), ESI-MS: 258.3 [MH]$^+$.

B. 1-[6-(4-Diethylamino-phenylamino)-pyrimidin-4-yl]-3-(2,6-difluoro-phenyl)-urea A mixture of N-(4-diethylamino-phenyl)-pyrimidine-4,6-diamine (257.4 mg, 1 mmol), 2,6-difluorophenyl isocyanate (170.6 mg, 1.1 mmol) in dry dioxane (4 mL) is shaken for 1.5 h at 80° C. After evaporation of the solvent in vacuo, the residue is distributed between CH$_2$Cl$_2$ and half-saturated K$_2$CO$_3$ solution. The organic layer is dried over Na$_2$SO$_4$, evaporated, and the residue purified by flash chromatography (CH$_2$Cl$_2$/CH$_3$OH). The combined pure fractions are evaporated, the residue triturated with CH$_2$Cl$_2$ and the solid filtered off and dried in vacuo to afford the title compound.

White solid, HPLC: $t_R$=3.35 min (purity: 100%, gradient F), ESI-MS: 413.4 [MH]$^+$.

Example 106

1-(2,6-Difluoro-phenyl)-3-[6-(3-dimethylamino-phenylamino)-pyrimidin-4-yl]-urea

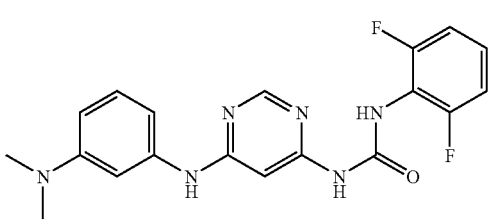 [SMILES: CN(C)c1cccc(Nc2cc(NC(=O)Nc3c(F)cccc3F)ncn2)c1]

A.
N-(3-Dimethylamino-phenyl)-pyrimidine-4,6-diamine

A mixture of N,N-dimethyl-m-phenylenediamine (1.36 g, 10 mmol), 6-chloro-pyrimidin-4-ylamine (1.30 g, 10 mmol), 2-propanol (10 mL) and HCl conc. (0.45 mL, ~5 mmol) is shaken for 16 h at 90° C. After cooling to room temperature, the reaction mixture is distributed between half-concentrated $Na_2CO_3$ solution and ethyl acetate. The organic layer is dried over $Na_2SO_4$, evaporated, and the residue purified by flash chromatography (ethyl acetate/$CH_3OH$). The combined pure fractions are evaporated to afford the title compound. Beige solid, HPLC: $t_R$=1.53 min (gradient F), ESI-MS: 230.3 $[MH]^+$.

B. 1-(2,6-Difluoro-phenyl)-3-[6-(3-dimethylamino-phenylamino)-pyrimidin-4-yl]-urea A mixture of N-(3-dimethylamino-phenyl)-pyrimidine-4,6-diamine (458.6 mg, 2 mmol), 2,6-difluorophenyl isocyanate (341.2 mg, 2.2 mmol) in dry dioxane (5 mL) is shaken for 2.5 h at 80° C. After cooling down, the reaction mixture is treated with ethyl acetate. The precipitate is filtered off and dried in vacuo to afford the title compound.

White solid, HPLC: $t_R$=3.39 min (purity: 100%, gradient F), ESI-MS: 385.4 $[MH]^+$.

Example 107

1-(2,6-Dichloro-phenyl)-3-[6-(4-diethylamino-phenylamino)-pyrimidin-4-yl]-urea

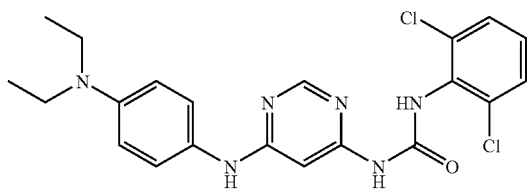 [SMILES: CCN(CC)c1ccc(Nc2cc(NC(=O)Nc3c(Cl)cccc3Cl)ncn2)cc1]

The title compound is prepared analogously as described in Example 105A from N-(4-diethylamino-phenyl)-pyrimidine-4,6-diamine and 2,6-dichlorophenyl isocyanate.

White solid, HPLC: $t_R$=3.61 min (purity: 100%, gradient F), ESI-MS: 445.3/447.3 $[MH]^+$.

Example 108

1-(2,6-Dichloro-Phenyl)-3-[6-(4-morpholin-4-yl-phenylamino)-pyrimidin-4-yl]-urea

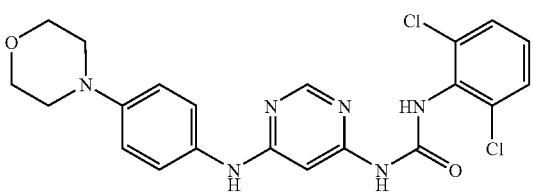 [SMILES: O=C(Nc1cc(Nc2ccc(N3CCOCC3)cc2)ncn1)Nc1c(Cl)cccc1Cl]

A.
N-(4-Morpholin-4-yl-phenyl)-pyrimidine-4,6-diamine

The title compound is prepared analogously as described in Example 105A from 6-chloro-pyrimidin-4-ylamine and 4-morpholinoaniline. The semi-solid reaction mixture received after cooling to room temperature is dissolved in warm methanol, basified with conc. aqueous ammonia solution and the mixture concentrated to half of its volume. The precipitate obtained after addition of $H_2O$ is filtered off, washed with $H_2O$ and dried in vacuo to afford the title compound. Faintly violet solid, ESI-MS: 272.3 $[MH]^+$.

B. 1-(2,6-Dichloro-phenyl)-3-[6-(4-morpholin-4-yl-phenylamino)-pyrimidin-4-yl]-urea The title compound is prepared analogously as described in Example 105B from N-(4-morpholin-4-yl-phenyl)-pyrimidine-4,6-diamine and 2,6-dichlorophenyl isocyanate. Faintly violet solid, HPLC: $t_R$=3.74 min (purity: 100%, gradient F), ESI-MS: 459.3/461.3 $[MH]^+$.

Example 109

1-(2,6-Difluoro-phenyl)-3-[6-(4-morpholin-4-yl-phenylamino)-pyrimidin-4-yl]-urea

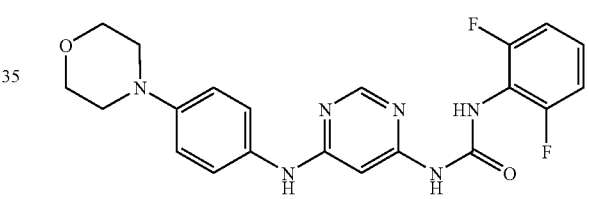

The title compound is prepared analogously as described in Example 105B from N-(4-morpholin-4-yl-phenyl)-pyrimidine-4,6-diamine and 2,6-difluorophenyl isocyanate. Slightly pink solid, HPLC: $t_R$=3.53 min (purity: 100%, gradient F), ESI-MS: 427.4 $[MH]^+$.

Example 110

3-(2,6-Dichloro-phenyl)-1-[6-(4-diethylamino-phenylamino)-pyrimidin-4-yl]-1-methyl-urea

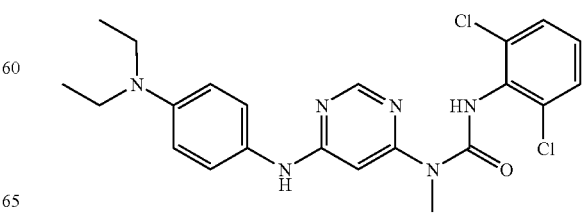

A. N-(4-Diethylamino-phenyl)-N'-methyl-pyrimidine-4,6-diamine

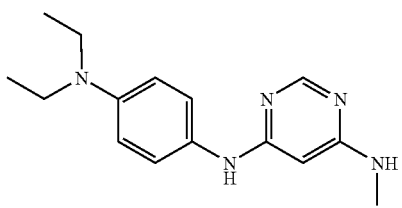 [SMILES: CCN(CC)c1ccc(Nc2cc(NC)ncn2)cc1]

The title compound is prepared analogously as described in Example 105A from (6-chloro-pyrimidin-4-yl)-methyl-amine and 4-amino-N,N-diethylaniline. The ethyl acetate layer is dried over $Na_2SO_4$ and evaporated in vacuo. The residue is suspended in $CH_2Cl_2$, filtered off and dried to afford the title compound.

White solid, HPLC: $t_R$=2.48 min (gradient F), ESI-MS: 272.3 $[MH]^+$.

B. 3-(2,6-Dichloro-phenyl)-1-[6-(4-diethylamino-phenylamino)-pyrimidin-4-yl]-1-methyl-urea The title compound is prepared analogously as described in Example 105B from N-(4-diethylamino-phenyl)-N'-methyl-pyrimidine-4,6-diamine and 2,6-dichlorophenyl isocyanate.

White solid, HPLC: $t_R$=2.46 min (purity: 95.6%, gradient H), ESI-MS: 459.2/461.2 $[MH]^+$.

Example 111

3-(2,6-Dichloro-Phenyl)-1-{6-[4-(1-hydroxy-1-methyl-ethyl)-phenylamino]-pyrimidin-4-yl}-1-methyl-urea

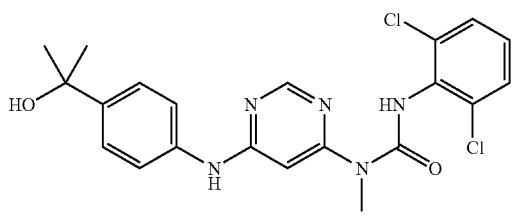 [SMILES: CN(C(=O)Nc1c(Cl)cccc1Cl)c1cc(Nc2ccc(C(C)(C)O)cc2)ncn1]

A. 1-[4-(6-Methylamino-pyrimidin-4-ylamino)-phenyl]-ethanone

A mixture of (6-chloro-pyrimidin-4-yl)-methylamine (5.76 g, 40.1 mmol), 4-amino-acetophenone (5.40 g, 40 mmol), 2-propanol (40 mL) and conc. HCl (1.8 mL, ~20 mmol) is stirred for 40 h at 90° C. Conc. HCl (0.9 mL, ~10 mmol) is added and stirring is continued for 56 h. After addition of $CH_3OH$ the reaction mixture is basified with conc. aqueous ammonia solution. $H_2O$ is added and the precipitate is filtered off, washed with $H_2O$ and dried in vacuo to afford the title compound. Yellow solid, ESI-MS: 243.4 $[MH]^+$.

B. 1-[6-(4-Acetyl-phenylamino)-pyrimidin-4-yl]-3-(2,6-dichloro-phenyl)-1-methyl-urea

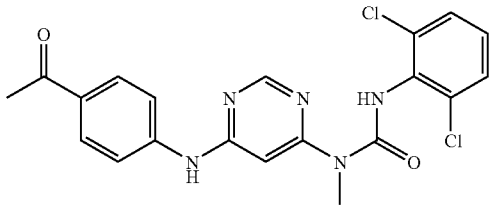 [SMILES: CC(=O)c1ccc(Nc2cc(N(C)C(=O)Nc3c(Cl)cccc3Cl)ncn2)cc1]

A mixture of 1-[4-(6-methylamino-pyrimidin-4-ylamino)-phenyl]-ethanone (3.77 g, 15.56 mmol), 2,6-dichlorophenyl isocyanate (3.22 g, 17.12 mmol) in dry dioxane (30 mL) is shaken for 16 h at 80° C. After evaporation of the solvent in vacuo, the residue is distributed between ethyl acetate and half-saturated $K_2CO_3$ solution. The precipitate is filtered off and washed with $H_2O$ and ethyl acetate. The solid residue is suspended in methanol, heated to reflux for several h and the hot yellow suspension filtered. This procedure is repeated once. The residue obtained after the second filtration is washed with $CH_3OH$ and dried in vacuo to afford the title compound.

Yellowish solid, HPLC: $t_R$=4.81 min (gradient G), ESI-MS: 430.3/432.3 $[MH]^+$.

C. 3-(2,6-Dichloro-phenyl)-1-{6-[4-(1-hydroxy-1-methyl-ethyl)-phenylamino]-pyrimidin-4-yl}-1-methyl-urea To a freshly prepared solution of methylmagnesium iodide in diethyl ether (8 mL, ~7 mmol) is added 1-[6-(4-acetyl-phenylamino)-pyrimidin-4-yl]-3-(2,6-dichloro-phenyl)-1-methyl-urea (0.5 g, 1.16 mmol) in several portions. After stirring for 5 h, THF (4 mL) is added. After 16 h the reaction is quenched by the addition of $H_2O$ and $CH_3OH$ and evaporated in vacuo. The residue is co-evaporated twice with toluene and purified by flash chromatography ($CH_2Cl_2/CH_3OH$). The combined pure fractions are evaporated to afford the title compound.

White solid, HPLC: $t_R$=4.39 min (purity: 100%, gradient G), ESI-MS: 446.4/448.4 $[MH]^+$.

Example 112

1-(2,6-Dichloro-phenyl)-3-[6-(6-methoxy-pyridin-3-ylamino)-pyrimidin-4-yl]-urea

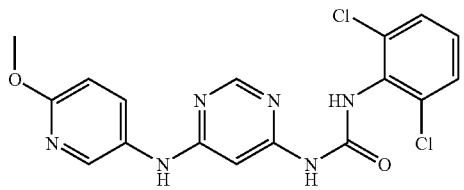 [SMILES: COc1ccc(Nc2cc(NC(=O)Nc3c(Cl)cccc3Cl)ncn2)cn1]

A.
N-(6-Methoxy-pyridin-3-yl)-pyrimidine-4,6-diamine

A mixture of 6-chloro-pyrimidin-4-ylamine (0.65 g, 5 mmol), 5-amino-2-methoxypyridine (0.62 g, 5 mmol) and 2-propanol (5 mL) is shaken for 36 h at 90° C. After cooling to room temperature, the reaction mixture is distributed between half-saturated Na$_2$CO$_3$-solution and ethyl acetate. The organic layer is dried over Na$_2$SO$_4$ and evaporated. The solid residue is washed consecutively with CH$_3$OH, ethyl acetate and CH$_2$Cl$_2$ and dried in vacuo.

Pinkish solid, HPLC: $t_R$=2.68 min (gradient F), ESI-MS: 218.3 [MH]$^+$.

B. 1-(2,6-Dichloro-phenyl)-3-[6-(6-methoxy-pyridin-3-ylamino)-pyrimidin-4-yl]-urea The title compound is prepared analogously as described in Example 105B from N-(6-methoxy-pyridin-3-yl)-pyrimidine-4,6-diamine and 2,6-dichlorophenyl isocyanate.

Slightly beige solid, HPLC: $t_R$=4.01 min (purity: 100%, gradient F), ESI-MS: 405.2/407.2 [MH]$^+$.

Example 113

3-(2,6-Dichloro-phenyl)-1-methyl-1-[6-(3-trifluoromethyl-phenylamino)-pyrimidin-4-yl]-urea

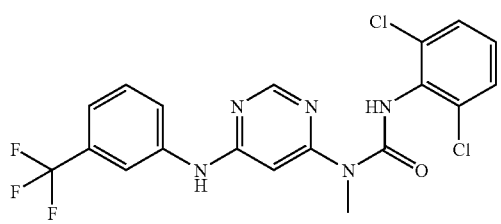 [SMILES: CN(C(=O)Nc1c(Cl)cccc1Cl)c1cc(Nc2cccc(C(F)(F)F)c2)ncn1]

A. (6-Chloro-pyrimidin-4-yl)-(3-trifluoromethyl-phenyl)-amine

A stirred mixture of 4,6-dichloropyrimidine (18.6 g, 125 mmol), 3-aminobenzotrifluoride (16.5 mL, 133 mmol), acetone (60 mL) and H$_2$O (90 mL) is kept at reflux for 3 h. Acetone is removed in vacuo, the remaining aqueous layer is basified with conc. aqueous ammonia solution and extracted with ethyl acetate. The organic extract is dried over Na$_2$SO$_4$ and evaporated. The residue is suspended in a small amount of acetone, filtered and the filter cake dried in vacuo to afford the title compound.

White solid, HPLC: $t_R$=4.82 min (gradient G), ESI-MS: 274.2/276.1 [MH]$^+$.

B. N-Methyl-N'-(3-trifluoromethyl-phenyl)-pyrimidine-4,6-diamine

A solution of methylamine in ethanol (32 mL, 256 mmol) is added to (6-chloro-pyrimidin-4-yl)-(3-trifluoromethyl-phenyl)-amine (3.49 g, 12.8 mmol) and the mixture is stirred for 5 h at 100° C. in a pressure bottle. The reaction mixture is concentrated in vacuo, the residue diluted with CH$_3$OH and basified using conc. aqueous ammonia solution. The product is filtered off, washed with H$_2$O and CH$_3$OH and dried in vacuo.

Greyish solid, HPLC: $t_R$=3.51 min (gradient G), ESI-MS: 269.2 [MH]$^+$.

C. 3-(2,6-Dichloro-phenyl)-1-methyl-1-[6-(3-trifluoromethyl-phenylamino)-pyrimidin-4-yl]-urea A mixture of N-methyl-N'-(3-trifluoromethyl-phenyl)-pyrimidine-4,6-diamine (536.5 mg, 2 mmol), 2,6-dichlorophenyl isocyanate (413.6 mg, 2.2 mmol) in dry dioxane (5 mL) is shaken for 1 h at 80° C. After evaporation of the solvent in vacuo, the residue is distributed between ethyl acetate and half-saturated K$_2$CO$_3$ solution. The organic layer is dried over Na$_2$SO$_4$, evaporated, and the residue recrystallized from CH$_2$Cl$_2$/CH$_3$OH. The solid residue is dried in vacuo to afford the title compound.

White solid, HPLC: $t_R$=5.08 min (purity: 100%, gradient H), ESI-MS: 456.3/458.3 [MH]$^+$.

Example 114

1-[6-(3-Cyano-phenylamino)-pyrimidin-4-yl]-3-(2,6-dichloro-phenyl)-1-methyl-urea

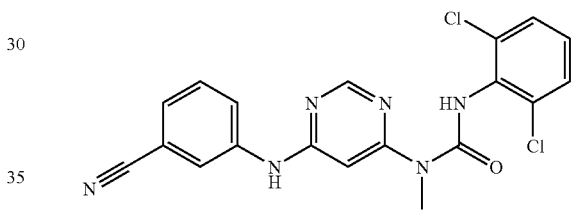

A. 3-(6-Methylamino-pyrimidin-4-ylamino)-benzonitrile

A mixture of (6-chloro-pyrimidin-4-yl)-methylamine (1.44 g, 10 mmol), 3-amino-benzonitrile. (1.18 g, 10 mmol), 2-propanol (10 mL) and conc. HCl (0.45 mL, ~5 mmol) is stirred for 36 h at 90° C. After cooling to room temperature, CH$_3$OH is added and the reaction mixture is basified with conc. aqueous ammonia solution. The precipitate which forms upon addition of H$_2$O is filtered off, washed with H$_2$O and dried in vacuo to afford the title compound.

Beige solid, HPLC: $t_R$=2.67 min (gradient G), ESI-MS: 226.2 [MH]$^+$.

B. 1-[6-(3-Cyano-phenylamino)-pyrimidin-4-yl]-3-(2,6-dichloro-phenyl)-1-methyl-urea A mixture of 3-(6-methylamino-pyrimidin-4-ylamino)-benzonitrile (450.5 mg, 2 mmol), 2,6-dichlorophenyl isocyanate (413.6 mg, 2.2 mmol) in dry dioxane (5 mL) is shaken for 1.5 h at 80° C. and then evaporated in vacuo. The residue is suspended in half-concentrated aqueous K$_2$CO$_3$ solution, filtered off, washed with H$_2$O and acetone and dried in vacuo to afford the title compound.

Beige solid, HPLC: $t_R$=4.34 min (purity: 100%, gradient H), ESI-MS: 413.3/415.3 [MH]⁺.

Example 115

1-(2,6-Dichloro-phenyl)-3-[6-(4-fluoro-phenylamino)-pyrimidin-4-yl]-urea

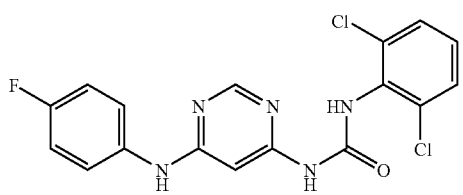 [SMILES: O=C(Nc1cc(Nc2ccc(F)cc2)ncn1)Nc1c(Cl)cccc1Cl]

A. N-(4-Fluoro-phenyl)-pyrimidine-4,6-diamine

The title compound is prepared analogously as described in Example 114A from 6-chloro-pyrimidin-4-ylamine and 4-fluoroaniline.

Brownish solid, HPLC: $t_R$=3.09 min (gradient F), ESI-MS: 205.2 [MH]⁺.

B. 1-(2,6-Dichloro-phenyl)-3-[6-(4-fluoro-phenylamino)-pyrimidin-4-yl]-urea

A suspension of N-(4-fluoro-phenyl)-pyrimidine-4,6-diamine (408.4 mg, 2 mmol), 2,6-dichlorophenyl isocyanate (413.6 mg, 2.2 mmol) in dry dioxane (5 mL) is shaken for 14 h at 80° C. After cooling to 5° C. the suspension is filtered, the residue washed with half-saturated K₂CO₃ solution, H₂O and acetone and dried in vacuo.

Greyish solid, HPLC: $t_R$=4.11 min (purity: 100%, gradient G), ESI-MS: 392.3/394.3 [MH]⁺.

Example 116

1-[6-(4-Fluoro-Phenylamino)-pyrimidin-4-yl]-3-(4-methoxy-phenyl)-1-methyl-urea

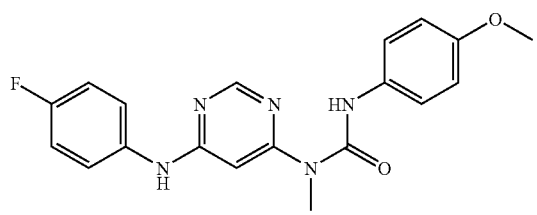 [SMILES: COc1ccc(NC(=O)N(C)c2cc(Nc3ccc(F)cc3)ncn2)cc1]

A mixture of N-(4-fluoro-phenyl)-N'-methyl-pyrimidine-4,6-diamine (2.18 g, 10 mmol), 4-methoxyphenyl isocyanate (1.29 mL, 10 mmol) and dibutyltin diacetate (0.54 mL, 2 mmol) in dry dioxane (20 mL) is shaken for 6 h at 100° C. After addition of a second portion of 4-methoxyphenyl isocyanate (0.9 mL, 7 mmol) stirring is continued at 100° C. for 9 h. The reaction mixture is treated with ethyl acetate and half-saturated Na₂CO₃ solution. The organic layer is filtered, dried over Na₂SO₄, evaporated, and the residue purified by flash chromatography (hexane/ethyl acetate). The combined pure fractions are evaporated, the residue is suspended in hot CH₃OH and the hot mixture filtered. This procedure is repeated several times. The solid thus obtained is dried in vacuo to afford the title compound.

White powder, HPLC: $t_R$=4.54 min (purity: 100%, gradient G), ESI-MS: 368.3 [MH]⁺.

Example 117

3-(2,6-Dichloro-phenyl)-1-methyl-1-[6-(4-morpholin-4-yl-phenylamino)-pyrimidin-4-yl]-urea

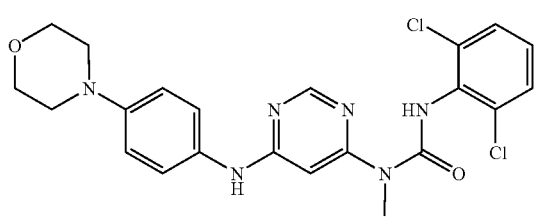 [SMILES: CN(C(=O)Nc1c(Cl)cccc1Cl)c1cc(Nc2ccc(N3CCOCC3)cc2)ncn1]

A. N-Methyl-N'-(4-morpholin-4-yl-phenyl)-pyrimidine-4,6-diamine

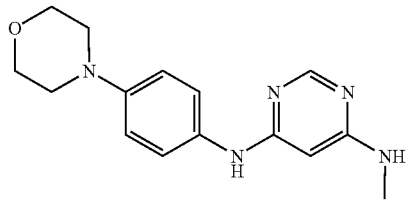 [SMILES: CNc1cc(Nc2ccc(N3CCOCC3)cc2)ncn1]

The title compound is prepared analogously as described in Example 114A from (6-chloro-pyrimidin-4-yl)-methylamine and 4-morpholinoaniline.

Slightly violet solid, HPLC: $t_R$=1.37 min (gradient G), ESI-MS: 286.3 [MH]⁺.

B. 3-(2,6-Dichloro-Phenyl)-1-methyl-1-[6-(4-morpholin-4-yl-phenylamino)-pyrimidin-4-yl]-urea A mixture of N-methyl-N'-(4-morpholin-4-yl-phenyl)-pyrimidine-4,6-diamine (428.0 mg, 1.5 mmol), 2,6-dichlorophenyl isocyanate (310.2 mg, 1.65 mmol) in dry dioxane (5 mL) is shaken for 1.5 h at 80° C. After evaporation of the solvent in vacuo, the residue is purified by flash chromatography (CH₂Cl₂/CH₃OH). The combined pure fractions are evaporated, the residue triturated with CH₂Cl₂ and the solid filtered off and dried in vacuo to afford the title compound.

White solid, HPLC: $t_R$=2.79 min (purity: 100%, gradient H), ESI-MS: 473.3/475.3 [MH]⁺.

Example 118

3-(2,6-Dichloro-phenyl)-1-[6-(2,4-difluoro-phenylamino)-pyrimidin-4-yl]-1-methyl-urea

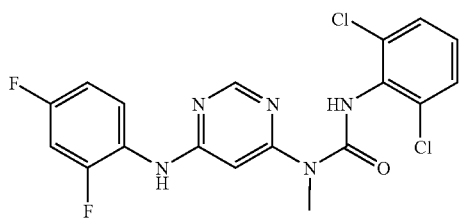 [SMILES: CN(C(=O)Nc1c(Cl)cccc1Cl)c1cc(Nc2ccc(F)cc2F)ncn1]

A. N-(2,4-Difluoro-phenyl)-N'-methyl-pyrimidine-4,6-diamine

The title compound is prepared analogously as described in Example 114A from (6-chloro-pyrimidin-4-yl)-methylamine and 2,4-difluoroaniline.

Pinkish solid, HPLC: $t_R$=3.21 min (gradient F), ESI-MS: 237.2 [MH]$^+$.

B. 3-(2,6-Dichloro-phenyl)-1-[6-(2,4-difluoro-phenylamino)-pyrimidin-4-yl]-1-methyl-urea The title compound is prepared analogously as described in Example 105B from N-(2,4-difluoro-phenyl)-N'-methyl-pyrimidine-4,6-diamine and 2,6-dichlorophenyl isocyanate.

White solid, HPLC: $t_R$=4.41 min (purity: 100%, gradient H), ESI-MS: 424.2/426.2 [MH]$^+$.

Example 119

1-(2,6-Dichloro-phenyl)-3-[6-(3-dimethylaminophenylamino)-pyrimidin-4-yl]-urea

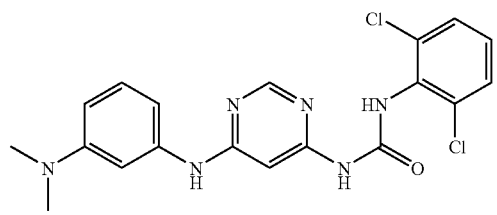

The title compound is prepared analogously as described in Example 105B from N-(3-dimethylamino-phenyl)-pyrimidine-4,6-diamine and 2,6-dichlorophenyl isocyanate using ethyl acetate instead of CH$_2$Cl$_2$ for the work-up procedure.

White solid, HPLC: $t_R$=3.61 min (purity: 100%, gradient F), ESI-MS: 417.3/419.2 [MH]$^+$.

Example 120

3-(2,6-Dichloro-phenyl)-1-[6-(3-dimethylaminophenylamino)-pyrimidin-4-yl]-1-methyl-urea

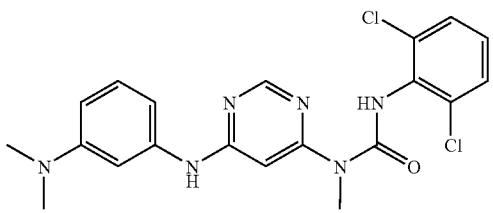

A. N-(3-Dimethylamino-phenyl)-N'-methyl-pyrimidine-4,6-diamine

The title compound is prepared analogously as described in Example 105A from (6-chloro-pyrimidin-4-yl)-methylamine and N,N-dimethyl-m-phenylenediamine. The crude product obtained after evaporation of the ethyl acetate layer is purified by flash chromatography (CH$_2$Cl$_2$/CH$_3$OH).

Beige solid, HPLC: $t_R$=2.45 min (gradient F), ESI-MS: 244.3 [MH]$^+$.

B. 3-(2,6-Dichloro-phenyl)-1-[6-(3-dimethylaminophenylamino)-pyrimidin-4-yl]-1-methyl-urea A mixture of N-(3-dimethylamino-phenyl)-N'-methyl-pyrimidine-4,6-diamine (243.3 mg, 1 mmol), 2,6-dichlorophenyl isocyanate (188 mg, 1 mmol) in dry dimethylformamide (2.5 mL) is shaken for 14 h at 90° C. Two additional portions (188 mg, 1 mmol each) of 2,6-dichlorophenyl isocyanate are added after 14 h and 26 h. After 38 h the reaction mixture is evaporated in vacuo and the residue is distributed between ethyl acetate and half-saturated K$_2$CO$_3$ solution. The organic layer is dried over Na$_2$SO$_4$, evaporated, and the residue purified by flash chromatography (hexane/ethyl acetate). The combined pure fractions are evaporated, the residue triturated with CH$_2$Cl$_2$ and the solid filtered off and dried in vacuo to afford the title compound.

White solid, HPLC: $t_R$=3.79 min (purity: 100%, gradient G), ESI-MS: 431.1/433.1 [MH]$^+$.

Example 121

1-[6-(4-Fluoro-phenylamino)-pyrimidin-4-yl]-1-methyl-3-(3-trifluoro-methyl-phenyl)-urea

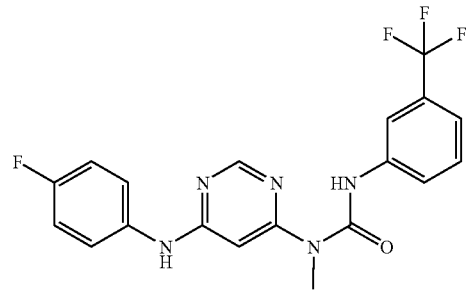 [SMILES: CN(C(=O)Nc1cccc(C(F)(F)F)c1)c1cc(Nc2ccc(F)cc2)ncn1]

A mixture of N-(4-fluoro-phenyl)-N'-methyl-pyrimidine-4,6-diamine (218.2 mg, 1 mmol), 3-trifluoromethyl)phenyl isocyanate (165.2 □L, 1.2 mmol) and dibutyltin diacetate (53.7 □L, 0.2 mmol) in dry dioxane (2.5 mL) is shaken for 14 h at 100° C. Two additional portions (82.6 □L, 0.6 mmol each) of 3-trifluoromethyl)phenyl isocyanate are added after 14 h and 20 h. After 26 h the reaction mixture is distributed between ethyl acetate and half-saturated Na₂CO₃ solution. The organic layer is dried over Na₂SO₄, evaporated, and the residue triturated with CH₂Cl₂. The solid is filtered off and the filtrate purified by flash chromatography (hexane/ethyl acetate). The combined pure fractions are evaporated, the residue recrystallized from CH₃OH/CH₂Cl₂ to afford the title compound.

White solid, HPLC: $t_R$=5.31 min (purity: 100%, gradient G), ESI-MS: 406.3 [MH]⁺.

Example 122

3-(3-Chloro-Phenyl)-1-[6-(4-fluoro-phenylamino)-pyrimidin-4-yl]-1-methyl-urea

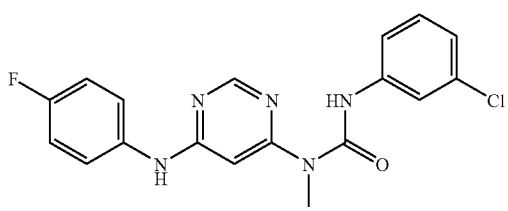 [SMILES: CN(C(=O)Nc1cccc(Cl)c1)c1cc(Nc2ccc(F)cc2)ncn1]

The title compound is prepared analogously as described in Example 121 from N-(4-fluoro-phenyl)-N'-methyl-pyrimidine-4,6-diamine and 3-chlorophenyl isocyanate.

White solid, HPLC: $t_R$=5.25 min ((purity: 100%, gradient G), ESI-MS: 372.2 [MH]⁺.

Example 123

3-(2,6-Dichloro-phenyl)-1-[6-(4-fluoro-phenylamino)-pyrimidin-4-yl]-1-methyl-urea

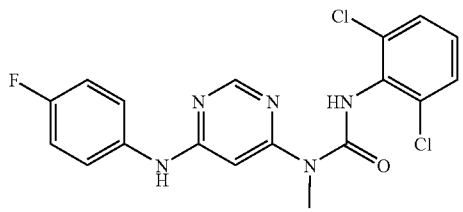 [SMILES: CN(C(=O)Nc1c(Cl)cccc1Cl)c1cc(Nc2ccc(F)cc2)ncn1]

A mixture of N-(4-fluoro-phenyl)-N'-methyl-pyrimidine-4,6-diamine (218.2 mg, 1 mmol), 2,6-dichlorophenyl isocyanate (188 mg, 1 mmol) and triethylamine (1.11 mL, 8 mmol) in dry dimethylformamide (2.5 mL) is shaken for 14 h at 90° C. The reaction mixture is evaporated in vacuo and the residue is distributed between ethyl acetate and half-saturated Na₂CO₃ solution. The organic layer is dried over Na₂SO₄, evaporated, and the residue purified by flash chromatography (CH₂Cl₂/CH₃OH). The combined pure fractions are evaporated, the residue triturated with CH₂Cl₂ and the solid filtered off and dried in vacuo to afford the title compound.

White solid, HPLC: $t_R$=4.33 min (purity: 100%, gradient H), ESI-MS: 406.1/408.1 [MH]⁺.

Example 124

1-[6-(3-Chloro-phenylamino)-pyrimidin-4-yl]-3-(2,6-dichloro-phenyl)-1-methyl-urea

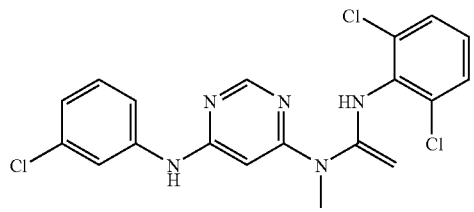 [SMILES: C=C(Nc1c(Cl)cccc1Cl)N(C)c1cc(Nc2cccc(Cl)c2)ncn1]

A. N-(3-Chloro-phenyl)-N'-methyl-pyrimidine-4,6-diamine

The title compound is prepared analogously as described in Example 105A from (6-chloro-pyrimidin-4-yl)-methyl-amine and 3-chloroaniline. The ethyl acetate layer is dried over Na₂SO₄ and evaporated. The solid residue is suspended in CH₂Cl₂, filtered off and dried in vacuo to afford the title compound.

White solid, HPLC: $t_R$=3.23 min (gradient G), ESI-MS: 235.2 [MH]⁺.

B. 1-[6-(3-Chloro-phenylamino)-pyrimidin-4-yl]-3-(2,6-dichloro-phenyl)-1-methyl-urea The title compound is prepared analogously as described in Example 105B from N-(3-chloro-phenyl)-N'-methyl-pyrimidine-4,6-diamine and 2,6-dichloroaniline. The oily residue received after evaporation of the CH₂Cl₂ layer is triturated with CH₂Cl₂ and the crystals thus obtained were filtered off and dried in vacuo to afford the title compound.

White solid, HPLC: $t_R$=4.97 min (purity: 100%, gradient H), ESI-MS: 422.3/424.3 [MH]⁺.

Example 125

1-(2-Chloro-Phenyl)-3-{6-[4-(3-morpholin-4-yl-propoxy)-phenylamino]-pyrimidin-4-yl}-urea bis-hydrochloride Salt

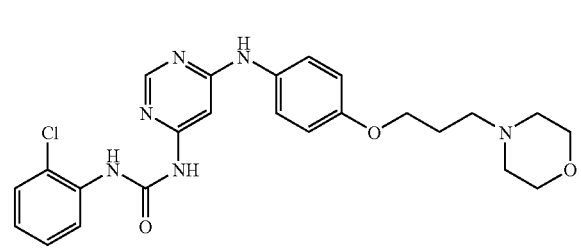 [SMILES: O=C(Nc1cc(Nc2ccc(OCCCN3CCOCC3)cc2)ncn1)Nc1ccccc1Cl]

A. 1-(2-Chloro-phenyl)-3-(6-chloro-pyrimidin-4-yl)-urea

A solution of 6-chloro-pyrimidin-4-ylamine (997 mg, 7.7 mmol) and 2-chlorophenyl isocyanate (0.46 mL, 3.85 mmol)

in THF (20 mL) is refluxed for 4 h. A further amount of 2-chlorophenyl isocyanate (0.46 mL, 3.85 mmol) is added and the reaction mixture is refluxed for 28 h. The reaction mixture is cooled to RT, the precipitate is filtered to afford the title compound (1.9 g, 86%).

White powder. HPLC: $t_R$=8.01 min (gradient I), ESI-MS: 281.1/283.1 [M–H]−

B 1-(2-Chloro-phenyl)-3-{6-[4-(3-morpholin-4-yl-propoxy)-phenylamino]-pyrimidin-4-yl}-urea A solution of 1-(2-chloro-phenyl)-3-(6-chloro-pyrimidin-4-yl)-urea (99 mg, 0.35 mmol), 4-(3-morpholin-4-yl-propoxy)-phenylamine [Chabrier et al. *Bull. Soc. Chim. Fr.* 1955; 1353] (83 mg, 0.35 mmol), and concentrated HCl (0.1 ml, 1.4 mmol) in ethanol (5 ml) was refluxed for 32 h. The reaction mixture is cooled to RT, and diluted with water. The acidic solution is washed with ethyl acetate, basified with aqueous ammoniac, and extracted with DCM. The combined organic phases are dried over sodium sulfate, evaporated in vacuo, the residue is crystallized from water/methanol/1 N HCl to afford the title compound.

Brownish crystalline powder. HPLC: $t_R$=5.92 min (gradient I), ESI-MS: 483 [MH]+

Example 126

1-(2-Chloro-phenyl)-3-{6-[4-(2-diethylamino-ethoxy)-phenylamino]-pyrimidin-4-yl}-urea

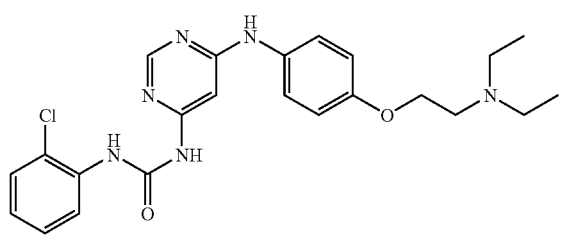 [SMILES: CCN(CC)CCOc1ccc(Nc2cc(NC(=O)Nc3ccccc3Cl)ncn2)cc1]

The title compound is prepared analogously as described in Example 125B using 4-(2-diethylamino-ethoxy)-phenylamine, crystallization from DCM afford the title compound.

White powder. HPLC: $t_R$=6.03 min (gradient I), ESI-MS: 455 [MH]+

Example 127

1-[6-(3-Chloro-phenylamino)-pyrimidin-4-yl]-3-(2,6-dimethyl-phenyl)-1-methyl-urea

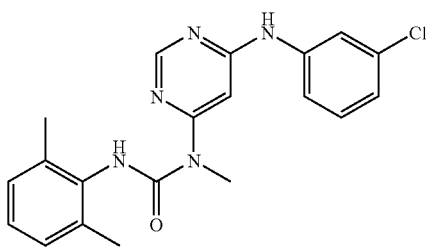 [SMILES: Cc1cccc(C)c1NC(=O)N(C)c1cc(Nc2cccc(Cl)c2)ncn1]

A solution of N-(3-chloro-phenyl)-N'-methyl-pyrimidine-4,6-diamine (Example 124A, 94 mg, 0.4 mmol) and 2,6-dimethylphenyl isocyanate (74 mg, 0.52 mmol) in diglyme was stirred at 80° C. for 18 h. The solvent is evaporated in vacuo, and the residue is purified by column flash chromatography on silica gel (ethyl acetate/hexane 1:2) to afford title compound (29 mg, 19

White powder. HPLC: $t_R$=9.60 min (gradient I), ESI-MS: 382.3 [MH]+

Example 128

3-(2-Chloro-phenyl)-1-[6-(3-chloro-phenylamino)-pyrimidin-4-yl]-urea

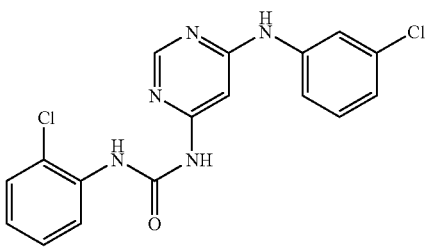 [SMILES: O=C(Nc1cc(Nc2cccc(Cl)c2)ncn1)Nc1ccccc1Cl]

A. N-(3-Chloro-phenyl)-pyrimidine-4,6-diamine

The title compound is prepared analogously as described in Example 105A from 6-chloro-pyrimidin-4-ylamine and 3-chloroaniline.

White powder. m.p. 171-172° C., HPLC: $t_R$=5.11 min (gradient I), ESI-MS: 221 [MH]+

B. 3-(2-Chloro-phenyl)-1-[6-(3-chloro-phenylamino)-pyrimidin-4-yl]-urea

A solution of N-(3-chloro-phenyl)-pyrimidine-4,6-diamine (110 mg, 0.5 mmol) and 2-chlorophenyl isocyanate (60 μL, 0.5 mmol) in diglyme (1.5 mL) is stirred at 80° C. for 18 h. The precipitate which formed over time is filtered and washed with hexane/ethyl acetate to afford the pure title compound (98 mg, 52%).

White powder. HPLC: $t_R$=8.95 min (gradient I), ESI-MS: 374.1/376.1 [MH]+

Example 129

1-(2-Bromo-phenyl)-3-[6-(3-chloro-phenylamino)-pyrimidin-4-yl]-urea

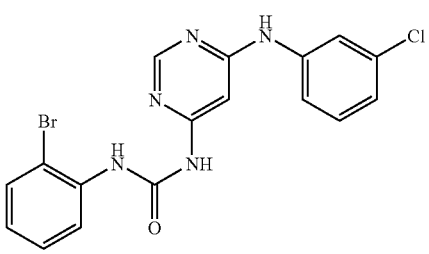 [SMILES: O=C(Nc1cc(Nc2cccc(Cl)c2)ncn1)Nc1ccccc1Br]

The title compound is prepared analogously as described in Example 128 using 2-bromophenyl isocyanate.

White powder. HPLC: $t_R$=9.03 min (gradient I), ESI-MS: 418.0/420.0 [MH]+

Example 130

1-[6-(3-Chloro-phenylamino)-pyrimidin-4-yl]-3-(2-fluoro-phenyl)-urea

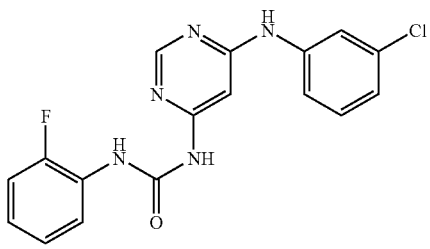 [SMILES: O=C(Nc1cc(Nc2cccc(Cl)c2)ncn1)Nc1ccccc1F]

The title compound is prepared analogously as described in Example 128 using 2-fluorophenyl isocyanate.
White powder. HPLC: $t_R$=8.24 min (gradient I), ESI-MS: 258.2 [MH]$^+$

Example 131

1-[6-(3-Chloro-phenylamino)-pyrimidin-4-yl]-3-(3-methoxy-Phenyl)-urea

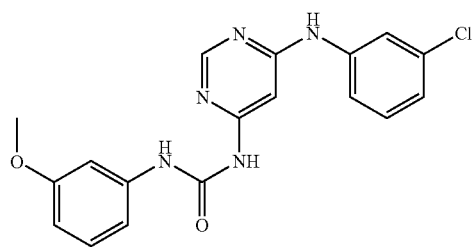 [SMILES: COc1cccc(NC(=O)Nc2cc(Nc3cccc(Cl)c3)ncn2)c1]

The title compound is prepared analogously as described in Example 128 using 3-methoxy-phenyl isocyanate.
White powder. HPLC: $t_R$=7.90 min (gradient I), ESI-MS: 370.2 [MH]$^+$

Example 132

1-[6-(3-Chloro-phenylamino)-pyrimidin-4-yl]-3-(2,5-dimethoxy-phenyl)-urea

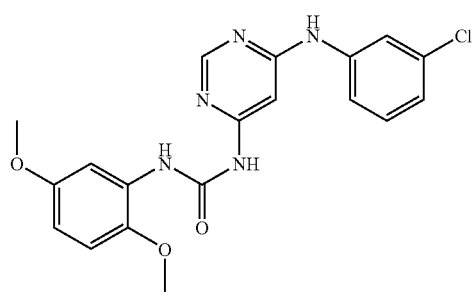 [SMILES: COc1ccc(OC)c(NC(=O)Nc2cc(Nc3cccc(Cl)c3)ncn2)c1]

The title compound is prepared analogously as described in Example 127 from N-(3-chloro-phenyl)-pyrimidine-4,6-diamine and 2,5-dimethoxyphenyl isocyanate.
White powder. HPLC: $t_R$=8.18 min (gradient I), ESI-MS: 400.2 [MH]$^+$

Example 133

1-[6-(3-Chloro-phenylamino)-pyrimidin-4-yl]-3-(2-trifluoromethyl-phenyl)-urea

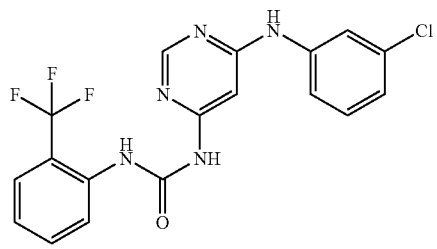 [SMILES: O=C(Nc1cc(Nc2cccc(Cl)c2)ncn1)Nc1ccccc1C(F)(F)F]

The title compound is prepared analogously as described in Example 128 using 3-trifluoromethylphenyl isocyanate.
White powder. HPLC: $t_R$=8.94 min (gradient I), ESI-MS: 408.1 [MH]$^+$

Example 134

1-[6-(3-Chloro-phenylamino)-pyrimidin-4-yl]-3-(5-methoxy-2-methyl-phenyl)-urea

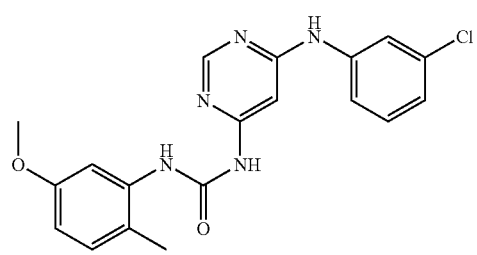 [SMILES: COc1ccc(C)c(NC(=O)Nc2cc(Nc3cccc(Cl)c3)ncn2)c1]

The title compound is prepared analogously as described in Example 2 from 5-methoxy-2-methylaniline and N-(3-chloro-phenyl)-pyrimidine-4,6-diamine.
White powder. HPLC: $t_R$=8.38 min (gradient I), ESI-MS: 384.2 [MH]$^+$

Example 135

1-(3-Chloro-phenyl)-3-[6-(3-chloro-phenylamino)-pyrimidin-4-yl]-urea

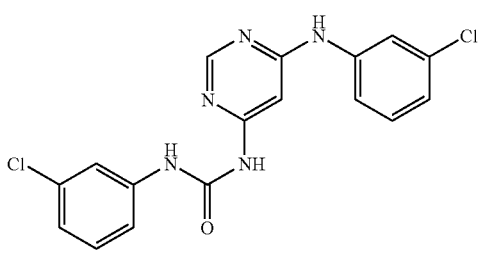 [SMILES: O=C(Nc1cccc(Cl)c1)Nc1cc(Nc2cccc(Cl)c2)ncn1]

The title compound is prepared analogously as described in Example 128 using 3-chlorophenyl isocyanate.
White powder. HPLC: $t_R$=8.75 min (gradient I), ESI-MS: 374.1/376.1 [MH]$^+$

Example 136

1-[6-(3-Chloro-phenylamino)-pyrimidin-4-yl]-3-(3,4,5-trimethoxy-phenyl)-urea

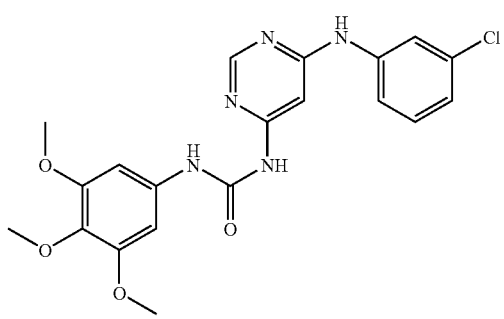 [SMILES: COc1cc(NC(=O)Nc2cc(Nc3cccc(Cl)c3)ncn2)cc(OC)c1OC]

The title compound is prepared analogously as described in Example 127 from N-(3-chloro-phenyl)-pyrimidine-4,6-diamine and 3,4,5-trimethoxyphenyl isocyanate.

White powder. HPLC: $t_R$=7.60 min (gradient I), ESI-MS: 430.2 [MH]$^+$

Example 137

1-[6-(3-Chloro-phenylamino)-pyrimidin-4-yl]-3-(2,6-dichloro-Phenyl)-urea

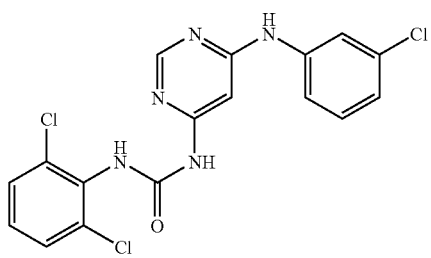 [SMILES: O=C(Nc1cc(Nc2cccc(Cl)c2)ncn1)Nc1c(Cl)cccc1Cl]

The title compound is prepared analogously as described in Example 127 from N-(3-chloro-phenyl)-pyrimidine-4,6-diamine and 2,6-dichlorophenyl isocyanate.

White powder. HPLC: $t_R$=8.30 min (gradient I), ESI-MS: 410 [MH]$^+$

Example 138

1-(4-Chloro-phenyl)-3-[6-(3-chloro-phenylamino)-pyrimidin-4-yl]-urea

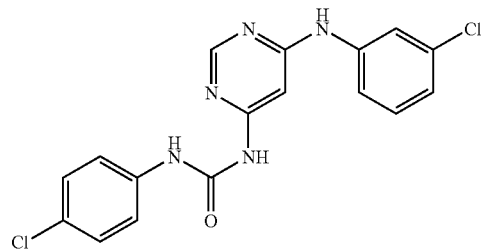 [SMILES: O=C(Nc1ccc(Cl)cc1)Nc1cc(Nc2cccc(Cl)c2)ncn1]

The title compound is prepared analogously as described in Example 128 using 4-chlorophenyl isocyanate.

White powder. HPLC: $t_R$=8.63 min (gradient I), ESI-MS: 374.1/376.1 [MH]$^+$

Example 139

1-[6-(3-Chloro-phenylamino)-pyrimidin-4-yl]-3-(3,5-dimethoxy-phenyl)-urea

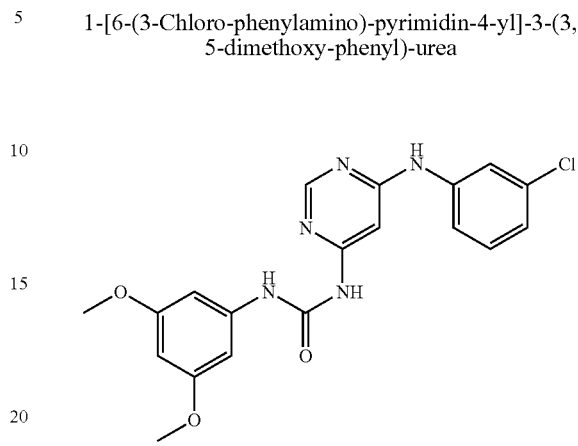

The title compound is prepared analogously as described in Example 128 using 3,5-dimethoxyphenyl isocyanate.

White powder. HPLC: $t_R$=8.06 min (gradient I), ESI-MS: 400.2 [MH]$^+$

Example 140

1-[6-(3-Chloro-phenylamino)-pyrimidin-4-yl]-3-(2,6-dimethyl-phenyl)-urea

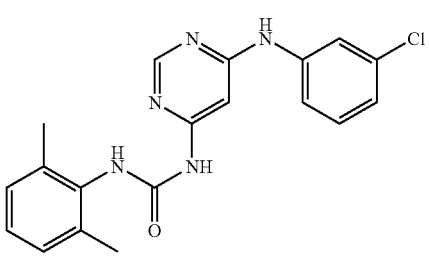 [SMILES: Cc1cccc(C)c1NC(=O)Nc1cc(Nc2cccc(Cl)c2)ncn1]

The title compound is prepared analogously as described in Example 127 from N-(3-chloro-phenyl)-pyrimidine-4,6-diamine and 2,6-dimethylphenyl isocyanate.

White powder. HPLC: $t_R$=7.97 min (gradient I), ESI-MS: 368.2 [MH]$^+$

Example 141

1-[6-(3-Chloro-phenylamino)-pyrimidin-4-yl]-3-phenyl-urea

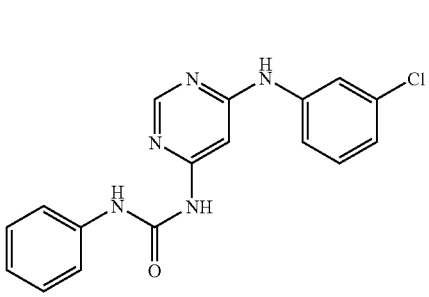 [SMILES: O=C(Nc1ccccc1)Nc1cc(Nc2cccc(Cl)c2)ncn1]

The title compound is prepared analogously as described in Example 128 using phenyl isocyanate.

White powder. HPLC: $t_R$=7.83 min (gradient I), ESI-MS: 338 [MH]$^+$

Example 142

1-(2-Chloro-phenyl)-3-{6-[4-(2-morpholin-4-yl-ethoxy)-phenylamino]-pyrimidin-4-yl}-urea

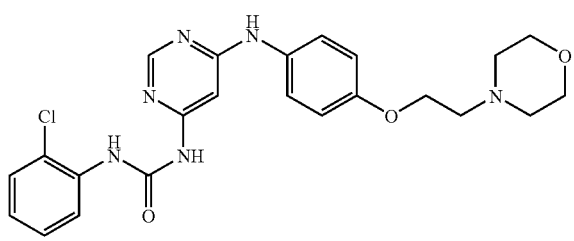

The title compound is prepared analogously as described in Example 125B using 4-(2-morpholin-4-yl-ethoxy)-phenylamine, crystallization from DCM afford the title compound.

White powder. HPLC: $t_R$=5.82 min (gradient I), ESI-MS: 469 [MH]$^+$

Example 143

3-(2,6-Dichloro-3,5-dimethoxy-phenyl)-1-ethyl-1-{6-[4-(4-methyl-piperazin-1-yl)-phenylamino]-pyrimidin-4-yl}-urea

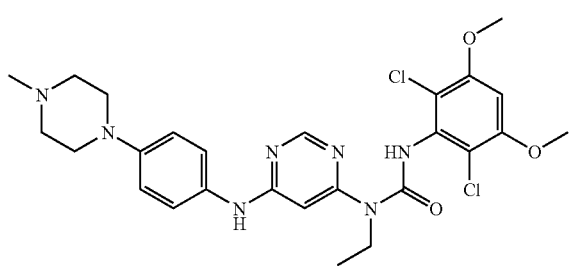

To a solution of 2,6-dichloro-3-methoxyphenylisocyanate (1.25 eq.) in toluene (1.9 ml) is added N-ethyl-N'-[4-(4-methyl-piperazin-1-yl)-phenyl]-pyrimidine-4,6-diamine (113 mg, 0.36 mmol), under an argon atmosphere. The resulting mixture is stirred at 70° C. for 18 h, allowed to cool to RT and filtered. The recovered solid is washed with diethyl ether, dried and further purified by MPLC (silica gel) (DCM/MeOH) to afford 10 mg of the title compound as a white solid: ESI-MS: 559.9/561.9 [MH]$^+$; $t_R$=3.53 min (purity: 100%, gradient J); TLC: $R_f$=0.28 (DCM/MeOH, 9:1).

A. N-Ethyl-N'-[4-(4-methyl-piperazin-1-yl)-phenyl]-pyrimidine-4,6-diamine

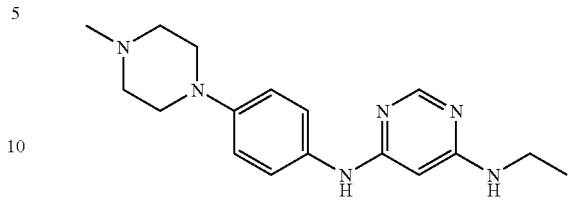

A mixture of (6-chloro-pyrimidin-4-yl)-ethyl-amine (363 mg, 2.30 mmol, 1.1 eq.) and 4-(4-methylpiperazin-1-yl)-aniline (400 mg, 2.09 mmol) in water (0.8 ml) and glacial acetic acid (3.2 ml) is heated to 100° C. 3 h. After solvent evaporation, the residue is taken up in methanol, made alkaline by addition of 25% NH$_3$ in water and concentrated. The residue is purified by MPLC (silica gel) (DCM/MeOH) to afford 395 mg of the title compound as a white solid: ESI-MS: 313.2 [MH]$^+$; $t_R$=1.25 min (purity: ~90%, gradient J); TLC: $R_f$=0.12 (DCM/MeOH, 9:1).

B. (6-Chloro-pyrimidin-4-yl)-ethyl-amine

Ethylamine (70% in water, 16 ml, 45.08 mmol, 2.5 eq.) is added dropwise (15 min) to a suspension of 4,6-dichloropyrimidine (12 g, 80.5 mmol) in EtOH (36 ml) at RT. The resulting yellowish solution is allowed to stir for 1 h at RT and then cooled to 0° C. The resulting white precipitate is collected by vacuum filtration, washed with water and dried in vacuo to afford 12.4 g of the title compound: ESI-MS: 157.9 [MH]$^+$; single peak at $t_R$=2.02 min (purity: 100%, gradient J).

Example 144

3-(2,6-Dichloro-3,5-dimethoxy-phenyl)-1-[6-(3-dimethylaminomethyl-phenylamino)-pyrimidin-4-yl]-1-methyl-urea

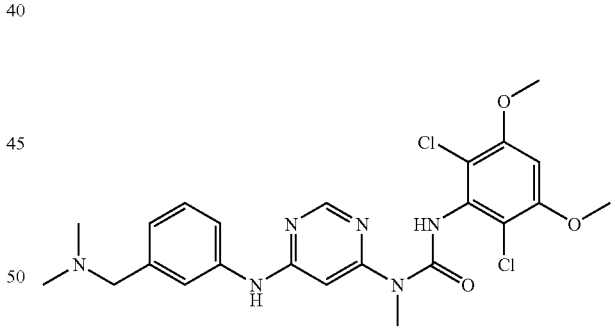

2,6-dichloro-3,5-dimethoxyphenylisocyanate (1.25 eq.) is added to a solution of N-(3-dimethylaminomethyl-phenyl)-N'-methyl-pyrimidine-4,6-diamine (93 mg, 0.36 mmol, 1 eq.) in toluene (3 ml), at 70° C. and under an argon atmosphere. The resulting mixture is stirred at 70° C. for 18 h, allowed to cool to RT, and diluted with DCM and a saturated aqueous solution of sodium bicarbonate. The aqueous layer is separated and extracted with DCM. The organic phase is washed with brine, dried (sodium sulfate), filtered and concentrated. Purification of the crude product by silica gel column chromatography (DCM/MeOH+1% NH$_3^{aq}$, 9:1) affords 121 mg of the title compound as a white solid: ESI-MS: 504.9/506.9 [MH]$^+$; $t_R$=3.64 min (purity: 100%, gradient J); TLC: $R_f$=0.12 (DCM/MeOH+1% NH$_3^{aq}$, 9:1).

A. N-(3-Dimethylaminomethyl-phenyl)-N'-methyl-pyrimidine-4,6-diamine

A mixture of (6-chloro-pyrimidin-4-yl)-methyl-amine (Example 1) (750 mg, 5.2 mmol), 3-dimethylaminomethyl-phenylamine (787 mg, 5.2 mmol) and 4N HCl in dioxane (15 ml) is heated in a sealed tube to 150° C. for 5 h. The reaction mixture is concentrated, diluted with DCM and a saturated aqueous solution of sodium bicarbonate. The aqueous layer is separated and extracted with DCM. The organic phase is washed with brine, dried (sodium sulfate), filtered and concentrated. Purification of the residue by silica gel column chromatography (DCM/MeOH+1% NH$_3$$^{aq}$, 9:1) affords 800 mg of the title compound as a white solid: ESI-MS: 258.1 [MH]$^+$; t$_R$=1.00 min (purity: 100%, gradient J); TLC: R$_f$=0.14 (DCM/MeOH+1% NH$_3$$^{aq}$, 9:1).

Example 145

3-(2,6-Dichloro-3,5-dimethoxy-phenyl)-1-{6-[4-(4-ethyl-piperazin-1-yl)-phenylamino]-pyrimidin-4-yl}-1-methyl-urea

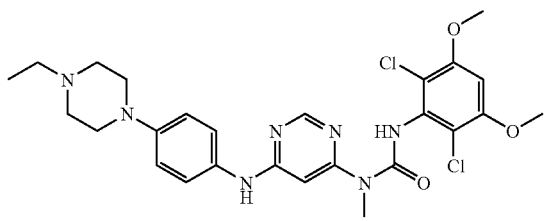 [SMILES: CCN1CCN(c2ccc(Nc3cc(N(C)C(=O)Nc4c(Cl)c(OC)cc(OC)c4Cl)ncn3)cc2)CC1]

The title compound is prepared as described in Example 144 but using N-[4-(4-ethyl-piperazin-1-yl)-phenyl]-N'-methyl-pyrimidine-4,6-diamine (2.39 g, 7.7 mmol, 1 eq.) and stirring the reaction mixture for 1.5 h at reflux. Purification of the crude product by silica gel column chromatography (DCM/MeOH+1% NH$_3$$^{aq}$, 95:5) affords the title compound as a white solid: ESI-MS: 560.0/561.9 [MH]$^+$; t$_R$=3.54 min (purity: 100%, gradient J); TLC: R$_f$=0.28 (DCM/MeOH+1% NH$_3$$^{aq}$, 95:5).

A. N-[4-(4-ethyl-piperazin-1-yl)-phenyl]-N'-methyl-pyrimidine-4,6-diamine

The title compound is prepared as described in Example 144A but using 4-(4-ethylpiperazin-1-yl)-aniline (1 g, 4.88 mmol) and (6-chloro-pyrimidin-4-yl)-methyl-amine (Example 1) (771 1.81 g, 12.68 mmol, 1.3 eq.). Purification of the residue by silica gel column chromatography (DCM/MeOH, 93:7) followed by trituration in diethyl ether affords the title compound as a white solid: ESI-MS: 313.2 [MH]$^+$; t$_R$=1.10 min (gradient J); TLC: R$_f$=0.21 (DCM/MeOH, 93:7).

B. 4-(4-Ethylpiperazin-1-yl)-aniline

A suspension of 1-ethyl-4-(4-nitro-phenyl)-piperazine (6.2 g, 26.35 mmol) and Raney Nickel (2 g) in MeOH (120 mL) is stirred for 7 h at RT, under a hydrogen atmosphere. The reaction mixture is filtered through a pad of celite and concentrated to afford 5.3 g of the title compound as a violet solid: ESI-MS: 206.1 [MH]$^+$; TLC: R$_f$=0.15 (DCM/MeOH+1% NH$_3$$^{aq}$, 9:1).

C. 1-Ethyl-4-(4-nitro-phenyl)-piperazine

A mixture of 1-bromo-4-nitrobenzene (6 g, 29.7 mmol) and 1-ethylpiperazine (7.6 ml, 59.4 mmol, 2 eq.) is heated to 80° C. for 15 h. After cooling to RT, the reaction mixture is diluted with water and DCM/MeOH, 9:1. The aqueous layer is separated and extracted with DCM/MeOH, 9:1. The organic phase is washed with brine, dried (sodium sulfate), filtered and concentrated. Purification of the residue by silica gel column chromatography (DCM/MeOH+1% NH$_3$$^{aq}$, 9:1) affords 6.2 g of the title compound as a yellow solid: ESI-MS: 236.0 [MH]$^+$; t$_R$=2.35 min (purity: 100%, gradient J); TLC: R$_f$=0.50 (DCM/MeOH+1% NH$_3$$^{aq}$, 9:1).

Example 146

3-(2,6-Dichloro-3,5-dimethoxy-phenyl)-1-methyl-1-(6-{4-[3-(4-methyl-piperazin-1-yl)-propoxy]-phenylamino}-pyrimidin-4-yl)-urea

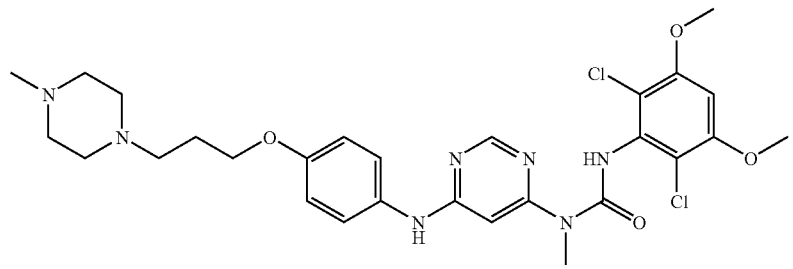

The title compound is prepared as described in Example 144 but using N-methyl-N'-{4-[3-(4-methyl-piperazin-1-yl)-propoxy]-phenyl}-pyrimidine-4,6-diamine (93 mg, 0.26 mmol, 1 eq.). Purification of the crude product by silica gel column chromatography (DCM/MeOH+1% NH$_3$$^{aq}$, 95:5) affords 86 mg of the title compound as a white solid: ESI-MS: 603.9/605.9 [MH]$^+$; t$_R$=3.21 min (purity: 100%, gradient J); TLC: R$_f$=0.19 (DCM/MeOH+1% NH$_3$$^{aq}$, 95:5).

A. N-Methyl-N'-{4-[3-(4-methyl-piperazin-1-yl)-propoxy]-phenyl}-pyrimidine-4,6-diamine The title compound is prepared as described in Example 143A but using 4-[3-(4-methylpiperazin-1-yl)-propoxy]-phenylamine (383 mg, 1.50 mmol, 1.1 eq.) and stirring the reaction mixture for 18 h at 100° C. The reaction mixture is allowed to cool to RT, poured onto a saturated aqueous solution of sodium bicarbonate, and extracted with EE and DCM. The organic phase is dried (sodium sulfate), filtered and concentrated.

The residue is triturated in diethyl ether to provide 115 mg of the title compound as a white solid: ESI-MS: 357.1 [MH]$^+$; $t_R$=1.10 min (gradient J); purity: 100%, gradient J); TLC: $R_f$=0.08 (DCM/MeOH, 9:1).

B. 4-[3-(4-Methylpiperazin-1-yl)-propoxy]-phenylamine

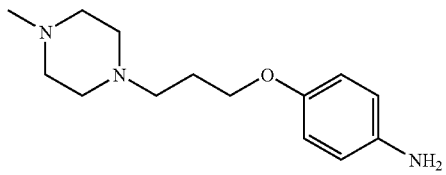 [SMILES: CN1CCN(CCCOc2ccc(N)cc2)CC1]

1-(3-Chloro-propyl)-4-methyl-piperazine hydrochloride (1.7 g, 9.6 mmol, 1.2 eq.) is added in one portion to a mixture of 4-aminophenol (893 mg, 8.0 mmol) and finely powdered sodium hydroxide (808 mg, 20 mmol, 2.5 eq.) in DMF (27 ml). The reaction mixture is stirred for 17 h at RT. The resulting dark suspension is filtered. The filtrate is diluted with DCM (200 ml) and washed with brine (2×50 ml). The aqueous layer is back-extracted with DCM. The organic phase is dried (sodium sulfate), filtered and concentrated. Purification of the residue by silica gel column chromatography (DCM/MeOH, 7:3) provides 1.86 g of the title compound as a yellow-brown oil: ESI-MS: 250.2 [MH]$^+$; TLC: $R_f$=0.31 (DCM/MeOH, 7:3).

Example 147

3-(2,6-Dichloro-3,5-dimethoxy-phenyl)-1-{6-[4-(3-dimethylamino-propyl)-phenylamino]-pyrimidin-4-yl}-1-methyl-urea

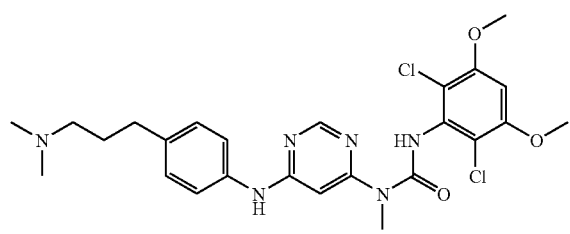

The title compound is prepared as described in Example 144 but using N-[4-(3-dimethylamino-propyl)-phenyl]-N'-pyrimidine-4,6-diamine (206 mg, 0.72 mmol, 1 eq.). Purification of the crude product by silica gel column chromatography (DCM/MeOH+1% NH$_3^{aq}$, 93:7) affords 84 mg of the title compound as a white solid: ESI-MS: 532.9/534.9 [MH]$^+$; $t_R$=3.70 min (purity: 100%, gradient J); TLC: $R_f$=0.15 (DCM/MeOH+1% NH$_3^{aq}$, 93:7).

A. N-[4-(3-Dimethylamino-propyl)-phenyl]-N'-pyrimidine-4,6-diamine

The title compound is prepared as described in Example 144A but using 4-(3-dimethylamino-propyl)-phenylamine (311 mg, 1.7 mmol). Purification of the residue by silica gel column chromatography (DCM/MeOH+1% NH$_3^{aq}$, 9:1), followed by trituration of the resulting solid in diethyl ether, affords 213 mg of the title compound as a white solid: ESI-MS: 286.1 [MH]$^+$; $t_R$=1.20 min (gradient J); purity: 100%, gradient J); TLC: $R_f$=0.08 (DCM/MeOH+1% NH$_3^{aq}$, 9:1).

B. 4-(3-Dimethylamino-propyl-phenylamine

A mixture of dimethyl-[3-(4-nitro-phenyl)-prop-2-ynyl]-amine (1.35 g, 6.6 mmol), 10% palladium on carbon (140 mg), and EtOH (25 ml) is stirred for 22 h at RT, under a hydrogen atmosphere. The reaction mixture is filtered through a pad of celite and concentrated. Purification of the residue by silica gel column chromatography (DCM/MeOH+1% NH$_3^{aq}$95:5) affords 797 mg of the title compound as a brown oil: ESI-MS: 179.0 [MH]$^+$; TLC: $R_f$=0.14 (DCM/MeOH+1% NH$_3^{aq}$, 95:5).

C. Dimethyl-[3-(4-nitro-phenyl)-prop-2-ynyl]-amine

Tri-t-butylphosphine (0.25 M in dioxane, 11.9 ml, 3.0 mmol, 0.2 eq.), 3-dimethylamino-1-propyne (2.2 ml, 20.8 mmol, 1.4 eq.), and diisopropylamine (2.7 ml, 19.3 mmol, 1.3 eq.) are added sequentially to a mixture of 4-bromonitrobenzene (3 g, 14.9 mmol), copper (I) iodide (198 mg, 1.0 mmol, 0.07 eq.), and Pd(PhCN)$_2$Cl$_2$ (570 mg, 1.5 mmol, 0.1 eq.) in dioxane (20 ml), under an argon atmosphere. The resulting mixture is stirred for 22 h at RT and concentrated. The residue is dissolved in EE and water and filtered through a pad of celite. The aqueous layer is separated and extracted with EE. The organic phase is washed with brine, dried (sodium sulfate), filtered and concentrated. Purification of the residue by silica gel column chromatography (DCM/MeOH+1% NH$_3^{aq}$, 95:5) affords 2.72 g of the title compound as a brown oil: ESI-MS: 205.0 [MH]$^+$; $t_R$=2.51 min (purity: 100%, gradient J); TLC: $R_f$=0.41 (DCM/MeOH+1% NH$_3^{aq}$, 95:5).

Example 148

3-(2,6-Dichloro-3,5-dimethoxy-phenyl)-1-methyl-1-{6-[4-(2-pyrrolidin-1-yl-ethoxy)-phenylamino]-pyrimidin-4-yl}-urea

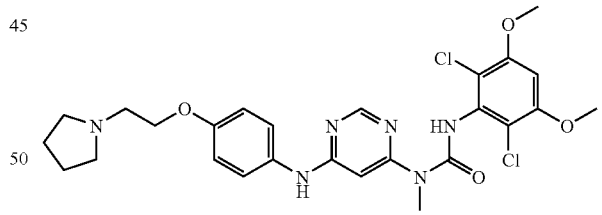

The title compound is prepared as described in Example 144 but using N-methyl-N'-[4-(2-pyrrolidin-1-yl-ethoxy)-phenyl]-pyrimidine-4,6-diamine (227 mg, 0.72 mmol, 1 eq.). Purification of the crude product by silica gel column chromatography (DCM/MeOH+1% NH$_3^{aq}$, 92:8) affords 156 mg of the title compound as a white solid: ESI-MS: 560.9/562.9 [MH]$^+$; $t_R$=3.64 min (purity: 100%, gradient J); TLC: $R_f$=0.42 (DCM/MeOH+1% NH$_3^{aq}$, 92:8).

A. N-Methyl-N'-[4-(2-pyrrolidin-1-yl-ethoxy)-phenyl]-pyrimidine-4,6-diamine The title compound is prepared as described in Example 143A but using 4-(2-pyrrolidin-1-yl-ethoxy)-phenylamine (360 mg, 1.70 mmol, 1 eq.) and stirring the reaction mixture for 18 h at 150° C. The reaction mixture is allowed to cool to RT and the top phase is discarded. The gluey bottom residue is diluted with a saturated aqueous solution of sodium bicarbonate and DCM. The aqueous layer is separated and extracted with DCM. The organic phase is dried (sodium sulfate), filtered and concentrated. Purification of the crude product by silica gel column chromatography (DCM/MeOH+1% $NH_3^{aq}$, 9:1), followed by trituration of the resulting solid in diethyl ether, affords 402 mg of the title compound as a grey solid: ESI-MS: 314.1 [MH]$^+$; $t_R$=1.15 min (gradient J); purity: 100%, gradient J); TLC: $R_f$=0.15 (DCM/MeOH+1% $NH_3^{aq}$, 9:1).

B. 4-(2-pyrrolidin-1-yl-ethoxy)-phenylamine

The title compound is prepared as described in Example 146B but using 1-(2-chloroethyl)-pyrrolidine hydrochloride (7.6 g, 44.9 mmol, 1.2 eq.) and stirring the reaction mixture for 2 h at 75° C. Purification of the residue by silica gel column chromatography (DCM/MeOH, 1:1) affords 7.7 g of the title compound as a brown oil: ESI-MS: 207.1 [MH]$^+$; TLC: $R_f$=0.22 (DCM/MeOH, 1:1).

Example 149

3-(2,6-Dichloro-3,5-dimethoxy-phenyl)-1-{6-[4-(4-ethyl-piperazin-1-ylmethyl)-phenylamino]-pyrimidin-4-yl}-1-methyl-urea

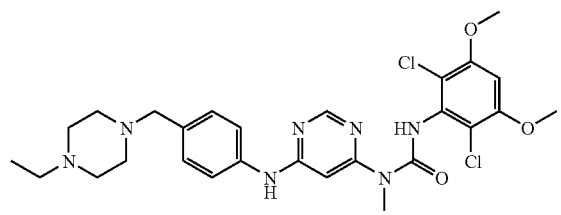 [SMILES: CCN1CCN(Cc2ccc(Nc3cc(N(C)C(=O)Nc4c(Cl)c(OC)cc(OC)c4Cl)ncn3)cc2)CC1]

The title compound is prepared as described in Example 144 but using N-[4-(4-ethyl-piperazin-1-ylmethyl)-phenyl]-N'-methyl-pyrimidine-4,6-diamine (140 mg, 0.43 mmol, 1 eq.). Purification of the crude product by MPLC (silica gel) (DCM/MeOH+1% $NH_3^{aq}$, 95:5) affords 24 mg of the title compound: ESI-MS: 573.9/575.9 [MH]$^+$; $t_R$=3.25 min (purity: 90%, gradient J); TLC: $R_f$=0.09 (DCM/MeOH+1% $NH_3^{aq}$, 9:1).

A. N-[4-(4-Ethyl-piperazin-1-ylmethyl)-phenyl]-N'-methyl-pyrimidine-4,6-diamine The title compound is prepared as described in Example 143A but using 4-(4-ethyl-piperazin-1-ylmethyl)-phenylamine (500 mg, 2.28 mmol, 1 eq.) and stirring the reaction mixture for 18 h at 150° C. Purification of the crude product by MPLC (silica gel) (DCM/MeOH+1% $NH_3^{aq}$, 9:1) affords 140 mg of impure product which is used without further purification.

B. 4-(4-Ethyl-piperazin-1-ylmethyl)-phenylamine

A suspension of 1-ethyl-4-(4-nitro-benzyl)-piperazine (7.2 g, 29.14 mmol) and Raney Nickel (1.5 g) in MeOH (100 mL) is stirred for 6 h at RT, under a hydrogen atmosphere. The reaction mixture is filtered through a pad of celite and concentrated to afford 6.3 g of the title compound as a yellow solid: ESI-MS: 220.1 [MH]$^+$; TLC: $R_f$=0.08 (DCM/MeOH+1% $NH_3^{aq}$, 9:1).

C. 1-Ethyl-4-(4-nitro-benzyl)-piperazine

A mixture of 4-nitrobenzylchloride (5 g, 29.14 mmol), N-ethylpiperazine (4.4 ml, 34.97 mmol, 1.2 eq.), potassium carbonate (8 g, 58.28, 2 eq.), and acetone (100 ml) is stirred for 15 h at reflux. The reaction mixture is allowed to cool to RT, filtered and concentrated to afford 7.2 g of the title compound as a brow oil: ESI-MS: 250.1 [MH]$^+$; TLC: $R_f$=0.31 (DCM/MeOH+1% $NH_3^{aq}$, 9:1).

Example 150

3-(2,6-Dichloro-3,5-dimethoxy-phenyl)-1-{6-[3-(4-ethyl-piperazin-1-ylmethyl)-phenylamino]-pyrimidin-4-yl}-1-methyl-urea

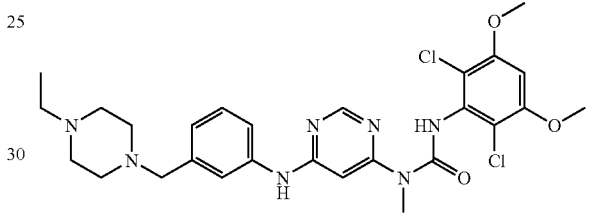

The title compound is prepared as described in Example 144 but using N-[3-(4-ethyl-piperazin-1-ylmethyl)-phenyl]-N'-methyl-pyrimidine-4,6-diamine (306 mg, 0.94 mmol, 1 eq.). Purification of the crude product by MPLC (silica gel) (DCM/MeOH+1% $NH_3^{aq}$, 95:5) affords 207 mg of the title compound: ESI-MS: 573.9/575.9 [MH]$^+$; $t_R$=3.28 min (purity: 100%, gradient J); TLC: $R_f$=0.24 (DCM/MeOH+1% $NH_3^{aq}$, 95:5).

A. N-[3-(4-Ethyl-piperazin-1-ylmethyl)-phenyl]-N'-methyl-pyrimidine-4,6-diamine The title compound is prepared as described in Example 143A but using 3-(4-ethyl-piperazin-1-ylmethyl)-phenylamine (500 mg, 2.28 mmol, 1 eq.) and stirring the reaction mixture for 15 h at 150° C. Purification of the crude product by MPLC (silica gel) (DCM/MeOH+1% $NH_3^{aq}$, 9:1) affords 306 mg of the title compound as a beige solid: ESI-MS: 327.2 [MH]$^+$; TLC: $R_f$=0.05 (DCM/MeOH+1% $NH_3^{aq}$, 9:1).

B. 3-(4-Ethyl-piperazin-1-ylmethyl)-phenylamine

The title compound is prepared as described in Example 149B: ESI-MS: 220.1 [MH]$^+$; $t_R$=0.79 min (purity: 100%, gradient J).

C. 1-Ethyl-4-(3-nitro-benzyl)-piperazine

The title compound is prepared as described in Example 149C: ESI-MS: 250.1 [MH]$^+$; $t_R$=1.50 min (purity: 100%, gradient J); TLC: $R_f$=0.32 (DCM/MeOH+1% $NH_3^{aq}$, 9:1).

Example 151

3-(2,6-Dichloro-3,5-dimethoxy-phenyl)-1-[6-(3-dimethylaminomethyl-phenylamino)-pyrimidin-4-yl]-1-ethyl-urea

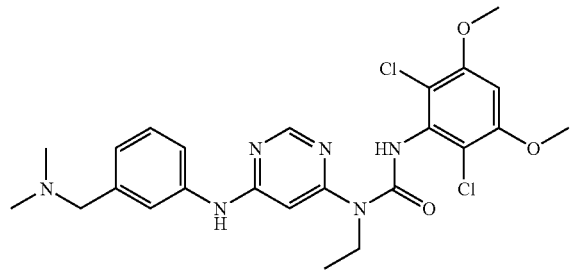

A suspension of 2,6-dichloro-3-methoxyphenylisocyanate (2 eq.) in toluene (3 ml) is added to a refluxing solution of N-(3-dimethylaminomethyl-phenyl)-N'-methyl-pyrimidine-4,6-diamine (216 mg, 0.80 mmol, 1 eq.) in toluene (3 ml), under an argon atmosphere. The resulting mixture is stirred at reflux for 2 h and allowed to cool to RT. The reaction mixture is diluted with EE and a saturated aqueous solution of sodium bicarbonate. The aqueous layer is separated and extracted with EE. The organic phase is washed with brine, dried (sodium sulfate), filtered and concentrated. Purification of the residue by silica gel column chromatography (DCM/MeOH+1% $NH_3^{aq}$, 95:5), followed by reversed phase MPLC purification (AcCN/$H_2$O/TFA) of the resulting product, affords 161 mg of the title compound as a white solid: ESI-MS: 518.9/520.9 [MH]$^+$; $t_R$=3.76 min (purity: 100%, gradient J); TLC: $R_f$=0.21 (DCM/MeOH+1% $NH_3^{aq}$, 95:5).

A. N-(3-Dimethylaminomethyl-phenyl)-N'-ethyl-pyrimidine-4,6-diamine

The title compound is prepared as described in Example 143A but using 3-dimethylaminomethyl-phenylamine (334 mg, 2.20 mmol, 1 eq.), (6-chloro-pyrimidin-4-yl)-ethyl-amine (Example 143B) and stirring the reaction mixture for 3 h at 160° C. Purification of the crude product by silica gel column chromatography (DCM/MeOH+1% $NH_3^{aq}$, 9:1) followed by trituration of the resulting solid in diethyl ether, affords 335 mg of the title compound as a beige solid: ESI-MS: 272.1 [MH]$^+$; $t_R$=1.18 min (purity: 100%, gradient J); TLC: $R_f$=0.16 (DCM/MeOH+1% $NH_3^{aq}$, 9:1).

Example 152

3-(2,6-Dichloro-3,5-dimethoxy-phenyl)-1-{6-[4-(2-diethylamino-ethoxy)-phenylamino]-pyrimidin-4-yl}-1-methyl-urea

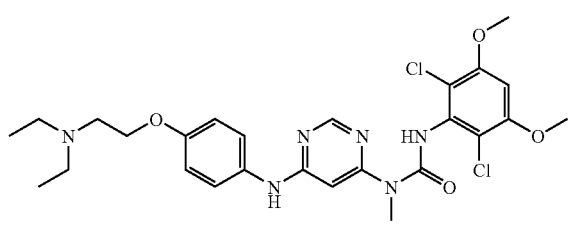 [SMILES: CCN(CC)CCOc1ccc(Nc2cc(N(C)C(=O)Nc3c(Cl)c(OC)cc(OC)c3Cl)ncn2)cc1]

The title compound is prepared as described in Example 151 but using N-[4-(2-diethylamino-ethoxy)-phenyl]-N'-methyl-pyrimidine-4,6-diamine (255 mg, 0.81 mmol, 1 eq.). Purification of the crude product by silica gel column chromatography (DCM/MeOH+1% $NH_3^{aq}$, 95:5), followed by trituration of the resulting solid in MeOH, affords 220 mg of the title compound as a white solid: ESI-MS: 562.9/564.9 [MH]$^+$; $t_R$=3.70 min (purity: 93%, gradient J); TLC: $R_f$=0.21 (DCM/MeOH+1% $NH_3^{aq}$, 95:5).

A. N-[4-(2-Diethylamino-ethoxy)-phenyl]-N'-methyl-pyrimidine-4,6-diamine

The title compound is prepared as described in Example 143A but using 4-(2-diethylamino-ethoxy)-phenylamine (271 mg, 1.3 mmol, 1 eq.) and stirring the reaction mixture for 18 h at 150° C. The reaction mixture is allowed to cool to RT and the top phase is discarded. The gluey bottom residue is diluted with a saturated aqueous solution of sodium bicarbonate and DCM. The aqueous layer is separated and extracted with DCM. The organic phase is dried (sodium sulfate), filtered and concentrated. Purification of the crude product by silica gel column chromatography (DCM/MeOH+1% $NH_3^{aq}$, 92:8) provides 261 mg of the title compound as a grey solid: ESI-MS: 316.1 [MH]$^+$; $t_R$=1.25 min (purity: 100%, gradient J); TLC: $R_f$=0.19 (DCM/MeOH+1% $NH_3^{aq}$, 92:8).

B. 4-(2-Diethylamino-ethoxy)-phenylamine

The title compound is prepared as described in Example 146B but using 1-(2-chloroethyl)-diethylamine hydrochloride (1.9 g, 11 mmol, 1.2 eq.) and stirring the reaction mixture for 1 h at RT. Purification of the residue by silica gel column chromatography (DCM/MeOH, 4:1→7:3) affords 1.52 g of the title compound as a brown oil: ESI-MS: 209.1 [MH]$^+$; TLC: $R_f$=0.12 (DCM/MeOH, 7:3).

Example 153

3-(2,6-Dichloro-3,5-dimethoxy-phenyl)-1-[6-(2,6-dimethyl-pyridin-3-ylamino)-pyrimidin-4-yl]-1-methyl-urea

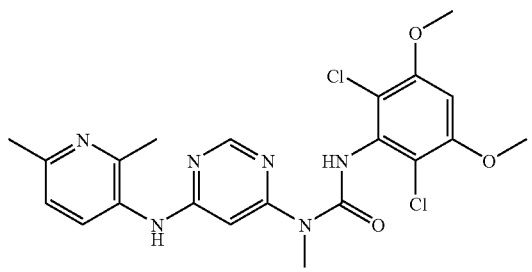

The title compound is prepared as described in Example 151 but using N-(2,6-dimethyl-pyridin-3-yl)-N'-methyl-pyrimidine-4,6-diamine.
ESI-MS: 476.9/478.9 [MH]$^+$; $t_R$=3.44 min (purity: 100%, gradient J); TLC: $R_f$=0.40 (DCM/MeOH+1% $NH_3^{aq}$, 9:1).

A. N-(2,6-Dimethyl-pyridin-3-yl)-N'-methyl-pyrimidine-4,6-diamine

The title compound is prepared as described in Example 152A but using 3-amino-2,6-dimethylpyrimidine and stirring the reaction mixture for 24 h at 150° C.
ESI-MS: 230.1 [MH]$^+$; TLC: $R_f$=0.22 (DCM/MeOH, 9:1).

Example 154

3-(2,6-Dichloro-3,5-dimethoxy-phenyl)-1-methyl-1-[6-(6-trifluoromethyl-pyridin-3-ylamino)-pyrimidin-4-yl]-urea

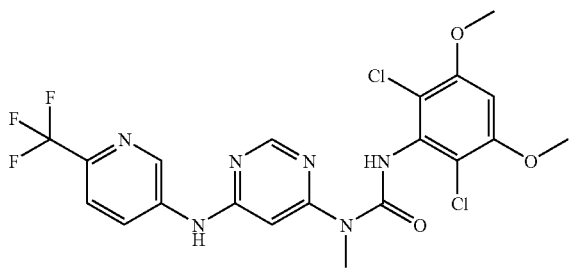 [SMILES: COc1cc(OC)c(Cl)c(NC(=O)N(C)c2cc(Nc3ccc(C(F)(F)F)nc3)ncn2)c1Cl]

The title compound is prepared as described in Example 151 but using N-methyl-N'-(6-trifluoromethyl-pyridin-3-yl)-pyrimidine-4,6-diamine.

ESI-MS: 514.8/516.8 [MH]$^-$; $t_R$=5.27 min (purity: 100%, gradient J); TLC: $R_f$=0.49 (DCM/MeOH, 9:1).

A. N-Methyl-N'-(6-trifluoromethyl-pyridin-3-yl)-pyrimidine-4,6-diamine

The title compound is prepared as described in Example 152A but using 3-amino-6-(trifluoromethyl)pyridine and stirring the reaction mixture for 24 h at 150° C.

ESI-MS: 270.0 [MH]$^+$; $t_R$=2.63 min (purity: 100%, gradient J); TLC: $R_f$=0.32 (DCM/MeOH, 9:1).

Example 155

1-(2,6-Dichloro-3,5-dimethoxy-phenyl)-3-{6-[4-(2-pyrrolidin-1-yl-ethoxy)-phenylamino]-pyrimidin-4-yl}-urea

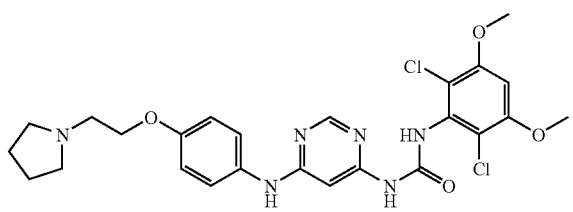 [SMILES: COc1cc(OC)c(Cl)c(NC(=O)Nc2cc(Nc3ccc(OCCN4CCCC4)cc3)ncn2)c1Cl]

The title compound is prepared as described in Example 151 but using N-[4-(2-pyrrolidin-1-yl-ethoxy)-phenyl]-pyrimidine-4,6-diamine.

ESI-MS: 546.9/548.8 [MH]$^-$; $t_R$=3.15 min (purity: 100%, gradient J); TLC: $R_f$=0.49 (DCM/MeOH+1% NH$_3^{aq}$, 95:5).

A. N-[4-(2-Pyrrolidin-1-yl-ethoxy)-phenyl]-pyrimidine-4,6-diamine

The title compound is prepared as described in Example 152A but using 6-chloro-pyrimidin-4-ylamine, 4-(2-pyrrolidin-1-yl-ethoxy)-phenylamine (Example 148B), and stirring the reaction mixture for 2 h at 150° C.

ESI-MS: 300.1 [MH]$^+$; $t_R$=1.10 min (purity: 100%, gradient J).

Example 156

3-(2,6-Dichloro-3,5-dimethoxy-phenyl)-1-ethyl-1-{6-[4-(2-pyrrolidin-1-yl-ethoxy)-phenylamino]-pyrimidin-4-yl}-urea

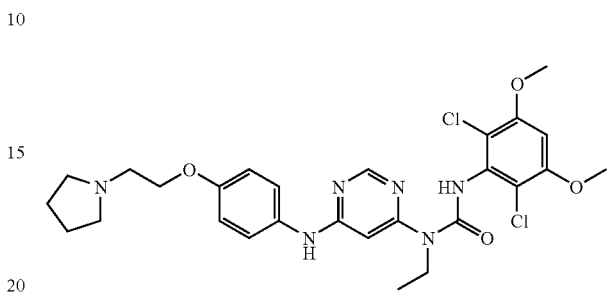

The title compound is prepared as described in Example 151 but using N-ethyl-N'-[4-(2-pyrrolidin-1-yl-ethoxy)-phenyl]-pyrimidine-4,6-diamine.

ESI-MS: 575.2/577.2 [MH]$^+$; $t_R$=3.74 min (purity: 100%, gradient J); TLC: $R_f$=0.42 (DCM/MeOH+1% NH$_3^{aq}$, 95:5).

A. N-Ethyl-N'-[4-(2-pyrrolidin-1-yl-ethoxy)-phenyl]-pyrimidine-4,6-diamine

The title compound is prepared as described in Example 152A but using 6-chloro-pyrimidin-4-yl)-ethyl-amine, 4-(2-pyrrolidin-1-yl-ethoxy)-phenylamine (Example 148B), and stirring the reaction mixture for 6 h at 150° C. The crude product is purified by trituration in diethyl ether.

ESI-MS: 326.1 [MH]$^-$; $t_R$=1.45 min (purity: 95%, gradient J).

Example 157

1-(2,6-Dichloro-3,5-dimethoxy-phenyl)-3-[6-(3-dimethylaminomethyl-phenylamino)-pyrimidin-4-yl]-urea

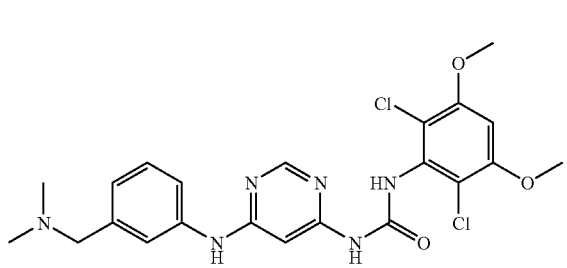

The title compound is prepared as described in Example 151 but using N-(3-dimethylaminomethyl-phenyl)-pyrimidine-4,6-diamine.

ESI-MS: 491.0/493.0 [MH]$^+$; $t_R$=3.17 min (purity: 97%, gradient J); TLC: $R_f$=0.25 (DCM/MeOH+1% NH$_3^{aq}$, 92:8).

A. N-(3-Dimethylaminomethyl-phenyl)-pyrimidine-4,6-diamine

The title compound is prepared as described in Example 152A but using 3-dimethylaminomethyl-phenylamine, 6-chloro-pyrimidin-4-ylamine, and stirring the reaction mixture for 2 h at 150° C. The crude product is purified by trituration in diethyl ether followed by silica gel column chromatography (DCM/MeOH+1% NH$_3$$^{aq}$, 92:8) of the resulting beige solid to afford the title compound as a white solid. ESI-MS: 242.1 [MH]$^-$; $t_R$=0.95 min (purity: 100%, gradient J); TLC: $R_f$=0.11 (DCM/MeOH+1% NH$_3$$^{aq}$, 92:8).

Example 158

1-(2,6-Dichloro-3,5-dimethoxy-phenyl)-3-(6-{4-[2-(4-methyl-piperazin-1-yl)-ethoxy]-phenylamino}-pyrimidin-4-yl)-urea

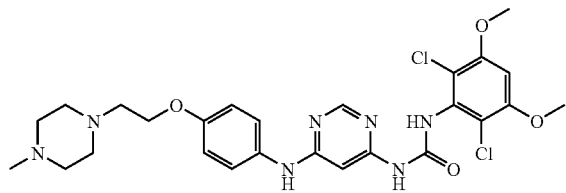

The title compound is prepared as described in Example 151 but using N-(3-dimethylaminomethyl-phenyl)-pyrimidine-4,6-diamine.

ESI-MS: 575.9/577.9 [MH]$^+$; $t_R$=2.83 min (purity: 100%, gradient J); TLC: $R_f$=0.03 (DCM/MeOH+1% NH$_3$$^{aq}$, 95:5).

A. N-{4-[2-(4-Methyl-piperazin-1-yl)-ethoxy]-phenyl}-pyrimidine-4,6-diamine

The title compound is prepared as described in Example 152A but using 4-[2-(4-methyl-piperazin-1-yl)-ethoxy]-phenylamine (300 mg, 1.28 mmol, 1 eq.), 6-chloro-pyrimidin-4-ylamine, water (0.5 ml), and stirring the reaction mixture for 2 h at 150° C. The crude product is purified by trituration in diethyl ether to afford the title compound as a white solid. ESI-MS: 329.1 [MH]$^+$; $t_R$=0.98 min (purity: 100%, gradient J).

Example 159

1-(2,6-Dichloro-3,5-dimethoxy-phenyl)-3-[6-(4-dimethylaminomethyl-3-trifluoromethyl-phenylamino)-pyrimidin-4-yl]-urea

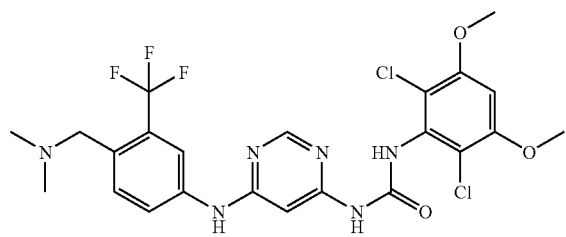

The title compound is prepared as described in Example 151 but using N-(4-dimethylaminomethyl-3-trifluoromethyl-phenyl)-pyrimidine-4,6-diamine.

ESI-MS: 558.9/560.9 [MH]$^+$; $t_R$=3.69 min (purity: 100%, gradient J); TLC: $R_f$=0.21 (DCM/MeOH+1% NH$_3$$^{aq}$, 95:5).

A. N-(4-Dimethylaminomethyl-3-trifluoromethyl-phenyl)-pyrimidine-4,6-diamine

The title compound is prepared as described in Example 152A but using 4-dimethylaminomethyl-3-trifluoromethyl-phenylamine (218 mg, 1.46 mmol, 1 eq.), 6-chloro-pyrimidin-4-ylamine, and stirring the reaction mixture for 5 h at 150° C. The crude product is purified by silica gel column chromatography (DCM/MeOH+1% NH$_3$$^{aq}$, 92:8) to afford the title compound as a white solid. ESI-MS: 312.1 [MH]$^+$; $t_R$=1.20 min (purity: 100%, gradient J); TLC: $R_f$=0.16 (DCM/MeOH+1% NH$_3$$^{aq}$, 92:8).

B. 4-(4-(N,N-Dimethylamino-methyl)-3-trifluoromethyl-phenyl-amine

N-(4-Dimethylaminomethyl-3-trifluoromethyl-phenyl)-pyrimidine-4,6-diamine (359 mg, 1.2 mmol) is dissolved in MeOH (12 mL) and treated with K$_2$CO$_3$ (6 mL of a 1N aqueous solution) at RT. The reaction is heated to reflux for 1.5 h until completion, cooled back to RT and concentrated. The residual oil is taken up in EtOAc and washed with brine. The organic layers are dried over Na$_2$SO$_4$, filtered and concentrated under reduced pressure. Drying under high vacuum gives the title compound as a yellow oil. ESI-MS: 219 [MH]$^+$.

C. N-(4-Dimethylaminomethyl-3-trifluoromethyl-phenyl)-pyrimidine-4,6-diamine 501 mg (1.5 mmol) N-(4-bromomethyl-3-trifluoromethyl-phenyl)-2,2,2-trifluoro-acetamide (Step 14.2) is added to 5 ml of a solution of dimethyl amine in EtOH (33%) at RT. The reaction is stirred at ambient temperature for 0.5 h until completion. It is concentrated and the residual crude product is purified by flash chromatography (SiO$_2$; CH$_2$Cl$_2$/MeOH, gradient 0-5% MeOH) to give the title compound as a yellow oil. ESI-MS: 315 [MH]$^+$.

D. N-(4-Bromomethyl-3-trifluoromethyl-phenyl)-2,2,2-trifluoro-acetamide

To a solution of 60.9 g (224.6 mmol) of N-(4-methyl-3-trifluoromethyl-phenyl)-2,2,2-trifluoro-acetamide in 830 ml n-butyl acetate under a nitrogen atmosphere, 44 g (247 mmol) N-bromosuccinimide and 830 mg (5 mmol) azo-iso-butyronitrile are added. The suspension is heated up to 60° C. and then illuminated for 30 min by a Phillips low-voltage lamp (500 W; 10500 lm), whereby the temperature rises to 70-75° C. and a clear brown solution is formed. There is still remaining educt detectable, therefore another 22 g N-bromosuccinimide are added in 3 portions. After totally 6 h illumination, the resulting solid is filtered off and discarded and the filtrate concentrated. The residue is distributed between 2 l CH$_2$Cl$_2$ and 1 l H$_2$O and the aqueous layer extracted with 1 l CH$_2$Cl$_2$. The organic phases are washed 4 times with 1 l H$_2$O, 0.5 l brine, dried (Na$_2$SO$_4$) and concentrated. Column chromatography (SiO$_2$; hexane/CH$_2$Cl$_2$ 2:1→1:1) and crystallization from CH$_2$Cl$_2$/hexane yields the title compound: m.p.: 119-120° C.

E. N-(4-Methyl-3-trifluoromethyl-Phenyl)-2,2,2-trifluoro-acetamide

To an ice-cooled solution of 320 g (1.827 Mol) of 5-amino-2-methylbenzotrifluoride and 1.47 l (18.27 mol) pyridine in 4.5 l of CH$_2$Cl$_2$ under N$_2$-atmosphere, 284 ml (2.01 Mol) of trifluoroacetic acid anhydride are added dropwise. After 50 min, the mixture is diluted with 5 l ice-cooled 2 N HCl. The organic phases are separated off and washed two times with 2 l cold 2 N HCl, then 1 l 2 N HCl and finally with 2 l brine. The aqueous layers are extracted twice with CH$_2$Cl$_2$, the organic phases dried (Na$_2$SO$_4$) and concentrated partially. Crystallization by addition of hexane yields the title compound: m.p.: 72-73° C.

Example 160

1-(2,6-Dichloro-3,5-dimethoxy-phenyl)-3-{6-[4-(4-ethyl-piperazin-1-yl)-phenylamino]-pyrimidin-4-yl}-urea

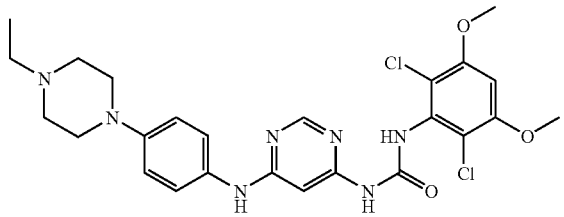 [SMILES: CCN1CCN(c2ccc(Nc3cc(NC(=O)Nc4c(Cl)c(OC)cc(OC)c4Cl)ncn3)cc2)CC1]

2,6-dichloro-3,5-dimethoxyphenylisocyanate (1.2 eq.) is added to a solution of N-[4-(4-ethyl-piperazin-1-yl)-phenyl]-pyrimidine-4,6-diamine (350 mg, 1.18 mmol) in NMP (2 ml), at 70° C. and under an argon atmosphere. The resulting mixture is stirred at 70° C. for 2 h, allowed to cool to RT and concentrated. The residue is diluted with DCM and a saturated aqueous solution of sodium bicarbonate. The aqueous layer is separated and extracted with DCM. The organic phase is washed with brine, dried (sodium sulfate), filtered and concentrated. Purification of the crude product by trituration in MeOH followed by silica gel column chromatography (DCM/MeOH+1% $NH_3^{aq}$, 97:3) affords the title compound as a white solid:
ESI-MS: 545.9/547.9 [MH]$^+$; $t_R$=3.10 min (purity: 100%, gradient J); TLC: $R_f$=0.18 (DCM/MeOH+1% $NH_3^{aq}$, 95:5).

A. N-[4-(4-Ethyl-piperazin-1-yl)-phenyl]-pyrimidine-4,6-diamine

A mixture of 6-chloro-pyrimidin-4-yl)-amine (500 mg, 3.87 mmol, 1.3 eq.) and 4-(4-ethylpiperazin-1-yl)-aniline (611 mg, 2.98 mmol) in water (3.0 ml) and glacial acetic acid (10 ml) is heated to 100° C. for 15 h. The reaction mixture is diluted with DCM and brine. The aqueous layer is made basic by addition of sodium bicarbonate. The aqueous layer is separated and extracted with DCM. The organic phase is washed with brine, dried (sodium sulfate), filtered and concentrated. Purification of the crude product by trituration in EE affords the title compound: ESI-MS: 299.2 [MH]$^+$; $t_R$=1.05 min (gradient J).

Example 161

3-(2,6-Dichloro-3,5-dimethoxy-phenyl)-1-{6-[3-(4-isopropyl-piperazin-1-ylmethyl)-phenylamino]-pyrimidin-4-yl}-1-methyl-urea

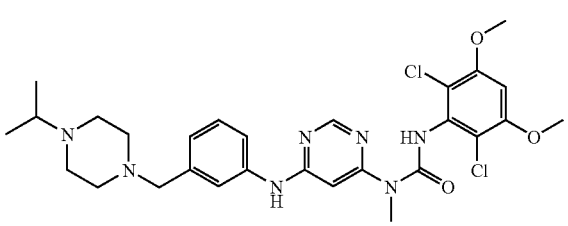 [SMILES: COc1cc(OC)c(Cl)c(NC(=O)N(C)c2cc(Nc3cccc(CN4CCN(C(C)C)CC4)c3)ncn2)c1Cl]

The title compound is prepared as described in Example 151 but using N-[3-(4-isopropyl-piperazin-1-ylmethyl)-phenyl]-N'-methyl-pyrimidine-4,6-diamine. Purification of the crude product by MPLC (silica gel) (DCM/MeOH+1% $NH_3^{aq}$, 95:5) affords the title compound as a white solid:
ESI-MS: 587.9/589.9 [MH]$^+$; $t_R$=3.35 min (purity: 100%, gradient J); TLC: $R_f$=0.17 (DCM/MeOH+1% $NH_3^{aq}$, 9:1).

A. N-[3-(4-Isopropyl-piperazin-1-ylmethyl)-phenyl]-N'-methyl-pyrimidine-4,6-diamine The title compound is prepared as described in Example 152A but using 3-(4-isopropyl-piperazin-1-ylmethyl)-phenylamine and stirring the reaction mixture for 17.5 h at 150° C. The crude product is purified by MPLC (silica gel) (DCM/MeOH+1% $NH_3^{aq}$, 95:5) to afford the title compound as a light yellow solid. ESI-MS: 341.2 [MH]$^+$; $t_R$=1.05 min (purity: 100%, gradient J); TLC: $R_f$=0.10 (DCM/MeOH+1% $NH_3^{aq}$, 9:1).

B. 3-(4-Isopropyl-piperazin-1-ylmethyl)-phenylamine

The title compound is prepared as described in Example 149B: ESI-MS: 234.2 [MH]$^+$.

C. 1-Isopropyl-4-(3-nitro-benzyl)-piperazine

The title compound is prepared as described in Example 149C. Purification of the crude product by silica gel column chromatography (DCM/MeOH+1% $NH_3^{aq}$, 9:1) affords the title compound as a yellow solid: ESI-MS: 264.1 [MH]$^+$; $t_R$=1.64 min (purity: 96.5%, gradient J);
TLC: $R_f$=0.35 (DCM/MeOH+1% $NH_3^{aq}$, 9:1).

Example 162

3-(2,6-Dichloro-3,5-dimethoxy-phenyl)-1-[6-(3-{[(2-dimethylamino-ethyl)-methyl-amino]-methyl}-phenylamino)-pyrimidin-4-yl]-1-methyl-urea

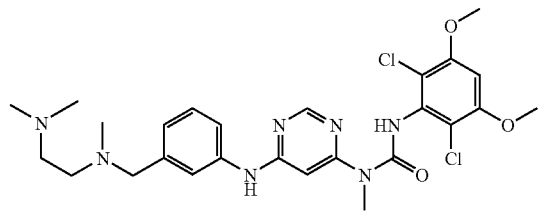

The title compound is prepared as described in Example 151 but using N-(3-{[(2-dimethylamino-ethyl)-methyl-amino]-methyl}-phenyl)-N'-methyl-pyrimidine-4,6-diamine. Purification of the crude product by MPLC (silica gel) (DCM/MeOH+1% $NH_3^{aq}$, 95:5) affords the title compound as a white solid: ESI-MS: 561.9/563.9 [MH]$^+$; $t_R$=3.24 min (purity: 100%, gradient J); TLC: $R_f$=0.10 (DCM/MeOH+1% $NH_3^{aq}$, 9:1).

A. N-(3-{[(2-Dimethylamino-ethyl)-methyl-amino]-methyl}-phenyl)-N'-methyl-pyrimidine-4,6-diamine The title compound is prepared as described in Example 152A but using N-(3-amino-benzyl)-N,N',N'-trimethyl-ethane-1,2-diamine and stirring the reaction mixture for 17.5 h at 150° C. The crude product is purified by MPLC (silica gel) (DCM/MeOH+1% NH$_3{}^{aq}$, 95:5) to afford the title compound as a beige solid. ESI-MS: 315.2 [MH]$^+$; TLC: R$_f$=0.05 (DCM/MeOH+1% NH$_3{}^{aq}$, 9:1).

B. N-(3-Amino-benzyl)-N,N',N'-trimethyl-ethane-1,2-diamine

The title compound is prepared as described in Example 149B: ESI-MS: 208.2 [MH]$^+$.

C. N,N',N'-Trimethyl-N'-(3-nitro-benzyl)-ethane-1,2-diamine

The title compound is prepared as described in Example 149C. Purification of the crude product by silica gel column chromatography (DCM→DCM/MeOH+1% NH$_3{}^{aq}$, 9:1) affords the title compound as a brown oil: ESI-MS: 238.1 [MH]$^+$; t$_R$=1.15 min (purity: 96.5%, gradient J); TLC: R$_f$=0.10 (DCM/MeOH, 9:1).

Example 163

3-(2,6-Dichloro-3,5-dimethoxy-phenyl)-1-{6-[4-(4-isopropyl-piperazin-1-yl)-phenylamino]-pyrimidin-4-yl}-1-methyl-urea

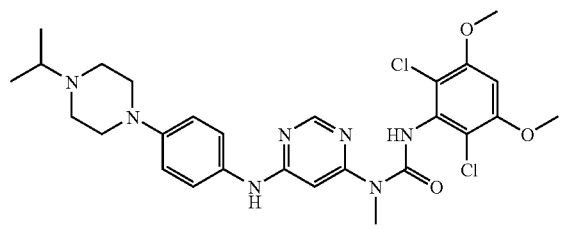 [SMILES: COc1cc(OC)c(Cl)c(NC(=O)N(C)c2cc(Nc3ccc(N4CCN(C(C)C)CC4)cc3)ncn2)c1Cl]

The title compound is prepared as described in Example 151 but using N-[4-(4-isopropyl-piperazin-1-yl)-phenyl]-N'-methyl-pyrimidine-4,6-diamine.
ESI-MS: 573.9/575.9 [MH]$^+$; t$_R$=3.65 min (purity: 97%, gradient J); TLC: R$_f$=0.10 (DCM/MeOH+1% NH$_3{}^{aq}$, 97:3).

A. N-[4-(4-Isopropyl-piperazin-1-yl)-phenyl]-N'-methyl-pyrimidine-4,6-diamine

The title compound is prepared as described in Example 152A but using N-(3-amino-benzyl)-N,N',N'-trimethyl-ethane-1,2-diamine and stirring the reaction mixture for 4 h at 150° C. The crude product is purified by silica gel column chromatography (DCM/MeOH+1% NH$_3{}^{aq}$, 92:8) to afford the title compound as a white solid. ESI-MS: 327.2 [MH]$^+$; TLC: R$_f$=0.26 (DCM/MeOH+1% NH$_3{}^{aq}$, 92:8).

B. 4-(4-Isopropyl-piperazin-1-yl)-phenylamine

The title compound is prepared as described in Example 149B: ESI-MS: 220.1 [MH]$^+$.

C. 1-Isopropyl-4-(4-nitro-phenyl)-piperazine

The title compound is prepared as described in Example 149C. Purification of the crude product by silica gel column chromatography (DCM/MeOH, 95:5) affords the title compound as a yellow solid: ESI-MS: 238.1 [MH]$^+$; t$_R$=2.57 min (purity: 100%, gradient J); TLC: R$_f$=0.16 (DCM/MeOH, 95:5).

Example 164

1-(2,6-Dichloro-3,5-dimethoxy-phenyl)-3-{6-[4-(1-methyl-piperidin-4-yloxy)-phenylamino]-pyrimidin-4-yl}-urea

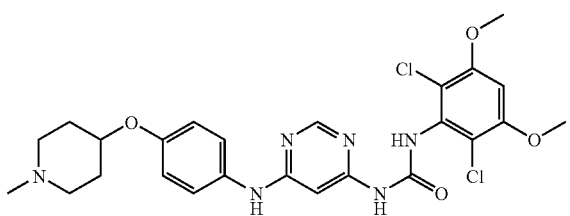

Example 165

3-(2,6-Dichloro-3,5-dimethoxy-phenyl)-1-methyl-{6-[4-(1-methyl-piperidin-4-yloxy)-phenylamino]-pyrimidin-4-yl}-urea

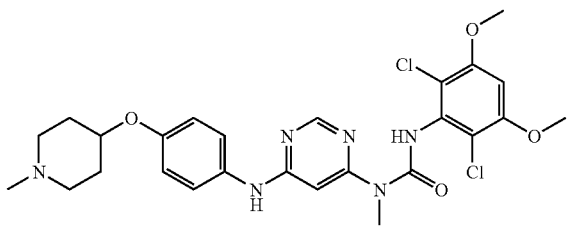

Example 166

3-(2,6-Dichloro-3,5-dimethoxy-phenyl)-1-ethyl-{6-[4-(1-methyl-piperidin-4-yloxy)-phenylamino]-pyrimidin-4-yl}-urea

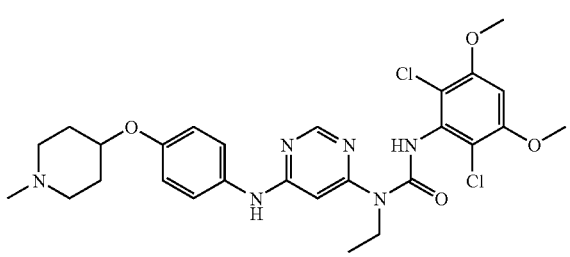

Example 167

3-(2,6-Dichloro-3,5-dimethoxy-phenyl)-1-[6-(4-dimethylaminomethyl-3-trifluoromethyl-phenylamino)-pyrimidin-4-yl]-1-methyl-urea

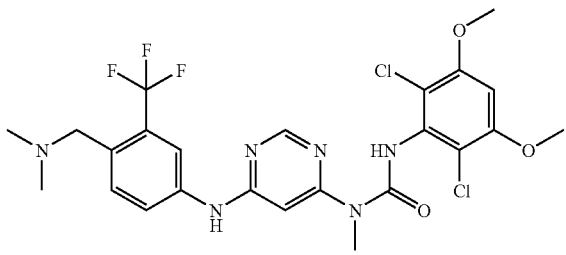

Example 168

1-(2,6-Dichloro-3,5-dimethoxy-phenyl)-3-{6-[4-(4-ethyl-piperazin-1-ylmethyl)-3-trifluoromethyl-phenylamino]-pyrimidin-4-yl}-urea

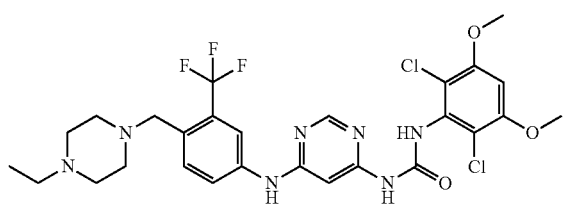 [SMILES: CCN1CCN(Cc2ccc(Nc3cc(NC(=O)Nc4c(Cl)c(OC)cc(OC)c4Cl)ncn3)cc2C(F)(F)F)CC1]

Example 169

3-(2,6-Dichloro-3,5-dimethoxy-phenyl)-1-{6-[4-(4-ethyl-piperazin-1-ylmethyl)-3-trifluoromethyl-phenylamino]-pyrimidin-4-yl}-1-methyl-urea

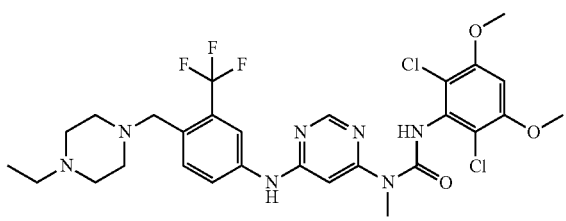 [SMILES: CCN1CCN(Cc2ccc(Nc3cc(N(C)C(=O)Nc4c(Cl)c(OC)cc(OC)c4Cl)ncn3)cc2C(F)(F)F)CC1]

Example 170

In Vitro Enzymatic Data

The compounds of Examples 1 to 169 were tested under the protocols as hereinbefore described for their inhibitory activity against KDR, FGFR3 and TEK. Measurements are made as described in the aforementioned methods in the general description. For KDR 67-100% inhibition at 10 μM, for FGFR3 (K650E) 27-100% inhibition at 10 μM and for Tek 12-100% inhibition at 10 μM is observed.

Method A: Examples 171-193

Example 171

N-[4-Methyl-3-(3-methyl-3-{6-[4-(4-methyl-piperazin-1-yl)-phenyl-amino]-pyrimidin-4-yl}-ureido)-phenyl]-3-trifluoromethyl-benzamide To a solution of N-(3-Amino-4-methyl-phenyl)-3-trifluoromethyl-benzamide (preparation 3, 62 mg, 0.21 mmol, 1.25 eq.) in dioxane is added 20% phosgene solution in toluene (110 μl, 0.21 mmol, 1.25 eq.) under argon. The reaction mixture is stirred for further 22 h at room temperature under argon. Then, the solvent is evaporated and the residue is taken up in dry toluene (2 ml). After the addition of N-Methyl-N'-[4-(4-methyl-piperazin-1-yl)-phenyl]-pyrimidine-4,6-diamine (50 mg, 0.168 mmol, 1.0 eq.) the suspension is refluxed for 24 h under argon. After cooling ether (2 ml) is added and the mixture is stirred for 30 min. The precipitated product is filtered off, washed (1× toluene/ether 1:1, 1× ether) and vacuum dried at 60° C. overnight to afford the title compound as colorless crystals: M.p. 189.5-191° C., HPLC: $t_R$=6.02 min (purity: >99%, gradient A), ESI-MS: 619.6 [MH]⁺.

N-Methyl-N'-[4-(4-methyl-piperazin-1-yl)-phenyl]-pyrimidine-4,6-diamine

A solution of (6-chloro-pyrimidin-4-yl)-methyl-amine (1.65 g, 11.5 mmol, 1.1 eq.) and commercially available 4-(4-methylpiperazin-1-yl)-aniline (2.0 g, 10.5 mmol, 1.0 eq.) in a mixture of water (4 ml) and glacial acetic acid (16 ml) is heated to 100° C. internal temperature for 16 h. After cooling the solvent is evaporated.

The residue is taken up in methanol (50 ml) and made alkaline by addition of 25% NH₃ in water. To this silica gel (11 g) is added and the solvent is evaporated. The silica adsorbed crude product is purified by medium pressure liquid chromatography (A: TBME; B: MeOH—NH₃ 99:1; gradient: 5% B->25% B in 180 min). The fractions containing the product are pooled and evaporated to dryness. The residue is triturated with ether. The product is filtered off, washed with ether, and vacuum dried at 50° C. over night to give the title compound as pale yellow powder: $t_R$=3.04 min (purity: 97%, gradient A), ESI-MS: 299.3 [MH]⁺.

(6-chloro-pyrimidin-4-yl)-methyl-amine

This material was prepared by a modified procedure published in the literature (*J. Appl. Chem.* 1955, 5, 358): To a suspension of commercially available 4,6-dichloropyrimidine (20 g, 131.6 mmol, 1.0 eq.) in isopropanol (60 ml) is added 33% methylamine in ethanol (40.1 ml, 328.9 mmol, 2.5 eq.) at such a rate that the internal temperature does not rise above 50° C. After completion of the addition the reaction mixture was stirred for 1 h at room temperature. Then, water (50 ml) is added and the suspension formed is chilled in an ice bath to 5° C. The precipitated product is filtered off, washed with cold isopropanol/water 2:1 (45 ml) and water. The collected material is vacuum dried over night at 45° C. to afford the title compound as colorless crystals: $t_R$=3.57 min (purity: >99%, gradient A), ESI-MS: 144.3/146.2 [MH]⁺.

By following the procedure of Example 171 but using the appropriate starting materials, examples 172-193 may be prepared:

Example 172

N-{4-Methyl-3-[3-(6-methylamino-pyrimidin-4-yl)-ureido]-phenyl}-3-trifluoromethyl-benzamide Colorless crystals, TLC: $R_f$=0.40 (TBME/MeOH/NH3 90:9:1), HPLC: $t_R$=5.88 min (purity: 85%, gradient A), ESI-MS: 445.4 [MH]⁺.

Example 173

N-{4-Methyl-3-[3-(6-phenylamino-pyrimidin-4-yl)-ureido]-phenyl}-3-trifluoromethyl-benzamide Colorless crystals, HPLC: $t_R$=6.94 min (purity: >99%, gradient A), ESI-MS: 507.4 [MH]⁺.

Example 174

N-[4-Methyl-3-(3-{6-[4-(4-methyl-piperazin-1-yl)-phenylamino]-pyrimidin-4-yl}-ureido)-phenyl]-3-trifluoromethyl-benzamide Colorless crystals, TLC: $R_f$=0.53 (TBME/MeOH/NH3 80:18:2), HPLC: $t_R$=5.79 min (purity: >99%, gradient A), ESI-MS: 605.5 [MH]⁺.

Example 175

N-[4-Methyl-3-(3-{6-[3-(4-methyl-piperazin-1-yl)-phenylamino]-pyrimidin-4-yl}-ureido)-phenyl]-3-trifluoromethyl-benzamide

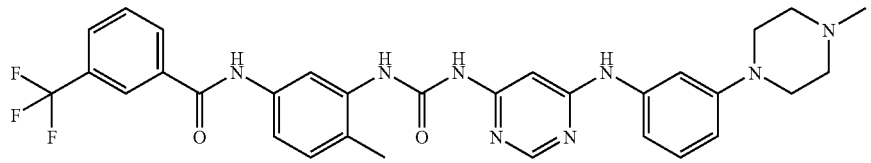

Colorless crystals, TLC: $R_f$=0.34 (TBME/MeOH/NH3 80:18:2), HPLC: $t_R$=5.72 min (purity: >99%, gradient A), ESI-MS: 605.5 [MH]⁺.

Example 176

N-[3-(3-{6-[4-(2-Diethylamino-ethoxy)-phenylamino]-pyrimidin-4-yl}-ureido)-4-methyl-phenyl]-3-trifluoromethyl-benzamide

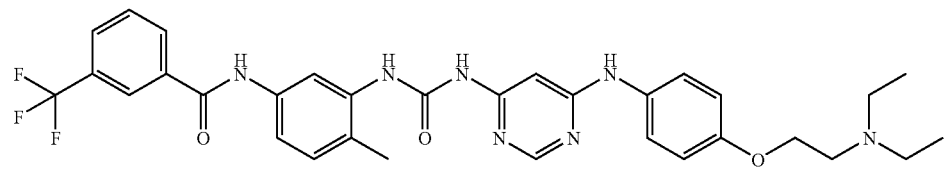 [SMILES: CCN(CC)CCOc1ccc(Nc2cc(NC(=O)Nc3cc(NC(=O)c4cccc(C(F)(F)F)c4)ccc3C)ncn2)cc1]

Colorless crystals, TLC: $R_f$=0.63 (TBME/MeOH/NH3 80:18:2), HPLC: $t_R$=5.84 min (purity: >99%, gradient A), ESI-MS: 622.4 [MH]⁺.

Example 177

N-[3-(3-{6-[4-(3-Dimethylamino-propoxy)-phenylamino]-pyrimidin-4-yl}-ureido)-4-methyl-phenyl]-3-trifluoromethyl-benzamide

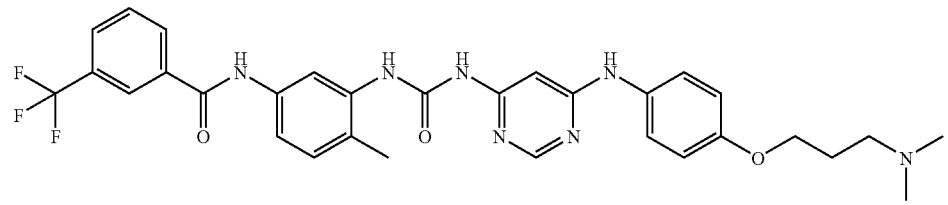 [SMILES: Cc1ccc(NC(=O)c2cccc(C(F)(F)F)c2)cc1NC(=O)Nc1cc(Nc2ccc(OCCCN(C)C)cc2)ncn1]

Colorless crystals, HPLC: $t_R$=5.75 min (purity: >99%, gradient A), ESI-MS: 608.4 [MH]⁺.

Example 178

N-[3-(3-{6-[3-(2-Dimethylamino-ethoxy)-phenylamino]-pyrimidin-4-yl}-ureido)-4-methyl-phenyl]-3-trifluoromethyl-benzamide

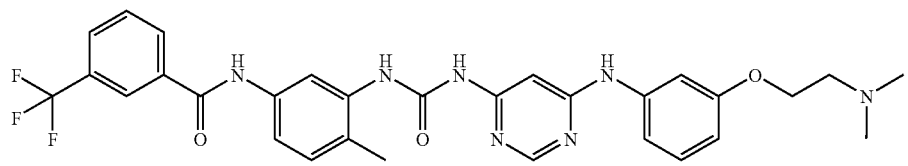

Colorless crystals, TLC: $R_f$=0.17 (TBME/MeOH 30:70), HPLC: $t_R$=5.72 min (purity: 95%, gradient A), ESI-MS: 594.5 [MH]$^+$.

Example 179

N-[4-Methyl-3-(3-{6-[4-(2-morpholin-4-yl-ethoxy)-phenylamino]-pyrimidin-4-yl}-ureido)-phenyl]-3-trifluoromethyl-benzamide

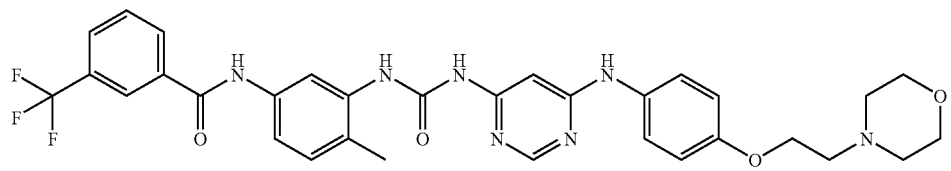 [SMILES: Cc1ccc(NC(=O)c2cccc(C(F)(F)F)c2)cc1NC(=O)Nc1cc(Nc2ccc(OCCN3CCOCC3)cc2)ncn1]

Colorless crystals, TLC: $R_f$=0.31 (TBME/MeOH 80:20), HPLC: $t_R$=5.66 min (purity: >99%, gradient A), ESI-MS: 636.5.4 [MH]$^+$.

Example 180

N-[4-Methyl-3-(3-{6-[3-(2-morpholin-4-yl-ethoxy)-phenylamino]-pyrimidin-4-yl}-ureido)-phenyl]-3-trifluoromethyl-benzamide

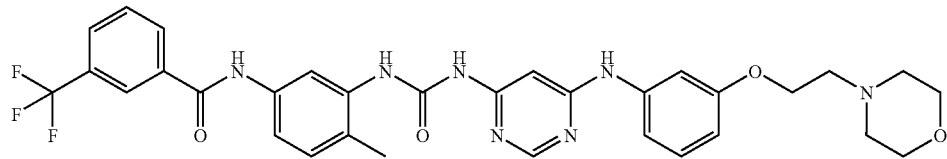 [SMILES: Cc1ccc(NC(=O)c2cccc(C(F)(F)F)c2)cc1NC(=O)Nc1cc(Nc2cccc(OCCN3CCOCC3)c2)ncn1]

Colorless crystals, TLC: $R_f$=0.42 (TBME/MeOH 75:25), HPLC: $t_R$=5.86 min (purity: >99%, gradient A), ESI-MS: 636.6 [MH]$^+$.

Example 181

N-{4-Methyl-3-[3-methyl-3-(6-phenylamino-pyrimidin-4-yl)-ureido]-phenyl}-3-trifluoromethyl-benzamide

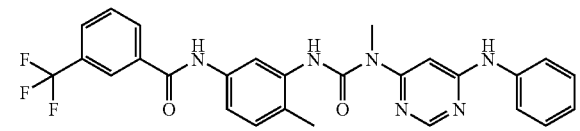 [SMILES: Cc1ccc(NC(=O)c2cccc(C(F)(F)F)c2)cc1NC(=O)N(C)c1cc(Nc2ccccc2)ncn1]

Colorless crystals, TLC: $R_f$=0.69 (TBME/MeOH90:10), HPLC: $t_R$=7.67 min (purity: >99%, gradient A), ESI-MS: 521.4 [MH]$^+$.

Example 182

N-[3-(3-{6-[3-(2-Dimethylamino-ethoxy)-phenylamino]-pyrimidin-4-yl}-3-methyl-ureido)-4-methyl-phenyl]-3-trifluoromethyl-benzamide

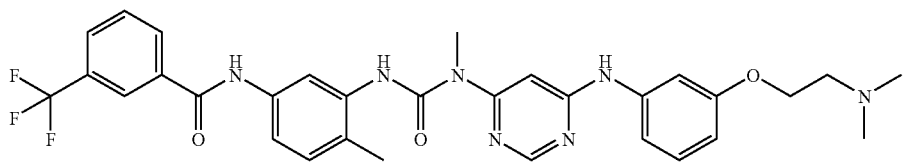 [SMILES: Cc1ccc(NC(=O)c2cccc(C(F)(F)F)c2)cc1NC(=O)N(C)c1cc(Nc2cccc(OCCN(C)C)c2)ncn1]

Colorless crystals, TLC: $R_f$=0.51 (TBME/MeOH/NH3 80:18:2), HPLC: $t_R$=6.02 min (purity: >99%, gradient A), ESI-MS: 608.4 [MH]$^+$.

Example 183

N-[3-(3-{6-[4-(2-Diethylamino-ethoxy)-phenylamino]-pyrimidin-4-yl}-3-methyl-ureido)-4-methyl-Phenyl]-3-trifluoromethyl-benzamide

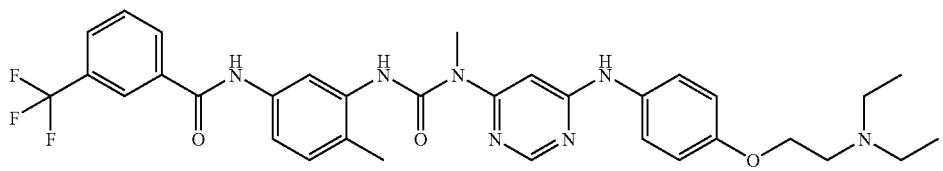 [SMILES: CCN(CC)CCOc1ccc(Nc2cc(N(C)C(=O)Nc3cc(NC(=O)c4cccc(C(F)(F)F)c4)ccc3C)ncn2)cc1]

Colorless crystals, TLC: $R_f$=0.24 (TBME/MeOH 75:25), HPLC: $t_R$=6.23 min (purity: 94%, gradient A), ESI-MS: 636.5 [MH]$^+$.

Example 184

N-{4-Methyl-3-[3-methyl-3-(6-{4-[2-(4-methyl-piperazin-1-yl)-ethoxy]-phenylamino}-pyrimidin-4-yl)-ureido]-phenyl}-3-trifluoromethyl-benzamide

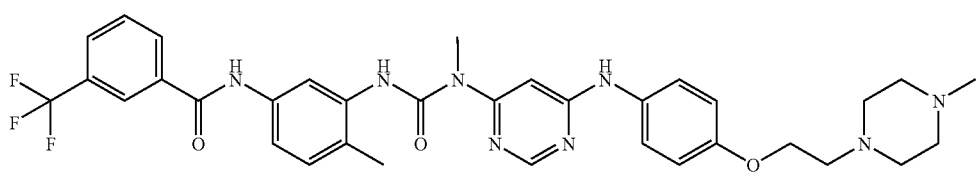 [SMILES: Cc1ccc(NC(=O)c2cccc(C(F)(F)F)c2)cc1NC(=O)N(C)c1cc(Nc2ccc(OCCN3CCN(C)CC3)cc2)ncn1]

Colorless crystals, TLC: $R_f$=0.21 (DCM/MeOH 80:20), HPLC: $t_R$=6.07 min (purity: 88%, gradient A), ESI-MS: 633.2 [MH]$^+$.

Example 185

N-{4-Methyl-3-[3-methyl-3-(6-{3-[2-(4-methyl-piperazin-1-yl)-ethoxy]-phenylamino}-pyrimidin-4-yl)-ureido]-phenyl}-3-trifluoromethyl-benzamide

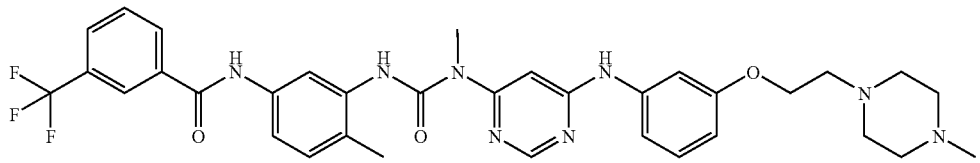 [SMILES: Cc1ccc(NC(=O)c2cccc(C(F)(F)F)c2)cc1NC(=O)N(C)c1cc(Nc2cccc(OCCN3CCN(C)CC3)c2)ncn1]

Colorless crystals, HPLC: $t_R$=6.15 min (purity: 92%, gradient A), ESI-MS: 633.3 [MH]$^+$.

Example 186

4-Methyl-3-(3-methyl-3-{6-[4-(4-methyl-piperazin-1-yl)-phenylamino]-pyrimidin-4-yl}-ureido)-N-(3-trifluoromethyl-phenyl)-benzamide

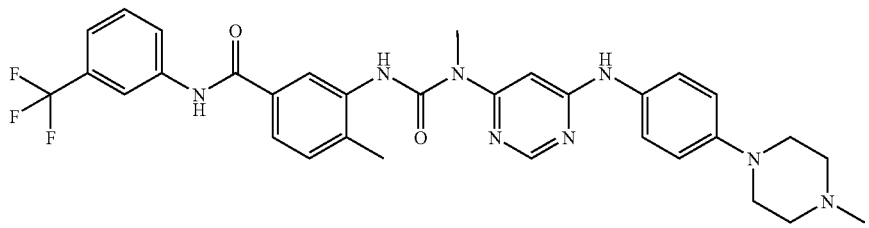 [SMILES: Cc1ccc(C(=O)Nc2cccc(C(F)(F)F)c2)cc1NC(=O)N(C)c1cc(Nc2ccc(N3CCN(C)CC3)cc2)ncn1]

Colorless powder, HPLC: $t_R$=6.19 min (purity: 96%, gradient A), ESI-MS: 619.3 [MH]$^+$.

Example 187

N-[4-Methyl-3-(3-methyl-3-{6-[4-(4-methyl-piperazine-1-carbonyl)-phenylamino]-pyrimidin-4-yl}-ureido)-phenyl]-3-trifluoromethyl-benzamide

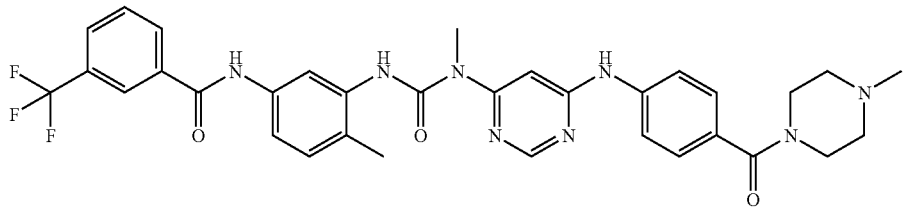 [SMILES: Cc1ccc(NC(=O)c2cccc(C(F)(F)F)c2)cc1NC(=O)N(C)c1cc(Nc2ccc(C(=O)N3CCN(C)CC3)cc2)ncn1]

Colorless crystals, TLC: $R_f$=0.50 (DCM/MeOH 80:20), HPLC: $t_R$=5.82 min (purity: 88%, gradient A), ESI-MS: 647.6 [MH]$^+$.

Example 188

N-[4-Methyl-3-(3-methyl-3-{6-[3-(4-methyl-piperazin-1-yl)-phenylamino]-pyrimidin-4-yl}-ureido)-phenyl]-3-trifluoromethyl-benzamide

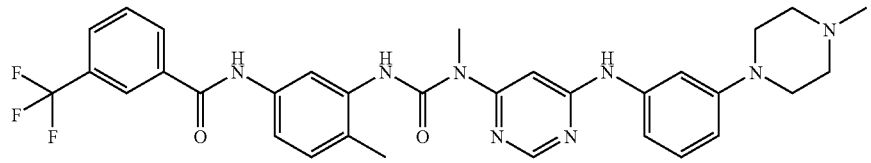 [SMILES: Cc1ccc(NC(=O)c2cccc(C(F)(F)F)c2)cc1NC(=O)N(C)c1cc(Nc2cccc(N3CCN(C)CC3)c2)ncn1]

Pale yellow crystals, TLC: R$_f$=0.50 (TBME/MeOH/NH3 80:18:2), HPLC: t$_R$=6.14 min (purity: 95%, gradient A), ESI-MS: 619.5 [MH]$^+$.

Example 189

N-{4-Methyl-3-[3-[2-(4-methyl-piperazin-1-yl)-ethyl]-3-(6-phenylamino-pyrimidin-4-yl)-ureido]-phenyl}-3-trifluoromethyl-benzamide

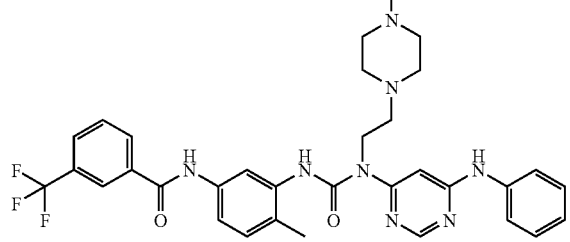

Colorless crystals, TLC: R$_f$=0.04 (TBME/MeOH 90:10), HPLC: t$_R$=6.26 min (purity: >100%, gradient A), ESI-MS: 633.5 [MH]$^+$.

Example 190

N-{4-Methyl-3-[3-(6-phenylamino-pyrimidin-4-yl)-3-(2-pyridin-2-yl-ethyl)-ureido]-phenyl}-3-trifluoromethyl-benzamide

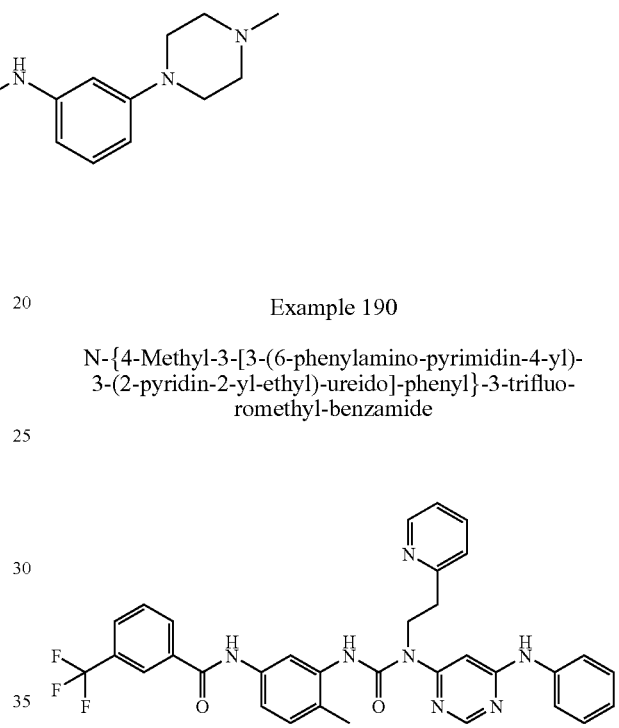

Colorless crystals, HPLC: t$_R$=7.58 min (purity: >100%, gradient A), ESI-MS: 612.4 [MH]$^+$.

Example 191

N-[4-Methyl-3-[3-{6-[4-(4-methyl-piperazin-1-yl)-phenylamino]-pyrimid-in-4-yl]-3-(2-pyridin-2-yl-ethyl)-ureido]-phenyl}-3-trifluoromethyl-benzamide

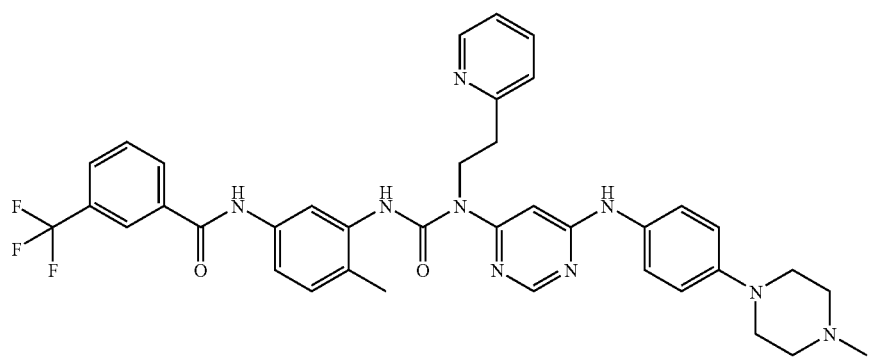 [SMILES: Cc1ccc(NC(=O)c2cccc(C(F)(F)F)c2)cc1NC(=O)N(CCc1ccccn1)c1cc(Nc2ccc(N3CCN(C)CC3)cc2)ncn1]

Pink crystals, TLC: R$_f$=0.54 (DCM/MeOH 80:20), HPLC: t$_R$=5.87 min (purity: 92%, gradient A), ESI-MS: 710.6 [MH]$^+$.

Example 192

N-[3-(3-Ethyl-3-{6-[4-(4-methyl-piperazin-1-yl)-phenylamino]-pyrimidin-4-yl}-ureido)-4-methyl-Phenyl]-3-trifluoromethyl-benzamide

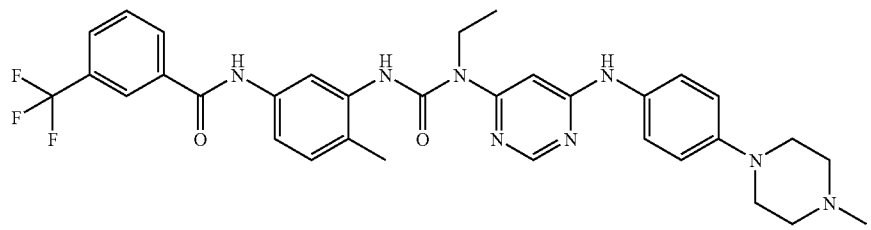 [SMILES: CCN(C(=O)Nc1cc(NC(=O)c2cccc(C(F)(F)F)c2)ccc1C)c1cc(Nc2ccc(N3CCN(C)CC3)cc2)ncn1]

Colorless crystals, TLC: $R_f$=0.45 (DCM/MeOH 80:20), HPLC: $t_R$=6.18 min (purity: >100%, gradient A), ESI-MS: 633.6 [MH]$^+$.

Example 193

N-[4-Methyl-3-(3-{6-[4-(4-methyl-piperazin-1-yl)-phenylamino]-pyrimid-in-4-yl}-3-thiophen-2-ylm-ethyl-ureido)-phenyl]-3-trifluoromethyl-benzamide

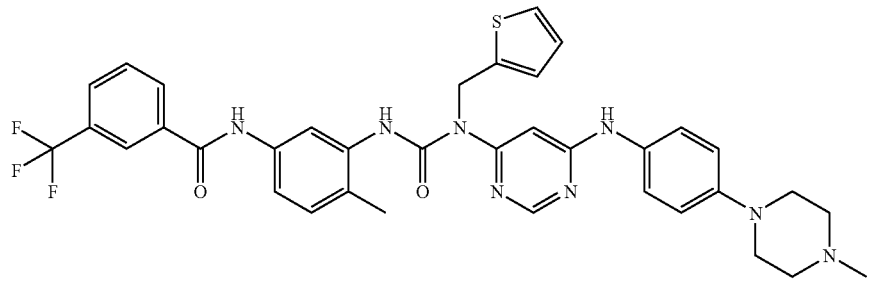 [SMILES: Cc1ccc(NC(=O)c2cccc(C(F)(F)F)c2)cc1NC(=O)N(Cc1cccs1)c1cc(Nc2ccc(N3CCN(C)CC3)cc2)ncn1]

Colorless crystals, TLC: $R_f$=0.26 (DCM/MeOH 90:10), HPLC: $t_R$=6.51 min (purity: >100%, gradient A), ESI-MS: 701.5 [MH]$^+$.
Method B: Examples 194-201

Example 194

N-{3-[3-(6-Amino-pyrimidin-4-yl)-3-methyl-ure-ido]-4-methyl-phenyl}-4-(4-methyl-piperazin-1-ylmethyl)-3-trifluoromethyl-benzamide

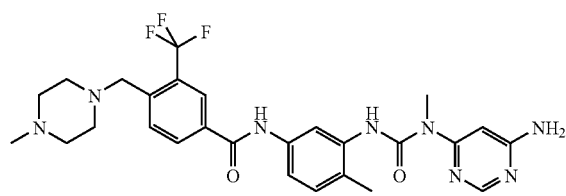 [SMILES: Cc1ccc(NC(=O)c2ccc(CN3CCN(C)CC3)c(C(F)(F)F)c2)cc1NC(=O)N(C)c1cc(N)ncn1]

To tert-butyl [6-(1-Methyl-3-{2-methyl-5-[4-(4-methyl-piperazin-1-ylmethyl)-3-trifluoro-methyl-benzoylamino]-phenyl}-ureido)-pyrimidin-4-yl]-carbamate (50 mg, 0.076 mmol) is added trifluoroacetic acid/DCM 2:3 (2 ml). The clear reaction mixture is stirred for 1 h at room temperature. Then, methanol/DCM 1:9 (20 ml) is added. The solution is washed with 50% aqueous $K_2CO_3$, dried over $MgSO_4$ and evaporated to give the title compound as a beige powder: M.p. 191.5-193° C., HPLC: $t_R$=5.27 min (purity: >99%, gradient A), ESI-MS: 557.3 [MH]$^+$, 400 MHz $^1$H-NMR (DMSO-d$_6$) δ: 2.19 (s, 3H, NMe), 2.30 (s, 3H, ArMe), 2.24-2.62 (br m, 8H, piperazine), 3.32 (s, 3H, urea-NMe), 3.69 (s, 2H, ArCH$_2$N), 6.09 (s, 1H, pyrimidine-H5), 7.02 (s, 2H, NH$_2$), 7.19 (d, 1H, Ar—H5), 7.50 (dd, 1H, Ar—H4), 7.91 (d, 1H, Ar'—H5), 8.23 (dd, 1H, Ar'—H6), 8.26 (d, 1H, Ar—H2), 8.30 (s, 1H, pyrimidine-H2), 8.41 (d, 1H, Ar'—H2), 10.41 (s, 1H, amide-NH).

tert-Butyl [6-(1-Methyl-3-{2-methyl-5-[4-(4-methyl-piperazin-1-ylmethyl)-3-trifluoro-methyl-benzoy-lamino]-phenyl}-ureido)-pyrimidin-4-yl]-carbamate To a solution of 4-(4-Methyl-piperazin-1-ylmethyl)-2-tri-fluoromethyl-benzoic acid (Preparation 2, 80 mg, 0.27 mmol, 1.1 eq.) in DMA is added HATU (138 mg, 0.36 mmol, 1.5 eq.) and diisopropylethylamine (83 µl, 0.48 mmol, 2.0 eq.) after 10 min stirring at room temperature tert-butyl {6-[3-(5-Amino-2-methyl-phenyl)-1-methyl-ureido]-pyrimidin-4-yl}-carbamate is added. The reaction mixture is sonicated for 5 min. After stirring at room temperature over night a grey suspension is formed. The precipitate is filtered off, washed with DMA and ether. Vacuum drying at 60° C. over night afforded a gray powder: HPLC: $t_R$=6.30 min (purity: >99%, gradient A), ESI-MS: 657.4 [MH]$^+$.

tert-Butyl {6-[3-(5-Amino-2-methyl-Phenyl)-1-me-thyl-ureido]-pyrimidin-4-yl}-carbamate A solution of tert-butyl {6-[3-(2-methyl-5-nitro-phenyl)-1-methyl-ureido]-pyrimidin-4-yl}-carbamate (330 mg, 0.82 mmol) in a mixture of methanol (20 ml) and DMF (50 ml) is hydrogenated in the presence of 10% palladium on charcoal (500 mg) at atmospheric pressure. After 20 h the hydrogenation is complete and the catalyst is filtered off. The filtrate is evaporated to dryness. The residue obtained is triturated with ether, filtered off, and vacuum dried to afford a gray powder: HPLC: $t_R$=5.38 min (purity: 97%, gradient A), ESI-MS: 373.4 [MH]$^+$.

tert-Butyl {6-[3-(2-methyl-5-nitro-phenyl)-1-methyl-ureido]-pyrimidin-4-yl}-carbamate A solution of tert-butyl (6-Methylamino-pyrimidin-4-yl)-carbamate (240 mg, 1.07 mmol, 1.0 eq.), commercially available 2-methyl-5-nitrophenylisocyanate (210 mg, 1.18 mmol, 1.1 eq.), and DMAP (26 mg, 0.21 mmol, 0.2 eq.) in toluene (10 ml) is stirred at 80° C. for 24 h. After cooling to room temperature methanol (10 ml) is added and the suspension formed is stirred for 10 min at 50° C. The precipitate is filtered off and washed with methanol (2×10 ml). After drying in vacuo an extremely insoluble colorless powder is obtained: HPLC: $t_R$=8.09 min (purity: 85%, gradient A), ESI-MS: 403.5 [MH]$^+$.

tert-Butyl
(6-Methylamino-pyrimidin-4-yl)-carbamate

A solution of bis(tert-butyl)-(6-chloro-4-pyrimidinyl)-imidodicarboxylate (1 g, 3.03 mmol, 1.0 eq.) in 33% methylamine in ethanol (5.63 ml, 45.5 mmol, 15 eq.) is heated to 80° C. in a sealed tube for 2 h and then allowed to reach room temperature. The precipitated product is filtered off, washed with cold ethanol and vacuum dried at 60° C. over night. The title compound is obtained as colorless crystals: HPLC: $t_R$=3.82 min (purity: 99%, gradient A), ESI-MS: 225.1 [MH]$^+$ (weak), 169.1 [MH-tBu]$^+$.

Bis(tert-butyl)-(6-chloro-4-pyrimidinyl)-imidodicarboxylate may be prepared according to a procedure published in the literature: J. M. Lehn et al., *Eur. J. Chem.* 2001, 1515-1521.

By following the procedure of Example 194 but using the appropriate starting materials, examples 195-201 may be prepared:

Example 195

N-{4-Methyl-3-[3-methyl-3-(6-phenylamino-pyrimidin-4-yl)-ureido]-phenyl}-4-(4-methyl-piperazin-1-ylmethyl)-3-trifluoromethyl-benzamide

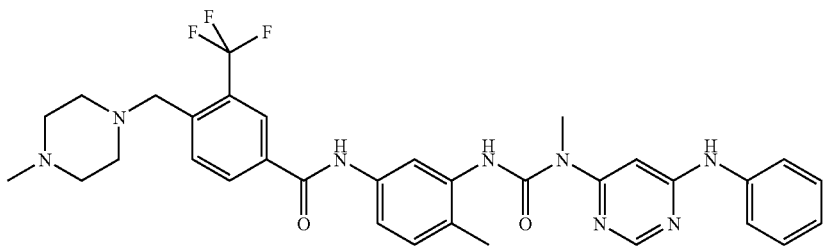 [SMILES: Cc1ccc(NC(=O)c2ccc(CN3CCN(C)CC3)c(C(F)(F)F)c2)cc1NC(=O)N(C)c1cc(Nc2ccccc2)ncn1]

Beige crystals, HPLC: $t_R$=6.33 min (purity: 96%, gradient A), ESI-MS: 633.8 [MH]$^+$.

Example 196

3-(5-Amino-2-methoxy-phenyl)-1-methyl-1-{6-[4-(4-methyl-piperazin-1-yl)-phenylamino]-pyrimidin-4-yl}-urea

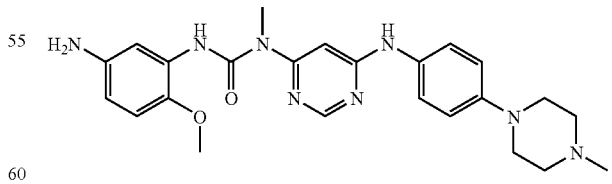

Beige crystals, TLC: $R_f$=0.19 (DCM/MeOH 85:15), HPLC: $t_R$=3.72 min (purity: >100%, gradient A), ESI-MS: 463.6 [MH]$^+$.

Example 197

N-[4-Methoxy-3-(3-methyl-3-{6-[4-(4-methyl-Piperazin-1-yl)-phenyl amino]-pyrimidin-4-yl}-ureido)-phenyl]-3-trifluoromethyl-benzamide

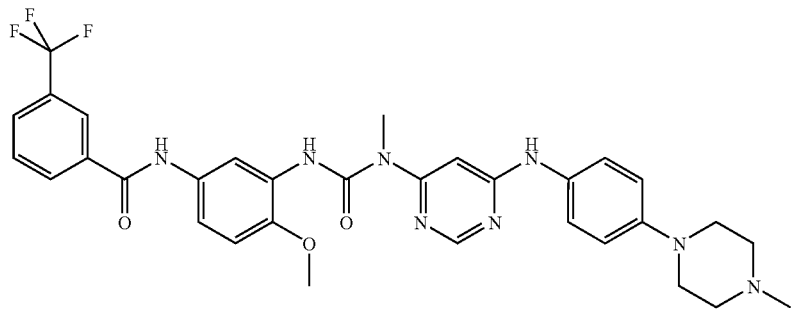 [SMILES: COc1ccc(NC(=O)c2cccc(C(F)(F)F)c2)cc1NC(=O)N(C)c1cc(Nc2ccc(N3CCN(C)CC3)cc2)ncn1]

Pale yellow crystals, TLC: $R_f$=0.21 (TBME/MeOH 60:40), HPLC: $t_R$=5.94 min (purity: 97%, gradient A), ESI-MS: 635.2 [MH]$^+$.

Example 198

N-[4-Methoxy-3-(3-methyl-3-{6-[4-(4-methyl-piperazin-1-yl)-phenyl-amino]-pyrimidin-4-yl}-ureido)-phenyl]-4-(4-methyl-piperazin-1-ylmethyl)-3-trifluoro-methyl-benzamide

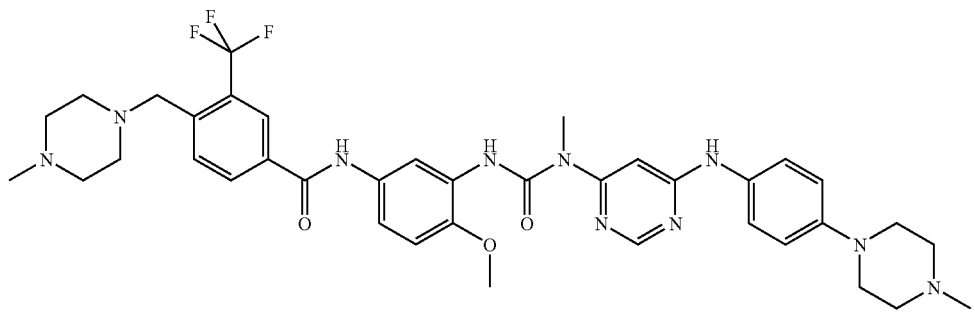

Pale yellow crystals, TLC: $R_f$=0.19 (TBME/MeOH/NEt3 50:50:1.5), HPLC: $t_R$=5.07 min (purity: 96%, gradient A), ESI-MS: 747.4 [MH]$^+$.

Example 199

N-{3-[3-(6-Amino-pyrimidin-4-yl)-3-methyl-ureido]-5-methoxy-phenyl}-4-(4-methyl-piperazin-1-ylmethyl)-3-trifluoromethyl-benzamide

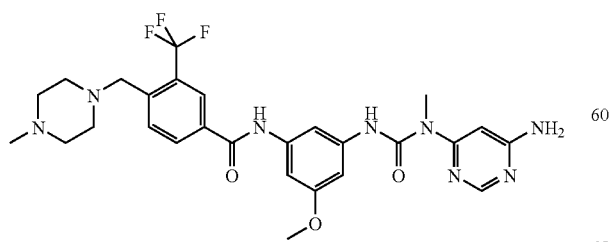

Colorless crystals, HPLC: $t_R$=5.12 min (purity: 97%, gradient A), ESI-MS: 573.2 [MH]$^+$.

Example 200

N-{3-Methoxy-5-[3-methyl-3-(6-phenylamino-pyrimidin-4-yl)-ureido]-phenyl}-4-(4-methyl-piperazin-1-ylmethyl)-3-trifluoromethyl-benzamide

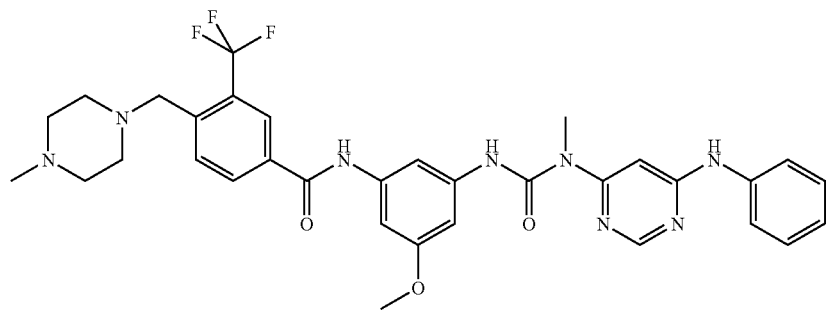 [SMILES: COc1cc(NC(=O)c2ccc(CN3CCN(C)CC3)c(C(F)(F)F)c2)cc(NC(=O)N(C)c2cc(Nc3ccccc3)ncn2)c1]

Yellow resin, HPLC: $t_R$=6.20 min (purity: 99%, gradient A), ESI-MS: 649.4 [MH]$^+$.

Example 201

N-[3-Methoxy-5-(3-methyl-3-{6-[4-(4-methyl-piperazin-1-yl)-phenyl-amino]-pyrimidin-4-yl}-ureido)-phenyl]-4-methyl-3-trifluoromethyl-benzamide

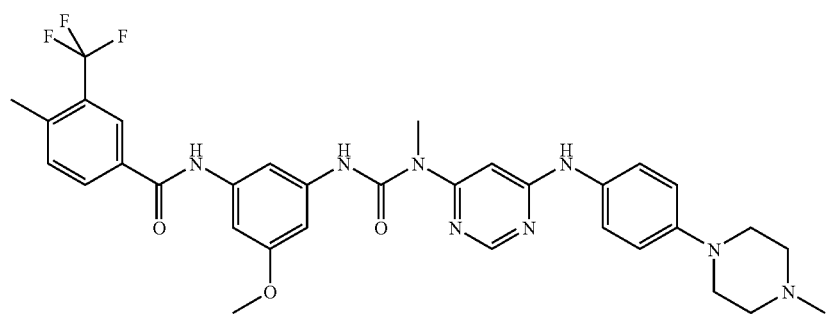

Beige crystals, TLC: $R_f$=0.39 (DCM/MeOH 85:15), HPLC: $t_R$=6.17 min (purity: >100%, gradient A), ESI-MS: 649.7 [MH]$^+$.

Example 202

N-[3-[3-(6-Acetylaminopyrimidin-4-yl)-3-methylureido]-4-methylphenyL]-4-(4-methylpiperazin-1-ylmethyl)-3-trifluoromethylbenzamide

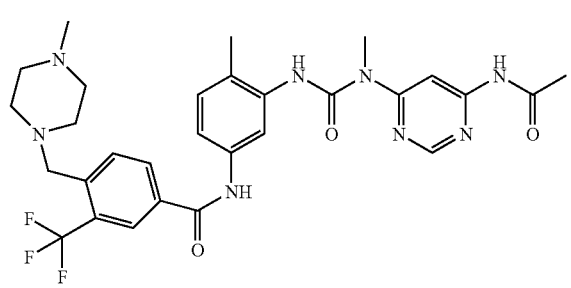 [SMILES: CC(=O)Nc1cc(N(C)C(=O)Nc2cc(NC(=O)c3ccc(CN4CCN(C)CC4)c(C(F)(F)F)c3)ccc2C)ncn1]

colourless crystalline solid, TLC: $R_f$=0.24 (DCM/EtOH/NH3 90:9:1), HPLC: $t_R$=10.57 min (purity: 100%, gradient B), ESI-MS: 599 [MH]$^+$.

Example 203

[6-(1-Methyl-3-{2-methyl-5-[4-(4-methyl-piperazin-1-ylmethyl)-3-trifluoromethyl-benzoylamino]-phenyl}-ureido)-pyrimidin-4-yl]-carbamic acid methyl ester

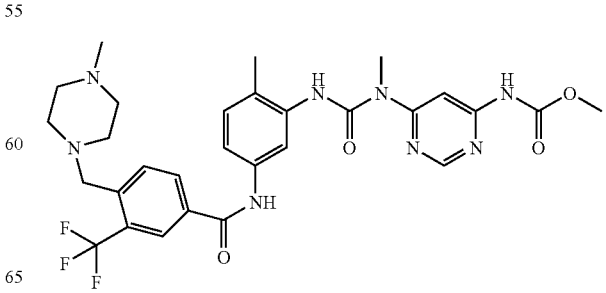

Colourless powder, TLC: $R_f$=0.20 (DCM/EtOH/NH3 90:9:1), HPLC: $t_R$=11.25 min (purity: 100%, gradient B), ESI-MS: 615 [MH]$^+$.

Example 204

[6-(1-Methyl-3-{2-methyl-5-[4-(4-methyl-piperazin-1-ylmethyl)-3-trifluoromethyl-phenylcarbamoyl]-phenyl}-ureido)-pyrimidin-4-yl]-carbamic acid methyl ester

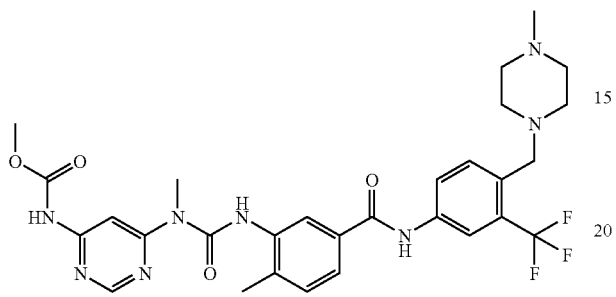

Colourless powder, TLC: $R_f$=0.33 (DCM/EtOH/NH3 90:9:1), HPLC: $t_R$=10.97 min (purity: 100%, gradient B), ESI-MS: 615 [MH]$^+$.

Example 205

3-[3-(6-Acetylamino-pyrimidin-4-yl)-3-methyl-ureido]-4-methyl-N-[4-(4-methyl-piperazin-1-ylmethyl)-3-trifluoromethyl-phenyl]-benzamide

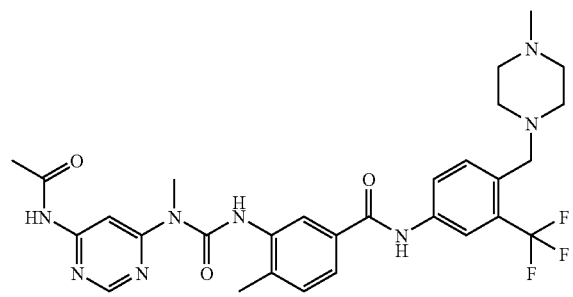 [SMILES: CC(=O)Nc1cc(N(C)C(=O)Nc2cc(C(=O)Nc3ccc(CN4CCN(C)CC4)c(C(F)(F)F)c3)ccc2C)ncn1]

Example 206

3-[3-(6-Amino-pyrimidin-4-yl)-3-methyl-ureido]-4-methyl-N-[4-(4-methyl-piperazin-1-ylmethyl)-3-trifluoromethyl-phenyl]-benzamide

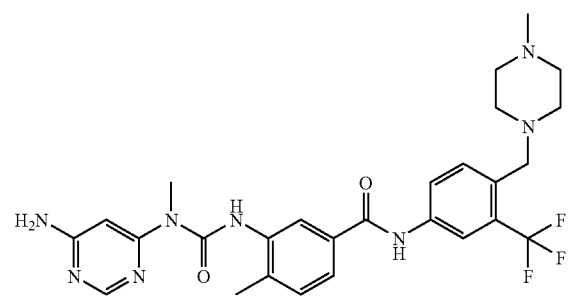 [SMILES: Cc1ccc(C(=O)Nc2ccc(CN3CCN(C)CC3)c(C(F)(F)F)c2)cc1NC(=O)N(C)c1cc(N)ncn1]

Example 207

In Vitro Inhibition Data

The compounds of Examples 171 to 206 were tested under the protocols as hereinbefore described for their inhibitory activity against c-Abl, KDR and FGFR3.

For c-Abl 79-100% inhibition at 10 µM, for KDR 87-100% inhibition at 10 µM and for FGFR3 56-98% inhibition at 10 µM is observed.

Example 208

N-[4-Methyl-3-(3-methyl-3-{6-[(tetrahydro-furan-2-ylmethyl)-amino]-pyrimidin-4-yl}-ureido)-phenyl]-3-trifluoromethyl-benzamide

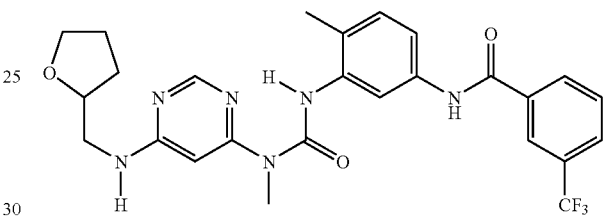

Pal-resin bearing C-(Tetrahydro-furan-2-yl)-methylamine (Ig, 1 mmol), DIEA (0.52 mL, 3 mmol), and 4,6-dichloropyrimidine (300 mg, 2 mmol) are mixed in n-BuOH (15 mL). The reaction vial is put into a heating shaker and heated up at 80° C. for 16 hours. The resultant mixture is filtered and the resin is washed with DMF (3×20 mL), MeOH (3×20 mL), CH$_2$Cl$_2$ (3×20 mL), and dried under vacuum. 10 mgs of the resin is treated with TFA/CH$_2$Cl$_2$/H$_2$O (45/50/5) (200 µL) for 1 hour. LC-MS revealed only one major peak: observed MS (M+H$^+$) is 214.2;

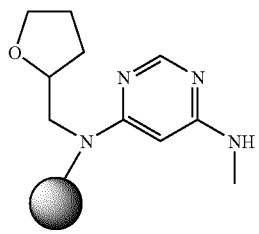 [SMILES: CNc1cc(N(C)CC2CCCO2)ncn1]

Pal-resin bearing (6-Chloro-pyrimidin-4-yl)-(tetrahydro-furan-2-ylmethyl)-amine (1 mmol), 40% methylamine water solution (1.95 mL, 25 mmol), 15 mL n-BuOH are mixed together in a sealed tube. The reaction vial is put into a heating shaker and heated up at 100° C. for 12 hours. After cooling, another 1.95 mL of 40% methylamine water solution is added into the reaction vial. The reaction is heated to 100° C. for 12 hours. The resultant mixture is filtered and the resin is washed with DMF (3×20 mL), MeOH (3×20 mL), CH$_2$Cl$_2$ (3×20 mL), and dried under vacuum. 10 mgs of the resin is treated with TFA/CH$_2$Cl$_2$/H$_2$O (45/50/5) (200 µL) for 1 hour. LC-MS revealed only one major peak: observed MS (M+H$^+$) is 209.2.

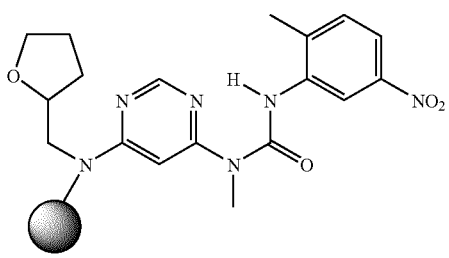

Pal-resin bearing N-Methyl-N'-(tetrahydro-furan-2-ylmethyl)-pyrimidine-4,6-diamine (1 mmol), 2-methyl-5-nitrophenyl-isocyanate (540 mg, 3 mmol), DIEA (0.52 mL, 3 mmol), 15 mL anhydrous DMF are mixed together. The reaction vial is heated with shaking to 60° C. for 14 hours. The resultant mixture is filtered and the resin is washed with DMF (3×20 mL), MeOH (3×20 mL), CH$_2$Cl$_2$ (3×20 mL), and dried under vacuum. 10 mgs of the resin is treated with TFA/CH$_2$Cl$_2$/H$_2$O (45/50/5) (200 µL) for 1 hour. LC-MS revealed only one major peak: observed MS (M+H$^+$) is 387.2.

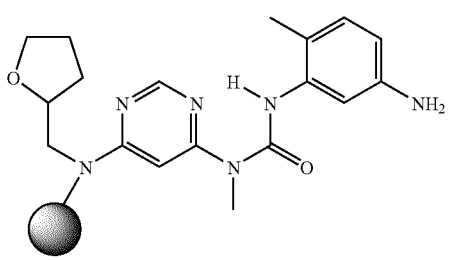 [SMILES: Cc1ccc([N+](=O)[O-])cc1NC(=O)N(C)c1cc(N(C)CC2CCCO2)ncn1]

Pal-resin bearing 1-Methyl-3-(2-methyl-5-nitro-phenyl)-1-{6-[(tetrahydro-furan-2-ylmethyl)-amino]-pyrimidin-4-yl}-urea (1 mmol), tin(II) chloride (1.55 g, 8 mmol), 15 mL NMP are mixed together. The reaction vial is shaken at room temperature for 16 hours. The resultant mixture is filtered and the resin is washed with DMF (3×20 mL), MeOH (3×20 mL), CH$_2$Cl$_2$ (3×20 mL), and dried under vacuum. 10 mgs of the resin is treated with TFA/CH$_2$Cl$_2$/H$_2$O (45/50/5) (200 µL) for 1 hour. LC-MS revealed only one major peak: observed MS (M+H$^+$) is 357.3.

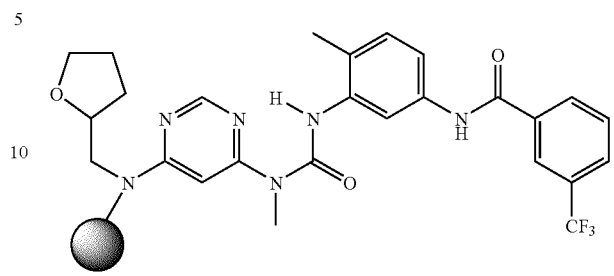

Pal-resin bearing 3-(5-Amino-2-methyl-phenyl)-1-methyl-1-{6-[(tetrahydro-furan-2-ylmethyl)-amino]-pyrimidin-4-yl}-urea (1 mmol), 3-trifluoromethyl-benzoyl chloride (630 mg, 3 mmol), DIEA (0.52 mL, 3 mmol) and 15 mL anhydrous DMF are mixed together. The reaction vial is shaking in room temperature for 16 hours. The resultant mixture is filtered and the resin is washed with DMF (3×20 mL), MeOH (3×20 mL), CH$_2$Cl$_2$ (3×20 mL), and dried under vacuum. 10 mgs of the resin is treated with TFA/CH$_2$Cl$_2$/H$_2$O (45/50/5) (200 µL) for 1 hour. LC-MS revealed only one major peak: observed MS (M+H$^+$) is 529.3.

All of the pal resin is treated with TFA/CH$_2$Cl$_2$/H$_2$O (45/50/5) (10 mL) for 2 hours. After removing the solvent under the vacuum, the crude product is dissolved in DMSO and purified by reverse phase preparative HPLC to give the final product N-[4-Methyl-3-(3-methyl-3-{6-[(tetrahydro-furan-2-ylmethyl)-amino]-pyrimidin-4-yl}-ureido)-phenyl]-3-trifluoromethyl-benzamide as the white solid, 241 mg. A summary of the procedure is described in the flow diagram below. The solid spheres indicate a solid support (Pal resin); $^1$H NMR (600 MHz, DMSO-d$_6$) δ 12.84 (s, 1H), 10.44 (s, 1H), 8.41 (s, 1H), 8.34 (s, 1H), 8.28 (s, 1H), 8.27 (d, J=7.9 Hz, 1H), 7.96 (d, J=8.0 Hz, 1H), 7.78 (t, J=7.4 Hz, 1H), 7.60 (s, 1H), 7.51 (d, J=8.2 Hz, 1H), 7.20 (d, J=8.0 Hz, 1H), 6.16 (s, 1H), 3.92-3.79 (m, 3H), 3.64-3.62 (m, 2H), 3.34 (s, 3H), 2.31 (s, 3H), 1.85-1.82 (m, 4H); ESIMS m/z 529.3 (M$^+$+1).

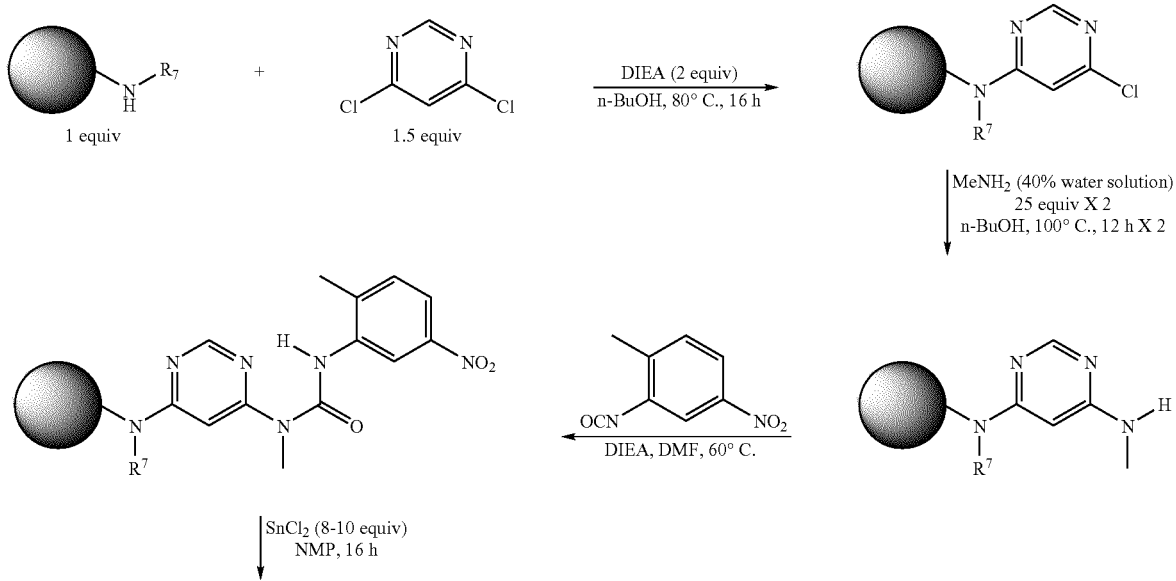

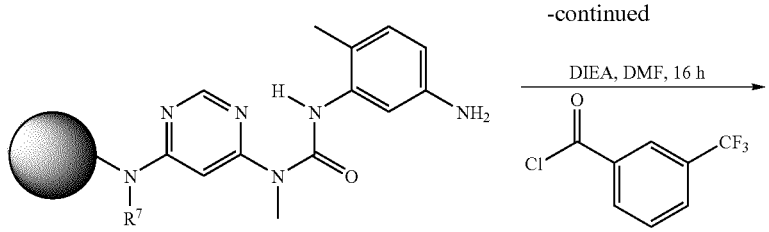

-continued

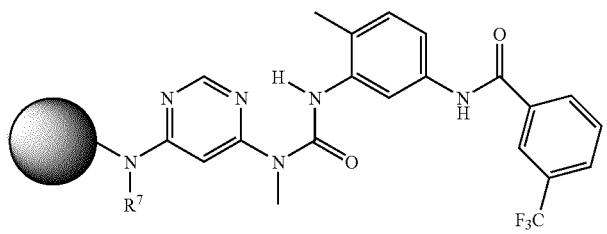

Example 209

N-(3-{3-[6-(Benzo[1,3]dioxol-5-ylamino)-pyrimidin-4-yl]-3-methyl-ureido}-4-methyl-phenyl)-3-trifluoromethyl-benzamide

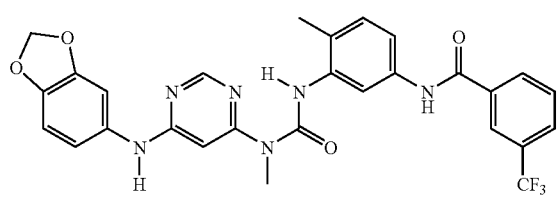 [SMILES: Cc1ccc(NC(=O)c2cccc(C(F)(F)F)c2)cc1NC(=O)N(C)c1cc(Nc2ccc3c(c2)OCO3)ncn1]

The general procedure is as same as example 208, except the Pal-resin is attached to benzo[1,3]dioxol-5-ylamine. All of the pal resin is treated with TFA/CH$_2$Cl$_2$/H$_2$O (45/50/5) (10 mL) for 2 hours. After removing the solvent under the vacuum, the crude product is dissolved into DMSO and purified by reverse phase preparative HPLC to give the final product N-(3-{3-[6-(Benzo[1,3]dioxol-5-ylamino)-pyrimidin-4-yl]-3-methyl-ureido}-4-methyl-phenyl)-3-trifluoromethyl-benzamide as the white solid; $^1$H NMR (400 MHz, DMSO-d$_6$) δ 12.70 (s, 1H), 10.44 (s, 1H), 9.58 (s, 1H), 8.49 (s, 1H), 8.40 (d, J=11.8 Hz, 2H), 8.30 (s, 1H), 8.27 (d, J=7.8 Hz, 1H), 7.95 (d, J=7.6 Hz, 1H), 7.78 (t, J=7.8 Hz, 1H), 7.51 (d, J=8.4 Hz, 1H), 7.37 (t, J=8.1 Hz, 1H), 7.25 (d, J=8.8 Hz, 1H), 6.88 (d, J=8.3 Hz, 1H), 6.35 (s, 1H), 6.00 (s, 2H), 3.33 (s, 3H), 2.32 (s, 3H); ESIMS m/z 565.3 (M$^+$+1).

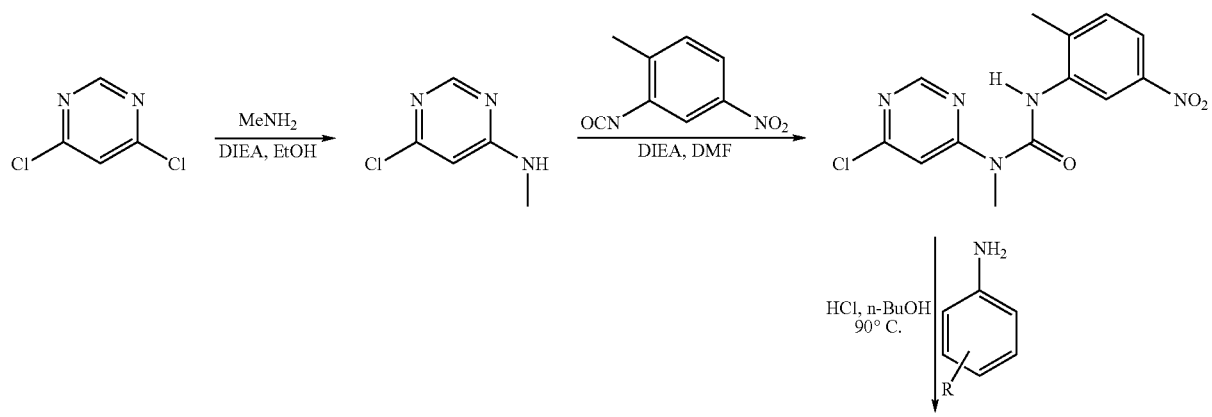

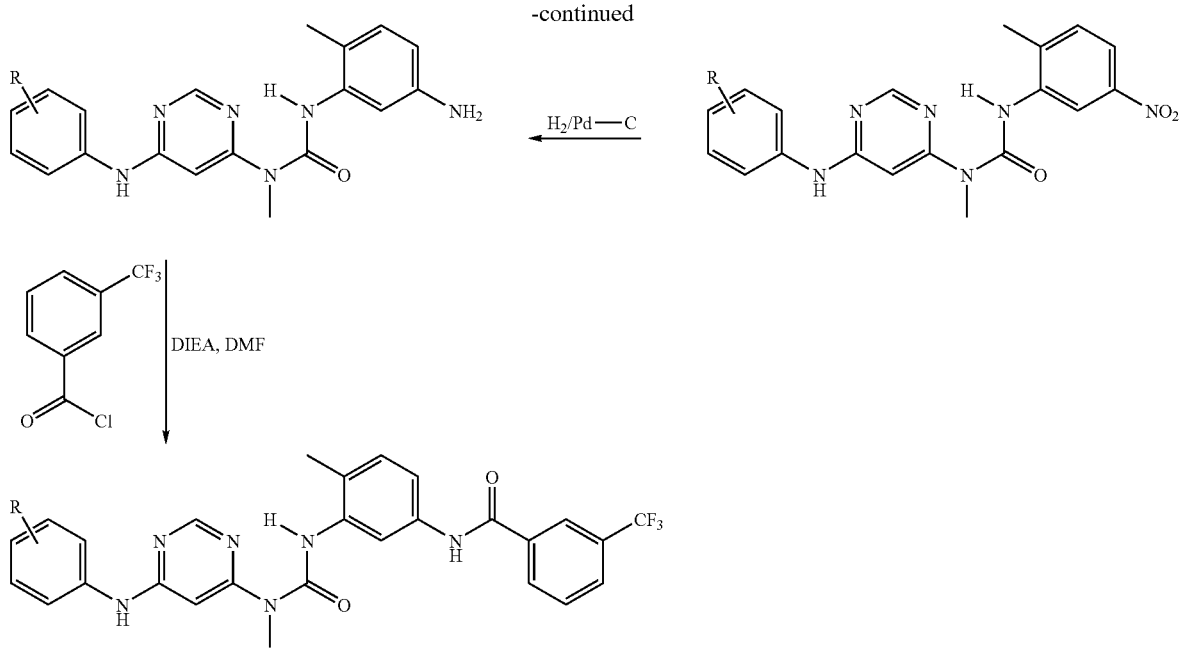

in which R represents an $R_7$ substituent as defined in the Summary of the Invention.

Example 210

N-(3-{3-[6-(3-Dimethylamino-phenylamino)-pyrimidin-4-yl]-3-methyl-ureido}-4-methyl-phenyl-3-trifluoromethyl-benzamide

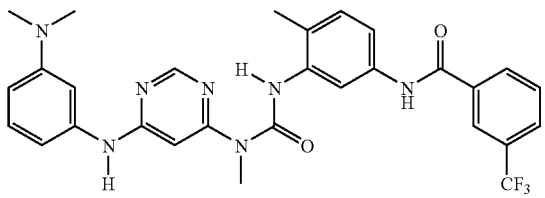 [SMILES: Cc1ccc(NC(=O)c2cccc(C(F)(F)F)c2)cc1NC(=O)N(C)c1cc(Nc2cccc(N(C)C)c2)ncn1]

A reaction scheme for this protocol is shown above. 4,6-dichloropyrimidine (1.0 g, 6.75 mmol), 2.0M methylamine in MeOH (3.38 mL, 6.75 mmol) and DIEA (1.76 mL, 10.13 mmol) are dissolved in 30 mL ethanol. The reaction is heated to 70° C. for 4 hours. After removing the solvent, the crude product is purified by flash chromatography using EA/Hexane (3:7) to get the final product (6-Chloro-pyrimidin-4-yl)-methyl-amine as the white solid.

(6-Chloro-pyrimidin-4-yl)-methyl-amine (940 mg, 6.57 mmol), 2-methyl-5-nitrophenyl-isocyanate (1.23 g, 6.90 mmol), DIEA (2.30 mL, 13.15 mmol) are dissolved in 30 mL anhydrous DMF. The reaction is stirred in room temperature for 14 hours. After removing the solvent, the crude product is purified by flash chromatography using EA/Hexane (4:6) to get the final product 1-(6-Chloro-pyrimidin-4-yl)-1-methyl-3-(2-methyl-5-nitro-phenyl)-urea as the white solid.

1-(6-Chloro-pyrimidin-4-yl)-1-methyl-3-(2-methyl-5-nitro-phenyl)-urea (100 mg, 0.31 mmol), N,N-Dimethyl-benzene-1,3-diamine HCl salt (82 mg, 0.47 mmol) are dissolved in 6 mL n-BuOH. The reaction is heated up to 90° C. for 16 hours. After removing the solvent, the crude product is purified by flash chromatography using EA/Hexane (1:1) to get the final product 1-[6-(3-dimethylamino-phenylamino)-pyrimidin-4-yl]-1-methyl-3-(2-methyl-5-nitro-phenyl)-urea as white solid.

1-[6-(3-Dimethylamino-phenylamino)-pyrimidin-4-yl]-1-methyl-3-(2-methyl-5-nitro-phenyl)-urea (110 mg, 0.26 mmol) and 10 mg 10% palladium carbon powder are mixed in 20 mL EtOH under hydrogen environment. The reaction is stirred at 50° C. for 4 hours. The reaction mixture is passed through a celite plug and washed by methanol. After removing the solvent under the vacuum, the crude product 3-(5-Amino-2-methyl-phenyl)-1-[6-(3-dimethylamino-phenylamino)-pyrimidin-4-yl]-1-methyl-urea is used for next step reaction without purification.

3-(5-Amino-2-methyl-phenyl)-1-[6-(3-dimethylamino-phenylamino)-pyrimidin-4-yl]-1-methyl-urea (0.26 mmol), 3-trifluoromethyl-benzoyl chloride (57 mg, 0.27 mmol) and DIEA (68 uL, 0.39 mmol) are dissolved in 10 mL anhydrous DMF. The reaction is stirred in the room temperature for 4 hours. After removing the solvent, the crude product is dissolved into DMSO and purified by reverse phase preparative HPLC to give the final product N-(3-{3-[6-(3-Dimethylamino-phenylamino)-pyrimidin-4-yl]-3-methyl-phenyl)-3-trifluoromethyl-benzamide as the white solid; $^1$H NMR (600 MHz, DMSO-$d_6$) δ 12.67 (s, 1H), 10.44 (s, 1H), 9.84 (s, 1H), 8.56 (s, 1H), 8.40 (d, J=11.8 Hz, 2H), 8.28 (s, 1H), 8.24 (d, J=8.2 Hz, 1H), 7.94 (d, J=7.7 Hz, 1H), 7.76 (t, J=7.8 Hz, 1H), 7.48 (d, J=8.4 Hz, 1H), 7.35 (t, J=8.1 Hz, 1H), 7.22 (d, J=8.8 Hz, 1H), 6.81 (d, J=7.5 Hz, 1H), 6.64 (s, 1H), 6.59 (d, J=8.2 Hz, 1H), 3.35 (s, 3H), 2.92 (s, 6H), 2.35 (s, 3H); ESIMS m/z 565.3 (M$^+$+1).

Example 211

N-(3-{3-[6-(3-Acetylamino-phenylamino)-pyrimidin-4-yl]-3-methyl-ureido}-4-methyl-phenyl)-3-trifluoromethyl-benzamide

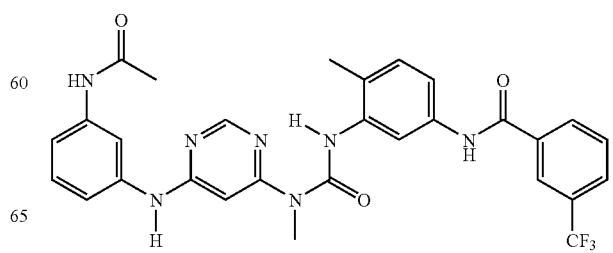

The general procedure is as same as example 3, except N-(3-Amino-phenyl)-acetamide (71 mg, 0.47 mmol) and 0.12 mL 4M HCl in dioxane solution are added in the reaction. The final product N-(3-{3-[6-(3-Acetylamino-phenylamino)-pyrimidin-4-yl]-3-methyl-ureido}-4-methyl-phenyl)-3-trifluoromethyl-benzamide is purified by reverse phase preparative HPLC to give the white solid; $^1$H NMR (600 MHz, DMSO-$d_6$) δ 12.67 (s, 1H), 10.44 (s, 1H), 9.84 (s, 1H), 8.56 (s, 1H), 8.40-8.36 (m, 2H), 8.31 (s, 1H), 8.28 (d, J=7.8 Hz, 1H), 8.07 (s, 1H), 7.95 (d, J=7.7 Hz, 1H), 7.84 (d, J=6.6 Hz, 1H), 7.78 (t, J=7.8 Hz, 1H), 7.52 (d, J=6.6 Hz, 1H), 7.47 (d, J=7.8 Hz, 1H), 7.41 (t, J=7.8 Hz, 1H), 7.22 (d, J=8.4 Hz, 1H), 6.48 (s, 1H), 3.37 (s, 3H), 2.79 (d, J=4.2, 3H), 2.34 (s, 3H); ESIMS m/z 578.3 (M$^+$+1).

4-methyl-3-nitroaniline (3.0 g, 20 mmol) is dissolved in 100 ml methylene chloride. 3 ml triethylamine (22 mmol) is added, the solution is cooled to 0° C., and 3-trifluorobenzioc chloride (4. Ig; 20 mmol) is added slowly to the above mixture while stirring. The reaction mixture was allowed raised to room temperature and the reaction was completed in 1 hr. The reaction mixture was washed with 10% NaHCO$_3$ solution, brine and dried over Na$_2$SO$_4$. The final product (3) N-(4-Methyl-3-nitro-phenyl)-3-trifluoromethyl-benzamide is a yellow solid, 6.28 g.

N-(4-Methyl-3-nitro-phenyl)-3-trifluoromethyl-benzamide (6.2 g, 19 mmol) was dissolved in 80 ml ethanol and 600 mg Pd/C was added to the solution. The mixture was stirred under hydrogen at room temperature for 4 hours. The Pd/C

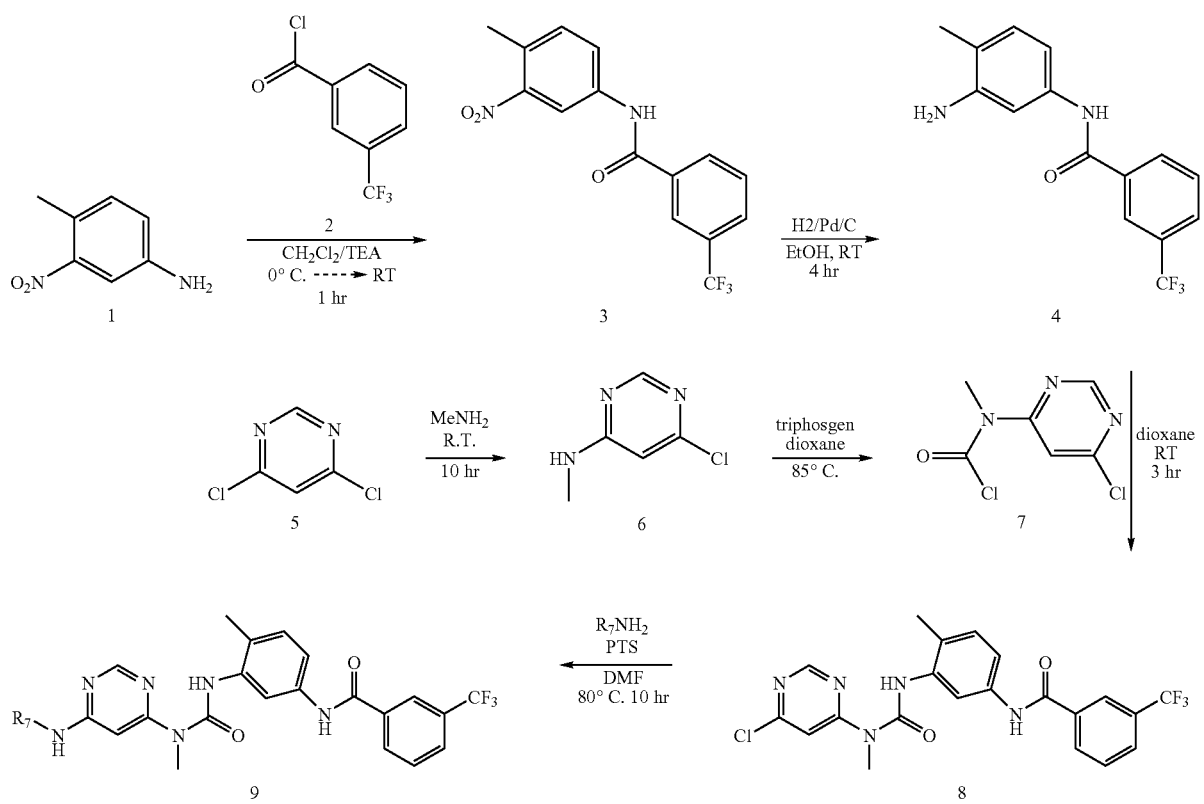

was removed by filtration. The crude product was recrystallized in ethyl acetate. The final product (4) N-(3-Amino-4-methyl-phenyl)-3-trifluoromethyl-benzamide is dark solid, 5.5 g.

4,6-dichloro-pyrimidine (10 g, 67 mmol) was dissolved in 50 ml methanol. Then 37 ml 2M methylamine THF solution Example 212

N-(4-Methyl-3-{3-methyl-3-[6-(4-morpholin-4-yl-phenylamino)-pyrimidin-4-yl]-ureido}-phenyl)-3-trifluoromethyl-benzamide

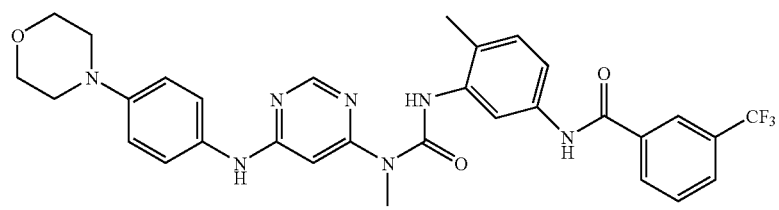 [SMILES: Cc1ccc(NC(=O)c2cccc(C(F)(F)F)c2)cc1NC(=O)N(C)c1cc(Nc2ccc(N3CCOCC3)cc2)ncn1]

was added to it. The reaction was stirred for 10 hours at room temperature. The solvent was removed by rotary evaporation and the crude product was recrystallized in methanol. The final product (5) (6-Chloro-pyrimidin-4-yl)methylamine was light yellow solid, 8.2 g.

(6-Chloro-pyrimidin-4-yl)-methyl-amine (1.43 g 10 mmol) was dissolved in 20 ml dioxane and mixed with 1.7 ml DIEA (15 mmol), then 1.2 g triphosgene was added to the solution. The reaction mixture was stirred at 85° C. for 3 hours. The reaction mixture was cooled down to room temperature. To this reaction mixture, 1.7 ml DIEA and 2.94 g N-(3-Amino-4-methyl-phenyl)-3-trifluoromethyl-benzamide (4) were added. The reaction was stirred at room temperature for 3 hours. The crude product was recrystallized in ethyl acetate. The final product (8) N-{3-[3-(6-Chloro-pyrimidin-4-yl)-3-methyl-ureido]-4-methyl-phenyl}-3-trifluoromethyl-benzamide is light yellow solid, 3.9 g.

N-{3-[3-(6-Chloro-pyrimidin-4-yl)-3-methyl-ureido]-4-methyl-phenyl}-3-trifluoromethyl-benzamide (50 mg, 0.107 mmol) and p-toluenesulfonic acid (20 mg, 0.105 mmol) were mixed and dissolved in 1 ml DMF. Then 4-Morpholin-4-yl-phenylamine (22 mg, 0.11 mmol) was added to it. The reaction was stirred at 80° C. for 10 hours. The crude product was purified by reverse phase HPLC to give final product N-(4-Methyl-3-{3-methyl-3-[6-(4-morpholin-4-yl-phenylamino)-pyrimidin-4-yl]-ureido}-phenyl)-3-trifluoromethyl-benzamide as grey solid, 48 mg; $^1$H NMR 600 MHz (DMSO) δ 12.74 (s, 1H), 10.46 (s, 1H), 9.53 (s, 1H), 8.47 (s, 1H), 8.41 (m, 1H), 8.31 (s, 1H), 8.28 (d, 1H, J=7.8 Hz), 7.97 (d, 1H, J=7.2 Hz), 7.79 (t, 1H, J=4.2 Hz), 7.52 (d, 1H, J=7.8 Hz), 7.47 (d, 2H, J=8.4 Hz), 7.22 (d, 1H, J=8.4 Hz), 6.99 (s, 1H), 6.98 (s, 1H), 6.34 (s, 1H), 4.15 (m, 4H), 3.76 (m, 4H), 3.10 (m, 3H), 2.32 (s, 3H); MS m/z 606.2 (M+1).

Example 213

N-[4-Methyl-3-(3-methyl-3-{6-[4-(4-methyl-piperazin-1-yl)-phenylamino]-pyrimidin-4-yl}-ureido)-phenyl]-3-trifluoromethyl-benzamide

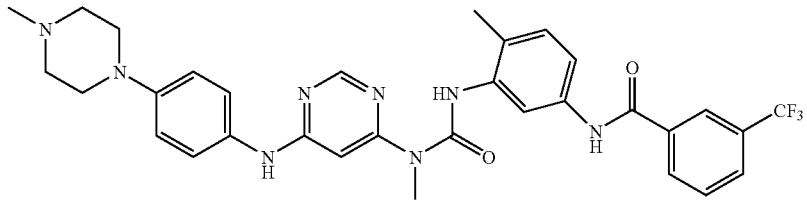 [SMILES: Cc1ccc(NC(=O)c2cccc(C(F)(F)F)c2)cc1NC(=O)N(C)c1cc(Nc2ccc(N3CCN(C)CC3)cc2)ncn1]

This compound was made using the same procedure as above, except that the 4-(4-Methyl-piperazin-1-yl)-phenylamine was used instead of 4-Morpholin-4-yl-phenylamine. The final compound N-[4-Methyl-3-(3-methyl-3-{6-[4-(4-methyl-piperazin-1-yl)-phenylamino]-pyrimidin-4-yl}-ureido)-phenyl]-3-trifluoromethyl-benzamide is white solid, 43 mg; $^1$H NMR 600 MHz (DMSO) δ 12.75 (s, 1H), 10.47 (s, 1H), 9.64 (s, 1H), 9.55 (s, 1H), 8.47 (s, 1H), 8.41 (m, 1H), 8.31 (s, 1H), 8.28 (d, 1H, J=7.8 Hz), 7.97 (d, 1H, J=7.2 Hz), 7.79 (t, 1H, J=4.2 Hz), 7.52 (d, 1H, J=7.8 Hz), 7.47 (d, 2H, J=8.4 Hz), 7.22 (d, 1H, J=8.4 Hz), 6.99 (s, 1H), 6.98 (s, 1H), 6.34 (s, 1H), 3.79 (m, 2H), 3.56 (m, 4H), 3.18 (m, 3H), 2.95 (m, 2H), 2.87 (s, 3H), 2.33 (s, 3H); MS m/z 620.2 (M+1).

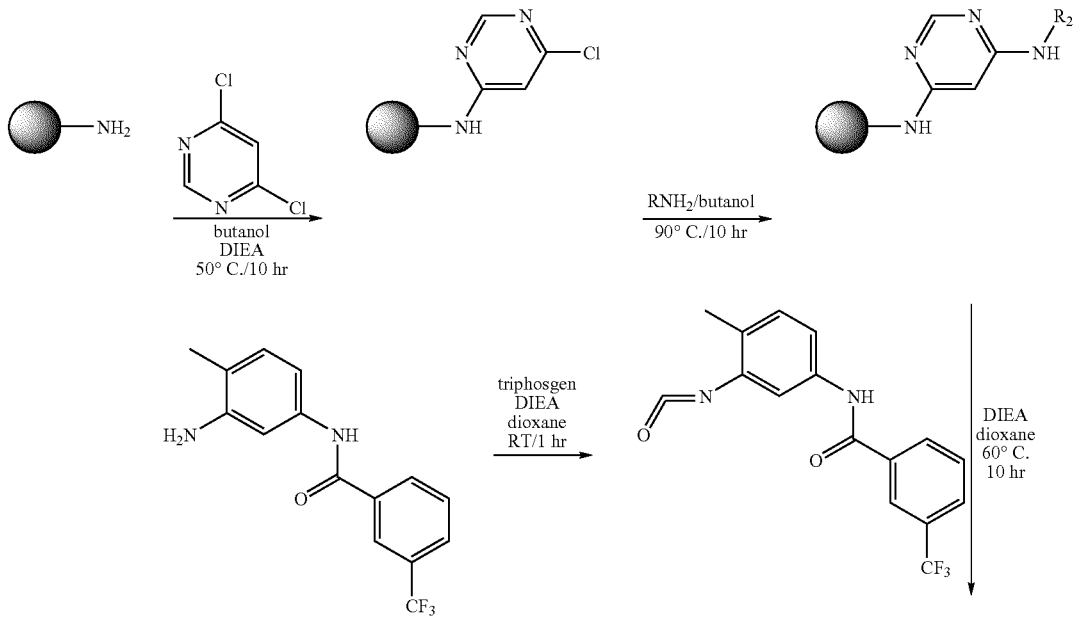

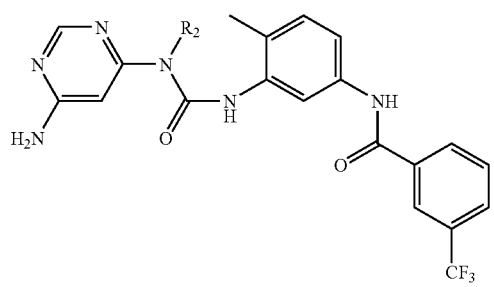 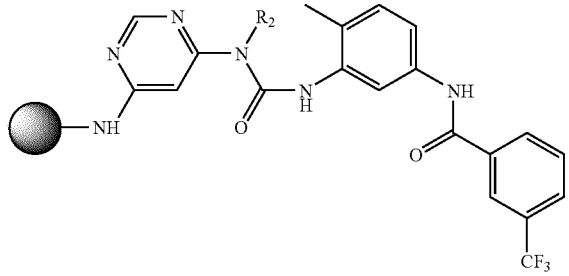

Example 214

N-{3-[3-(6-Amino-pyrimidin-4-yl)-3-(2-morpholin-4-yl-ethyl)-ureido]-4-methyl-phenyl}-3-trifluoromethyl-benzamide

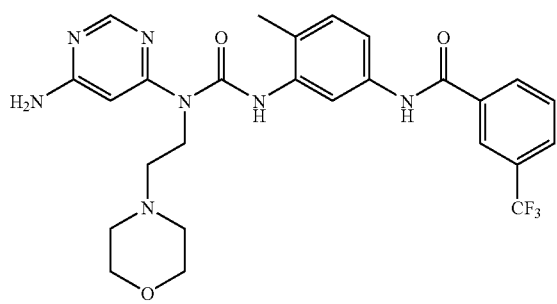 [SMILES: Cc1ccc(NC(=O)c2cccc(C(F)(F)F)c2)cc1NC(=O)N(CCN1CCOCC1)c1cc(N)ncn1]

Rink resin with free amino group (50 g, 53 mmol) is mixed with 4,6-dichloropyrimidine (23 g, 159 mmol) in 60 ml butanol and 28 ml DIEA. The reaction mixture was shaken on heating block at 50° C. for 10 hours. The resin was washed with DMF, methanol and methylene chloride. Then to 1 g of the resin is added 3 equivalent amine and 3 ml butanol, the reaction was shaken at 90° C. for 10 hours. The resin was washed with DMF, methanol and methylene chloride.

N-(3-Amino-4-methyl-phenyl)-3-trifluoromethyl-benzamide (880 mg, 3 mmol) was dissolved in 8 ml dioxane with 0.52 ml DIEA added. Then triphosgene (357 mg, 1.2 mmol) was added to this solution. The reaction was stirred at room temperature for 1 hour. This reaction mixture was then added to the above resin. The reaction was shaken at 60° C. for 10 hours. The resin was washed with DMF, methanol and methylene chloride. The resin was cleaved with TFA at room temperature for 1 hour. The crude product was purified by RP-HPLC.

Example 214 is prepared using 2-morpholin-4-yl-ethylamine as amine in the procedure above. The final product N-{3-[3-(6-Amino-pyrimidin-4-yl)-3-(2-morpholin-4-yl-ethyl)-ureido]-4-methyl-phenyl}-3-trifluoromethyl-benzamide was white solid, 63 mg; $^1$H NMR 600 MHz (DMSO) δ 12.95 (s, 1H), 10.46 (s, 1H), 8.41 (s, 1H), 8.31 (s, 1H), 8.28 (s, 1H), 8.27 (s, 1H), 7.95 (d, 1H, J=7.7 Hz), 7.77 (t, 1H, J=7.8 Hz), 7.54 (d, 1H, J=6.8 Hz), 7.20 (d, 2H, J=8.3 Hz), 7.03 (s, 2H), 6.99 (s, 1H), 6.17 (s, 1H), 3.98 (s, 2H), 3.59 (s, 4H), 3.35 (m, 2H), 2.50 (m, 4H), 2.30 (s, 3H); MS m/z 544.2 (M+1).

Example 215

N-(3-{3-(6-Amino-pyrimidin-4-yl)-3-[3-(2-oxo-pyrrolidin-1-yl)-propyl]-ureido}-4-methyl-phenyl)-3-trifluoromethyl-benzamide

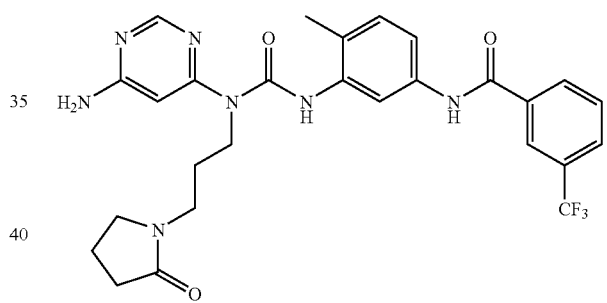

This compound was prepared using 1-(3-Amino-propyl)-pyrrolidin-2-one as amine in the procedure above. The final product N-(3-{3-(6-Amino-pyrimidin-4-yl)-3-[3-(2-oxo-pyrrolidin-1-yl)-propyl]-ureido}-4-methyl-phenyl)-3-trifluoromethyl-benzamide is white solid, 14 mg; $^1$H NMR 600 MHz (DMSO) δ 12.51 (s, 1H), 10.40 (s, 1H), 8.38 (s, 1H), 8.31 (s, 1H), 8.28 (s, 1H), 8.27 (s, 1H), 7.95 (d, 1H, J=7.7 Hz), 7.77 (t, 1H, J=7.8 Hz), 7.54 (d, 1H, J=6.8 Hz), 7.20 (d, 2H, J=8.3 Hz), 7.03 (s, 2H), 6.99 (s, 1H), 6.17 (s, 1H), 3.70 (m, 2H), 3.31 (t, 2H, J=7.2 Hz), 3.24 (t, 2H, J=7.2 Hz), 2.23 (s, 3H), 2.16 (t, 2H, J=8.4 Hz), 1.87 (m, 2H), 1.74 (m, 2H); MS m/z 556.2 (M+1).

Example 216

By repeating the procedures described in the above examples 208 to 215, using appropriate starting materials, the following compounds of Formula I, as identified in Table 1, are obtained.

TABLE 1

| Compound Number | Structure | Physical Data |
|---|---|---|
| 1 | 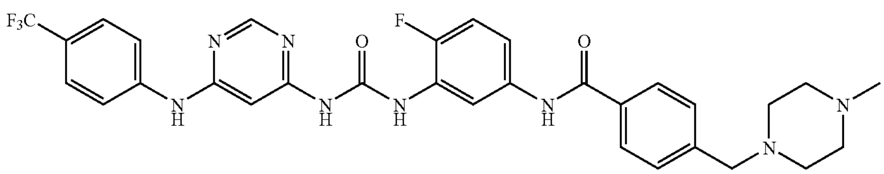 [SMILES: CN1CCN(Cc2ccc(C(=O)Nc3ccc(F)c(NC(=O)Nc4cc(Nc5ccc(C(F)(F)F)cc5)ncn4)c3)cc2)CC1] | $^1$H NMR (400 MHz, CD$_3$OH-d$_4$) δ 9.92 (d, J = 5.1 Hz, 1 H), 9.80 (s, 1 H), 9.20 (d, J = 8.1 Hz, 2 H), 8.93 (d, J = 8.5 Hz, 2 H), 8.85 (d, J = 8.6 Hz, 2 H), 8.79 (d, J = 5.0 Hz, 2 H), 8.76 (d, J = 8.0 Hz, 2 H), 8.75 (s, 1 H), 8.46 (t, J = 9.0 Hz, 1 H), 8.08 (s, 1 H), 4.92 (s, 2 H), 4.71 (s, 2 H), 3.66 (m, 6 H); ESIMS m/z 623.20 (M$^+$ + 1). |
| 2 | 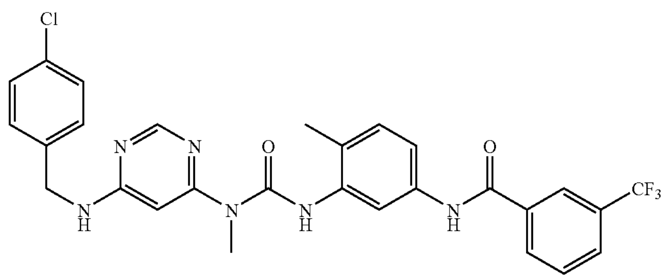 [SMILES: Cc1ccc(NC(=O)c2cccc(C(F)(F)F)c2)cc1NC(=O)N(C)c1cc(NCc2ccc(Cl)cc2)ncn1] | $^1$H NMR (600 MHz, DMSO-d$_6$) δ 12.82 (s, 1 H), 10.44 (s, 1 H), 8.40 (s, 1 H), 8.36 (s, 1 H), 8.31 (s, 1 H), 8.28 (d, J = 7.9 Hz, 1 H), 7.96 (d, J = 7.8 Hz, 1 H), 7.78 (t, 7.8 Hz, 1 H), 7.50 (d, J = 8.2 Hz, 1 H), 7.40 (d, J = 8.1 Hz, 2 H), 7.38 (d, J = 8.1 Hz, 2 H), 7.20 (d, J = 8.1 Hz, 1 H), 6.21 (s, 1 H), 4.57 (s, 2 H), 3.18 (s, 3 H), 2.39 (s, 3 H); ESIMS m/z 569.10 (M$^+$ + 1). |
| 3 | 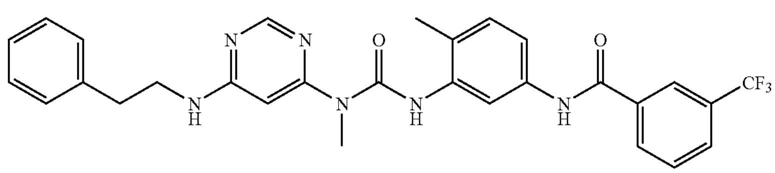 [SMILES: Cc1ccc(NC(=O)c2cccc(C(F)(F)F)c2)cc1NC(=O)N(C)c1cc(NCCc2ccccc2)ncn1] | $^1$H NMR (600 MHz, DMSO-d$_6$) δ 12.85 (s, 1 H), 10.44 (s, 1 H), 8.41 (s, 1 H), 8.34 (s, 1 H), 8.31 (s, 1 H), 8.28 (d, J = 7.4 Hz, 1 H), 7.96 (d, J = 7.7 Hz, 1 H), 7.78 (t, J = 7.9 Hz, 1 H), 7.62 (s, 1 H), 7.51 (d, J = 8.1 Hz, 1 H), 7.33 (s, 1 H), 7.31 (d, J = 7.1 Hz, 1 H), 7.28 (s, 1 H), 7.27 (s, 1 H), 7.22 (d, J = 9.2 Hz, 1 H), 7.20 (d, J = 8.6 Hz, 1 H), 6.15 (s, 1 H), 3.30 (m, 2 H), 3.18 (s, 3 H), 2.86 (t, J = 6.7 Hz, 2 H), 2.24 (s, 3 H); ESIMS m/z 549.20 (M$^+$ + 1). |

TABLE 1-continued

| Compound Number | Structure | Physical Data |
|---|---|---|
| 4 | 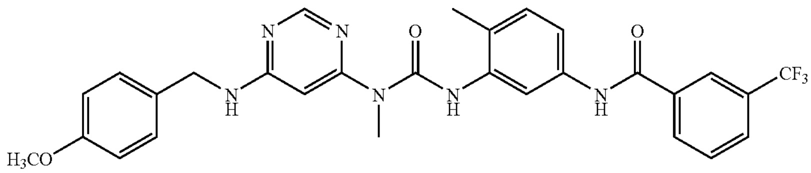 [SMILES: COc1ccc(CNc2cc(N(C)C(=O)Nc3cc(NC(=O)c4cccc(C(F)(F)F)c4)ccc3C)ncn2)cc1] | $^1$H NMR (600 MHz, DMSO-d$_6$) δ 12.83 (s, 1 H), 10.44 (s, 1 H), 8.40 (s, 1 H), 8.36 (s, 1 H), 8.31 (s, 1 H), 8.27 (d, J = 7.9 Hz, 1 H), 7.99 (s, 1 H), 7.96 (d, J = 7.5 Hz, 1 H), 7.78 (t, J = 7.7 Hz, 1 H), 7.50 (d, J = 8.2 Hz, 1 H), 7.28 (s, 1 H), 7.27 (s, 1 H), 7.20 (d, J = 8.4 Hz, 1 H), 6.91 (s, 1 H), 6.90 (s, 1 H), 6.15 (s, 1 H), 4.50 (s, 2 H), 3.73 (s, 3 H), 3.29 (s, 3 H), 2.20 (3 H); ESIMS m/z 565.20 (M$^+$ + 1). |
| 5 | 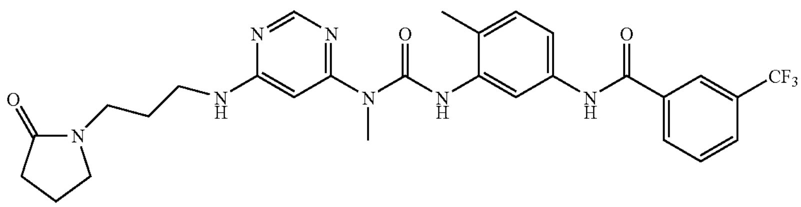 [SMILES: Cc1ccc(NC(=O)c2cccc(C(F)(F)F)c2)cc1NC(=O)N(C)c1cc(NCCCN2CCCC2=O)ncn1] | $^1$H NMR (600 MHz, DMSO-d$_6$) δ 12.86 (s, 1 H), 10.44 (s, 1 H), 8.41 (s, 1 H), 8.35 (br, 1 H), 8.31 (s, 1 H), 8.28 (d, J = 7.8 Hz, 1 H), 7.96 (d, J = 7.9 Hz, 1 H), 7.78 (t, J = 7.8 Hz, 1 H), 7.54 (s, 1 H), 7.51 (d, J = 8.2 Hz, 1 H), 7.20 (d, J = 8.3 Hz, 2 H), 6.12 (s, 1 H), 3.34 (s, 3 H), 3.31 (t, J = 7.0 Hz, 2 H), 3.25 (t, J = 7.0 Hz, 4 H), 2.31 (s, 3 H), 2.22 (t, J = 8.1 Hz, 2 H), 1.93 (dt, J = 7.6, 14.1 Hz, 2 H), 1.73 (m, 2 H); ESIMS m/z 570.20 (M$^+$ + 1). |
| 6 | 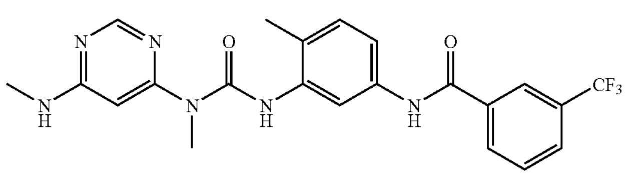 | ESIMS m/z 559.10 (M$^+$ + 1). |
| 7 | 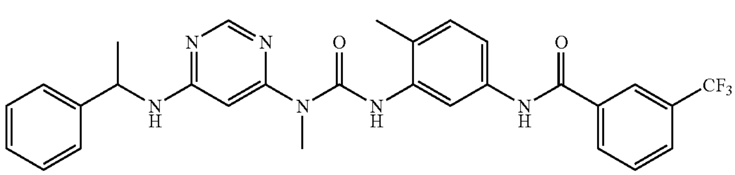 [SMILES: Cc1ccc(NC(=O)c2cccc(C(F)(F)F)c2)cc1NC(=O)N(C)c1cc(NC(C)c2ccccc2)ncn1] | ESIMS m/z 549.20 (M$^+$ + 1). |

TABLE 1-continued

| Compound Number | Structure | Physical Data |
|---|---|---|
| 8 | 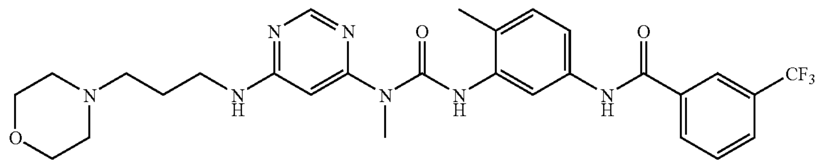 [SMILES: Cc1ccc(NC(=O)c2cccc(C(F)(F)F)c2)cc1NC(=O)N(C)c1cc(NCCCN2CCOCC2)ncn1] | ESIMS m/z 572.30 (M+ + 1). |
| 9 | 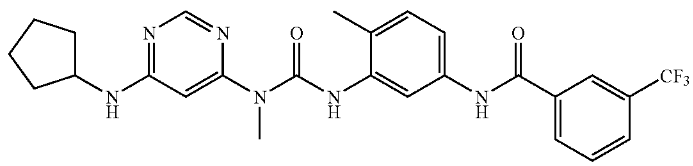 [SMILES: Cc1ccc(NC(=O)c2cccc(C(F)(F)F)c2)cc1NC(=O)N(C)c1cc(NC2CCCC2)ncn1] | ESIMS m/z 513.20 (M+ + 1). |
| 10 | 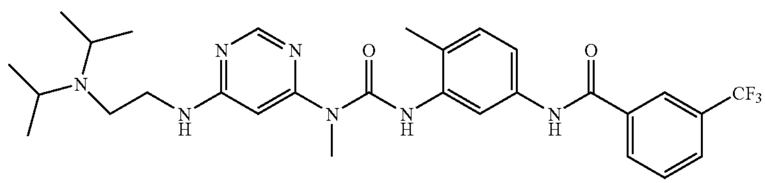 [SMILES: Cc1ccc(NC(=O)c2cccc(C(F)(F)F)c2)cc1NC(=O)N(C)c1cc(NCCN(C(C)C)C(C)C)ncn1] | ESIMS m/z 572.30 (M+ + 1). |
| 11 | 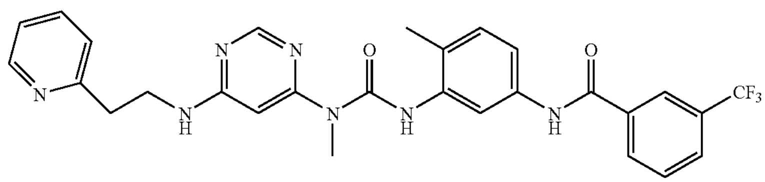 [SMILES: Cc1ccc(NC(=O)c2cccc(C(F)(F)F)c2)cc1NC(=O)N(C)c1cc(NCCc2ccccn2)ncn1] | ESIMS m/z 550.20 (M+ + 1). |
| 12 | 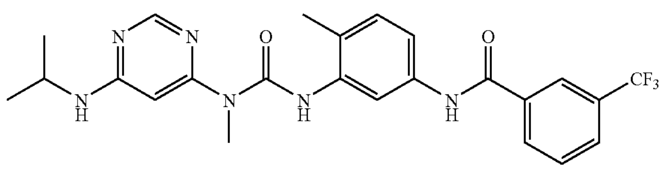 [SMILES: Cc1ccc(NC(=O)c2cccc(C(F)(F)F)c2)cc1NC(=O)N(C)c1cc(NC(C)C)ncn1] | ESIMS m/z 487.20 (M+ + 1). |
| 13 | 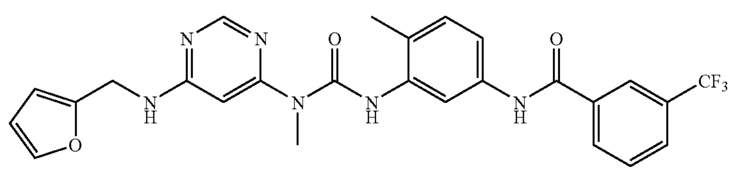 [SMILES: Cc1ccc(NC(=O)c2cccc(C(F)(F)F)c2)cc1NC(=O)N(C)c1cc(NCc2ccco2)ncn1] | ESIMS m/z 525.20 (M+ + 1). |
| 14 | 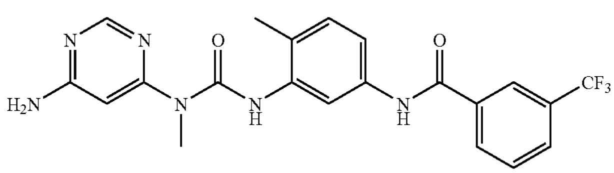 [SMILES: Cc1ccc(NC(=O)c2cccc(C(F)(F)F)c2)cc1NC(=O)N(C)c1cc(N)ncn1] | $^1$H NMR (400 MHz, DMSO-d$_6$) δ 10.47 (s, 1 H), 8.40 (d, J = 2.1 Hz, 1 H), 8.33 (s, 1 H), 8.31-8.25 (m, 2 H), ), 7.96 (t, J = 7.8 Hz, 1 H), 7.78 (t, J = 7.8 Hz, 1 H), 7.54 (d, J = 6.0, 1 H), 7.52 (d, J = 8.2 Hz, 1 H), 7.21 (d, J = 8.3 Hz, 2 H) 6.13 (s, 1 H), 3.31 (s, 3 H), 2.31 (s, 3 H), 2.17 (s, 2 H); ESIMS m/z 445.10 (M+ + 1). |

TABLE 1-continued

| Compound Number | Structure | Physical Data |
|---|---|---|
| 15 | 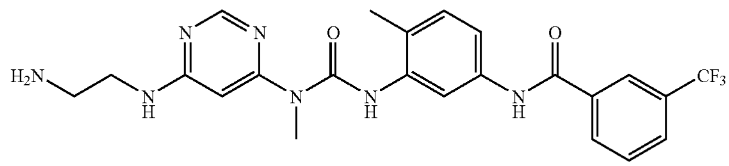 [SMILES: Cc1ccc(NC(=O)c2cccc(C(F)(F)F)c2)cc1NC(=O)N(C)c1cc(NCCN)ncn1] | ESIMS m/z 488.10 (M⁺ + 1). |
| 16 | 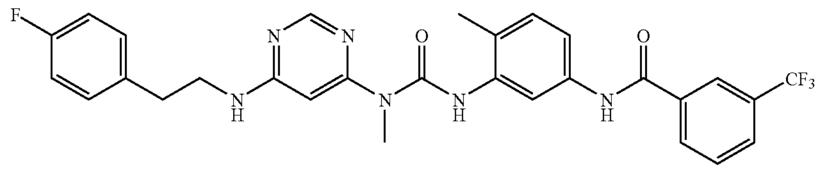 [SMILES: Cc1ccc(NC(=O)c2cccc(C(F)(F)F)c2)cc1NC(=O)N(C)c1cc(NCCc2ccc(F)cc2)ncn1] | ESIMS m/z 567.10 (M⁺ + 1). |
| 17 | 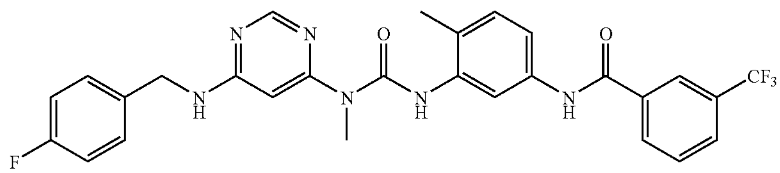 [SMILES: Cc1ccc(NC(=O)c2cccc(C(F)(F)F)c2)cc1NC(=O)N(C)c1cc(NCc2ccc(F)cc2)ncn1] | ESIMS m/z 553.10 (M⁺ + 1). |
| 18 | 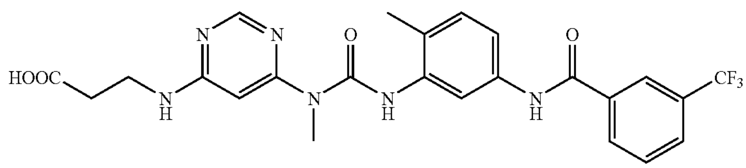 [SMILES: Cc1ccc(NC(=O)c2cccc(C(F)(F)F)c2)cc1NC(=O)N(C)c1cc(NCCC(=O)O)ncn1] | ESIMS m/z 517.10 (M⁺ + 1). |
| 19 | 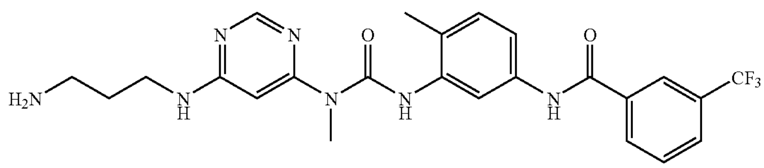 [SMILES: Cc1ccc(NC(=O)c2cccc(C(F)(F)F)c2)cc1NC(=O)N(C)c1cc(NCCCN)ncn1] | ESIMS m/z 502.20 (M⁺ + 1). |
| 20 | 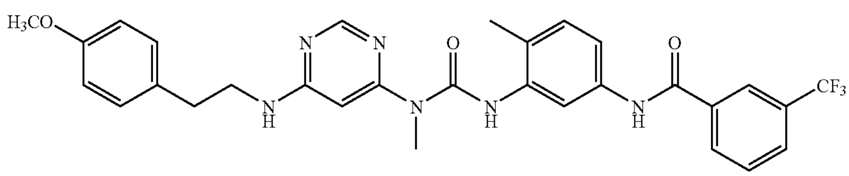 [SMILES: COc1ccc(CCNc2cc(N(C)C(=O)Nc3cc(NC(=O)c4cccc(C(F)(F)F)c4)ccc3C)ncn2)cc1] | ESIMS m/z 579.20 (M⁺ + 1). |
| 21 | 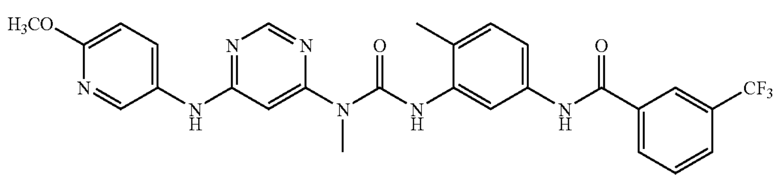 [SMILES: COc1ccc(Nc2cc(N(C)C(=O)Nc3cc(NC(=O)c4cccc(C(F)(F)F)c4)ccc3C)ncn2)cn1] | ESIMS m/z 552.10 (M⁺ + 1). |
| 22 | 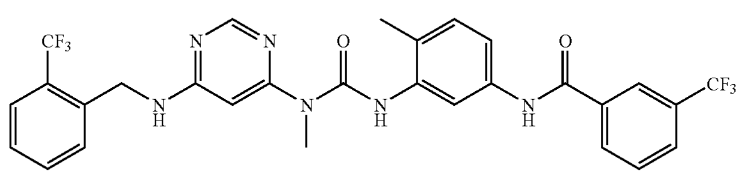 [SMILES: Cc1ccc(NC(=O)c2cccc(C(F)(F)F)c2)cc1NC(=O)N(C)c1cc(NCc2ccccc2C(F)(F)F)ncn1] | ESIMS m/z 603.10 (M⁺ + 1). |

TABLE 1-continued

| Compound Number | Structure | Physical Data |
|---|---|---|
| 23 | 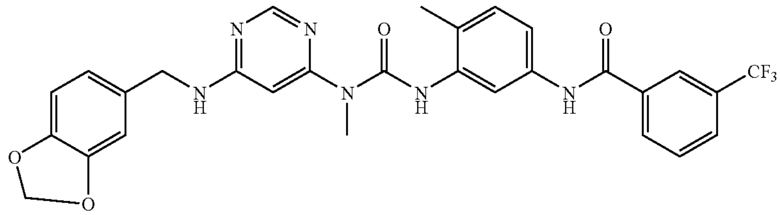 [SMILES: Cc1ccc(NC(=O)c2cccc(C(F)(F)F)c2)cc1NC(=O)N(C)c1cc(NCc2ccc3c(c2)OCO3)ncn1] | ESIMS m/z 579.15 (M$^+$ + 1). |
| 24 | 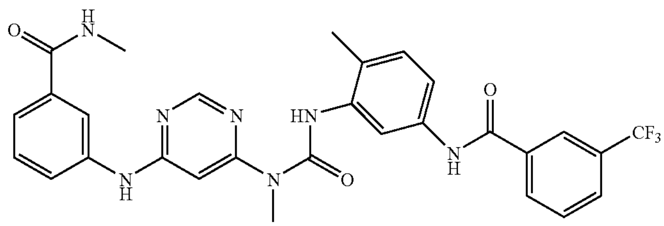 [SMILES: CNC(=O)c1cccc(Nc2cc(N(C)C(=O)Nc3cc(NC(=O)c4cccc(C(F)(F)F)c4)ccc3C)ncn2)c1] | ESIMS m/z 578.30 (M$^+$ + 1). |
| 25 | 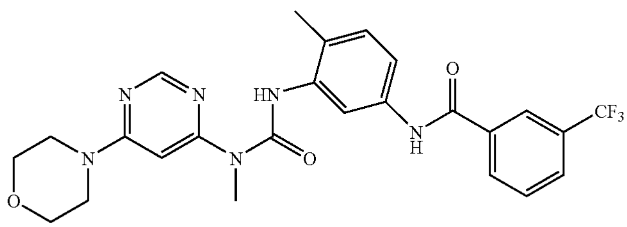 [SMILES: Cc1ccc(NC(=O)c2cccc(C(F)(F)F)c2)cc1NC(=O)N(C)c1cc(N2CCOCC2)ncn1] | ESIMS m/z 515.20 (M$^+$ + 1). |
| 26 | 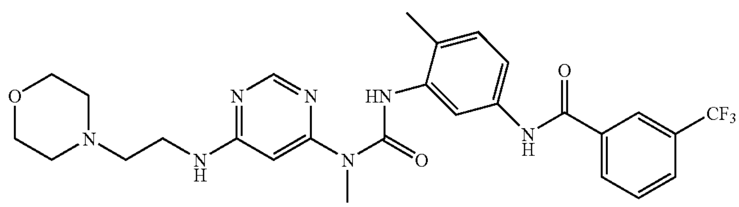 [SMILES: Cc1ccc(NC(=O)c2cccc(C(F)(F)F)c2)cc1NC(=O)N(C)c1cc(NCCN2CCOCC2)ncn1] | ESIMS m/z 558.30 (M$^+$ + 1). |
| 27 | 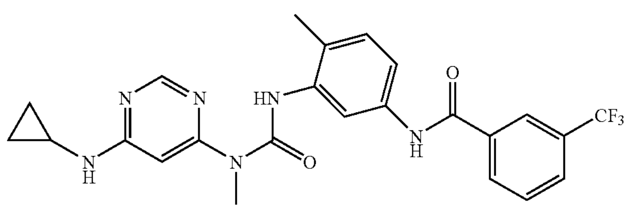 [SMILES: Cc1ccc(NC(=O)c2cccc(C(F)(F)F)c2)cc1NC(=O)N(C)c1cc(NC2CC2)ncn1] | ESIMS m/z 485.20 (M$^+$ + 1). |
| 28 | 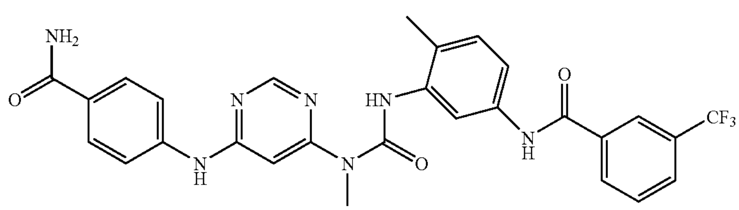 [SMILES: Cc1ccc(NC(=O)c2cccc(C(F)(F)F)c2)cc1NC(=O)N(C)c1cc(Nc2ccc(C(N)=O)cc2)ncn1] | ESIMS m/z 564.20 (M$^+$ + 1). |
| 29 | 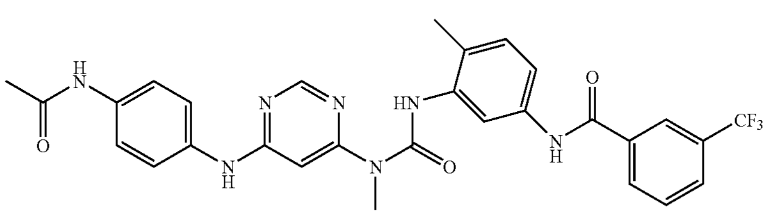 [SMILES: CC(=O)Nc1ccc(Nc2cc(N(C)C(=O)Nc3cc(NC(=O)c4cccc(C(F)(F)F)c4)ccc3C)ncn2)cc1] | ESIMS m/z 578.20 (M$^+$ + 1). |

TABLE 1-continued

| Compound Number | Structure | Physical Data |
|---|---|---|
| 30 | 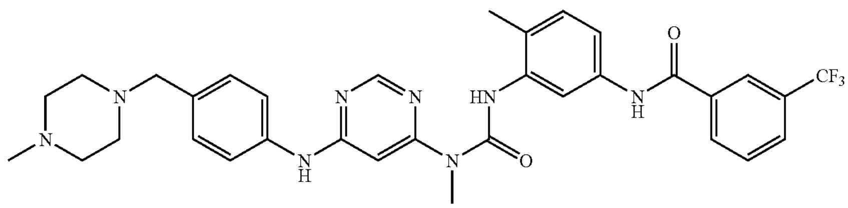 [SMILES: Cc1ccc(NC(=O)c2cccc(C(F)(F)F)c2)cc1NC(=O)N(C)c1cc(Nc2ccc(CN3CCN(C)CC3)cc2)ncn1] | ESIMS m/z 633.30 ($M^+ + 1$). |
| 31 | 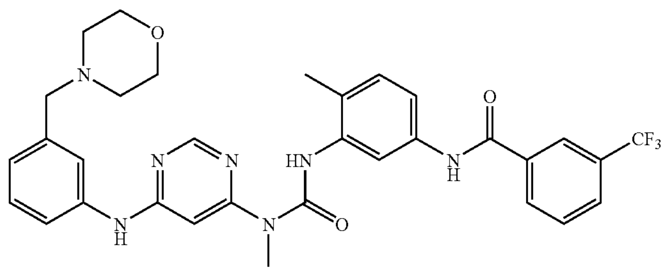 [SMILES: Cc1ccc(NC(=O)c2cccc(C(F)(F)F)c2)cc1NC(=O)N(C)c1cc(Nc2cccc(CN3CCOCC3)c2)ncn1] | ESIMS m/z 620.30 ($M^+ + 1$). |
| 32 | 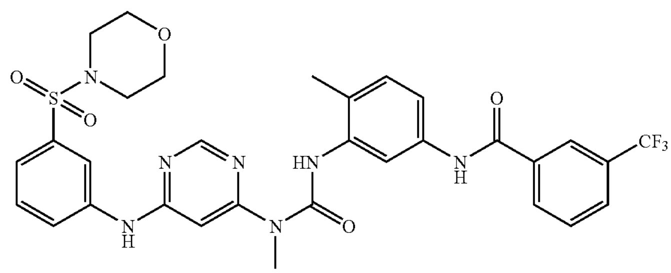 [SMILES: Cc1ccc(NC(=O)c2cccc(C(F)(F)F)c2)cc1NC(=O)N(C)c1cc(Nc2cccc(S(=O)(=O)N3CCOCC3)c2)ncn1] | ESIMS m/z 670.30 ($M^+ + 1$). |
| 33 | 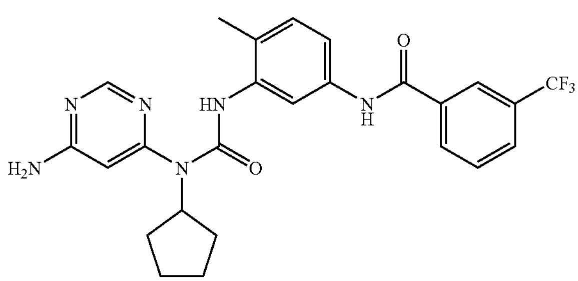 [SMILES: Cc1ccc(NC(=O)c2cccc(C(F)(F)F)c2)cc1NC(=O)N(c1cc(N)ncn1)C1CCCC1] | ESIMS m/z 499.2 ($M^+ + 1$). |
| 34 | 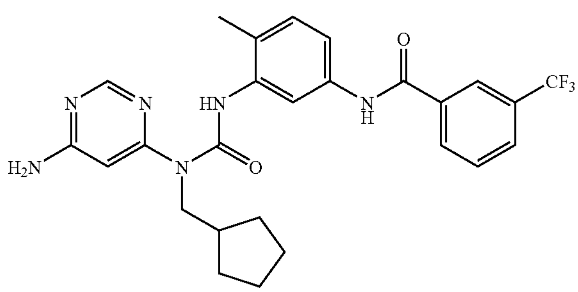 [SMILES: Cc1ccc(NC(=O)c2cccc(C(F)(F)F)c2)cc1NC(=O)N(CC1CCCC1)c1cc(N)ncn1] | ESIMS m/z 515.2 ($M^+ + 1$). |

TABLE 1-continued
| Compound Number | Structure | Physical Data |
|---|---|---|
| 35 | 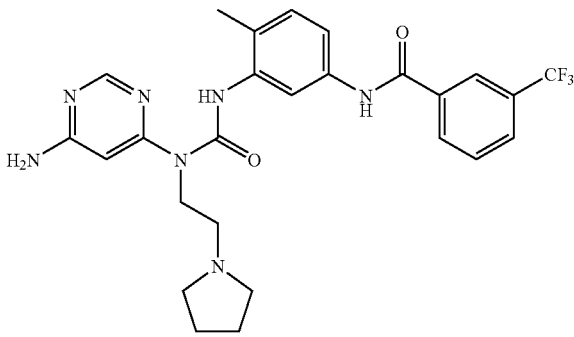 [SMILES: Cc1ccc(NC(=O)c2cccc(C(F)(F)F)c2)cc1NC(=O)N(CCN1CCCC1)c1cc(N)ncn1] | ESIMS m/z 528.3 (M+ + 1). |
| 36 | 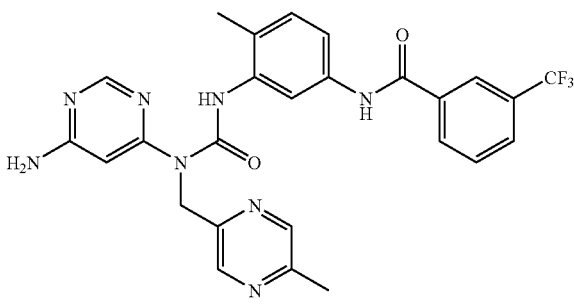 [SMILES: Cc1cnc(CN(C(=O)Nc2cc(NC(=O)c3cccc(C(F)(F)F)c3)ccc2C)c2cc(N)ncn2)cn1] | ESIMS m/z 537.2 (M+ + 1). |
| 37 | 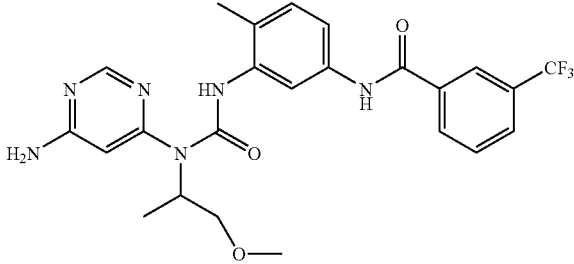 [SMILES: COCC(C)N(C(=O)Nc1cc(NC(=O)c2cccc(C(F)(F)F)c2)ccc1C)c1cc(N)ncn1] | ESIMS m/z 503.2 (M+ + 1). |
| 38 | 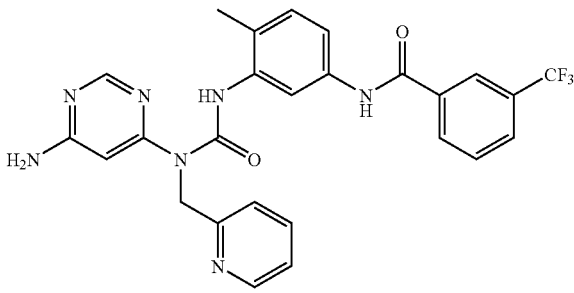 [SMILES: Cc1ccc(NC(=O)c2cccc(C(F)(F)F)c2)cc1NC(=O)N(Cc1ccccn1)c1cc(N)ncn1] | ESIMS m/z 522.2 (M+ + 1). |
| 39 | 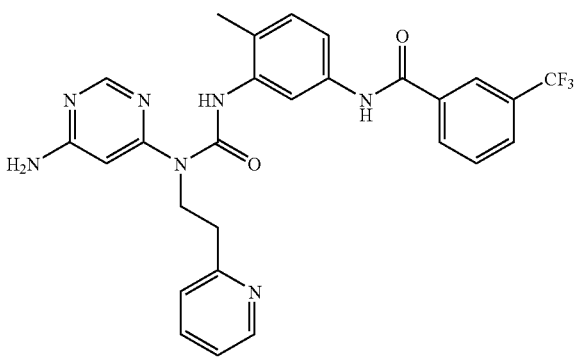 [SMILES: Cc1ccc(NC(=O)c2cccc(C(F)(F)F)c2)cc1NC(=O)N(CCc1ccccn1)c1cc(N)ncn1] | ESIMS m/z 536.2 (M+ + 1). |

TABLE 1-continued

| Compound Number | Structure | Physical Data |
|---|---|---|
| 40 | 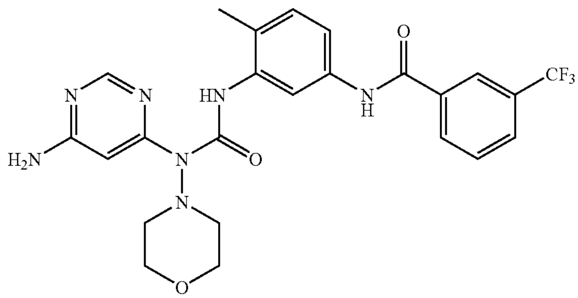 [SMILES: Cc1ccc(NC(=O)c2cccc(C(F)(F)F)c2)cc1NC(=O)N(c1cc(N)ncn1)N1CCOCC1] | ESIMS m/z 516.2 (M$^+$ + 1). |
| 41 | 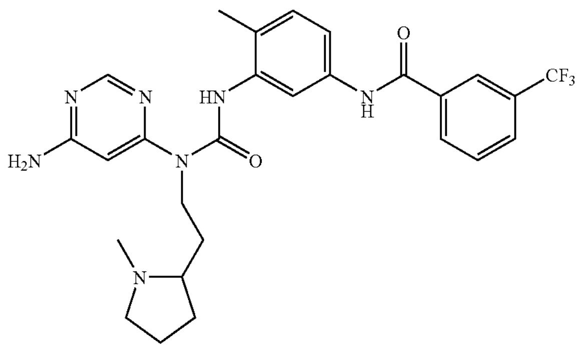 [SMILES: Cc1ccc(NC(=O)c2cccc(C(F)(F)F)c2)cc1NC(=O)N(CCC1CCCN1C)c1cc(N)ncn1] | ESIMS m/z 542.30 (M$^+$ + 1). |
| 42 | 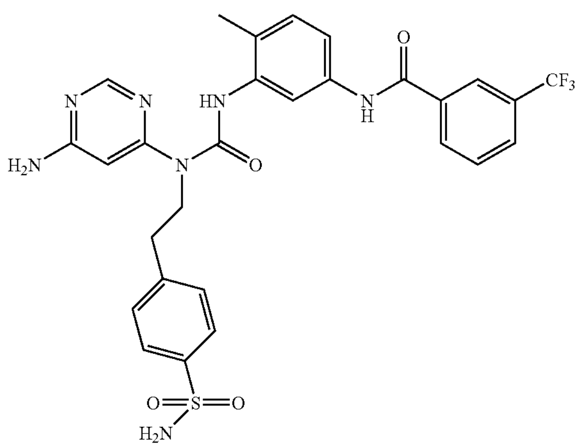 [SMILES: Cc1ccc(NC(=O)c2cccc(C(F)(F)F)c2)cc1NC(=O)N(CCc1ccc(S(N)(=O)=O)cc1)c1cc(N)ncn1] | ESIMS m/z 614.30 (M$^+$ + 1). |
| 43 | 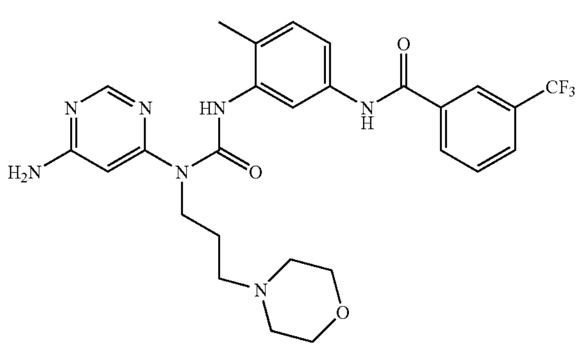 [SMILES: Cc1ccc(NC(=O)c2cccc(C(F)(F)F)c2)cc1NC(=O)N(CCCN1CCOCC1)c1cc(N)ncn1] | ESIMS m/z 558.30 (M$^+$ + 1). |

TABLE 1-continued

| Compound Number | Structure | Physical Data |
|---|---|---|
| 44 | 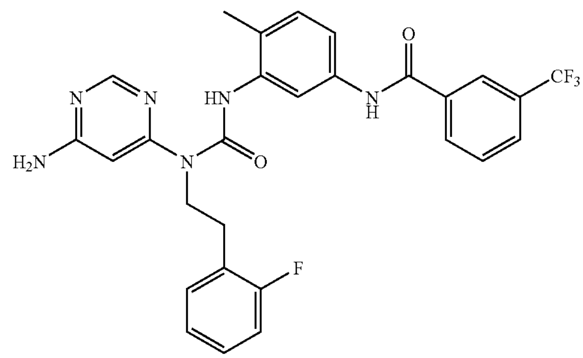 [SMILES: Cc1ccc(NC(=O)c2cccc(C(F)(F)F)c2)cc1NC(=O)N(CCc1ccccc1F)c1cc(N)ncn1] | ESIMS m/z 553.30 (M$^+$ + 1). |
| 45 | 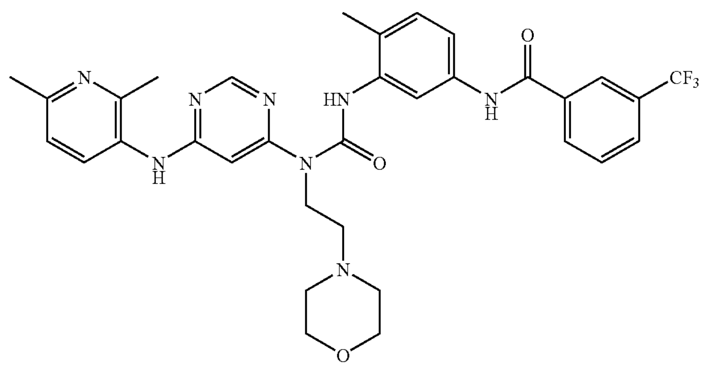 [SMILES: Cc1ccc(Nc2cc(N(CCN3CCOCC3)C(=O)Nc3cc(NC(=O)c4cccc(C(F)(F)F)c4)ccc3C)ncn2)c(C)n1] | ESIMS m/z 649.30 (M$^+$ + 1). |
| 46 | 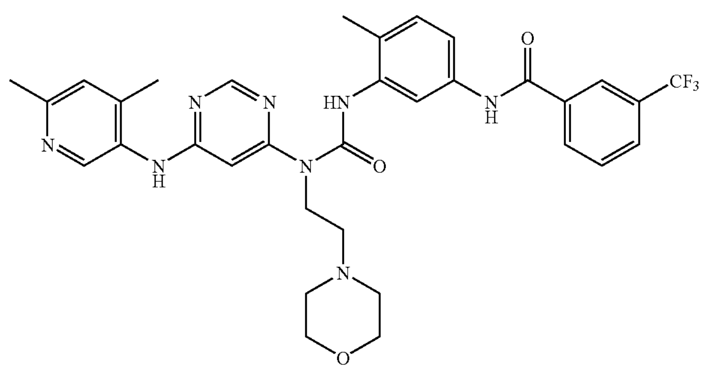 [SMILES: Cc1cc(C)c(Nc2cc(N(CCN3CCOCC3)C(=O)Nc3cc(NC(=O)c4cccc(C(F)(F)F)c4)ccc3C)ncn2)cn1] | ESIMS m/z 649.30 (M$^+$ + 1). |
| 47 | 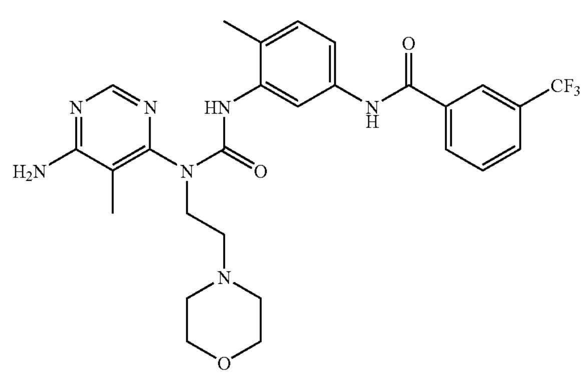 [SMILES: Cc1ccc(NC(=O)c2cccc(C(F)(F)F)c2)cc1NC(=O)N(CCN1CCOCC1)c1ncnc(N)c1C] | ESIMS m/z 558.30 (M$^+$ + 1). |

TABLE 1-continued
| Compound Number | Structure | Physical Data |
|---|---|---|
| 48 | 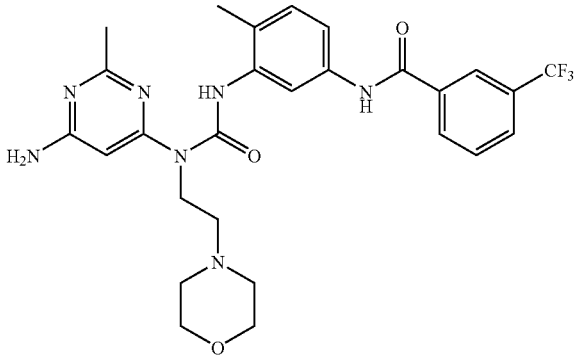 [SMILES: Cc1nc(N)cc(N(CCN2CCOCC2)C(=O)Nc2cc(NC(=O)c3cccc(C(F)(F)F)c3)ccc2C)n1] | ESIMS m/z 558.30 (M$^+$ + 1). |
| 49 | 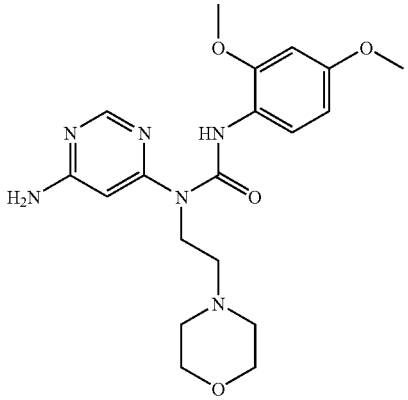 [SMILES: COc1ccc(NC(=O)N(CCN2CCOCC2)c2cc(N)ncn2)c(OC)c1] | ESIMS m/z 403.30 (M$^+$ + 1). |
| 50 | 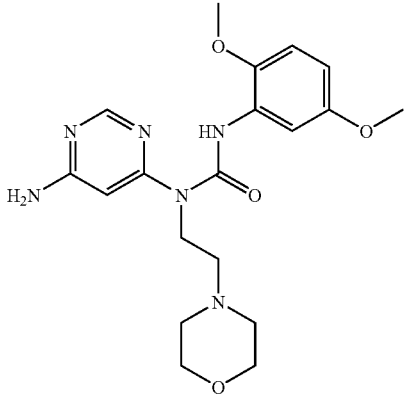 [SMILES: COc1ccc(OC)c(NC(=O)N(CCN2CCOCC2)c2cc(N)ncn2)c1] | ESIMS m/z 403.30 (M$^+$ + 1). |

TABLE 1-continued
| Compound Number | Structure | Physical Data |
|---|---|---|
| 51 | 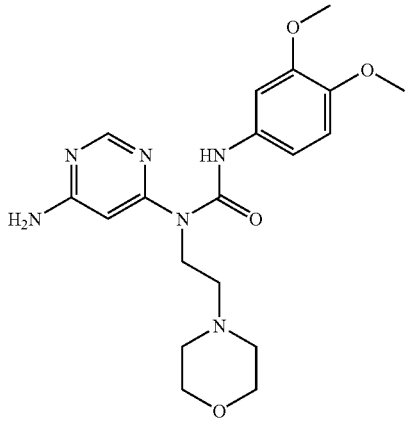 [SMILES: COc1ccc(NC(=O)N(CCN2CCOCC2)c2cc(N)ncn2)cc1OC] | ESIMS m/z 403.30 (M+ + 1). |
| 52 | 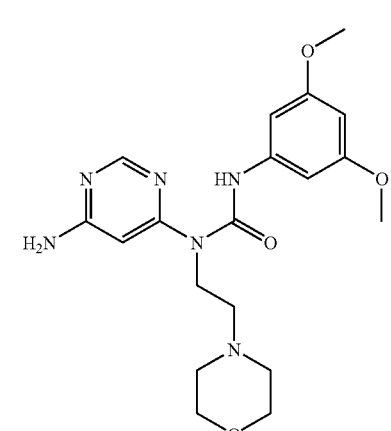 | ESIMS m/z 403.30 (M+ + 1). |
| 53 | 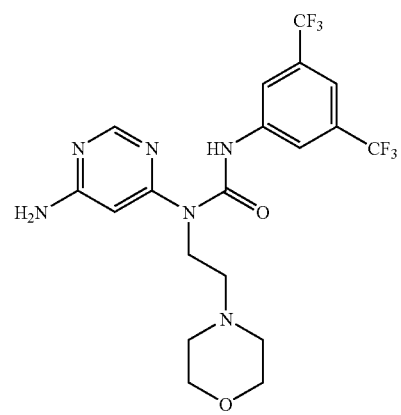 [SMILES: Nc1cc(N(CCN2CCOCC2)C(=O)Nc2cc(C(F)(F)F)cc(C(F)(F)F)c2)ncn1] | ESIMS m/z 495.3 (M+ + 1). |

TABLE 1-continued

| Compound Number | Structure | Physical Data |
|---|---|---|
| 54 | (pyrimidine with H₂N and N-substituted thiourea bearing 3,5-bis(trifluoromethyl)phenyl group and morpholinoethyl chain) | ESIMS m/z 479.30 (M$^+$ + 1). |

1. Assays

Compounds of Examples 208 to 216 are assayed to measure their capacity to selectively inhibit cell proliferation of 32D cells expressing BCR-Abl (32D-p210) compared with parental 32D cells. Compounds selectively inhibiting the proliferation of these BCR-Abl transformed cells are tested for anti-proliferative activity on Ba/F3 cells expressing either wild type or the mutant forms of Bcr-abl. In addition, compounds are assayed to measure their capacity to inhibit FGFR35 (in an enzyme and cellular assay), FLT3, PDGFRβ, trkB, c-SRC, BMX, SGK, Tie2, Lck, JNK2α2, MKK4, c-RAF, MKK6, SAPK2α and SAPK2β kinases.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 μg/mL, streptomycin 50 μg/mL and L-glutamine 200 mM. Untransformed 32D cells are similarly maintained with the addition of 15% of WEHI conditioned medium as a source of IL3.

50 μl of a 32D or 32D-p210 cells suspension are plated in Greiner 384 well microplates (black) at a density of 5000 cells per well. 50 nl of test compound (1 mM in DMSO stock solution) is added to each well (STI571 is included as a positive control). The cells are incubated for 72 hours at 37° C., 5% CO$_2$. 10 μl of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular BCR-Abl Dependent Proliferation 32D-p210 cells are plated into 96 well TC plates at a density of 15,000 cells per well. 50 μL of two fold serial dilutions of the test compound ($C_{max}$ is 40 μM) are added to each well (STI571 is included as a positive control). After incubating the cells for 48 hours at 37° C., 5% CO$_2$, 15 μL of MTT (Promega) is added to each well and the cells are incubated for an additional 5 hours. The optical density at 570 nm is quantified spectrophotometrically and IC$_{50}$ values, the concentration of compound required for 50% inhibition, determined from a dose response curve.

Effect on Cell Cycle Distribution 32D and 32D-p210 cells are plated into 6 well TC plates at 2.5×10$^6$ cells per well in 5 ml of medium and test compound at 1 or 10 μM is added (STI571 is included as a control). The cells are then incubated for 24 or 48 hours at 37° C., 5% CO$_2$. 2 ml of cell suspension is washed with PBS, fixed in 70% EtOH for 1 hour and treated with PBS/EDTA/RNase A for 30 minutes. Propidium iodide (Cf=10 μg/ml) is added and the fluorescence intensity is quantified by flow cytometry on the FACScalibur system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at 2×10$^5$ cells per well in 50 μL of medium. 50 μL of two fold serial dilutions of test compounds ($C_{max}$ is 10 μM) are added to each well (STI571 is included as a positive control). The cells are incubated for 90 minutes at 37° C., 5% CO$_2$. The cells are then treated for 1 hour on ice with 150 μL of lysis buffer (50 mM Tris-HCl, pH 7.4, 150 mM NaCl, 5 mM EDTA, 1 mM EGTA and 1% NP-40) containing protease and phosphatase inhibitors. 50 μL of cell lysate is added to 96 well optiplates previously coated with anti-abl specific antibody and blocked. The plates are incubated for 4 hours at 4° C. After washing with TBS-Tween 20 buffer, 50 μL of alkaline-phosphatase conjugated anti-phosphotyrosine antibody is added and the plate is further incubated overnight at 4° C. After washing with TBS-Tween 20 buffer, 90 μL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of Bcr-abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant-BCR-Abl expressing cells and on the non transformed cells were tested at 10, 3.3, 1.1 and 0.37 µM as described above (in media lacking IL3). The $IC_{50}$ values of the compounds lacking toxicity on the untransformed cells were determined from the dose response curves obtained as describe above.

FGFR35 (Enzymatic Assay)

Kinase activity assay with purified FGFR35 (Upstate) is carried out in a final volume of 10 µL containing 0.25 µg/mL of enzyme in kinase buffer (30 mM Tris-HCl pH7.5, 15 mM $MgCl_2$, 4.5 mM $MnCl_2$, 15 µM $Na_3VO_4$ and 50 µg/mL BSA), and substrates (5 µg/mL biotin-poly-EY(Glu, Tyr) (CIS-US, Inc.) and 3 µM ATP). Two solutions are made: the first solution of 5 µl contains the FGFR35 enzyme in kinase buffer was first dispensed into 384—format ProxiPlate® (Perkin-Elmer) followed by adding 50 nL of compounds dissolved in DMSO, then 5 µl of second solution contains the substrate (poly-EY) and ATP in kinase buffer was added to each wells. The reactions are incubated at room temperature for one hour, stopped by adding 10 µL of HTRF detection mixture, which contains 30 mM Tris-HCl pH7.5, 0.5 M KF, 50 mM ETDA, 0.2 mg/mL BSA, 15 µg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 µM to 0.28 nM). In this assay, compounds of the invention have an $IC_{50}$ in the range of 10 nM to 2 µM.

FGFR35 (Cellular Assay)

Compounds of the invention are tested for their ability to inhibit transformed Ba/F3-TEL-FGFR35 cells proliferation, which is depended on FGFR35 cellular kinase activity. Ba/F3-TEL-FGFR35 are cultured up to 800,000 cells/mL in suspension, with RPMI 1640 supplemented with 10% fetal bovine serum as the culture medium. Cells are dispensed into 384-well format plate at 5000 cell/well in 50 µL culture medium. Compounds of the invention are dissolved and diluted in dimethylsulfoxide (DMSO). Twelve points 1:3 serial dilutions are made into DMSO to create concentrations gradient ranging typically from 10 mM to 0.05 µM. Cells are added with 50 nL of diluted compounds and incubated for 48 hours in cell culture incubator. AlamarBlue® (TREK Diagnostic Systems), which can be used to monitor the reducing environment created by proliferating cells, are added to cells at final concentration of 10%. After additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

Upstate KinaseProfiler™—Radio-Enzymatic Filter Binding Assay

Compounds of the invention are assessed for their ability to inhibit individual members of a panel of kinases (a partial, non-limiting list of kinases includes: Abl, BCR-Abl, BMX, FGFR35, Lck, JNK1, JNK2, CSK, RAF, MKK6 and P38). The compounds are tested in duplicates at a final concentration of 10 µM following this generic protocol. Note that the kinase buffer composition and the substrates vary for the different kinases included in the "Upstate KinaseProfiler™" panel. The compounds are tested in duplicates at a final concentration of 10 µM following this generic protocol. Note that the kinase buffer composition and the substrates vary for the different kinases included in the "Upstate KinaseProfiler™" panel. Kinase buffer (2.5 µL, 10x—containing $MnCl_2$ when required), active kinase (0.001-0.01 Units; 2.5 µL), specific or Poly(Glu4-Tyr) peptide (5-500 µM or 0.01 mg/ml) in kinase buffer and kinase buffer (50 µM; 5 µL) are mixed in an eppendorf on ice. A Mg/ATP mix (10 µL; 67.5 (or 33.75) mM $MgCl_2$, 450 (or 225) µM ATP and 1 µCi/µl [$\gamma$-$^{32}$P]-ATP (3000 Ci/mmol)) is added and the reaction is incubated at about 30° C. for about 10 minutes. The reaction mixture is spotted (20 µL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Compounds of Formula I, in free form or in pharmaceutically acceptable salt form, exhibit valuable pharmacological properties, for example, as indicated by the in vitro tests described in this application. For example, compounds of Formula I preferably show an $IC_{50}$ in the range of $1\times10^{10}$ to $1\times10^{-5}$ M, preferably less than 50 nM for wild type BCR-Abl and G250E, E255V, T315I, F317L and M35IT BCR-Abl mutants. Compounds of Formula I** preferably, at a concentration of 10 mM, preferably show a percentage inhibition of greater than 50%, preferably greater than about 70%, against Abl, Bcr-abl, c-RAF, c-SRC, JNK2α2, lck, MKK6, PDGFRα, SAPK2α, SAPK2β, Tie2 and TrkB kinases. For example: N-(3-{3-[6-(3-Acetylamino-phenylamino)-pyrimidin-4-yl]-3-methyl-ureido}-4-methyl-phenyl)-3-trifluoromethyl-benzamide (Example 4) has an $IC_{50}$ of <0.5 nM, 38 nM, 44 nM, 41 nM, <0.5 nM and <0.5 nM for wild type, G250E, E255V, T315J, F317L and M351T Bcr-abl, respectively;

b). N-{3-[3-(6-Amino-pyrimidin-4-yl)-3-(2-morpholin-4-yl-ethyl)-ureido]-4-methyl-phenyl}-3-trifluoromethyl-benzamide (Example 214) has an $IC_{50}$ of 65 nM and 49 nM for the FGFR35 enzyme and cellular assays, respectively, and 14.9 nM and 0.4 nM for Bcr-abl wild type and PDGFRβ, respectively;

c). N-(3-{3-(6-Amino-pyrimidin-4-yl)-3-[3-(2-oxo-pyrrolidin-1-yl)-propyl]-ureido}-4-methyl-phenyl)-3-trifluoromethyl-benzamide (Example 215) has an IC50 of 16 nM and 15 nM for the FGFR35 enzyme and cellular assays, respectively, and 10 nM and 2 nM for Bcr-abl wild type and PDGFRβ, respectively;

d). N-(3-{3-(6-Amino-pyrimidin-4-yl)-3-[3-(2-oxo-pyrrolidin-1-yl)-propyl]-ureido}-4-methyl-phenyl)-3-trifluoromethyl-benzamide (Example 215), at a concentration of 10 µM, inhibits the following kinases by the percentage shown in brackets (for example, 100% means complete inhibition, 0% means no inhibition): wild-type Abl (99%), c-RAF (99%), CSK (97%), c-SRC (100%), FGFR35 (99%), JNK2α2 (93%), lck (100%), MKK6 (88%), p70S6K (81%), ROS (95%), SAPK2α (99%), SAPK2β, (99%), Tie2 (100%) and TrkB (99%). It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

Example 217

1-(2,6-Dichloro-3,5-dimethoxy-Phenyl)-3-{6-[4-(4-isopropyl-piperazin-1-yl)-phenylamino]-pyrimidin-4-yl}-urea

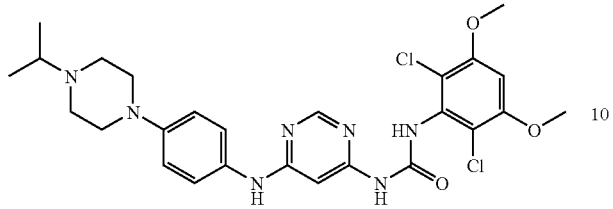

The title compound is prepared as described in Example 160 but using N-[4-(4-isopropyl-piperazin-1-yl)-phenyl]-pyrimidine-4,6-diamine (385 mg, 1.23 mmol, 1 eq.), and stirring the reaction mixture for 0.5 h at 70° C. The title compound: ESI-MS: 560.0/562.0 [MH]$^+$; $t_R$=3.17 min (purity: 98%, gradient J); TLC: $R_f$=0.31 (DCM/MeOH+1% NH$_3^{aq}$, 95:5).

A. N-[4-(4-Isopropyl-piperazin-1-yl)-phenyl]-pyrimidine-4,6-diamine

The title compound is prepared as described in Example 144A but using 4-(4-isopropyl-piperazin-1-yl)-phenylamine (400 mg, 1.83 mmol, 1 eq.), 6-chloro-pyrimidin-4-yl)-amine (1.3 eq.), and stirring the reaction mixture at 150° C. for 18 h. Purification of the crude product by trituration in diethyl ether affords the title compound as a white solid: ESI-MS: 313.2 [MH]$^+$; $t_R$=1.00 min (gradient J).

B. 4-(4-Isopropylpiperazin-1-yl)-aniline

A suspension of 1-isopropyl-4-(4-nitro-phenyl)-piperazine (5.18 g, 20.80 mmol) and Palladium (5%) on carbon (0.5 g) in MeOH (100 mL) is stirred for 2.7 h at RT, under a hydrogen atmosphere. The reaction mixture is filtered through a pad of celite and concentrated to afford the title compound as a violet solid: ESI-MS: 220.1 [MH]$^+$; $t_R$=0.95 min (gradient J).

C. 1-Isopropyl-4-(4-nitro-phenyl)-piperazine

A mixture of 1-bromo-4-nitrobenzene (6 g, 29.7 mmol) and 1-ethylpiperazine (7.6 ml, 59.4 mmol, 2 eq.) is heated to 80° C. for 15 h. After cooling to RT, the reaction mixture is concentrated. Purification of the residue by silica gel column chromatography (DCM/MeOH, 95:5) affords 5.18 g of the title compound as a yellow solid: ESI-MS: 250.1 [MH]$^+$; $t_R$=2.57 min (purity: 100%, gradient J); TLC: $R_f$=0.16 (DCM/MeOH, 95:5).

Example 218

3-(2,6-Dichloro-3,5-dimethoxy-Phenyl)-1-methyl-1-(6-{4-[2-(4-methyl-piperazin-1-yl)-ethoxy]-phenylamino}-pyrimidin-4-yl)-urea

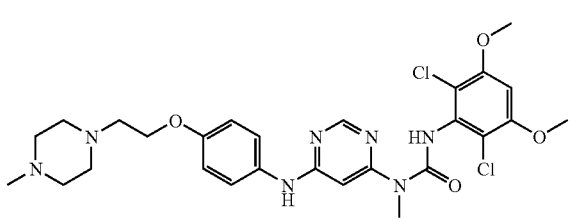

The title compound is prepared as described in Example 144 but using N-{4-[2-(4-methyl-piperazin-1-yl)-ethoxy]-phenyl}-pyrimidine-4,6-diamine (227 mg, 1.23 mmol, 1 eq.), and stirring the reaction mixture for 18 h at 70° C. Purification of the crude product by silica gel column chromatography (DCM/MeOH+1% NH$_3^{aq}$, 95:5) affords the title compound as a white solid: ESI-MS: 589.9/591.9 [MH]$^+$; $t_R$=3.11 min (purity: 100%, gradient J); TLC: $R_f$=0.12 (DCM/MeOH+1% NH$_3^{aq}$, 95:5).

A. N-Methyl-N'-{4-[2-(4-methyl-piperazin-1-yl)-ethoxy]-phenyl}-pyrimidine-4,6-diamine The title compound is prepared as described in Example 160A but using 4-[2-(4-methyl-piperazin-1-yl)-ethoxy]-phenylamine (500 mg, 2.13 mmol, 1 eq.), (6-chloro-pyrimidin-4-yl)-ethyl-amine and stirring the reaction mixture at 150° C. for 20 h. Purification of the crude product by silica gel column chromatography (DCM/MeOH+1% NH$_3^{aq}$, 9:1) followed by trituration in diethyl ether affords 250 mg of the title compound as a white solid: ESI-MS: 343.2 [MH]$^+$; $t_R$=1.00 min (gradient J); TLC: $R_f$=0.23 (DCM/MeOH+1% NH$_3^{aq}$, 9:1).

Example 219

3-(2,6-Dichloro-3,5-dimethoxy-phenyl)-1-{6-[4-(4-isopropyl-piperazin-1-yl)-phenylamino]-pyrimidin-4-yl}-1-methyl-urea

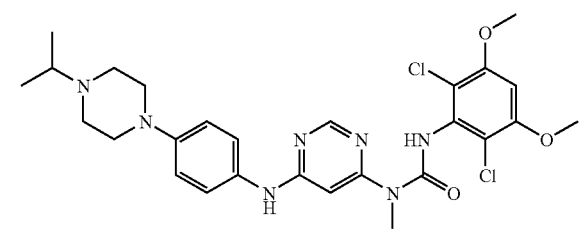 [SMILES: COc1cc(OC)c(Cl)c(NC(=O)N(C)c2cc(Nc3ccc(N4CCN(C(C)C)CC4)cc3)ncn2)c1Cl]

The title compound is prepared as described in Example 144 but using N-[4-(4-isopropyl-piperazin-1-yl)-phenyl]-N'-methyl-pyrimidine-4,6-diamine (1.71 g, 5.25 mmol, 1 eq.) and performing the reaction mixture for 45 min at reflux. Purification of the crude product by trituration in MeOH followed by silica gel column chromatography (DCM/MeOH+1% NH$_3^{aq}$, 97:3) affords the title compound as a white solid: ESI-MS: 573.9/575.9 [MH]$^+$; $t_R$=3.65 min (purity: 100%, gradient J); TLC: $R_f$=0.10 (DCM/MeOH+1% NH$_3^{aq}$, 97:3).

A. N-[4-(4-Isopropyl-piperazin-1-yl)-phenyl]-N'-methyl-pyrimidine-4,6-diamine The title compound is prepared as described in Example 144A but using 4-(4-isopropylpiperazin-1-yl)-aniline (Example 217B) (2.6 g, 11.9 mmol). Purification of the residue by silica gel column chromatography (DCM/MeOH, 93:7) affords 1.71 g of the title compound as a white solid: ESI-MS: 327.2 [MH]$^+$; $t_R$=1.30 min (gradient J); TLC: $R_f$=0.26 (DCM/MeOH, 93:7).

Example 220

1-(2,6-Dichloro-3,5-dimethoxy-phenyl)-3-[6-(4-dimethylaminomethyl-3-trifluoromethyl-phenylamino)-pyrimidin-4-yl]-urea

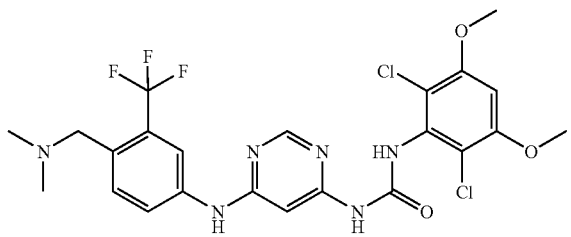

The title compound is prepared as described in Example 144 but using N-(4-dimethylaminomethyl-3-trifluoromethyl-phenyl)-pyrimidine-4,6-diamine (250 mg, 0.80 mmol, 1 eq.), 2 eq. of isocyanate, and performing the reaction mixture for 30 min at reflux. Purification of the crude product by silica gel column chromatography (DCM/MeOH+1% $NH_3{}^{aq}$, 95:5) affords the title compound as a white solid: ESI-MS: 558.9/560.9 $[MH]^+$; $t_R$=3.69 min (purity: 100%, gradient J); TLC: $R_f$=0.21 (DCM/MeOH+1% $NH_3{}^{aq}$, 95:5).

A. N-(4-Dimethylaminomethyl-3-trifluoromethyl-phenyl)-pyrimidine-4,6-diamine The title compound is prepared as described in Example 144A but using 4-dimethylaminomethyl-3-trifluoromethyl-phenylamine (300 mg, 1.46 mmol) and 6-chloro-pyrimidin-4-yl)-amine (1.3 eq.). Purification of the crude product by silica gel column chromatography (DCM/MeOH, 93:7) affords the title compound as a white solid: ESI-MS: 312.1 $[MH]^+$; TLC: $R_f$=0.16 (DCM/MeOH, 93:7).

Example 164

3-(2,6-Dichloro-3,5-dimethoxy-phenyl)-1-[6-(4-dimethylaminomethyl-3-trifluoromethyl-phenylamino)-pyrimidin-4-yl]-1-methyl-urea

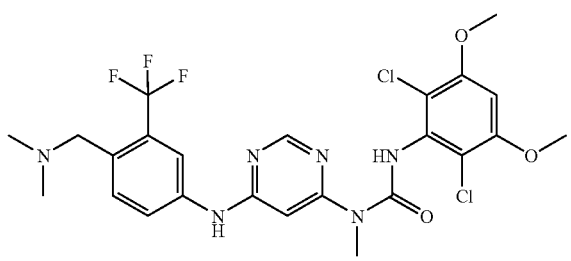

The title compound is prepared as described in Example 144 but using N-(4-dimethylaminomethyl-3-trifluoromethyl-phenyl)-N'-methyl-pyrimidine-4,6-diamine (200 mg, 0.62 mmol, 1 eq.), and performing the reaction mixture for 1 h at reflux. Purification of the crude product by trituration in MeOH followed by silica gel column chromatography (DCM/MeOH+1% $NH_3{}^{aq}$, 95:5) affords the title compound as a white solid: ESI-MS: 572.8/574.8 $[MH]^+$; $t_R$=4.14 min (purity: 100%, gradient J); TLC: $R_f$=0.24 (DCM/MeOH+1% $NH_3{}^{aq}$, 95:5).

A. N-(4-Dimethylaminomethyl-3-trifluoromethyl-phenyl)-N'-methyl-pyrimidine-4,6-diamine The title compound is prepared as described in Example 144A but using 4-dimethylaminomethyl-3-trifluoromethyl-phenylamine (300 mg, 1.46 mmol) and 1.3 eq. of 6-chloro-pyrimidin-4-yl)-methyl-amine. Purification of the crude product by silica gel column chromatography (DCM/MeOH, 93:7) affords the title compound as a white solid: ESI-MS: 326.1 $[MH]^+$; TLC: $R_f$=0.27 (DCM/MeOH, 93:7).

Example 222

3-(2,6-Dichloro-3,5-dimethoxy-phenyl)-1-[6-(3-{[(2-dimethylamino-ethyl)-methyl-amino]-methyl}-phenylamino)-pyrimidin-4-yl]-1-methyl-urea

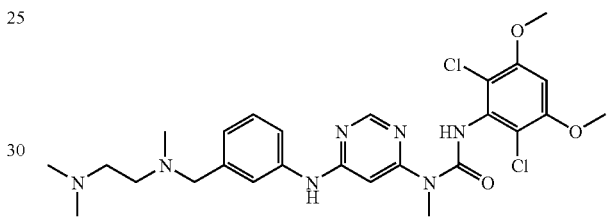

The title compound is prepared as described in Example 144 but using N-(3-{[(2-dimethylamino-ethyl)-methyl-amino]-methyl}-phenyl)-pyrimidine-4,6-diamine (250 mg, 0.80 mmol, 1 eq.), 1.5 eq. of isocynaze, and performing the reaction mixture for 6 h at reflux. Purification of the crude product by MPLC (by silica gel) (DCM/MeOH+1% $NH_3{}^{aq}$, 95:5) followed by trituration in diethyl ether affords the title compound as a white solid: ESI-MS: 561.9/563.9 $[MH]^+$; $t_R$=3.24 min (purity: 100%, gradient J); TLC: $R_f$=0.10 (DCM/MeOH+1% $NH_3{}^{aq}$, 9:1).

A. N-(3-{[(2-Dimethylamino-ethyl)-methyl-amino]-methyl}-phenyl)-N'-methyl-pyrimidine-4,6-diamine The title compound is prepared as described in Example 144A but using N-(3-amino-benzyl)-N,N',N'-trimethyl-ethane-1,2-diamine (500 mg, 2.41 mmol), 1.1 eq. of 6-chloro-pyrimidin-4-yl)-methyl-amine, and stirring the reaction mixture for 17.5 h. Purification of the crude product by silica gel column chromatography (DCM/MeOH+1% $NH_3{}^{aq}$, 95:5) affords the title compound as a beige solid: ESI-MS: 315.2 $[MH]^+$; TLC: $R_f$=0.05 (DCM/MeOH+1% $NH_3{}^{aq}$, 9:1).

B. N-(3-Amino-benzyl)-N,N',N'-trimethyl-ethane-1,2-diamine

A suspension of N,N',N'-trimethyl-N'-(3-nitro-benzyl)-ethane-1,2-diamine (4.5 g, 18.96 mmol) and Raney Nickel (1.2 g) in MeOH (100 mL) is stirred for 2 h at RT, under a hydrogen atmosphere. The reaction mixture is filtered through a pad of celite and concentrated to afford the title compound as a yellow oil: ESI-MS: 208.2.

C. N,N',N'-Trimethyl-N'-(3-nitro-benzyl)-ethane-1,2-diamine

A mixture of 3-nitrobenzylchloride (4.5 g, 26.23 mmol), N,N,N-trimethylethylendiamine (4.1 ml, 31.47 mmol, 1.2 eq.), potassium carbonate (7.3 g, 52.46, 2 eq.), and acetone (90 ml) is stirred for 19 h at 80° C. The reaction mixture is allowed to cool to RT, filtered and concentrated. Purification of the crude product by silica gel column chromatography (DCM/MeOH+1% $NH_3^{aq}$, 9:1) affords the title compound as a brown oil: ESI-MS: 238.1 $[MH]^+$; $t_R$=1.10 min (gradient J); TLC: $R_f$=0.10 (DCM/MeOH+1% $NH_3^{aq}$, 9:1).

Example 223

3-(2,6-Dichloro-3,5-dimethoxy-phenyl)-1-{6-[3-(4-isopropyl-piperazin-1-ylmethyl)-phenylamino]-pyrimidin-4-yl}-1-methyl-urea

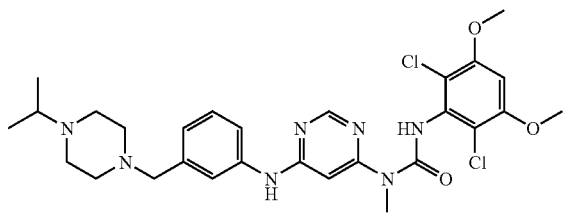 [SMILES: COc1cc(OC)c(Cl)c(NC(=O)N(C)c2cc(Nc3cccc(CN4CCN(C(C)C)CC4)c3)ncn2)c1Cl]

The title compound is prepared as described in Example 144 but using N-[3-(4-isopropyl-piperazin-1-ylmethyl)-phenyl]-N'-methyl-pyrimidine-4,6-diamine (250 mg, 0.73 mmol, 1 eq.). Purification of the crude product by MPLC (silica gel) (DCM/MeOH+1% $NH_3^{aq}$, 95:5) followed by trituration in diethyl ether affords the title compound as a white solid: ESI-MS: 587.9/589.9 $[MH]^+$; $t_R$=3.35 min (purity: 100%, gradient J); TLC: $R_f$=0.17 (DCM/MeOH+1% $NH_3^{aq}$, 9:1).

A. N-[3-(4-Isopropyl-piperazin-1-ylmethyl)-phenyl]-N'-methyl-pyrimidine-4,6-diamine The title compound is prepared as described in Example 143A but using 3-(4-isopropyl-piperazin-1-ylmethyl)-phenylamine (500 mg, 2.14 mmol, 1 eq.) and stirring the reaction mixture for 17.5 h at 150° C. Purification of the crude product by MPLC (silica gel) (DCM/MeOH+1% $NH_3^{aq}$, 95:5) affords the title compound as a light yellow solid: TLC: $R_f$=0.10 (DCM/MeOH+1% $NH_3^{aq}$, 9:1).

B. 3-(4-Isopropyl-piperazin-1-ylmethyl)-phenylamine

The title compound is prepared as described in Example 149B: ESI-MS: 234.1 $[MH]^+$; $t_R$=0.95 min (gradient J).

C. 1-Isopropyl-4-(3-nitro-benzyl)-piperazine

The title compound is prepared as described in Example 222C: ESI-MS: 264.1 $[MH]^+$; TLC: $R_f$=0.35 (DCM/MeOH+1% $NH_3^{aq}$, 9:1).

Example 224

1-(2,6-Dichloro-3,5-dimethoxy-phenyl)-3-{6-[3-(1-methyl-piperidin-4-yloxy)-phenylamino]-pyrimidin-4-yl}-urea

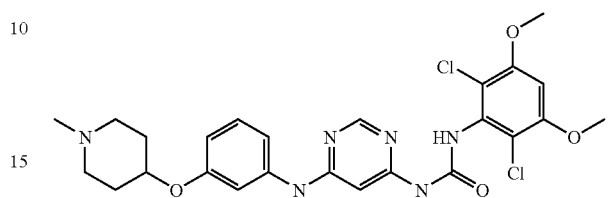

The title compound is prepared as described in Example 160 but using N-[3-(1-methyl-piperidin-4-yloxy)-phenyl]-pyrimidine-4,6-diamine (205 mg, 0.69 mmol, 1 eq.). Purification of the crude product by silica gel column chromatography (DCM/MeOH+1% $NH_3^{aq}$, 95:5) followed by trituration in MeOH affords the title compound as a white solid: ESI-MS: 546.9/548.9 $[MH]^+$; $t_R$=3.14 min (purity: 100%, gradient J); TLC: $R_f$=0.13 (DCM/MeOH+1% $NH_3^{aq}$, 95:5).

A. N-[3-(1-Methyl-piperidin-4-yloxy)-phenyl]-pyrimidine-4,6-diamine

The title compound is prepared as described in Example 160A but using 3-(1-methyl-piperidin-4-yloxy)-phenylamine (500 mg, 2.43 mmol, 1 eq.) and stirring the reaction mixture for 20 h at 100° C. Trituration of the crude product in EE affords the title compound as a red solid: ESI-MS: 300.2 $[MH]^+$; $t_R$=0.85 min (gradient J).

B. 3-(1-Methyl-piperidin-4-yloxy)-phenylamine

The title compound is prepared as described in Example 217B: ESI-MS: 207.1 $[MH]^+$.

C. 1-Methyl-4-(3-nitro-phenoxy)-piperidine

A mixture of 4-fluoro-nitrobenzene (10 g, 71.0 mmol), 4-hydroxy-1-methyl-piperidine (16.6 ml, 141.8 mmol, 2 eq.), tetrabutylammonium bromide (4.6 g, 14.2 mmol, 0.2 eq.), toluene (50 ml) and a 25% aqueous solution of potassium hydroxide (50 ml) is stirred for 15 h at 60° C. The reaction mixture is cooled to RT and poured onto ice/water. The resulting suspension is filtered and the filtrate is extracted with EE. The organic phase is washed with 0.5 N HCl, brine, then dried (sodium sulfate), filtered, and concentrated to afford 6 g of the title compound. The aqueous layer is made neutral by addition of sodium bicarbonate and extracted with EE. The organic phase is washed with brine, dried (sodium sulfate), filtered, and concentrated to afford additional 10 g of the title compound: ESI-MS: 237.0 $[MH]^+$; $t_R$=2.61 min (purity: 90%, gradient J).

Example 225

3-(2,6-Dichloro-3,5-dimethoxy-phenyl)-1-methyl-{6-[3-(1-methyl-piperidin-4-yloxy)-phenylamino]-pyrimidin-4-yl}-urea

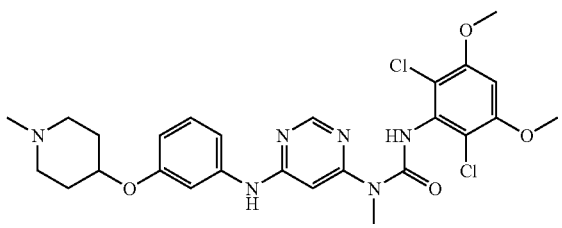

The title compound is prepared as described in Example 144 but using N-methyl-N'-[3-(1-methyl-piperidin-4-yloxy)-phenyl]-pyrimidine-4,6-diamine (130 mg, 0.41 mmol, 1 eq.). Purification of the crude product by silica gel column chromatography (DCM/MeOH+1% $NH_3^{aq}$, 95:5) followed by trituration in MeOH affords the title compound as a white solid: ESI-MS: 561.0/563.0 $[MH]^+$; $t_R$=3.66 min (purity: 97%, gradient J).

A. N-Methyl-N'-[3-(1-methyl-piperidin-4-yloxy)-phenyl]-pyrimidine-4,6-diamine The title compound is prepared as described in Example 160A but using 3-(1-methyl-piperidin-4-yloxy)-phenylamine (Example 224B). The title compound as a red solid: ESI-MS: 314.2 $[MH]^+$; TLC: $R_f$=0.16 (DCM/MeOH+1% $NH_3^{aq}$, 9:1).

Example 226

3-(2,6-Dichloro-3,5-dimethoxy-phenyl)-1-[6-(3-diethylaminomethyl-phenylamino)-pyrimidin-4-yl]-1-methyl-urea

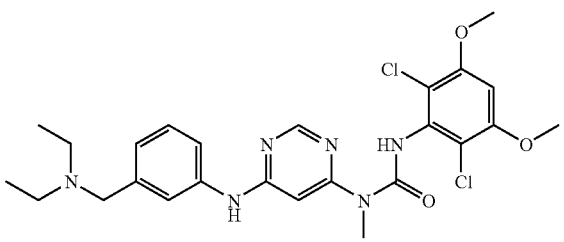 [SMILES: CCN(CC)Cc1cccc(Nc2cc(N(C)C(=O)Nc3c(Cl)c(OC)cc(OC)c3Cl)ncn2)c1]

The title compound is prepared as described in Example 144 but using N-(3-diethylaminomethyl-phenyl)-N'-methyl-pyrimidine-4,6-diamine (128 mg, 0.45 mmol, 1 eq.). The title compound: ESI-MS: 533.0/535.0 $[MH]^+$; $t_R$=3.94 min (purity: 100%, gradient J); TLC: $R_f$=0.37 (DCM/MeOH+1% $NH_3^{aq}$, 92:8).

A. N-(3-Diethylaminomethyl-phenyl)-N'-methyl-pyrimidine-4,6-diamine

The title compound is prepared as described in Example 144A but using 3-diethylaminomethyl-phenylamine. The title compound: ESI-MS: 286.1 $[MH]^+$; TLC: $R_f$=0.05 (DCM/MeOH+1% $NH_3^{aq}$, 9:1).

B. 3-Diethylaminomethyl-phenylamine

The title compound is prepared as described in Example 149B but using diethyl-(3-nitrobenzyl)-amine. The title compound contains 30% of 3-methyl-aniline and is used as a crude impure material.

C. Diethyl-(3-nitrobenzyl)-amine

The title compound is prepared as described in Example 149C but using diethylamine. The title compound: $t_R$=1.83 min (purity: 100%, gradient J); TLC: $R_f$=0.38 (DCM/MeOH, 9:1).

Example 227

3-(2,6-Dichloro-3,5-dimethoxy-phenyl)-1-methyl-1-{4-[4-(4-methyl-piperazin-1-yl)-phenylamino]-[1,3,5]triazin-2-yl}-urea

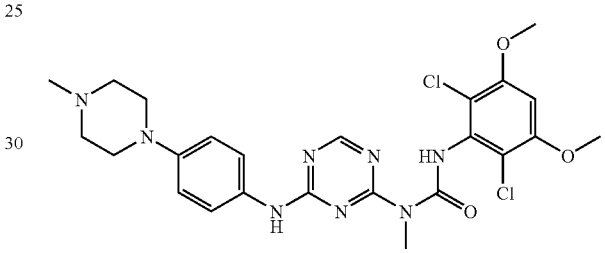

To a solution of 2,6-dichloro-3,5-dimethoxy-aniline (124 mg, 0.56 mmol; Preparation 2) in 2 ml of dioxane under a nitrogene atmosphere, phosgene (0.52 ml 20% in toluene, 0.98 mmol) is added. The mixture is stirred for 70 min at 100° C., cooled to RT and concentrated in vacuo, yielding 2,6-dichloro-3,5-dimethoxyphenylisocyanate. The resulting solid is added portion-wise to a boiling solution of N-methyl-N'-[4-(4-methyl-piperazin-1-yl)-phenyl]-[1,3,5]triazine-2,4-diamine (140 mg, 0.47 mmol) in 8 ml of toluene during 20 min. After 3 h, another 2 eq of 2,6-dichloro-3,5-dimethoxyphenylisocyanate are added and stirring is continued for totally 5 h. Then the reaction mixture is diluted with DCM and a saturated aqueous solution of $NaHCO_3$. The aqueous layer is separated and extracted twice with DCM. The organic phases are washed with water and brine, dried ($Na_2SO_4$) and concentrated. Column chromatography ($SiO_2$; DCM/MeOH/$NH_3^{aq}$, 97:3:0.2) gives the title compound: ESI-MS: 547/549 $[MH]^+$; $t_R$=3.5 min (purity: 100%, gradient J); TLC: $R_f$=0.40 (DCM/MeOH+1% $NH_3^{aq}$, 95:5).

A. N-Methyl-N'-[4-(4-methyl-piperazin-1-yl)-phenyl]-[1,3,5]triazine-2,4-diamine A solution of (4-chloro-[1,3,5]triazin-2-yl)-methyl-amine (290 mg, 2.00 mmol) and 4-(4-methylpiperazin-1-yl)-aniline (570 mg, 3.0 mmol) in EtOH (20 ml) and N-ethyl-diisopropyl amine (530 µl, 3.1 mmol) is heated to 80° C. for 2 h under a nitrogen atmosphere. The reaction mixture is concentrated and the residue re-dissolved in EE and water. The separated off aqueous phase is extracted twice with EE, the organic layer washed with water and brine, dried ($Na_2SO_4$) and concentrated. Column chromatography ($SiO_2$; DCM/MeOH/

NH₃ q 95:5:0.2) gives the title compound: TLC: R_f=0.07 (DCM/MeOH+1% NH₃^aq, 95:5).

B. (4-Chloro-[1.3.5]triazin-2-yl)-methyl-amine

To an ice cooled solution of 2,4-dichlor-[1,3,5]triazine (2.25 g, 15 mmol; WO 2004/072063, Expl. 9) in 20 ml of THF, MeNH₂ (15 ml of 2 M solution in THF) is added. After 1 h the mixture is diluted with 15 ml of water and concentrated partially in vacuo. The precipitated title compound can be filtered off, washed with ice-water and dried: ESI-MS: 143 [M–H.

Example 228

3-(2,6-Dichloro-3,5-dimethoxy-phenyl)-1-methyl-1-{4-[4-(4-ethyl-piperazin-1-yl)-phenylamino]-[1,3,5]triazin-2-yl}-urea

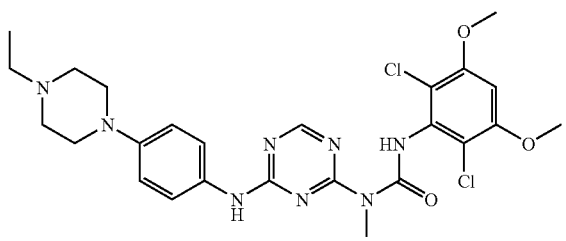 [SMILES: CCN1CCN(c2ccc(Nc3ncnc(N(C)C(=O)Nc4c(Cl)c(OC)cc(OC)c4Cl)n3)cc2)CC1]

To a solution of 2,6-dichloro-3,5-dimethoxy-aniline (133 mg, 0.60 mmol; Preparation 2) in 2 ml of dioxane under a nitrogen atmosphere, phosgene (0.54 ml 20% in toluene, 1.0 mmol) is added. The mixture is stirred for 60 min at 100° C., cooled to RT and concentrated in vacuo, yielding 2,6-dichloro-3,5-dimethoxyphenylisocyanate.

The resulting solid is added portion-wise to a boiling solution of N-methyl-N'-[4-(4-ethyl-piperazin-1-yl)-phenyl]-[1,3,5]triazine-2,4-diamine (156 mg, 0.50 mmol) in 7 ml of toluene during 15 min. After 5 h, the reaction mixture is diluted with DCM and a saturated aqueous solution of NaHCO₃. The aqueous layer is separated and extracted twice with DCM. The organic phases are washed with water and brine, dried (Na₂SO₄) and concentrated. Column chromatography (SiO₂; DCM/MeOH/NH₃^aq, 95:5:0.2) gives the title compound: ESI-MS: 561/563 [MH]⁺; t_R=3.6 min (gradient J); TLC: R_f=0.4 (DCM/MeOH+1% NH₃^aq, 95:5).

A. N-Methyl-N'-[4-(4-ethyl-piperazin-1-yl)-phenyl]-[1,3,5]triazine-2,4-diamine

A mixture of (4-chloro-[1,3,5]triazin-2-yl)-methyl-amine (290 mg, 2.00 mmol), NaI (28 mg) and 4-(4-ethylpiperazin-1-yl)-aniline (410 mg, 2.0 mmol) in EtOH (20 ml) and N-ethyl-diisopropyl amine (350 µl, 2.0 mmol) is heated to 80° C. for 3 h under a nitrogen atmosphere. The reaction mixture is cooled to RT, concentrated partially in vacuo and diluted with hexane at 0° C. The precipitate is filtered off, washed with Et₂O and re-dissolved in EE and water. The separated off aqueous phase is extracted twice with EE, the organic layer washed with water and brine, dried (Na₂SO₄) and concentrated, yielding the title compound: ESI-MS: 314 [MH]⁺; TLC: R_f=0.10 (DCM/MeOH 9:1).

Example 229

3-(4-Fluoro-3-trifluoromethyl-Phenyl)-1-methyl-1-{4-[4-(4-ethyl-piperazin-1-yl)-phenylamino]-[1,3,5]triazin-2-yl}-urea

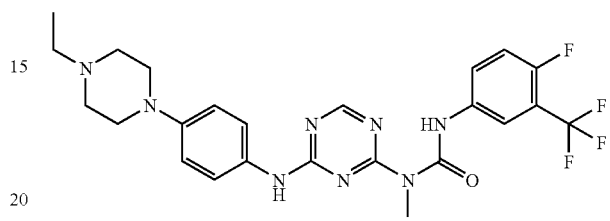

To a solution of N-methyl-N'-[4-(4-ethyl-piperazin-1-yl)-phenyl]-[1,3,5]triazine-2,4-diamine (24 mg, 0.077 mmol) in 1.5 ml THF and 2.5 ml toluene, 4-fluoro-3-trifluoromethyl-phenyl-isocyanate (25 µl, 0.17 mmol) is added and the mixture is stirred for 5 h at 100° C. Workup analogously as described in Example 171 gives the title compound: ESI-MS: 519 [MH]⁺; t_R=4.3 min (purity: 100%, gradient J); TLC: R_f=0.43 (DCM/MeOH 9).

Example 230

3-(2,6-Dichloro-3,5-dimethoxy-phenyl)-1-methyl-1-{4-[4-(4-isopropyl-piperazin-1-yl)-phenylamino]-[1,3,5]triazin-2-yl}-urea

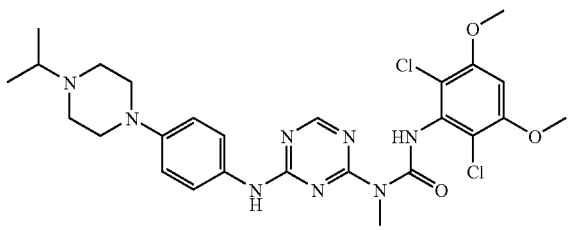 [SMILES: COc1cc(OC)c(Cl)c(NC(=O)N(C)c2ncnc(Nc3ccc(N4CCN(C(C)C)CC4)cc3)n2)c1Cl]

As described in Example 230, 2,6-dichloro-3,5-dimethoxy-aniline (133 mg, 0.60 mmol; Preparation 2) and N-methyl-N'-[4-(4-isopropyl-piperazin-1-yl)-phenyl]-[1,3,5]triazine-2,4-diamine (163 mg, 0.50 mmol) are converted to the title compound: ESI-MS: 575/577 [MH]⁺; t_R=3.7 min (gradient J); TLC: R_f=0.32 (DCM/MeOH+1% NH₃^aq, 95:5).

A. N-Methyl-N'-[4-(4-isopropyl-piperazin-1-yl)-phenyl]-[1,3,5]triazine-2,4-diamine A mixture of (4-chloro-[1,3,5]triazin-2-yl)-methyl-amine (290 mg, 2.00 mmol), NaI (28 mg) and 4-(4-propylpiperazin-1-yl)-aniline (500 mg, 2.0 mmol) in EtOH (20 ml) and N-ethyl-diisopropyl amine (350 µl, 2.0 mmol) is heated to 80° C. for 3 h under a nitrogen atmosphere. Workup as described in Example 228A gives the title compound: ESI-MS: 328 [MH]⁺; TLC: $R_f$=0.14 (DCM/MeOH, 9:1).

Example 231

3-(2,6-Dichloro-3-trifluoromethyl-Phenyl)-1-{6-[4-(4-ethyl-piperazin-1-yl)-phenylamino]-pyrimidin-4-yl}-1-methyl-urea

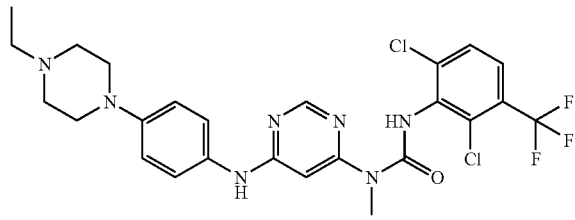 [SMILES: CCN1CCN(c2ccc(Nc3cc(N(C)C(=O)Nc4c(Cl)ccc(C(F)(F)F)c4Cl)ncn3)cc2)CC1]

To a solution of 2,6-dichloro-3-trifluoromethyl-aniline (138 mg, 0.60 mmol) in 2 ml of dioxane under a nitrogen atmosphere, phosgene (0.54 ml 20% in toluene, 1.0 mmol) is added. The mixture is stirred for 2 h at 100° C., cooled to rt and concentrated in vacuo, yielding 2,6-dichloro-3-trifluoromethyl-phenylisocyanate.

This oil is re-dissolved in 2 ml of toluene and added portion-wise to a boiling solution of N-[4-(4-ethyl-piperazin-1-yl)-phenyl]-N'-methyl-pyrimidine-4,6-diamine (156 mg, 0.50 mmol; Example 145A) in 6 ml of toluene during 10 min. After 1.5 h, another 2 eq of 2,6-dichloro-3-trifluoromethyl-phenylisocyanate are added and stirring is continued for totally 2 h. Then the reaction mixture is diluted with DCM and a saturated aqueous solution of NaHCO₃. The aqueous layer is separated and extracted twice with DCM. The organic phases are washed with water and brine, dried (Na₂SO₄) and concentrated. Column chromatography (SiO₂; CH₂Cl₂/MeOH/NH₃$^{aq}$, 95:5:0.5) gives the title compound: ESI-MS: 568/570 [MH]⁺; $t_R$=4.1 min (gradient J); TLC: $R_f$=0.3 (DCM/MeOH+1% NH₃$^{aq}$, 95:5).

A. 2,6-Dichloro-3-trifluoromethyl-anilin

Hydrogenation of 2,4-dichloro-3-nitro-benzotrifluoride (5.0 g, 19.2 mmol; ABCR, Karlsruhe/Germany) in 100 ml MeOH in the presence of 1 g Raney-nickel, filtration and concentration of the filtrate gives the title compound: TLC: $R_f$=0.67 (EE).

The invention claimed is:
1. A compound of Formula (I):

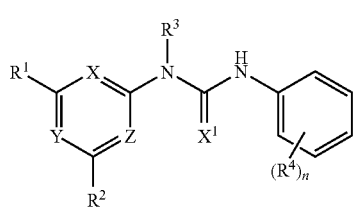

where
the following fragments referred to hereinafter as the "left hand ring" and the "right hand ring", respectively:

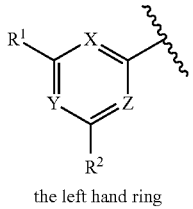 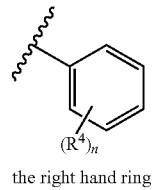

the left hand ring      the right hand ring wherein X is C—R⁵, and Y and Z are both N, whereby the left hand ring has the structure of Fragment (A):

Fragment (A)

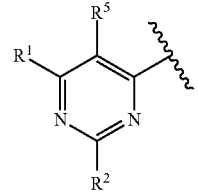

n is 0, 1, 2, 3, 4 or 5;
X¹ is oxygen,
R¹ is of the formula R$^z$—NR$^a$— wherein R$^a$ is hydrogen, hydroxy, hydrocarbyloxy or hydrocarbyl, wherein hydrocarbyl has from 1 to 15 carbon atoms, is optionally interrupted by an —O— or —NH— linkage and is unsubstituted or is substituted by hydroxy, halo, amino or mono- or di-(C₁-C₄)alkylamino, alkanoyl having 4 in-chain atoms, trifluoromethyl, cyano, azo or nitro; and R$^z$ is selected from:
(i) linear or branched alkyl having 1, 2, 3 or 4 carbon atoms,
(ii) linear or branched alkyl having 1, 2, 3 or 4 carbon atoms substituted by one or more halogens and/or one or two functional groups selected from hydroxy, amino, amidino, guanidino, hydroxyguanidino, formamidino, isothioureido, ureido, mercapto, acyl having 1, 2, 3 or 4 carbon atoms, acyloxy having 1, 2, 3 or 4 carbon atoms, carboxy, sulfo, sulfamoyl, carbamoyl, cyano, azo, or nitro, which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or, where possible, more linear or branched alkyl groups having 1, 2, 3 or 4 carbon atoms, and
(iii) a group of the formula

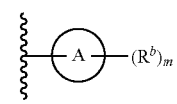

where:
ring A represents a 6-membered carbocyclic or heterocyclic ring;
m is 0, 1 or 2;
each R$^b$ is independently selected from -L²-NR$^c$R$^d$; -L²-RING where RING is a mono- or bi-cyclic ring optionally substituted as defined below; halogen; hydroxy; protected hydroxyl; amino; amidino; guanidino; hydroxyguanidino; formamidino; isothioureido; ureido;

mercapto; acyl having 4 in-chain atoms; acyloxy having 4 in-chain atoms; carboxy; sulfo; sulfamoyl; carbamoyl; cyano; azo; or nitro; and linear or branched alkyl having 1, 2, 3 or 4 carbon atoms optionally substituted by one or more halogens and/or one or two functional groups selected from hydroxy, protected hydroxy, amino, amidino, guanidino, hydroxyguanidino, formamidino, isothioureido, ureido, mercapto, acyl having 4 in-chain atoms, acyloxy having 4 in-chain atoms, carboxy, sulfo, sulfamoyl, carbamoyl, cyano, azo, or nitro; all of which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or, where possible, more $C_1$-$C_7$ aliphatic groups, wherein $L^2$ is a direct bond; a linkage selected from —O—; —S—; —C(O)—; —OC(O)—; —NR$^a$C(O)—; —C(O)—NR$^a$ —; —OC(O)—NR$^a$ —; cyclopropyl and —NR$^a$—; or is a linear or branched alkyl group having 1, 2, 3 or 4 carbon atoms optionally interrupted and/or terminated at a single end or at both ends by a said linkage;

and wherein R$^c$ and R$^d$ are each independently selected from hydrogen, and linear or branched alkyl having 1, 2, 3 or 4 carbon atoms optionally substituted by one or more halogens, by an optionally substituted 5- or 6- membered heterocyclic or carbocyclic ring, and/or one or two functional groups selected from hydroxy, protected hydroxy, amino, amidino, guanidino, hydroxyguanidino, formamidino, isothioureido, ureido, mercapto, acyl having 4 in-chain atoms, acyloxy having 4 in-chain atoms, carboxy, sulfo, sulfamoyl, carbamoyl, cyano, azo, or nitro, which hydroxy, amino, amidino, guanidino, hydroxyguanidino, formamidino, isothioureido, ureido, mercapto, carboxy, sulfo, sulfamoyl, carbamoyl and cyano groups are in turn optionally substituted on at least one heteroatom by one or more $C_1$-$C_7$ aliphatic groups, or R$^c$ and R$^d$ together with their adjoining nitrogen form a 5- or 6- membered ring optionally substituted as described below, said optionally substituted rings independently of each other being substituted by 0, 1, 2, 3, 4 or 5 substituents selected from halogen; hydroxy; protected hydroxy; amino; amidino; guanidino; hydroxyguanidino; formamidino; isothioureido; ureido; mercapto; acyl having 4 in-chain atoms;

acyloxy having 4 in-chain atoms; carboxy; sulfo; sulfamoyl; carbamoyl; cyano; azo; nitro; $C_1$-$C_7$ aliphatic optionally substituted by one or more halogens and/or one or two functional groups selected from hydroxy, protected hydroxy, amino, amidino, guanidino, hydroxyguanidino, formamidino, isothioureido, ureido, mercapto, acyl having 4 in-chain atoms, acyloxy having 4 in-chain atoms, carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or, where possible, more $C_1$-$C_7$ aliphatic groups;

R$^2$ is H, halo, alkyl, alkyl interrupted by an —O— or —NH— linkage and/or linked to the left hand ring by a said linkage, trifluoromethyl, hydroxy, amino, mono- or dialkylamino; any alkyl moiety (interrupted or not) having 1, 2, 3 or 4 carbon atoms;

R$^3$ is H, a straight chain or branched $C_1$-$C_4$ alkyl or a straight chain or branched $C_1$-$C_4$ alkyl substituted by a 5- or 6- membered saturated or unsaturated carbocyclic or heterocyclic ring;

R$^4$ is selected from hydroxy, protected hydroxy, alkoxy, alkyl, trifluoromethyl and halo, wherein alkyl and the alkyl part of alkoxy are branched or straight chain and have 1, 2, 3, or 4 carbon atoms, or;

R$^5$ is H, halo, alkyl, alkyl interrupted by an —O— or —NH— linkage and/or linked to the left hand ring by a said linkage, trifluoromethyl, hydroxy, amino, mono- or dialkylamino; any alkyl moiety (interrupted or not) having 1, 2, 3 or 4 carbon atoms, or pharmaceutically acceptable salts, esters, N-oxides, protected derivatives, individual isomers and mixture of isomers thereof.

2. The compound of claim 1 wherein R$^5$ is H or halo.

3. The compound of claim 2 wherein R$^5$ is H.

4. The compound of claim 1 wherein, R$^2$ is H.

5. The compound of claim 1 wherein the left hand ring has the structure of Fragment (B):

Fragment (B)

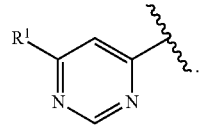

6. The compound of claim 1 wherein R$^z$ is of the formula

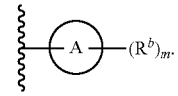

7. The compound of claim 6 which comprises at least one R$^b$ which is -L$^2$-NR$^c$R$^d$ or -L$^2$-RING, wherein L$^2$ is a direct bond, linear alkyl, linear alkyl terminated adjacent ring A by a linkage selected from —O—; —S—; —C(O)—; —OC(O)—; —NR$^a$C(O)—; —C(O)—NR$^a$ —;

—OC(O)—NR$^a$ —; cyclopropyl and —NR$^a$—; or is a linkage selected from —O—; —S—; —C(O)—; —OC(O)—; —NR$^a$C(O)—; —C(O)—NR$^a$—; —OC(O)—NR$^a$—; cyclopropyl and —NR$^a$—.

8. The compound of claim 7 wherein said linkage is —O—.

9. The compound of claim 6 wherein ring A is phenyl, cyclohexenyl or cyclohexyl.

10. The compound of claim 6 wherein there is a single R$^b$ group which is selected from -L$^2$-NR$^c$R$^d$ and -L$^2$-RING and there are 0, 1 or 2 additional substituents which are selected from halogen, alkyl, alkoxy, hydroxy, amino and trifluoromethyl, wherein alkyl and the alkyl part of alkoxy have 1, 2, 3 or 4 carbon atoms.

11. The compound of claim 1 wherein m is 1.

12. The compound of claim 11 wherein ring A is phenyl or cyclohexyl and R$^b$ is selected from -L$^2$-NR$^c$R$^d$ and -L$^2$-RING.

13. The compound of claim 12 wherein the substituent is at the 3-position or 4-position of ring A.

14. The compound of claim 1 wherein the left hand ring has a structure corresponding to Fragment (D1), (D2), (E1) or (E2):

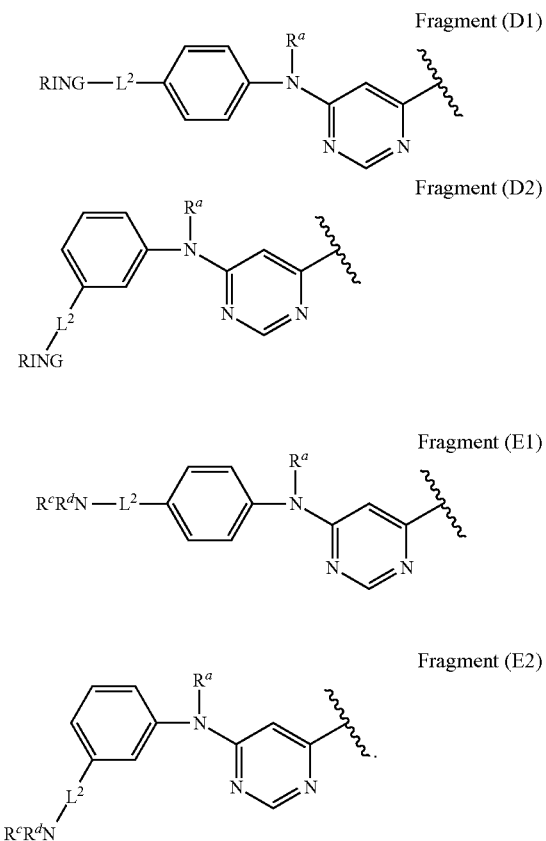

Fragment (D1)

Fragment (D2)

Fragment (E1)

Fragment (E2)

15. The compound of claim 14 wherein $R^a$ is H.

16. The compound of claim 14 wherein the phenyl ring of said Fragments has 1, 2, 3 or 4 further substituents, selected from halogen, methyl, methoxy and trifluoromethyl.

17. The compound of claim 14 wherein RING is a saturated heterocycle which contains an in-ring nitrogen.

18. The compound of claim 14 which contains a moiety $NR^cR^d$ and wherein $R^c$ and $R^d$ are the same or different and selected from straight chain or branched alkyl having 1, 2, 3 or 4 carbon atoms.

19. The compound of claim 14 which contains a moiety $NR^cR^d$ and wherein $R^c$ and $R^d$ together with the adjoining nitrogen form a 5- or 6- membered heterocyclic ring, optionally substituted as by 0, 1, 2, 3, 4 or 5 substituents selected from straight chain or branched $C_1$, $C_2$, $C_3$ or $C_4$ alkyl, halogen and $C_1$, $C_2$, $C_3$ or $C_4$ alkoxy, wherein alkyl and the alkyl part of alkoxy are unsubstituted or substituted by halogen.

20. The compound of claim 19 wherein the heterocycle is saturated.

21. The compound of claim 20 wherein $L^2NR^cR^d$ is selected from the group consisting of piperazine, morpholine, —OCH₂piperazine, —OCH₂morpholine, —OCH₂CH₂piperazine, —OCH₂CH₂morpholine, —OCH₂CH₂CH₂piperazine, —OCH₂CH₂CH₂morpholine, —CH₂piperazine, —CH₂morpholine, —CH₂CH₂piperazine, —CH₂CH₂morpholine, —CH₂CH₂CH₂piperazine, —CH₂CH₂CH₂morpholine, —C(O)piperazine and —C(O)morpholine, piperazine optionally being N-substituted by straight chain or branched $C_1$, $C_2$, $C_3$ or $C_4$ alkyl.

22. The compound of claim 14 wherein the left hand ring has the structure of the following Fragment (F):

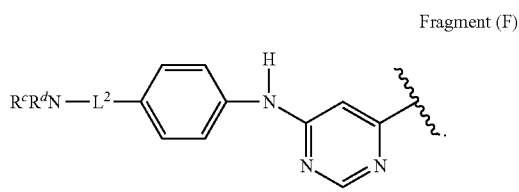

Fragment (F)

23. The compound of claim 1 wherein n is 1, 2, 3 or 4.

24. The compound of claim 1 wherein $R^4$ is selected from hydroxy, protected hydroxy, alkoxy, alkyl, trifluoromethyl and halo, wherein alkyl and the alkyl part of alkoxy are branched or straight chain and have 1, 2, 3, or 4 carbon atoms.

25. The compound of claim 24 wherein $R^4$ is selected from Cl, F, hydroxy, methyl, methoxy and trifluoromethyl.

26. The compound of claim 1 wherein the right hand ring corresponds to Fragment (G):

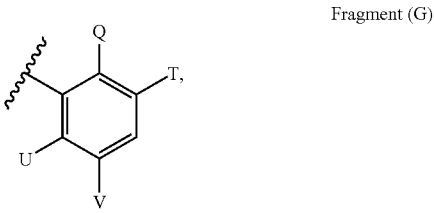

Fragment (G)

where:
Q is selected from F and Cl;
U is selected from H, F, Cl, methyl, trifluoromethyl and methoxy;
T and V are the same or different and selected from H, methyl, trifluoromethyl and methoxy.

27. The compound of claim 26 wherein the right hand ring is Fragment (H):

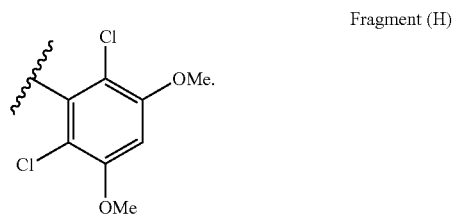 [SMILES: *c1c(Cl)c(OC)cc(OC)c1Cl]

Fragment (H)

28. The compound of claim 1 wherein the right hand ring corresponds to Fragment (I):

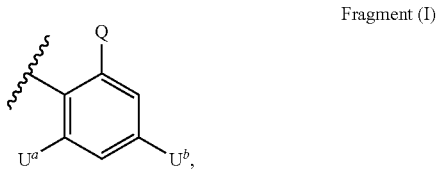

Fragment (I)

where:
Q is selected from F and Cl;
$U^a$ and $U^b$ are each independently selected from H, F, Cl, methyl, trifluoromethyl and methoxy.

29. The compound of claim 1 which is selected from the following formulae (IV), (V), (VI) and (VII):

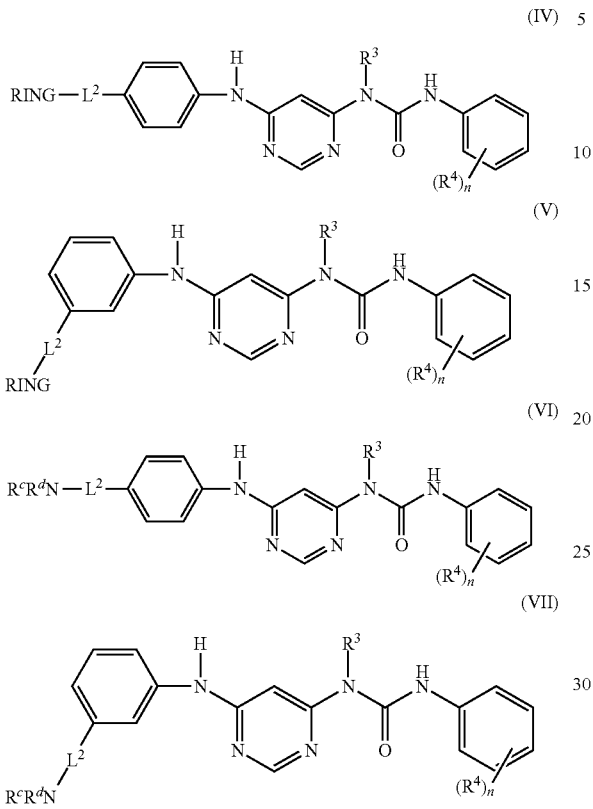

where
L²NRᶜRᵈ is piperazine, morpholine, —OCH₂piperazine, —OCH₂morpholine, —OCH₂CH₂piperazine, —OCH₂CH₂morpholine, —OCH₂CH₂CH₂piperazine, —OCH₂CH₂CH₂ morpholine, —CH₂piperazine, —CH₂morpholine, —CH₂CH₂piperazine, —CH₂CH₂morpholine, —CH₂CH₂CH₂piperazine, —CH₂CH₂CH₂morpholine, —C(O)piperazine or —C(O)morpholine, wherein morpholine is optionally substituted by C₁-C₄ alkyl and piperazine is optionally substituted by C₁-C₄ alkyl;
L²RING is -RING, —OCH₂RING, —OCH₂CH₂RING, —OCH₂CH₂CH₂RING, —CH₂RING, —CH₂CH₂RING, —CH₂CH₂CH₂RING, and, or is —C(O)RING, where RING is a heterocycle optionally substituted by C₁-C₄ alkyl or C₁-C₄ haloalkyl and selected from pyrrolidine, piperidine, piperazine or morpholine;
R³ is H;
R⁴ is selected from Cl, F, hydroxy, methyl, methoxy and trifluoromethyl;
n is 0, 1, 2, 3, 4 or 5.
30. A combination of the compound of claim 1 with (N—{5-[4-(4-methyl-piperazino-methyl)-benzoylamido]-2-methylphenyl}-4-(3-pyridyl)-2-pyrimidine-amine.
31. A compound of claim 1 selected from
3-(2,6-Dichloro-3-methoxy-phenyl)-1-methyl-1-{6-[4-(4-methyl-piperazin-1-yl)-phenylamino]-pyrimidin-4-yl}-urea;
3-(2,6-Dichloro-3,5-dimethoxy-phenyl)-1-methyl-1-{6-[4-(4-methyl-piperazin-1-yl)-phenylamino]-pyrimidin-4-yl}-urea;
3-(2,6-Dichloro-3,5-dimethoxy-phenyl)-1-methyl-1-{6-[(4-methyl-piperazin-1-yl)-phenylamino]-pyrimidin-4-yl}-urea;
1-(2,6-Dichloro-phenyl)-3-{6-[4-(4-methyl-piperazin-1-yl)-phenylamino]-pyrimidin-4-yl}-urea;
1-(2,6-Dichloro-phenyl)-3-{6-[3-(4-methyl-piperazin-1-yl)-phenylamino]-pyrimidin-4-yl}-urea;
1-(2-Chloro-6-methyl-phenyl)-3-{6-[4-(4-methyl-piperazin-1-yl)-phenyl-amino]-pyrimidin-4-yl}-urea;
1-(2-Chloro-6-methyl-phenyl)-3-{6-[3-(4-methyl-piperazin-1-yl)-phenyl-amino]-pyrimidin-4-yl}-urea;
1-(3-Methoxy-phenyl)-3-{6-[4-(4-methyl-piperazin-1-yl)-phenylamino]-py-rimidin-4-yl}-urea;
1-(3-Methoxy-phenyl)-3-{6-[3-(4-methyl-piperazin-1-yl)-phenylamino]-pyrimidin-4-yl}-urea;
1-(3,5-Dichloro-phenyl)-3-{6-[4-(4-methyl-piperazin-1-yl)-phenylamino]-pyrimidin-4-yl}-urea;
1-(3,5-Dichloro-phenyl)-3-{6-[3-(4-methyl-piperazin-1-yl)-phenylamino]-pyrimidin-4-yl}-urea;
1-(2,5-Dimethoxy-phenyl)-3-{6-[4-(4-methyl-piperazin-1-yl)-phenyl-amino]-pyrimidin-4-yl}-urea;
1-(2,5-Dimethoxy-phenyl)-3-{6-[3-(4-methyl-piperazin-1-yl)-phenyl-amino]-pyrimidin-4-yl}-urea;
1-{6-[4-(4-Methyl-piperazin-1-yl)-phenylamino]-pyrimidin-4-yl}-3-(3,4,5-trimethoxy-phenyl)-urea;
1-{6-[3-(4-Methyl-piperazin-1-yl)-phenylamino]-pyrimidin-4-yl}-3-(3,4,5-trimethoxy-phenyl)-urea;
1-(2,4-Dimethoxy-phenyl)-3-{6-[4-(4-methyl-piperazin-1-yl)-phenyl-amino]-pyrimidin-4-yl}-urea;
1-(2,4-Dimethoxy-phenyl)-3-{6-[3-(4-methyl-piperazin-1-yl)-phenyl-amino]-pyrimidin-4-yl}-urea;
1-(3,5-Dimethoxy-phenyl)-3-{6-[4-(4-methyl-piperazin-1-yl)-phenyl-amino]-pyrimidin-4-yl}-urea;
1-(3,5-Dimethoxy-phenyl)-3-{6-[3-(4-methyl-piperazin-1-yl)-phenyl-amino]-pyrimidin-4-yl}-urea;
1-(3,5-Bis-trifluoromethyl-phenyl)-3-{6-[4-(4-methyl-piperazin-1-yl)-phenylamino]-pyrimidin-4-yl}-urea;
1-(3,5-Bis-trifluoromethyl-phenyl)-3-{6-[3-(4-methyl-piperazin-1-yl)-phenylamino]-pyrimidin-4-yl}-urea;
1-(3,5-Dimethyl-phenyl)-3-{6-[4-(4-methyl-piperazin-1-yl)-phenyl-amino]-pyrimidin-4-yl}-urea;
1-(3,5-Dimethyl-phenyl)-3-{6-[3-(4-methyl-piperazin-1-yl)-phenyl-amino]-pyrimidin-4-yl}-urea;
1-(3-Chloro-4-methoxy-phenyl)-3-{6-[4-(4-methyl-piperazin-1-yl)-phenyl-amino]-pyrimidin-4-yl}-urea;
1-(3-Chloro-4-methoxy-phenyl)-3-{6-[3-(4-methyl-piperazin-1-yl)-phenyl-amino]-pyrimidin-4-yl}-urea;
1-(5-Methoxy-2-methyl-phenyl)-3-{6-[4-(4-methyl-piperazin-1-yl)-phenyl-amino]-pyrimidin-4-yl}-urea;
1-(5-Methoxy-2-methyl-phenyl)-3-{6-[3-(4-methyl-piperazin-1-yl)-phenyl-amino]-pyrimidin-4-yl}-urea;
1-(2-Chloro-5-methoxy-phenyl)-3-{6-[4-methyl-piperazin-1-yl)-phenyl-amino]-pyrimidin-4-yl}-urea;
1-(2-Chloro-5-methoxy-phenyl)-3-{6-[3-methyl-piperazin-1-yl)-phenyl-amino]-pyrimidin-4-yl}-urea;
1-(3,4-Dimethoxy-phenyl)-3-{6-[4-(4-methyl-piperazin-1-yl)-phenyl-amino]-pyrimidin-4-yl}-urea;
1-(3,4-Dimethoxy-phenyl)-3-{6-[3-(4-methyl-piperazin-1-yl)-phenyl-amino]-pyrimidin-4-yl}-urea ;
1-(4-Fluoro-3-methoxy-phenyl)-3-{6-[4-(4-methyl-piperazin-1-yl)-phenyl-amino]-pyrimidin-4-yl}-urea;
1-(4-Fluoro-3-methoxy-phenyl)-3-{6-[3-(4-methyl-piperazin-1-yl)-phenyl-amino]-pyrimidin-4-yl}-urea;
1-(4,5-Dimethoxy-2-methyl-phenyl)-3-{6-[4-(4-methyl-piperazin-1-yl)-phenyl-amino]-pyrimidin-4-yl}-urea;
1-(4,5-Dimethoxy-2-methyl-phenyl)-3-{6-[3-(4-methyl-piperazin-1-yl)-phenyl-amino]-pyrimidin-4-yl}-urea;

1-(2,6-Dichloro-3-methoxy-phenyl)-3-{6-[4-(4-methyl-piperazin-1-yl)-phenyl-amino]-pyrimidin-4-yl}-urea;
1-(2,6-Dichloro-3-methoxy-phenyl)-3-{6-[3-(2-morpholin-4-yl-ethoxy)-phenylamino]-pyrimidin-4-yl}-urea;
1-(2-Chloro-3,5-dimethoxy-phenyl)-3-(6-methylamino-pyrimidin-4-yl)-urea;
1-(2-Chloro-3,5-dimethoxy-phenyl)-3-(6-phenylamino-pyrimidin-4-yl)-urea;
1-(2-Chloro-3,5-dimethoxy-phenyl)-3-{6-[4-(4-methyl-piperazin-1-yl)-phenyl-amino]pyrimidin-4-yl}-urea;
1-(2-Chloro-3,5-dimethoxy-2-methyl-phenyl)-3-{6-[3-(4-methyl-piperazin-1-yl)-phenyl-amino]-pyrimidin-4-yl}-urea;
1-(2-Chloro-3,5-dimethoxy-phenyl)-3-{6-[4-(2-diethylamino-ethoxy)-phenylamino]pyrimidin-4-yl}-urea;
1-(2-Chloro-3,5-dimethoxy-phenyl)-3-{6-[3-(2-dimethylamino-ethoxy)-phenylamino]-pyrimidin-4-yl}-urea;
1-(2-Chloro-3,5-dimethoxy-phenyl)-3-{6-[4-(2-morpholin-4-yl-ethoxy)-phenylamino]-pyrimidin-4-yl}-urea;
1-(2-Chloro-3,5-dimethoxy-phenyl)-3-{6-[3-(2-morpholin-4-yl-ethoxy)-phenylamino]-pyrimidin-4-yl}-urea;
3-(2,3-Dimethoxy-phenyl)-1-ethyl-1-{6-[4-(4-methyl-piperazin-1-yl)-phenylamino]-pyrimidin-4-yl}-urea;
3-(3,5-Dimethoxy-phenyl)-1-methyl-1-{6-[4-(4-methyl-piperazin-1-yl)-phenylamino]-pyrimidin-4-yl}-urea;
3-(3,5-Dimethoxy-phenyl)-1-methyl-1-{6-[3-(4-methyl-piperazin-1-yl)-phenylamino]-pyrimidin-4-yl}-urea;
3-(2-Chloro-3,5-dimethoxy-phenyl)-1-methyl-1-(6-phenylamino-pyrimidin-4-yl)-urea;
3-(2-Chloro-3,5-dimethoxy-phenyl)-1-methyl-1-{6-[4-(4-methyl-piperazin-1-yl)-phenylamino]-pyrimidin-4-yl}-urea;
3-(2-Chloro-3,5-dimethoxy-phenyl)-1-methyl-1-{6-[3-(4-methyl-piperazin-1-yl)-phenylamino]-pyrimidin-4-yl}-urea;
3-(2-Chloro-3,5-dimethoxy-phenyl)-1-methyl-1-{6-[4-(4-methyl-piperazine-1-carbonyl)-phenylamino]-pyrimidin-4-yl}-urea;
3-(2-Chloro-3,5-dimethoxy-phenyl)-1-{6-[4-(2-diethylamino-ethoxy)-phenylamino]-pyrimidin-4-}1-1-methyl-urea;
3-(2-Chloro-3,5-dimethoxy-phenyl)-1-{6-[3-(2-dimethylamino-ethoxy)-phenylamino]-pyrimidin-4-yl}-1-methyl-urea;
3-(2-Chloro-3,5-dimethoxy-phenyl)-1-ethyl-1-{6-[4-(4-methyl-piperazin-1-yl)-phenylamino]-pyrimidin-4-yl}-urea;
3-(2-Chloro-3,5-dimethoxy-phenyl)-1-{6-[4-(4-methyl-piperazin-1-yl)-phenylamino]-pyrimidin-4-yl}-1-thiophen-2-ylmethyl-urea;
3-(2-Chloro-3,5-dimethoxy-phenyl)-1-[2-(4-methyl-piperazin-1-yl)-ethyl]-1-(6-phenylamino-pyrimidin-4-yl)-urea;
3-(2-Chloro-3,5-dimethoxy-phenyl)-1-(6-phenylamino-pyrimidin-4-yl)-1-(2-pyridin-2-yl-ethyl)-urea;
3-(2,6-Dichloro-3-methoxy-phenyl)-1-ethyl-1-{6-[4-(4-methyl-piperazin-1-yl)-phenylamino]-pyrimidin-4-yl}-urea;
3-(2,6-Dichloro-3-methoxy-phenyl)-1-methyl-1-{6-[3-(4-methyl-piperazin-1-yl)-phenylamino]-pyrimidin-4-yl}-urea;
3-(2,6-Dichloro-3-methoxy-phenyl)-1-methyl-1-{6-[4-(4-methyl-piperazine-1-carbonyl)-phenylamino]-pyrimidin-4-yl}-urea;
3-(2,6-Dichloro-3-methoxy-phenyl)-1-methyl-1-{6-[4-(4-methyl-piperazin-1-yl-methyl)-phenylamino]-pyrimidin-4-yl}-urea;
3-(2,6-Dichloro-3-methoxy-phenyl)-1-(6-methoxy-pyridin-3--yl-methyl)-1-{6-[4-(4-methyl-piperazin-1-yl)-phenylamino]-pyrimidin-4-yl}-urea;
3-(2,6-Dichloro-3,5-dimethoxy-phenyl)-1-ethyl-1-{6-[4-(4-methyl-piperazine-1-carbonyl)-phenylamino]-pyrimidin-4-yl}-urea;
1-(2-Chloro-6-methyl-phenyl)-3-(6-isopropylamino-pyrimidin-4-yl)-urea;
(2,6-dichloro-phenyl)-carbarnic acid 4-{6-[3-(2,6-dichloro-phenyl)-ureido]-pyrimidin-4yl-amino}-cyclohexylester;
1-(6-Isopropylamino-pyrimidin-4-yl)-3-(2,4,6-trichloro-phenyl)-urea;
1-(2,6-Dichloro-phenyl)-3-(6-isopropylamino-pyrimidin-4-yl)-urea;
1-{6-[4-(1-Methyl-piperidin-4-yl-methoxy)-phenylamino]-pyrimidin-4-yl}-3-(2,4,6-trichloro-phenyl)-urea;
1-(2-Chloro-6-methyl-phenyl)-3-{6-[4-(1-methyl-piperidin-4-yl-methoxy)-phenylamino]pyrimidin-4-yl}-urea;
1-(2,6-Dichloro-phenyl)-3-{6[4-(1-methyl-piperidin-4-yl-methoxy)-phenylamino]-pyrimidin-4-yl}-urea;
1-(2,5-Dichloro-phenyl)-3-{6[4-(4-methyl-piperazin-1-yl)-phenylamino]-pyrimidin-4-yl}-urea;
1-{6-[4-(4-Methyl-piperazin-1-yl)-phenylamino]-pyrimidin-4-yl}-3-(2,4,6-trichloro-phenyl)-urea;
1-{6-[4-(4-Methyl-piperazin-1-yl)-phenylamino]-pyrimidin-4-yl}-3-(2,4,5-trichloro-phenyl)-urea;
1-(3,4-Dichloro-phenyl)-3-{6-[4-(4-methyl-piperazin-1-yl)-phenylamino]-pyrimidin-4-yl}-urea;
1-(2,3-Dichloro-phenyl)-3-{6-[4-(4-methyl-piperazin-1-yl)-phenylamino]-pyrimidin-4-yl}-urea;
1-(5-Chloro-2-methoxy-phenyl)-3-{6-[4-(4-methyl-piperazin-1-yl)-phenylamino]-pyrimidin-4-yl}-urea;
1-(2-Chloro-6-methyl-phenyl)-3-{6-[3-(1-methyl-piperidin-4yl-methoxy)-phenylamino]-pyrimidin-4-yl}-urea;
1-(2,6-Dichloro-phenyl)-3-{6-[3-(1-methyl-piperidin-4-yl-methoxy)-phenylamino]-pyrimidin-4-yl}-urea;
1-{6-[3-(1-Methyl-piperidin-4-yl-methoxy)-phenylamino]-pyrimidin-4-yl}-3-(2,4,6-trichloro-phenyl)-urea;
1-(2-Chloro-6-methyl-phenyl)-3-{6-[4-(4-methyl-piperazin-1-yl-methyl)-phenylamino]-pyrimidin-4-yl}-urea;
1-(2,6-Dichloro-phenyl)-3-{6-[3-(4-methyl-piperazin-1-yl-methyl)-phenylamino]-pyrimidin-4-yl}-urea;
1-{6-[4-(4-Methyl-piperazin-1-ylmethy-phenylamino]-pyrimidin-4-yl}-3-(2,4,6-trichloro-phenyl)-urea;
1-{6-[4-(4-Methyl-piperazin-1-carbonyl)-phenylamino]-pyrimidin-4-yl}-3-(2,4,6-trichloro-phenyl)-urea;
1-{6-[3-(4-Methyl-piperazin-1-yl)-phenylamino]-pyrimidin-4-}-3-(2,4,6-trichloro-phenyl)-urea;
1-{6-[(trans)-4-(tert-Butyl-dimethyl-silanyloxy)-cyclohexylamino]pyrimidin-4-yl}-3-(2,4,6-trichloro-phenyl)-urea;
1-[6-((trans)-4-Hydroxy-cyclohexylamino)-pyrimidin-4-yl]-3-(2,4,6-trichloro-phenyl)-urea;
1-{6-[(trans)-4-(tert-Butyl-dimethyl-silanyloxy)-cyclohexylamino]-pyrimidin-4-yl}-3-(2-chloro-6-methyl-phenyl)-urea;
1-(2-Chloro-6-methyl-phenyl)-3-[6-((trans)-4-hydroxy-cyclohexylamino)-pyrimidin-4-yl]-urea;
1-{6-[(trans)-4-(tert-Butyl-dimethyl-silanyloxy)-cyclohexylamino]-pyrimidin-4-yl}-3-(2,6-dichloro-phenyl)-urea;
1-(2,6-Dichloro-phenyl)-3[6-((trans)-4-hydroxy-cyclohexylamino)-pyrimidin-4-yl]-urea;

1-(2-Chloro-phenyl)-3-{6-[4-(4-methyl-piperazin-1-yl)-phenylamino]-pyrimidin-4-yl}-urea;
1-(2-Bromo-phenyl)-3-{6-[4-(4-methyl-piperazin-1-yl)-phenylamino]-pyrimidin-4-yl}-urea;
1-(2,6-Dichloro-phenyl)-3-{6-[4-(2-morpholin-4-yl-ethoxy)-phenylamino]-pyrimidin-4-yl}-urea;
1-(2-Bromo-phenyl)-3-{6-[4-(2-morpholin-4-yl-ethoxy)-phenylamino]-pyrimidin-4-yl}-urea;
1-(2,6-Dichloro-phenyl)-3-{6-[4-(3-morpholin-4-yl-propoxy)-phenylamino]-pyrimidin-4-yl}-urea;
1-(2-Bromo-phenyl)-3-{6-[4-(3-morpholin-4-yl-propoxy)-phenylamino]-pyrimidin-4-yl}- urea;
1-(2,6-Dichloro-phenyl)-3-{6-[4-(2-diethylamino-ethoxy)-phenylamino]-pyrimidin-4-yl}-urea;
1-(2-Bromo-phenyl)-3-{6-[4-(2-diethylamino-ethoxy)-phenylamino]-pyrimidin-4-yl}-urea;
1-(2-Chloro-phenyl)-3-{6-[4-(3-diethylamino-propoxy)-phenylamino]-pyrimidin-4-yl}-urea;
1-(2,6-Dichloro-phenyl)-3-{6-[4-(3-diethylamino-propoxy)-phenylamino]-pyrimidin-4-yl}-urea;
1-(2-Bromo-phenyl)-3-{6-[4-(3-diethylamino-propoxy)-phenylamino]-pyrimidin-4-yl}-urea;
1-[6-(4-Diethylamino-phenylamino)-pyrimidin-4-yl]-3-(2,6-difluoro-phenyl) -urea;
1-(2,6-Difluoro-phenyl)-3-[6-(3-dirnethylamino-phenylamino)-pyrimidin-4-yl]-urea;
1-(2,6-Dichloro-phenyl)-3-[6-(4-diethylamino-phenylamino)-pyrimidin-4-yl]-urea;
1-(2,6-Dichloro-phenyl)-3-[6-(4-morpholin-4-yl-phenylamino)-pyrimidin-4-yl]-urea;
1-(2,6-Difluoro-phenyl)-3-[6-(4-morpholin-4-yl-phenylamino)-pyrimidin-4-yl]-urea;
3-(2,6-Dichloro-phenyl)-1-[6-(4-diethylamino-phenylamino)-pyrimidin-4-yl]-1-methyl-urea;
3-(2,6-Dichloro-phenyl)-1-{6-[4-(1-hydroxy-1-methyl-ethyl)-phenylamino]-pyrimidin-4-yl}-1-methyl-urea;
1-(2,6-Dichloro-phenyl)-3-[6-(6-methoxy-pyridin-3-ylamino)-pyrimidin-4-yl]urea;
3-(2,6-Dichloro-phenyl)-1-methyl-1-[6-(3-trifluoromethyl-phenylamino)-pyrimidin-4-yl]urea;
1-[6-(3-Cyano-phenylamino)-pyrimidin-4-yl]-3-(2,6-dichloro-phenyl)-1-methyl-urea;
1-(2,6-Dichloro-phenyl)-3-[6-(4-fluoro-phenylamino)-pyrimidin-4-yl]urea;
1-[6-(4-Fluoro-phenylamino)-pyrimidin-4-yl]-3-(4-methoxy-phenyl)-1-methyl-urea;
3-(2,6-Dichloro-phenyl)-1-methyl-1-[6-(4-morpholin-4-yl-phenylamino)-pyrimidin-4-yl]urea;
3-(2,6-Dichloro-phenyl)-1-[6-(2,4-difluoro-phenylamino)-pyrimidin-4-yl]-1-methyl-urea;
1-(2,6-Dichloro-phenyl)-3-[6-(3-dimethylamino-phenylamino)-pyrimidin-4-yl]urea;
3-(2,6-Dichloro-phenyl)-1-[6-(3-dimethylamino-phenylamino)-pyrimidin-4-yl]-1-methyl-urea;
1-[6-(4-Fluoro-phenylamino)-pyrimidin-4-yl]-1-methyl-3-(3-trifluoro-methyl-phenyl)-urea;
3-(3-Chloro-phenyl)-1-[6-(4-fluoro-phenylamino)-pyrimidin-4-yl]-1-methyl-urea ;
3-(2,6-Dichloro-phenyl)-1-[6-(4-fluoro-phenylamino)-pyrimidin-4-yl]-1-methyl-urea;
1-[6-(3-Chloro-phenylamino)-pyrimidin-4-yl]-3-(2,6-dichloro-phenyl)-1-methyl-urea;
1-(2-Chloro-phenyl)-3-{6-[4-(3-morpholin-4-yl-propoxy)-phenylamino]-pyrimidin-4-yl}-urea bis-hydrochloride salt;
1-(2-Chloro-phenyl)-3-{6-[4-(2-diethylamino-ethoxy)-phenylamino]-pyrimidin-4-yl}-urea;
1-[6-(3-Chloro-phenylamino)-pyrimidin-4-yl]-3-(2,6-dimethyl-phenyl)-1-methyl-urea;
3-(2-Chloro-phenyl)-1-[6-(3-chloro-phenylamino)-pyrimidin-4-yl]urea;
1-(2-Bromo-phenyl)-3-[6-(3-chloro-phenylamino)-pyrimidin-4-yl]-urea;
1-[6-(3-Chloro-phenylamino)-pyrimidin-4-yl]-3-(2-fluoro-phenyl)-urea;
1-[6-(3-Chloro-phenylamino)-pyrimidin-4-yl]-3-(3-methoxy-phenyl)-urea;
1-[6-(3-Chloro-phenylamino)-pyrimidin-4-yl]-3-(2,5-dimethoxy-phenyl)-urea;
1-[6-(3-Chloro-phenylamino)-pyrimidin-4-yl]-3-(2-trifluoromethyl-phenyl)-urea;
1-[6-(3-Chloro-phenylamino)-pyrimidin-4-yl]-3-(5-methoxy-2-methyl-phenyl)-urea;
1-(3-Chloro-phenyl)-3-[6-(3-chloro-phenylamino)-pyrimidin-4-yl]-urea;
1-[6-(3-Chloro-phenylamino)-pyrimidin-4-yl]-3-(3,4,5-trimethoxy-phenyl)-urea;
1-[6-(3-Chloro-phenylamino)-pyrimidin-4-yl]-3-(2,6-dichloro-phenyl)-urea;
1-(4-Chloro-phenyl)-3-[6-(3-chloro-phenylamino)-pyrimidin-4-yl]-urea;
1-[6-(3-Chloro-phenylamino)-pyrimidin-4-yl]-3-(3,5-dimethoxy-phenyl)-urea;
1-[6-(3-Chloro-phenylamino)-pyrimidin-4-yl]-3-(2,6-dimethyl-phenyl)-urea;
1-[6-(3-Chloro-phenylamino)-pyrimidin-4-yl]-3-phenyl-urea;
1-(2-Chloro-phenyl)-3-{6-[4-(2-morpholin-4-yl-ethoxy)-phenylamino]-pyrimidin-4-yl}-urea;
3-(2,6-Dichloro-3,5-dimethoxy-phenyl)-1-ethyl-1-{6[4-(4-methyl-piperazin-1-yl)-phenylamino]-pyrimidin-4-yl}-urea;
3-(2,6-Dichloro-3,5-dimethoxy-phenyl)-1-[6-(3-dimethylaminomethyl-phenylamino)-pyrimidin-4-yl]-1-methyl-urea;
3-(2,6-Dichloro-3,5-dimethoxy-phenyl)-1-{6-[4-(4-ethyl-piperazin-1-yl)-phenylamino]-pyrimidin-4-yl}-1-methyl-urea;
3-(2,6-Dichloro-3,5-dimethoxy-phenyl)-1-methyl-1-(6-{4-[3-(4-methyl-piperazin-1-yl)-propoxy]-phenylamino}-pyrimidin-4-yl)-urea;
3-(2,6-Dichloro-3,5-dimethoxy-phenyl)-1-{6-[4-(3-dimethylamino-propyl)-phenylamino]-pyrimidin-4-yl}-1-methyl-urea;
3-(2,6-Dichloro-3,5-dimethoxy-phenyl)-1-methyl-1-{6-[4-(2-pyrrolidin-1-yl-ethoxy)-phenylamino]-pyrimidin-4-yl}-urea;
3-(2,6-Dichloro-3,5-dimethoxy-phenyl)-1-{6-[4-(4-ethyl-piperazin-1-yl-methyl)-phenylamino]-pyrimidin-4-yl}-1-methyl-urea;
3-(2,6-Dichloro-3,5-dimethoxy-phenyl)-1-{6-[3-(4-ethyl-piperazin-1-yl-methyl)-phenylamino]-pyrimidin-4-yl}-1-methyl-urea;
3-(2,6-Dichloro-3,5-dimethoxy-phenyl)-1-[6-(3-dimethylaminomethyl-phenylamino)-pyrimidin-4-yl]-1-ethyl-urea;
3-(2,6-Dichloro-3,5-dimethoxy-phenyl)-1-{6-[4-(2-diethylamino-ethoxy)-phenylamino]-pyrimidin-4-yl}-1-methyl-urea;
3-(2,6-Dichloro-3,5-dimethoxy-phenyl)-1-[6-(2,6-dimethyl-pyridin-3yl-amino)-pyrimidin-4-yl]-1-methyl-urea;

3-(2,6-Dichloro-3,5-dimethoxy-phenyl)-1-methyl-1-[6-(6-trifluoromethyl-pyridin-3-yl-amino)-pyrimidin-4-yl]urea;

1-(2,6-Dichloro-3,5-dimethoxy-phenyl)-3-{6-[4-(2-pyrrolidin-1-yl-ethoxy)-phenylamino]-pyrimidin-4-yl}-urea;

3-(2,6-Dichloro-3,5-dimethoxy-phenyl)-1-ethyl-1-{6[4-(2-pyrrolidin-1-yl-ethoxy)-phenylamino]-pyrimidin-4-yl}-urea;

1-(2,6-Dichloro-3,5-dimethoxy-phenyl)-3-[6-(3-dimethylaminomethyl-phenylamino)-pyrimidin-4-yl]-urea;

1-(2,6-Dichloro-3,5-dimethoxy-phenyl)-3-(6-{4-[2-(4-methyl-piperazin-1-yl)-ethoxy]-phenylaminol}-pyrimidin-4-yl)-urea;

1-(2,6-Dichloro-3,5-dimethoxy-phenyl)-3-[6-(4-dimethylaminomethyl-3-trifluoromethyl-phenylamino)-pyrimidin-4-yl]-urea;

1-(2,6-Dichloro-3,5-dimethoxy-phenyl)-3-{6-[4-(4-ethyl-piperazin-1-yl)-phenylamino]-pyrimidin-4-yl}-urea;

3-(2,6-Dichloro-3,5-dimethoxy-phenyl)-1-{6[3-(4-isopropyl-piperazin-1-yl-methyl)-phenylamino]-pyrimidin-4-yl}-1-methyl-urea;

3-(2,6-Dichloro-3,5-dimethoxy-phenyl)-1-[6-(3-{[(2-dimethylamino-ethyl)-methyl-amino]-methyl}-phenylamino)-pyrimidin-4-yl]-1-methyl-urea;

3-(2,6-Dichloro-3,5-dimethoxy-phenyl)-1-{6-[4-(4-isopropyl-piperazin-1-yl)-phenylamino]-pyrimidin-4-yl}-1-methyl-urea;

1-(2,6-Dichloro-3,5-dimethoxy-phenyl)-3-{6-[4-(1-methyl-piperidin-4-yl-oxy)-phenylamino]-pyrimidin-4-yl}-urea;

3-(2,6-Dichloro-3,5-dimethoxy-phenyl)-1-methyl-{6-[4-(1-methyl-piperidin-4-yl-oxy)-phenylamino]-pyrimidin-4-yl}-urea;

3-(2,6-Dichloro-3,5-dimethoxy-phenyl)-1-ethyl-{6-[4-(1-methyl-piperidin-4-yl-oxy)-phenylamino]-pyrimidin-4-yl}-urea;

3-(2,6-Dichloro-3,5-dimethoxy-phenyl)-1-[6-(4-dimethylaminomethyl-3-trifluoromethyl-phenylamino)-pyrimidin-4-yl]-1-methyl-urea;

1-(2,6-Dichloro-3,5-dimethoxy-phenyl)-3-{6[4-(4-ethyl-piperazin-1-yl-methyl)-3-trifluoromethyl-phenylamino]-pyrimidin-4-yl}-urea;

3-(2,6-Dichloro-3,5-dimethoxy-phenyl)-1-{6-[4-(4-ethyl-piperazin-1-yl-methyl)-3-trifluoromethyl-phenylamino]-pyrimidin-4-yl}-1-methyl-urea;

1-(2,6-Dichloro-3,5-dimethoxy-phenyl)-3-{6-[4-(4-isopropyl-piperazin-1-yl)-phenylamino]-pyrimidin-4-yl}-urea;

3-(2,6-Dichloro-3,5-dimethoxy-phenyl)-1-methyl-1-(6-{4-[2-(4-methyl-piperazin-1-yl)-ethoxy]-phenylamino}-pyrimidin-4-yl)-urea;

3-(2,6-Dichloro-3,5-dimethoxy-phenyl)-1-{6-[4-(4-isopropyl-piperazin-1-yl)-phenylamino]-pyrimidin-4-yl}-1-methyl-urea;

1-(2,6-Dichloro-3,5-dimethoxy-phenyl)-3-[6-(4-dimethylaminomethyl-3-trifluoromethyl-phenylamino)-pyrimidin-4-yl]-urea;

3-(2,6-Dichloro-3,5-dimethoxy-phenyl)-1-[6-(4-dimethylaminomethyl-3-trifluoromethyl-phenylamino)-pyrimidin-4-yl]-1-methyl-urea;

3-(2,6-Dichloro-3,5-dimethoxy-phenyl)-1-[6-(3-{[(2-dimethylamino-ethyl)-methyl-amino]-methyl}-phenylamino)-pyrimidin-4-yl]-1-methyl-urea;

3-(2,6-Dichloro-3,5-dimethoxy-phenyl)-1-{6-[3-(4-isopropyl-piperazin-1-yl-methyl)-phenylamino]-pyrimidin-4-yl}-1-methyl-urea;

1-(2,6-Dichloro-3,5-dimethoxy-phenyl)-3-{6-[3-(1-methyl-piperidin-4-yl-oxy)-phenylamino]-pyrimidin-4-yl}-urea;

3-(2,6-Dichloro-3,5-dimethoxy-phenyl)-1-methyl-{6-[3-(1-methyl-piperidin-4-yl-oxy)-phenylamino]-pyrimidin-4-yl}-urea;

3-(2,6-Dichloro-3,5-dimethoxy-phenyl)-1-[6-(3-diethylaminomethyl-phenylamino)-pyrimidin-4-yl]-1-methyl-urea; and 3-(2,6-Dichloro-3-trifluoromethyl-phenyl)-1-{6-[4-(4-ethyl-piperazin-1-yl)-phenylamino]-pyrimidin-4-yl}-1-methyl-urea.

32. The compound 3-(2,6-Dichloro-3,5-dimethoxy-phenyl)-1-{6-[4-(4-ethyl-piperazin-1-yl)-phenylamino]-pyrimidin-4-yl}-1-methyl-urea or a pharmaceutically acceptable salt or N-oxide thereof.

33. The compound 3-(2,6-Dichloro-3,5-dimethoxy-phenyl)-1-{6-[4-(4-ethyl-piperazin-1-yl)-phenylamino]-pyrimidin-4-yl}-1-methyl-urea or a pharmaceutically acceptable salt thereof.

34. The compound 3-(2,6-Dichloro-3,5-dimethoxy-phenyl)-1-{6-[4-(4-ethyl-piperazin-1-yl)-phenylamino]-pyrimidin-4-yl}-1-methyl-urea.

35. The compound 1-(2,6-Dichloro-3,5-dimethoxy-phenyl)-3-{6-[4-(4-ethyl-piperazin-1-yl)-phenylamino]-pyrimidin-4-yl}-urea or a pharmaceutically acceptable salt or N-oxide thereof.

36. The compound 1-(2,6-Dichloro-3,5-dimethoxy-phenyl)-3-{6-[4-(4-ethyl-piperazin-1-yl)-phenylamino]-pyrimidin-4-yl}-urea or a pharmaceutically acceptable salt thereof.

37. The compound 1-(2,6-Dichloro-3,5-dimethoxy-phenyl)-3-{6-[4-(4-ethyl-piperazin-1-yl)-phenylamino]-pyrimidin-4-yl}-urea.

38. A pharmaceutical composition comprising a compound according to claim 32, or pharmaceutically acceptable salt or N-oxide thereof, and a pharmaceutically acceptable carrier or diluent.

39. A pharmaceutical composition comprising a compound according to claim 33, or pharmaceutically acceptable salt thereof, and a pharmaceutically acceptable carrier or diluent.

40. A pharmaceutical composition comprising a compound according to claim 34 and a pharmaceutically acceptable carrier or diluent.

41. A pharmaceutical composition comprising a compound according to claim 35, or pharmaceutically acceptable salt or N-oxide thereof, and a pharmaceutically acceptable carrier or diluent.

42. A pharmaceutical composition comprising a compound according to claim 36, or pharmaceutically acceptable salt thereof, and a pharmaceutically acceptable carrier or diluent.

43. A pharmaceutical composition comprising a compound according to claim 37 and a pharmaceutically acceptable carrier or diluent.

\* \* \* \* \*

UNITED STATES PATENT AND TRADEMARK OFFICE
CERTIFICATE OF CORRECTION

PATENT NO.        : 8,552,002 B2         Page 1 of 1
APPLICATION NO.   : 11/570983
DATED             : October 8, 2013
INVENTOR(S)       : Ding et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,524 days.

Signed and Sealed this
Twenty-sixth Day of August, 2014

Michelle K. Lee
*Deputy Director of the United States Patent and Trademark Office*